US012140598B2

(12) United States Patent
De Bruin et al.

(10) Patent No.: US 12,140,598 B2
(45) Date of Patent: Nov. 12, 2024

(54) BIOMARKER IDENTIFICATION FOR IMMINENT AND/OR IMPENDING HEART FAILURE

(71) Applicant: Endothelium Scanning Nanotechnology Limited, Melbourne (AU)

(72) Inventors: Leo De Bruin, Balwyn (AU); Gustav De Bruin, Highton (AU); Andrew Coats, Richmond (AU)

(73) Assignee: Endothelium Scanning Nanotechnology Limited, Melbourne (AU)

( * ) Notice: Subject to any disclaimer, the term of this patent is extended or adjusted under 35 U.S.C. 154(b) by 0 days.

(21) Appl. No.: 17/545,112

(22) PCT Filed: Jun. 3, 2021

(86) PCT No.: PCT/IB2021/000378
§ 371 (c)(1),
(2) Date: Dec. 8, 2021

(87) PCT Pub. No.: WO2021/245459
PCT Pub. Date: Dec. 9, 2021

(65) Prior Publication Data
US 2023/0128775 A1 Apr. 27, 2023

Related U.S. Application Data

(60) Provisional application No. 63/034,264, filed on Jun. 3, 2020.

(51) Int. Cl.
| | | |
|---|---|---|
| G01N 33/68 | (2006.01) | |
| G06N 3/08 | (2023.01) | |
| G06N 7/01 | (2023.01) | |
| G06N 20/00 | (2019.01) | |
| G16H 10/40 | (2018.01) | |
| G16H 20/10 | (2018.01) | |
| G16H 20/30 | (2018.01) | |
| G16H 20/60 | (2018.01) | |
| G16H 50/20 | (2018.01) | |
| G16H 50/30 | (2018.01) | |

(52) U.S. Cl.
CPC ......... *G01N 33/6893* (2013.01); *G06N 20/00* (2019.01); *G16H 20/10* (2018.01); *G16H 20/30* (2018.01); *G16H 20/60* (2018.01); *G16H 50/20* (2018.01); *G16H 50/30* (2018.01); *G01N 2800/325* (2013.01); *G06N 3/08* (2013.01); *G06N 7/01* (2023.01); *G16H 10/40* (2018.01)

(58) Field of Classification Search
None
See application file for complete search history.

(56) References Cited

U.S. PATENT DOCUMENTS

| | | | |
|---|---|---|---|
| 2004/0033582 A1 | 2/2004 | Edmonds et al. | |
| 2008/0057590 A1 | 3/2008 | Urdea et al. | |
| 2014/0045714 A1 | 2/2014 | Gerszten et al. | |
| 2015/0199491 A1* | 7/2015 | Snider | G16H 50/50 703/11 |
| 2015/0216471 A1* | 8/2015 | Goldstein | A61B 5/682 600/573 |
| 2016/0202190 A1* | 7/2016 | Hein | G01N 21/78 422/69 |
| 2018/0095067 A1* | 4/2018 | Huff | G01N 33/48721 |
| 2019/0183927 A1* | 6/2019 | Cummings | A61K 31/7004 |

FOREIGN PATENT DOCUMENTS

| | | |
|---|---|---|
| WO | WO-03042358 A2 | 5/2003 |
| WO | WO-2005114207 A2 | 12/2005 |
| WO | WO-2006026074 A2 | 3/2006 |
| WO | WO-2008026409 A1 | 3/2008 |
| WO | WO-2008131039 A2 | 10/2008 |
| WO | WO-2019028507 A1 | 2/2019 |
| WO | WO-2019057756 A1 | 3/2019 |
| WO | WO-2021245459 A1 | 12/2021 |
| WO | WO-2022261705 A1 | 12/2022 |

OTHER PUBLICATIONS

Zhang et al (Theranostics 2017, vol. 7, Issue 18).*
Jorba (PloS One Feb. 15, 2020:e0228926) (Year: 2020).*
Abdul Rehman, S. et al., "Role of Salivary Biomarkers in Detection of Cardiovascular Diseases (CVD)." Proteomes. Aug. 7, 2017;5(3):21.
Agarwal, S. et al., "Prediction of Incident Heart Failure in General Practice." Circulation: Heart Failure. Jul. 2012, vol. 5, DOI: 10.1161/CIRCHEARTFAILURE.111.964841.
Bakhshi, H. et al., "Targeted Discovery Proteomics in Malignant Left Ventricular Hypertrophy." Journal of the American College of Cardiology. Mar. 2020, vol. 75, Issue 11, Presentation No. 1039-05.
Baldan-Martin, M. et al., "Plasma Molecular Signatures in Hypertensive Patients With Renin-Angiotensin System Suppression." Hypertension. May 2016, DOI: 10.1161/HYPERTENSIONAHA.116.07412.
Bhattarai, KR. et al., "Compliance with Saliva Collection Protocol in Healthy Volunteers: Strategies for Managing Risk and Errors." International Journal of Medical Sciences. 2018;15(8):823-31.
Dobre, D. et al., "Albuminuria in heart failure: what do we really know?" Current Opinion in Cardiology. Mar. 2009, vol. 24, DOI 10.1097/HCO.0b013e328323aa9a.
Foo, JY. et al., "NT-ProBNP levels in saliva and its clinical relevance to heart failure." PLoS One. 2012;7(10):e48452.

(Continued)

*Primary Examiner* — Changhwa J Cheu
(74) *Attorney, Agent, or Firm* — Wilson Sonsini Goodrich & Rosati

(57) ABSTRACT

Disclosed herein are methods and compositions for the detection of biomarkers for cardiac diseases. Disclosed herein are sample collection devices comprising detection devices for heart failure. Disclosed herein are methods of detecting, monitoring, preventing, or treating heart failure.

20 Claims, 19 Drawing Sheets

(56) References Cited

OTHER PUBLICATIONS

Friedrich, FW. et al., "A new polymorphism in human calmodulin III gene promoter is a potential modifier gene for familial hypertrophic cardiomyopathy." Eur Heart J. Jul. 2009;30(13):1648-55.
Gaggin, HK. and Januzzi, JL. Jr., "Cardiac biomarkers and heart failure." Am College Cardiol 2015. Available at https://www.acc.org/%2Flatest-in-cardiology%2Farticles%2F2015%2F02%2F09%2F13%2F00%2Fcardiac-biomarkers-and-heart-failure.
Gaggin HK, Januzzi JL Jr. "Biomarkers and diagnostics in heart failure." Biochim Biophys Acta. 2013;1832(12):2442-2450. doi:10.1016/j.bbadis.2012.12.014.
Guo, F. et al., "The interplay of LncRNA ANRIL and miR-181b on the inflammation-relevant coronary artery disease through mediating NF-kappaB signalling pathway." J Cell Mol Med. Oct. 2018;22(10):5062-5075.
Hippisley-Cox, J. et al., "Development and validation of risk predication equations to estimate future risk of heart failure in patients with diabetes: a prospective cohort study." BMJ Open. 2015, vol. 5, doi:10.1136/bmjopen-2015-008503.
International Search Report dated Sep. 16, 2021 for International Application No. PCT/IB2021/000378, (8 pages).
Khurshid, Z. et al., "Human Saliva Collection Devices for Proteomics: An Update." Int J Mol Sci. Jun. 6, 2016;17(6):846.
Li, L. et al., "Characterization of LncRNA expression profile and identification of novel LncRNA biomarkers to diagnose coronary artery disease." Atherosclerosis. Aug. 2018;275:359-367.
Liu, TF. et al., "Association between CMTM5 gene and coronary artery disease and the relative mechanism." Beijing Da Xue Xue Bao Yi Xue Ban. Dec. 18, 2020;52(6):1082-1087. Chinese with English abstract.
Malon, R. et al., "Saliva-Based Biosensors: Noninvasive Monitoring Tool for Clinical Diagnostics." Hindawi. 2014, DOI 10.1155/2014/962903.
McMurray, J. et al., "Heart failure." Lancet. May 28-Jun. 3, 2005;365(9474):1877-89.
Mitulovic, Goran. "Proteomics of the Salivary Fluid, Salivary Glands—New Approaches in Diagnostics and Treatment." IntechOpen, (Dec. 20, 2017), DOI: 10.5772/intechopen.72309. Available from: https://www.intechopen.com/books/salivary-glands-new-approaches-in-diagnostics-and-treatment/proteomics-of-the-salivary-fluid.
Nadar, Sunil K, and Muhammed Mujtaba Shaikh. "Biomarkers in Routine Heart Failure Clinical Care." Cardiac failure review vol. 5,1 (2019): 50-56. doi:10.15420/cfr.2018.27.2.
Pappa, E. et al., "Saliva Proteomics Analysis Offers Insights on Type 1 Diabetes Pathology in a Pediatric Population." Frontiers in physiology. 2018;9:444.
Raghuraman, G. et al., "Enhanced Neuropeptide Y Synthesis During Intermittent Hypoxia in the Rat Adrenal Medulla: Role of Reactive Oxygen Species-Dependent Alterations in Precursor Peptide Processing." Antioxidants & Redox Signaling. Apr. 2011, DOI: 10.1089/ars.2010.3353.
Ritterhoff, J. and Most, P., "Targeting S100A1 in heart failure." Gene Ther. Jun. 2012;19(6):613-21.
Rosello-Lleti, E. et al., "Human Ischemic Cardiomyopathy Shows Cardiac Nos. 1 Translocation and its Increased Levels are Related to Left Ventricular Performance." Scientific Reports. Apr. 2016, vol. 6, DOI: 10.1038/srep24060.
Shi, X. et al., "Abstract 13293: Acyl-coa Binding Protein is Marker of Myocardial Ischemia." Circulation. Mar. 2018, DOI: 10.1161/circ.130.suppl_2.1329.
Shirai, T. et al., "The glycolytic enzyme PKM2 bridges metabolic and inflammatory dysfunction in coronary artery disease." J Exp Med. Mar. 7, 2016;213(3):337-54.
"Treatment—Heart Failure." NHS Choices, NHS, Oct. 26, 2018, https://www.nhs.uk/conditions/heart-failure/treatment/.
Wang, L. et al., "Identification of circular RNA Hsa_circ_0001879 and Hsa_circ_0004104 as novel biomarkers for coronary artery disease." Atherosclerosis. Jul. 2019;286:88-96.

Watson, C. et al., "Biomarker profiling for risk of future heart failure (HFpEF) development." Journal of Translational Medicine. Feb. 2021, vol. 19, DOI:10.1186/s12967-021-02735-3.
Yoshizawa, JM. et al., "Salivary biomarkers: toward future clinical and diagnostic utilities." Clin Microbiol Rev. Oct. 2013;26(4):781-91.
Zhang, Xi et al. "Identification and Validation of a Salivary Protein Panel to Detect Heart Failure Early." Theranostics vol. 7,18 4350-4358. Sep. 26, 2017, doi:10.7150/thno.21727.
Zhang, YH. et al., "Identifying the RNA signatures of coronary artery disease from combined IncRNA and mRNA expression profiles." Genomics. Nov. 2020;112(6):4945-4958.
Agarwal et al., Prediction of incident heart failure in general practice: the atherosclerosis risk in communities (ARIC) study. Circ Heart Fail. 5(4):422-429 (2012).
Bakhshi et al., Targeted discovery proteomics in malignant left ventricular hypertrophy. J Am Coll Cardiol. Presentation No. 1039-05, 75(11_Supplement_1):667, p. 1 (2020).
Baldan-Martin et al., Plasma molecular signatures in hypertensive patients with renin-angiotensin system suppression. Hypertension. 68(1):157-166 (2016).
Bhattarai et al., Compliance with saliva collection protocol in healthy volunteers: Strategies for managing risk and errors. Int J Med Sci. 15(8):823-831 (2018).
Dobre et al., Albuminuria in heart failure: what do we really know? Curr Opin Cardiol. 24(2):148-154 (2009).
Foo et al., NT-ProBNP levels in saliva and its clinical relevance to heart failure. PLoS One. 7(10):e48452, pp. 1-6 (2012).
Hoofnagle et al., Recommendations for the generation, quantification, storage and handling of peptides used for mass spectrometry-based assays. Clin Chem. 62(1):48-69 (2016).
Friedrich et al., A new polymorphism in human calmodulin III gene promoter is a potential modifier gene for familial hypertrophic cardiomyopathy. Eur Heart J. 30(13):1648-1655 (2009).
Gaggin et al., Biomarkers and diagnostics in heart failure. Biochim Biophys Acta. 1832(12):2442-2450 (2013).
Gaggin et al., Cardiac biomarkers and heart failure. Am College Cardiol. pp. 1-14 (2015). Accessed Dec. 9, 2021; available at https://www.acc.org/Latest-in-Cardiology/Articles/2015/02/09/13/00/Cardiac-Biomarkers-and-Heart-Failure.
Guo et al., The interplay of LncRNA ANRIL and miR-181b on the inflammation-relevant coronary artery disease through mediating NF-κB signalling pathway. J Cell Mol Med. 22(10):5062-5075 (2018).
Hippisley-Cox et al., Development and validation of risk prediction equations to estimate future risk of heart failure in patients with diabetes: a prospective cohort study. BMJ Open. 5(9):e008503, pp. 1-10 (2015).
Khurshid et al., Human saliva collection devices for proteomics: An update. Int J Mol Sci. 17(6):846, pp. 1-10 (2016).
Kitzman et al., Rationale and design for a phase 2 trial of verinurad plus allopurinol in patients with heart failure with preserved ejection fraction and hyperuricemia. J Am Coll Cardiol (JACC). 77(18_Supplement_1): 597-597 (2021).
Li et al., Characterization of LncRNA expression profile and identification of novel LncRNA biomarkers to diagnose coronary artery disease. Atherosclerosis. 275:359-367 (2018).
Liu et al., [Association between CMTM5 gene and coronary artery disease and the relative mechanism]. Beijing Da Xue Xue Bao Yi Xue Ban. 52(6):1082-1087 (2020). Chinese with English abstract.
Malon et al., Saliva-based biosensors: noninvasive monitoring tool for clinical diagnostics. Biomed Res Int. 2014:962903, pp. 1-20 (2014).
Mcmurray et al., Heart failure. Lancet. 365(9474):1877-1889 (2005).
Mitulović, Proteomics of the salivary fluid. Salivary Glands (Ed. Güvenç) Chapter 5, pp. 67-87 (2017).
Nadar et al., Biomarkers in routine heart failure clinical care. Card Fail Rev. 5(1):50-56 (2019).
Nelander et al., Early clinical experience with AZD4831, a novel myeloperoxidase inhibitor, developed for patients with heart failure with preserved ejection fraction. Clin Transl Sci. 14(3):812-819 (2021).

(56) References Cited

OTHER PUBLICATIONS

NHS, Treatment—Heart Failure. NHS.UK, Page reviewed Oct. 26, 2018. Accessed on Dec. 9, 2021 at https://www.nhs.uk/conditions/heart-failure/treatment/.
Ouyang et al., A review of biosensor technologies for blood biomarkers toward monitoring cardiovascular diseases at the point-of-care. Biosens Bioelectron. 171:112621, pp. 1-19 (2020).
Pappa et al., Saliva proteomics analysis offers insights on type 1 diabetes pathology in a pediatric population. Front Physiol. 9:444, pp. 1-14 (2018).
Patel et al., Drug targets for heart failure with preserved ejection fraction: A mechanistic approach and review of contemporary clinical trials. Annu Rev Pharmacol Toxicol. 6:59:41-63 (2019).
PCT/IB2021/000378 International Search Report and Written Opinion dated Sep. 16, 2021.
Raghuraman et al., Enhanced neuropeptide Y synthesis during intermittent hypoxia in the rat adrenal medulla: role of reactive oxygen species-dependent alterations in precursor peptide processing. Antioxid Redox Signal. 14(7):1179-1190 (2011).
Rehman et al., Role of salivary biomarkers in detection of cardiovascular diseases (CVD). Proteomes. 5(3):21, pp. 1-6 (2017).
Ritterhoff et al., Targeting S100A1 in heart failure. Gene Ther. 19(6):613-621 (2012).
Rosello-Lleti et al., Human ischemic cardiomyopathy shows cardiac NOS1 translocation and its increased levels are related to left ventricular performance. Sci Rep. 6:24060, pp. 1-9 (2016).
Shi et al., Abstract 13293: Acyl-CoA binding protein is marker of myocardial ischemia. Circulation. 130(suppl_2.13293) 1pg. (2018).
Shirai et al., The glycolytic enzyme PKM2 bridges metabolic and inflammatory dysfunction in coronary artery disease. J Exp Med. 213(3):337-354 (2016).
Spertus et al., Mavacamten for treatment of symptomatic obstructive hypertrophic cardiomyopathy (EXPLORER-HCM): health status analysis of a randomised, double-blind, placebo-controlled, phase 3 trial. Lancet. 397(10293):2467-2475 (2021).
Stienen et al., Enhanced clinical phenotyping by mechanistic bioprofiling in heart failure with preserved ejection fraction: insights from the MEDIA-DHF study (the metabolic road to diastolic heart failure). Biomarkers. 25(2):201-211 (2020).
Wang et al., Identification of circular RNA Hsa_circ_0001879 and Hsa_circ_0004104 as novel biomarkers for coronary artery disease. Atherosclerosis. 286:88-96 (2019).
Watson et al., Biomarker profiling for risk of future heart failure (HFpEF) development. J Transl Med. 19(1):61, pp. 1-10 (2021).
Yoshizawa et al., Salivary biomarkers: toward future clinical and diagnostic utilities. Clin Microbiol Rev. 26(4):781-791 (2013).
Zhang et al., Identification and validation of a salivary protein panel to detect heart failure early. Theranostics. 7(18):4350-4358 (2017).
Zhang et al., Identifying the RNA signatures of coronary artery disease from combined lncRNA and mRNA expression profiles. Genomics. 112(6):4945-4958 (2020).
Ansara et al., Neprilysin Inhibition With Sacubitril/valsartan in the Treatment of Heart Failure: Mortality Bang for Your Buck. Journal of Clinical Pharmacy and Therapeutics. vol. 41, Issue No. 2 (2016): 119-127.
Bozkurt et al., Neprilysin Inhibitors in Heart Failure: The Science, Mechanism of Action, Clinical Studies, and Unanswered Questions. JACC: Basic to translational science. vol. 8, Issue No. 1 (2023): 88-105.
EP21818377.0 Partial European search report pursuant to Rule 164(1) EPC, dated Apr. 25, 2024.
Greenberg, Angiotensin Receptor-Neprilysin Inhibition (ARNI) in Heart Failure. International journal of heart failure. vol.2, Issue No. 2 (2020): 73-90.
Kim et al., Update on the Pharmacotheraphy of Heart Failure with Reduced Ejection Fraction. Cardiovascular prevention and Pharmacotheraphy. vol. 2, Issue No. 4 (2020): 113-133.
PCT/AU2022/050591 International Search Report and Written Opinion dated Aug. 22, 2022.
Prenner et al., Role of Angiotensin Receptor-Neprilysin Inhibition in Heart Failure. Current Atherosclerosis Reports. vol. 18, Issue No. 48 (2016): 1-10.
U.S. Appl. No. 18/471,849 Office Action dated Jan. 30, 2024.

* cited by examiner

A0 evaluation results (1=Y; 0=N)

FIG. 3A

A1 evaluation results (1=Y; 0=N)

FIG. 3B

A2 evaluation results (1=Y; 0=N)

FIG. 3C

A3 evaluation results (1=Y; 0=N)

FIG. 4A

A4 evaluation results (1=Y; 0=N)

FIG. 4B

A5 evaluation results (1=Y; 0=N)

FIG. 4C

CALM3 high:

CALM3 low:

ACBP low:

ACBP high:

AMPN low:

AMPN high:

IGA2 low:

IGA2 high:

AMD high:

AMD low:

200 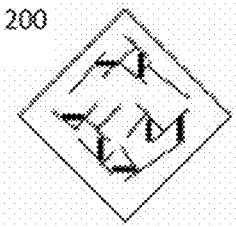 Electronic biosensor that collects data that can be installed onto any platform such as skin, clothing, smart-device, phone case, laptop, sports gear, sports equipment, gym apparatus, or any other usable device or platform where the sensors can be placed onto/into for use.

FIG. 13A

210  Electronic biosensor installed into/onto swab for use to detect diseases. The swab also has electronics to transmit data to a software

FIG. 13B

220 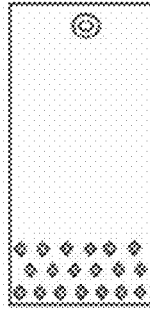 Electronic biosensor installed into/onto phone casing/other relevant usable device for use to detect diseases. The device also has electronics to transmit data to a software application.

BIOMARKER IDENTIFICATION FOR IMMINENT AND/OR IMPENDING HEART FAILURE

CROSS REFERENCE

This application claims priority to PCT/IB2021/000378, filed Jun. 3, 2021, which claims the benefit of U.S. Provisional Application No. 63/034,264, filed Jun. 3, 2020, which applications are incorporated herein by reference.

BACKGROUND OF THE INVENTION

There are limited tests conducted for specific disease detection. The most commonly used tests can be ineffective in terms of time and cost, and as a preventative measure. The shortcomings of these methods are that they are not disease specific tests and therefore lack the preventative impact. In addition, they are not applied at early stages of a disease where less invasive treatments or interventions would be effective in preventing or delaying onset of the disease. For example, testing for heart failure is primarily tested in patients after a significant cardiovascular adverse event, diagnosis of Type 2 diabetes, or heart failure symptoms have occurred, e.g. after a stroke, severe pain in the body, or chest pain. At this point, survival rates are lower. Current methods of collecting and analyzing health/medical or biological data is inefficient which has meant that correlations between diseases and specific biomarkers are not well understood and lack precision over a large population over a long time horizon. There is a need for tests that can provide clinically actionable information without the invasiveness, cost, and accessibility issues presented by testing through echocardiograph, blood tests, or cardiopulmonary exercise.

SUMMARY OF THE INVENTION

The disclosure herein provides compositions and methods to calculate a risk for the development of a disease condition before it is present in a subject or has been diagnosed, by the detection of biomarkers, such as those associated with a risk of the disease. Determining that patients are at risk allows earlier intervention, to improve outcomes. It is beneficial to detect imminent risk that is clinically actionable before it is too late, so that treatment can be administered early. Earlier detection also allows for less invasive treatments to be administered. Patients can be stratified into risk categories such as no risk, low risk, medium risk, and high risk, with appropriate therapies administered based at least in part on the level of risk of developing heart failure. In some embodiments, a treatment can prevent or delay heart failure developing in a subject.

Disclosed herein in some embodiments is a method of treating heart failure comprising measuring one or more compounds present in a biological sample from a subject that does not currently have heart failure or that has not been diagnosed with heart failure. In some embodiments, an increased or decreased level of the compound relative to a reference level can be indicative of a risk of developing heart failure within a time period. In some embodiments, a method can further comprise determining a risk of a subject developing heart failure within a time period based on an increased or decreased level of one or more compounds. In some embodiments, a method can further comprise administering a treatment for a heart failure to a subject based on a risk score. In some embodiments, one or more compounds can comprise one or more biomarkers. In some embodiments, one or more biomarkers can comprise a polypeptide comprising at least 70% sequence identity to AMPN, AMD, CALM3, KI21A, ACBP, IGA2, a salt of any of these, or any combination thereof. In some embodiments, one or more biomarkers can comprise at least two polypeptides comprising at least 70% sequence identity to at least two of AMPN, AMD, CALM3, KI21A, ACBP, IGA2, S10A7, a salt of any of these, or any combination thereof. In some embodiments, one or more biomarkers can comprise at least three polypeptides comprising at least 70% sequence identity to at least three of AMPN, AMD, CALM3, KI21A, ACBP, IGA2, S10A7, a salt of any of these, or any combination thereof. In some embodiments, one or more biomarkers can comprise at least four polypeptides comprising at least 70% sequence identity to at least four of AMPN, AMD, CALM3, KI21A, ACBP, IGA2, S10A7, a salt of any of these, or any combination thereof. In some embodiments, one or more biomarkers can comprise at least five polypeptides comprising at least 70% sequence identity to at least five of AMPN, AMD, CALM3, KI21A, ACBP, IGA2, S10A7, a salt of any of these, or any combination thereof. In some embodiments, a polypeptide can comprise at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity to AMPN, AMD, CALM3, KI21A, ACBP, IGA2, a salt of any of these, or any combination thereof. In some embodiments, polypeptides comprise at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity to AMPN, AMD, CALM3, KI21A, ACBP, IGA2, S10A7, a salt of any of these, or any combination thereof. In some embodiments, a treatment for the heart failure administered to the subject can be determined at least in part by the number of biomarkers that are expressed at an increased or decreased level relative to a reference level. In some embodiments, a treatment for the heart failure administered to the subject can be determined at least in part by the quantitative level of a biomarker relative to a reference level. In some embodiments, a subject can be classified as being low risk, medium risk or high risk of developing heart failure within a time period. In some embodiments, a subject can be determined to be at low risk of developing heart failure, and the treatment prescribed can comprise dietary intervention, exercise, or a combination thereof. In some embodiments, a subject can be determined to be at medium risk of developing heart failure, and the treatment prescribed can comprise administering a statin, an anti-inflammatory, a blood thinner, dietary intervention, exercise, or any combination thereof. In some embodiments, a subject can be determined to be at high risk of developing heart failure within the next six months, and the treatment prescribed can comprise administering a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator, cardioxyl, omecamtiv mecarbil, relaxin, serelaxin, staroxime, bucindolol, a phosphodiesterase 5 inhibitor, a vasopressin inhibitor, levosimendan, a sodium-glucose cotransporter-2 (SGLT2) inhibitor, an If channel blocker, an alpha blocker, a beta blocker, a beta receptor blocker, an ACE inhibitor, a stereoisomer of any of these, or a salt of any of these, or any combination thereof. In some embodiments, a biological sample can comprise amniotic fluid, amniotic sac, aqueous humor, bile, blood, blood plasma, breast milk, cerebrospinal fluid (CSF), cerebrospinal fluid rhinorrhea, chyle, chyme, endolymph, extracellular fluid, exudate, gastric acid, hemolacria, hemolymph, interstitial fluid, lymph, mucus, pericardial fluid, perilymph, peritoneal fluid, perspiration, phlegm, pus, rheum, saliva, semen, sweat, synovial fluid, tears, transcellular fluid, transudate, urine, vaginal lubricant, vitreous body, vomit, or any combination thereof. In some embodiments, a biological sample can comprise urine. In some embodiments, a biological sample can comprise saliva. In some embodiments, a biological sample can be obtained using an oral sample collection device. In some embodiments, an oral sample collection device can comprise a detection compound, and wherein the device can be configured to perform the contacting when the saliva is input into the oral sample collection device. In some embodiments, an oral sample collection device can comprise a wireless transmitter. In some embodiments, a wireless transmitter can comprise a Bluetooth transmitter, an RF transmitter, a cellular signal transmitter, a Wi-fi transmitter, or any combination thereof. In some embodiments, an oral sample collection device can comprise a wireless receiver. In some embodiments, a wireless receiver can comprise a Bluetooth receiver, an RF transmitter, a cellular signal receiver, a Wi-fi receiver, or any combination thereof. In some embodiments, an oral sample collection device can comprise an oral swab. In some embodiments, a concentration of the one or more compounds present in a biological sample can be enriched in the oral sample collection device after binding to the detection compound, relative to the concentration of the compound present in the biological sample. In some embodiments, a method can further comprise, with the aid of a computer processor, executing an algorithm selecting a treatment from a database prior to the administering. In some embodiments, a database can be at least transiently stored on a computer readable memory. In some embodiments, a database can comprise a treatment formulary of medicaments or interventions. In some embodiments, a treatment can comprise a medicament. In some embodiments, medicament can comprise a drug or a biologic that can be licensed or approved for a condition by the United States Federal Drug Agency (USFDA) anytime as of or after Apr. 1, 2020. In some embodiments, a drug or the biologic is not licensed or approved by the USFDA for heart failure anytime as of or after May 1, 2020. In some embodiments, a medicament can comprise a drug or a biologic that is not licensed or approved by the USFDA for any condition anytime as of or after May 1, 2020. In some embodiments, a medicament can comprise a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator cardioxyl, an omecamtiv mecarbil, a relaxin, a serelaxin, a staroxime, bucindolol, a phosphodiesterase 5 inhibitor, a vasopressin inhibitor, a levosimendan, a sodium-glucose cotransporter-2 (SGLT2) inhibitor, an If channel blocker, an alpha blocker, a beta receptor blocker, a beta blocker, an ACE inhibitor, a stereoisomer of any of these, a salt of any of these, or any combination thereof. In some embodiments, a medicament can comprise the beta receptor blocker or the salt thereof, wherein the beta receptor blocker or salt thereof comprise at least one stereocenter in an S-configuration. In some embodiments, a beta receptor blocker can comprise a long acting beta blocker. In some embodiments, a beta receptor blocker can comprise a short acting beta blocker. In some embodiments, a long acting beta blocker or salt thereof or the short acting beta blocker or the salt thereof can comprise pindolol, oxprenolol, atenolol, acebutolol, bisoprolol, bucindolol, carvedilol, metoprolol, nadolol, nebivolol, oxprenolol, propranolol, a stereoisomer of any of these, a polymorph of any of these, a diastereomer of any of these, a salt of any of these, or any combination thereof. In some embodiments, a long acting or short acting beta blocker or the salt thereof comprise S-pindolol, S-oxprenolol, S-atenolol, S-acebutolol, S-bisoprolol, S-bucindolol, S-carvedilol, S-metoprolol, S-nadolol, S-nebivolol, S-Oxprenolol, S-propranolol, a stereoisomer of any of these, a polymorph of any of these, a diastereomer of any of these, a salt of any of these, or any combination thereof. In some embodiments, a medicament can comprise the statin or the salt thereof, wherein the statin or the salt thereof can comprise atorvastatin, fluvastatin, lovastatin, pravastatin, rosuvastatin, simvastatin, pitavastatin, a salt of any of these, or any combination thereof. In some embodiments, a medicament can comprise the blood thinner or the salt thereof, wherein the blood thinner or the salt thereof can comprise apixaban, dabigatran, edoxaban, fondaparinux, heparin, rivaroxaban, warfarin, a salt of any of these, or any combination thereof. In some embodiments, a medicament can comprise the phosphodiesterase 5 inhibitor or the salt thereof, wherein the phosphodiesterase 5 inhibitor or the salt thereof can comprise amrinone, milrinone, avanafil, lodenafil, mirodenafil, sildenafil, tadalafil, vardenafil, udenafil, zaprinast, benzaminenafil, a salt of any of these, or any combination thereof. In some embodiments, a medicament can comprise the vasopressin inhibitor or the salt thereof, wherein the vasopressin inhibitor or the salt thereof can comprise conivaptan, relcovaptan, nelivaptan, lixivaptan, mozavaptan, satavaptan, tolvaptan, demeclocycline, lithium, a salt of any of these, or any combination thereof. In some embodiments, a medicament can comprise the SGLT2 inhibitor or the salt thereof, wherein the SGLT2 inhibitor or the salt thereof can comprise dapagliflozin, empagliflozin, canagliflozin, sotagliflozin, ertugliflozin, ipragliflozin, luseogliflozin, remogliflozin etabonate, sergliflozin etabonate, tofogliflozin a stereoisomer of any of these, a salt of any of these, or any combination thereof. In some embodiments, a medicament can comprise the aldosterone antagonist or the salt thereof, wherein the aldosterone antagonist or the salt thereof can comprise spironolactone, eplerenone, finerenone, canrenoate, a stereoisomer of any of these, a salt of any of these, or any combination thereof. In some embodiments, a medicament can comprise the aldosterone synthesis inhibitor or the salt thereof, wherein the aldosterone synthesis inhibitor or the salt thereof can comprise fadrozol, FAD 286, LCI699, a salt of any of these, or any combination thereof. In some embodiments, a medicament can comprise the angiotensin receptor antagonist or the salt thereof, wherein the angiotensin receptor antagonist or salt thereof can comprise a sartan, candesartan, irbesartan, valsartan, telmisartan, eprosartan, olmesartan, azilsartan, fimasartan, sacubitril/valsartan, losartan, EXP 3174, amlodipine, a stereoisomer of any of these, a salt of any of these, or any combination thereof. In some embodiments, a medicament can comprise the ACE inhibitor or the salt thereof, wherein the ACE inhibitor or the salt thereof can comprise benazepril, captopril, enalapril, fosinopril, lisinopril, moexipril, omapatrilat, perindopril, quinapril, ramipril, trandolapril, a salt of any of these, or any combination thereof. In some embodiments, a medicament can comprise the alpha blocker or the salt thereof, wherein the alpha blocker or the salt thereof can comprise phenoxybenzamine, phentolamine, tolazoline, trazodone, alfuzosin, doxazosin, prazosin, tamsulosin, terazosin, silodosin, atipamezole, idazoxan, mirtazapine, yohimbine, a salt of any of these, or any combination thereof. In some embodiments, a medicament can comprise the guanylate cyclase stimulator or the salt thereof, wherein the guanylate cyclase stimulator or the salt thereof can comprise a guanylate cyclase activator, adempas, riociguat, a salt of any of these or a combination thereof. In some embodiments, a medicament can comprise the inotrope or the salt thereof, wherein the inotrope can comprise a cardiac inotrope or a salt thereof. In some embodiments, a cardiac inotrope or salt thereof can comprise a positive cardiac inotrope or a salt thereof. In some embodiments, a positive cardiac inotrope or a salt thereof can comprise a cardiotonic drug, a cardiotonic agent, a cardiostimulatory drug, a cardiostimulatory agent, any salt thereof, or any combination thereof. In some embodiments, a positive cardiac inotrope or a salt thereof can comprise a cardiac glycoside or a salt thereof. In some embodiments, a cardiac glycoside or the salt thereof can comprise a cardenolide, a bufadienolide, a salt of either of these, or any combination thereof. In some embodiments, a cardiac glycoside or the salt thereof can comprise the cardenolide or the salt thereof, and wherein the cardenolide or the salt thereof can comprise a convallotoxin, an antiarin, a strophanthin, a digoxin, a digitoxin, an oleandrin, an adonitoxin, a salt of any of these, or any combination thereof. In some embodiments, a cardiac glycoside or a salt thereof can comprise the bufadienolide or the salt thereof, and wherein the bufadienolide or the salt thereof can comprise a scillarenin, a proscillaridine A, a daigremontianin, a hellebore, a salt of any of these, or any combination thereof. In some embodiments, a medicament can comprise the cardiac inotrope or the salt thereof, wherein the cardiac inotrope or the salt thereof can comprise a myosin activator or a salt thereof. In some embodiments, a myosin activator or the salt thereof can comprise an omecamtiv mecarbil or a salt thereof. In some embodiments, a medicament can comprise the cardiac inotrope or the salt thereof, wherein the cardiac inotrope or the salt thereof can comprise a negative cardiac inotrope or a salt thereof. In some embodiments, a negative cardiac inotrope or the salt thereof can comprise a beta-blocker, a calcium-channel blocker, an anti-arrhythmic medicine, a salt of any of these, or any combination thereof. In some embodiments, a treatment can comprise an intervention. In some embodiments, an intervention can comprise exercise, a selective diet, meditation, instructions to see a cardiologist, instructions to dispense a medicament, instructions to receive an ultrasound, or any combination thereof. In some embodiments, a database can comprise a plurality of the compounds present in the biological sample from the subject. In some embodiments, a treatment can prevent or delay heart failure developing in a subject.

Disclosed herein in some embodiments, is a method of using a machine learning model to determine a risk of a subject developing heart failure. In some embodiments, a method can comprise measuring a level of one or more compounds present in a biological sample from a subject that does not currently have heart failure or that has not been diagnosed with heart failure, wherein an increased or decreased level of the compound relative to a reference level can be indicative of a risk of developing heart failure within a time period. In some embodiments, a method can further comprise clustering the level of the one or more compounds present in the biological sample using the machine learning model. In some embodiments, a method can further comprise identifying a cluster of the one or more compound present in the biological sample, wherein the cluster represents the plurality of biomarker levels associated with a risk of a subject developing heart failure. In some embodiments, a method can further comprise determining the risk of the subject developing heart failure within a time period. In some embodiments, a machine learning model clusters the level of the one or more compounds present in the biological sample using linear regression, a neural network, ensemble, or any combination thereof. In some embodiments a method of using a machine learning model can comprise using a system comprising: a computer processor, a computer readable memory operatively coupled to a computer processor, wherein a computer readable memory at least transiently stores: a database that can comprise a treatment formulary of medicaments or interventions, and a plurality of biomarkers predictive of a probability of developing heart failure within a time period of from about 1 week to about 5 years; and an algorithm that, when executed by a computer processor, selects a treatment from a treatment formulary based on a biomarker selected from a plurality of compounds. In some embodiments, a system further can comprise a wireless transmitter or a wireless receiver. In some embodiments, a system can be configured for wireless communication to a device. In some embodiments, a system can be configured for wired communication to a device. In some embodiments, a device can be an oral sample collection device. In some embodiments, an oral sample collection device can comprise a compound, and wherein an oral sample collection device can be configured to contact a compound with a biomarker present in saliva when saliva is input into an oral sample collection device. In some embodiments, an oral sample collection device can comprise a wireless transmitter. In some embodiments, a wireless transmitter can comprise a Bluetooth transmitter, an RF transmitter, a cellular signal transmitter, a Wi-fi transmitter, or any combination thereof. In some embodiments, an oral sample collection device can comprise a wireless receiver. In some embodiments, a wireless receiver can comprise a Bluetooth receiver, an RF transmitter, a cellular signal receiver, a Wi-fi receiver, or any combination thereof. In some embodiments, an oral sample collection device can comprise an oral swab. In some embodiments, a system can be configured to access a database via a wireless transmitter or a wireless receiver, wherein a database can be stored on a server. In some embodiments, a server can comprise a cloud-based server. In some embodiments, an increased or decreased level of the compound relative to a reference level can be indicative of a risk of developing heart failure within a time period. In some embodiments, a method can further comprise determining a risk of a subject developing heart failure within a time period based on an increased or decreased level of one or more compounds. In some embodiments, a method can further comprise administering a treatment for a heart failure to a subject based on a risk score. In some embodiments, one or more compounds can comprise one or more biomarkers. In some embodiments, one or more biomarkers can comprise a polypeptide comprising at least 70% sequence identity to AMPN, AMD, CALM3, KI21A, ACBP, IGA2, a salt of any of these, or any combination thereof. In some embodiments, one or more biomarkers can comprise at least two polypeptides comprising at least 70% sequence identity to at least two of AMPN, AMD, CALM3, KI21A, ACBP, IGA2, S10A7, a salt of any of these, or any combination thereof. In some embodiments, one or more biomarkers can comprise at least three polypeptides comprising at least 70% sequence identity to at least three of AMPN, AMD, CALM3, KI21A, ACBP, IGA2, S10A7, a salt of any of these, or any combination thereof. In some embodiments, one or more biomarkers can comprise at least four polypeptides comprising at least 70% sequence identity to at least four of AMPN, AMD, CALM3, KI21A, ACBP, IGA2, S10A7, a salt of any of these, or any combination thereof. In some embodiments, one or more biomarkers can comprise at least five polypeptides comprising at least 70% sequence identity to at least five of AMPN, AMD, CALM3, KI21A, ACBP, IGA2, S10A7, a salt of any of these, or any combination thereof. In some embodiments, a polypeptide can comprise at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity to AMPN, AMD, CALM3, KI21A, ACBP, IGA2, a salt of any of these, or any combination thereof. In some embodiments, polypeptides comprise at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity to AMPN, AMD, CALM3, KI21A, ACBP, IGA2, S10A7, a salt of any of these, or any combination thereof. In some embodiments, a treatment for the heart failure administered to the subject can be determined at least in part by the number of biomarkers that are expressed at an increased or decreased level relative to a reference level. In some embodiments, a treatment for the heart failure administered to the subject can be determined at least in part by the quantitative level of a biomarker relative to a reference level. In some embodiments, a subject can be classified as being low risk, medium risk or high risk of developing heart failure within a time period. In some embodiments, a subject can be determined to be at low risk of developing heart failure, and the treatment prescribed can comprise dietary intervention, exercise, or a combination thereof. In some embodiments, a subject can be determined to be at medium risk of developing heart failure, and the treatment prescribed can comprise administering a statin, an anti-inflammatory, a blood thinner, dietary intervention, exercise, or any combination thereof. In some embodiments, a subject can be determined to be at high risk of developing heart failure within the next six months, and the treatment prescribed can comprise administering a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator, cardioxyl, omecamtiv mecarbil, relaxin, serelaxin, staroxime, bucindolol, a phosphodiesterase 5 inhibitor, a vasopressin inhibitor, levosimendan, a sodium-glucose cotransporter-2 (SGLT2) inhibitor, an If channel blocker, an alpha blocker, a beta blocker, a beta receptor blocker, an ACE inhibitor, a stereoisomer of any of these, or a salt of any of these, or any combination thereof. In some embodiments, a biological sample can comprise amniotic fluid, amniotic sac, aqueous humor, bile, blood, blood plasma, breast milk, cerebrospinal fluid (CSF), cerebrospinal fluid rhinorrhea, chyle, chyme, endolymph, extracellular fluid, exudate, gastric acid, hemolacria, hemolymph, interstitial fluid, lymph, mucus, pericardial fluid, perilymph, peritoneal fluid, perspiration, phlegm, pus, rheum, saliva, semen, sweat, synovial fluid, tears, transcellular fluid, transudate, urine, vaginal lubricant, vitreous body, vomit, or any combination thereof. In some embodiments, a biological sample can comprise urine. In some embodiments, a biological sample can comprise saliva. In some embodiments, a biological sample can be obtained using an oral sample collection device. In some embodiments, an oral sample collection device can comprise a detection compound, and wherein the device can be configured to perform the contacting when the saliva is input into the oral sample collection device. In some embodiments, an oral sample collection device can comprise a wireless transmitter. In some embodiments, a wireless transmitter can comprise a Bluetooth transmitter, an RF transmitter, a cellular signal transmitter, a Wi-fi transmitter, or any combination thereof. In some embodiments, an oral sample collection device can comprise a wireless receiver. In some embodiments, a wireless receiver can comprise a Bluetooth receiver, an RF transmitter, a cellular signal receiver, a Wi-fi receiver, or any combination thereof. In some embodiments, an oral sample collection device can comprise an oral swab. In some embodiments, a concentration of the one or more compounds present in a biological sample can be enriched in the oral sample collection device after binding to the detection compound, relative to the concentration of the compound present in the biological sample. In some embodiments, a method can further comprise, with the aid of a computer processor, executing an algorithm selecting a treatment from a database prior to the administering. In some embodiments, a database can be at least transiently stored on a computer readable memory. In some embodiments, a database can comprise a treatment formulary of medicaments or interventions. In some embodiments, a treatment can comprise a medicament. In some embodiments, medicament can comprise a drug or a biologic that is licensed or approved for a condition by the United States Federal Drug Agency (USFDA) anytime as of or after Apr. 1, 2020. In some embodiments, a drug or the biologic is not licensed or approved by the USFDA for heart failure anytime as of or after May 1, 2020. In some embodiments, a medicament can comprise a drug or a biologic that is not licensed or approved by the USFDA for any condition anytime as of or after May 1, 2020. In some embodiments, a medicament can comprise a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator cardioxyl, an omecamtiv mecarbil, a relaxin, a serelaxin, staroxime, bucindolol, a phosphodiesterase 5 inhibitor, a vasopressin inhibitor, a levosimendan, a sodium-glucose cotransporter-2 (SGLT2) inhibitor, an If channel blocker, an alpha blocker, a beta receptor blocker, a beta blocker, an ACE inhibitor, a stereoisomer of any of these, a salt of any of these, or any combination thereof. In some embodiments, a medicament can comprise the beta receptor blocker or the salt thereof, wherein the beta receptor blocker or salt thereof comprise at least one stereocenter in an S-configuration. In some embodiments, a beta receptor blocker can comprise a long acting beta blocker. In some embodiments, a beta receptor blocker can comprise a short acting beta blocker. In some embodiments, a long acting beta blocker or salt thereof or the short acting beta blocker or the salt thereof can comprise pindolol, oxprenolol, atenolol, acebutolol, bisoprolol, bucindolol, carvedilol, metoprolol, nadolol, nebivolol, oxprenolol, propranolol, a stereoisomer of any of these, a polymorph of any of these, a diastereomer of any of these, a salt of any of these, or any combination thereof. In some embodiments, a long acting or short acting beta blocker or the salt thereof comprise S-pindolol, S-oxprenolol, S-atenolol, S-acebutolol, S-bisoprolol, S-bucindolol, S-carvedilol, S-metoprolol, S-nadolol, S-nebivolol, S-Oxprenolol, S-propranolol, a stereoisomer of any of these, a polymorph of any of these, a diastereomer of any of these, a salt of any of these, or any combination thereof. In some embodiments, a medicament can comprise the statin or the salt thereof, wherein the statin or the salt thereof can comprise atorvastatin, fluvastatin, lovastatin, pravastatin, rosuvastatin, simvastatin, pitavastatin, a salt of any of these, or any combination thereof. In some embodiments, a medicament can comprise the blood thinner or the salt thereof, wherein the blood thinner or the salt thereof can comprise apixaban, dabigatran, edoxaban, fondaparinux, heparin, rivaroxaban, warfarin, a salt of any of these, or any combination thereof. In some embodiments, a medicament can comprise the phosphodiesterase 5 inhibitor or the salt thereof, wherein the phosphodiesterase 5 inhibitor or the salt thereof can comprise amrinone, milrinone, avanafil, lodenafil, mirodenafil, sildenafil, tadalafil, vardenafil, udenafil, zaprinast, benzaminenafil, a salt of any of these, or any combination thereof. In some embodiments, a medicament can comprise the vasopressin inhibitor or the salt thereof, wherein the vasopressin inhibitor or the salt thereof can comprise conivaptan, relcovaptan, nelivaptan, lixivaptan, mozavaptan, satavaptan, tolvaptan, demeclocycline, lithium, a salt of any of these, or any combination thereof. In some embodiments, a medicament can comprise the SGLT2 inhibitor or the salt thereof, wherein the SGLT2 inhibitor or the salt thereof can comprise dapagliflozin, empagliflozin, canagliflozin, sotagliflozin, ertugliflozin, ipragliflozin, luseogliflozin, remogliflozin etabonate, sergliflozin etabonate, tofogliflozin a stereoisomer of any of these, a salt of any of these, or any combination thereof. In some embodiments, a medicament can comprise the aldosterone antagonist or the salt thereof, wherein the aldosterone antagonist or the salt thereof can comprise spironolactone, eplerenone, finerenone, canrenoate, a stereoisomer of any of these, a salt of any of these, or any combination thereof. In some embodiments, a medicament can comprise the aldosterone synthesis inhibitor or the salt thereof, wherein the aldosterone synthesis inhibitor or the salt thereof can comprise fadrozol, FAD 286, LCI699, a salt of any of these, or any combination thereof. In some embodiments, a medicament can comprise the angiotensin receptor antagonist or the salt thereof, wherein the angiotensin receptor antagonist or salt thereof can comprise a sartan, candesartan, irbesartan, valsartan, telmisartan, eprosartan, olmesartan, azilsartan, fimasartan, sacubitril/valsartan, losartan, EXP 3174, amlodipine, a stereoisomer of any of these, a salt of any of these, or any combination thereof. In some embodiments, a medicament can comprise the ACE inhibitor or the salt thereof, wherein the ACE inhibitor or the salt thereof can comprise benazepril, captopril, enalapril, fosinopril, lisinopril, moexipril, omapatrilat, perindopril, quinapril, ramipril, trandolapril, a salt of any of these, or any combination thereof. In some embodiments, a medicament can comprise the alpha blocker or the salt thereof, wherein the alpha blocker or the salt thereof can comprise phenoxybenzamine, phentolamine, tolazoline, trazodone, alfuzosin, doxazosin, prazosin, tamsulosin, terazosin, silodosin, atipamezole, idazoxan, mirtazapine, yohimbine, a salt of any of these, or any combination thereof. In some embodiments, a medicament can comprise the guanylate cyclase stimulator or the salt thereof, wherein the guanylate cyclase stimulator or the salt thereof can comprise a guanylate cyclase activator, adempas, riociguat, a salt of any of these or a combination thereof. In some embodiments, a medicament can comprise the inotrope or the salt thereof, wherein the inotrope can comprise a cardiac inotrope or a salt thereof. In some embodiments, a cardiac inotrope or salt thereof can comprise a positive cardiac inotrope or a salt thereof. In some embodiments, a positive cardiac inotrope or a salt thereof can comprise a cardiotonic drug, a cardiotonic agent, a cardiostimulatory drug, a cardiostimulatory agent, any salt thereof, or any combination thereof. In some embodiments, a positive cardiac inotrope or a salt thereof can comprise a cardiac glycoside or a salt thereof. In some embodiments, a cardiac glycoside or the salt thereof can comprise a cardenolide, a bufadienolide, a salt of either of these, or any combination thereof. In some embodiments, a cardiac glycoside or the salt thereof can comprise the cardenolide or the salt thereof, and wherein the cardenolide or the salt thereof can comprise a convallotoxin, an antiarin, a strophanthin, a digoxin, a digitoxin, an oleandrin, an adonitoxin, a salt of any of these, or any combination thereof. In some embodiments, a cardiac glycoside or a salt thereof can comprise the bufadienolide or the salt thereof, and wherein the bufadienolide or the salt thereof can comprise a scillarenin, a proscillaridine A, a daigremontianin, a hellebore, a salt of any of these, or any combination thereof. In some embodiments, a medicament can comprise the cardiac inotrope or the salt thereof, wherein the cardiac inotrope or the salt thereof can comprise a myosin activator or a salt thereof. In some embodiments, a myosin activator or the salt thereof can comprise an omecamtiv mecarbil or a salt thereof. In some embodiments, a medicament can comprise the cardiac inotrope or the salt thereof, wherein the cardiac inotrope or the salt thereof can comprise a negative cardiac inotrope or a salt thereof. In some embodiments, a negative cardiac inotrope or the salt thereof can comprise a beta-blocker, a calcium-channel blocker, an anti-arrhythmic medicine, a salt of any of these, or any combination thereof. In some embodiments, a treatment can comprise an intervention. In some embodiments, an intervention can comprise exercise, a selective diet, meditation, instructions to see a cardiologist, instructions to dispense a medicament, instructions to receive an ultrasound, or any combination thereof. In some embodiments, a database can comprise a plurality of the compounds present in the biological sample from the subject. In some embodiments, a treatment can prevent or delay heart failure developing in a subject.

Disclosed herein is a method comprising: contacting a first compound with a second compound present in a biological sample from a subject that does not currently have or has not been diagnosed with heart failure, wherein a second compound when present in a biological sample at an increased level or a decreased level, relative to a reference level, can be indicative of developing heart failure within a time period of from about 1 week to about 5 years; detecting binding of a first compound with a second compound; and administering a treatment to a subject, wherein an administering prevents an occurrence of a heart failure over a time period when a treatment can be administered over a time period. In some embodiments, a reference level can be derived from a plurality of biological samples that are each from a different subject to a first subject. In some embodiments, a second subject does not currently have or has not been diagnosed with heart failure. In some embodiments, a second subject has a non-heart failure disease condition. In some embodiments, a non-heart failure disease condition can comprise a cardiac disease. In some embodiments, a second subject has heart failure. In some embodiments, a second subject was not hospitalized within 12 months prior to a collection of a biological sample from a second subject. In some embodiments, a second subject was not hospitalized from about 1 week to about 3 months prior to a collection of a biological sample from a second subject. In some embodiments, a heart failure can be mild. In some embodiments, a heart failure can be severe. In some embodiments, a time period can comprise from about one month to about three months. In some embodiments, a time period can comprise from about three months to about eighteen months. In some embodiments, a treatment can further prevent an occurrence of a heart failure over a period of time that can be longer than a time period of a treatment. In some embodiments, a first compound can comprise a polypeptide. In some embodiments, a polypeptide can comprise an antibody, an aptamer, or a functional fragment thereof. In some embodiments, a first compound can comprise a fluorophore, a chromophore, fluorescence-resonance energy transfer (FRET) donor, a FRET acceptor, or any combination thereof. In some embodiments, a second compound can be not substantially present in a subject with heart failure. In some embodiments, a second compound can be at least partially present in a subject with heart failure. In some embodiments, a second compound can be present at a decreased level in a biological sample from a subject, relative to a reference level. In some embodiments, a second compound can be present at an increased level in a biological sample from a subject, relative to a reference level. In some embodiments, a second compound can be present at a decreased level in a biological sample from a subject, relative to a reference level, wherein a reference level can be derived from a biological sample from a second subject that developed heart disease within a time period of 12 months prior to a collection of a biological sample from a second subject. In some embodiments, a second compound can be present at an increased level in a biological sample from a subject, relative to a reference level, wherein a reference level can be derived from a biological sample from a second subject that developed heart disease within a time period of 12 months prior to a collection of a biological sample from a second subject. In some embodiments, a second compound can comprise a polypeptide. In some embodiments, a polypeptide does not comprise a natriuretic peptide. In some embodiments, a polypeptide can comprise at least about 70% sequence identity to a polypeptide recited in Table 1, Table 7, or a combination thereof, as determined by BLAST. In some embodiments, a method distinguishes a first subject who develops heart failure without an administering over a time period from a second subject who does not develop heart failure over a time period. In some embodiments, a method distinguishes a first subject from a second subject with an accuracy of at least about 90%, with a confidence level of at least about 95%. In some embodiments, a biological sample can comprise amniotic fluid, amniotic sac, aqueous humor, bile, blood, blood plasma, breast milk, cerebrospinal fluid (CSF), cerebrospinal fluid rhinorrhea, chyle, chyme, endolymph, extracellular fluid, exudate, gastric acid, hemolacria, hemolymph, interstitial fluid, lymph, mucus, pericardial fluid, perilymph, peritoneal fluid, perspiration, phlegm, pus, rheum, saliva, semen, sweat, synovial fluid, tears, transcellular fluid, transudate, urine, vaginal lubricant, vitreous body, vomit, or any combination thereof. In some embodiments, a biological sample can comprise urine. In some embodiments, a biological sample can comprise saliva. In some embodiments, a biological sample can be obtained using an oral sample collection device. In some embodiments, an oral sample collection device can comprise a first compound, and wherein a device can be configured to perform a contacting when saliva is input into an oral sample collection device. In some embodiments, an oral sample collection device can comprise a wireless transmitter. In some embodiments, a wireless transmitter can comprise a Bluetooth transmitter, an RF transmitter, a cellular signal transmitter, a Wi-fi transmitter, or any combination thereof. In some embodiments, an oral sample collection device can comprise a wireless receiver. In some embodiments, a wireless receiver can comprise a Bluetooth receiver, an RF transmitter, a cellular signal receiver, a Wi-fi receiver, or any combination thereof. In some embodiments, an oral sample collection device can comprise an oral swab. In some embodiments, a concentration of a second compound can be enriched in an oral sample collection device after binding to a first compound, relative to a concentration of a second compound present in a biological sample. In some embodiments, a method can further comprise with an aid of a computer processor, executing an algorithm selecting a treatment from a database prior to an administering. In some embodiments, a database can be at least transiently stored on a computer readable memory. In some embodiments, a database can comprise a treatment formulary of medicaments or interventions. In some embodiments, a treatment can comprise a medicament. In some embodiments, a medicament can comprise a drug or biologic that can be licensed or approved for a condition by the United States Federal Drug Agency (USFDA) anytime as of or after Apr. 1, 2020. In some embodiments, a drug or a biologic is not licensed or approved by the USFDA for heart failure anytime as of or after May 1, 2020. In some embodiments, a medicament can comprise a drug or biologic that is not licensed or approved by the USFDA for any condition anytime as of or after May 1, 2020. In some embodiments, a medicament can comprise a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator cardioxyl, omecamtiv mecarbil, relaxin, serelaxin, staroxime, bucindolol, a phosphodiesterase 5 inhibitor, a vasopressin inhibitor, levosimendan, a sodium-glucose cotransporter-2 (SGLT2) inhibitor, an If channel blocker, an alpha blocker, a beta receptor blocker, a beta blocker, an ACE inhibitor, a stereoisomer of any of these, a salt of any of these, or any combination thereof. In some embodiments, a beta receptor blocker or salt thereof, wherein a beta receptor blocker or salt thereof comprise at least one stereocenter in an S-configuration. In some embodiments, a beta receptor blocker can comprise a long acting beta blocker. In some embodiments, a beta receptor blocker can comprise a short acting beta blocker. In some embodiments, a long acting beta blocker or a short acting beta blocker can comprise pindolol, oxprenolol, atenolol, acebutolol, bisoprolol, bucindolol, carvedilol, metoprolol, nadolol, nebivolol, oxprenolol, propranolol, a stereoisomer of any of these, a polymorph of any of these, a diastereomer of any of these, a salt of any of these, or any combination thereof. In some embodiments, a long acting or short acting beta blocker can comprise S-pindolol, S-oxprenolol, S-atenolol, S-acebutolol, S-bisoprolol, S-bucindolol, S-carvedilol, S-metoprolol, S-nadolol, S-nebivolol, S-Oxprenolol, S-propranolol, a stereoisomer of any of these, a polymorph of any of these, a diastereomer of any of these, a salt of any of these, or any combination thereof. In some embodiments, a statin or salt thereof can comprise atorvastatin, fluvastatin, lovastatin, pravastatin, rosuvastatin, simvastatin, pitavastatin, a salt of any of these, or any combination thereof. In some embodiments, a blood thinner or salt thereof can comprise apixaban, dabigatran, edoxaban, fondaparinux, heparin, rivaroxaban, warfarin, a salt of any of these, or any combination thereof.

In some embodiments, a phosphodiesterase 5 inhibitor can comprise amrinone, milrinone, avanafil, lodenafil, mirodenafil, sildenafil, tadalafil, vardenafil, udenafil, zaprinast, benzaminenafil, a salt of any of these, or any combination thereof. In some embodiments, a vasopressin inhibitor can comprise conivaptan, relcovaptan, nelivaptan, lixivaptan, mozavaptan, satavaptan, tolvaptan, demeclocycline, lithium, a salt of any of these, or any combination thereof. In some embodiments, a SGLT2 inhibitor can comprise dapagliflozin, empagliflozin, canagliflozin, sotagliflozin, ertugliflozin, ipragliflozin, luseogliflozin, remogliflozin etabonate, sergliflozin etabonate, tofogliflozin a stereoisomer of any of these, a salt of any of these, or any combination thereof. In some embodiments, an aldosterone antagonist, or salt thereof, wherein an aldosterone antagonist or salt thereof can comprise spironolactone, eplerenone, finerenone, canrenoate, a stereoisomer of any of these, a salt of any of these, or any combination thereof. In some embodiments, an aldosterone synthesis inhibitor or a salt thereof, wherein an aldosterone synthesis inhibitor or salt thereof can comprise fadrozol, FAD 286, LCI699, a salt of any of these, or any combination thereof. In some embodiments, an angiotensin receptor antagonist or a salt thereof, wherein an angiotensin receptor antagonist or salt thereof can comprise a sartan, candesartan, irbesartan, valsartan, telmisartan, eprosartan, Olmesartan, azilsartan, fimasartan, sacubitril/valsartan, losartan, EXP 3174, amlodipine, a stereoisomer of any of these, a salt of any of these, or any combination thereof. In some embodiments, an ACE inhibitor can comprise benazepril, captopril, enalapril, fosinopril, lisinopril, moexipril, omapatrilat, perindopril, quinapril, ramipril, trandolapril, a salt of any of these, or any combination thereof. In some embodiments, an alpha blocker, wherein an alpha blocker can comprise phenoxybenzamine, phentolamine, tolazoline, trazodone, alfuzosin, doxazosin, prazosin, tamsulosin, terazosin, silodosin, atipamezole, idazoxan, mirtazapine, yohimbine, a salt of any of these, or any combination thereof. In some embodiments, a guanylate cyclase stimulator or a salt thereof can comprise a guanylate cyclase activator, adempas, riociguat, a salt of any of these or a combination thereof. In some embodiments, an inotrope can comprise a cardiac inotrope or a salt thereof. In some embodiments, a cardiac inotrope or a salt thereof, wherein a cardiac inotrope can comprise a positive inotrope or a salt thereof. In some embodiments, a positive cardiac inotrope or a salt thereof, wherein a positive cardiac inotrope or a salt thereof can comprise a cardiotonic drug, a cardiotonic agent, a cardiostimulatory drug, a cardiostimulatory agent, any salt thereof, or any combination thereof. In some embodiments, a positive cardiac inotrope or a salt thereof can comprise a cardiac glycoside or a salt thereof. In some embodiments, a cardiac glycoside or a salt thereof can comprise a cardenolide, a bufadienolide, a salt of either of these, or any combination thereof. In some embodiments, a cardenolide can comprise a convallotoxin, an antiarin, a strophanthin, a digoxin, a digitoxin, an oleandrin, an adonitoxin, a salt of any of these, or any combination thereof. In some embodiments, a bufadienolide can comprise a scillarenin, a proscillaridine A, a daigremontianin, a hellebore, a salt of any of these, or any combination thereof. In some embodiments, a cardiac inotrope can comprise a myosin activator or a salt thereof. In some embodiments, a myosin activator can comprise an omecamtiv mecarbil or a salt thereof. In some embodiments, a cardiac inotrope can comprise a negative cardiac inotrope, or a salt thereof. In some embodiments, a negative cardiac inotrope can comprise a beta-blocker, a calcium-channel blocker, an anti-arrhythmic medicine, a salt of any of these, or any combination thereof. In some embodiments, a treatment can comprise an intervention. In some embodiments, an intervention can comprise exercise, a selective diet, meditation, instructions to see a cardiologist, instructions to dispense a medicament, instructions to receive an ultrasound, or any combination thereof. In some embodiments, a database can comprise a plurality of second compounds. Disclosed herein in some embodiments, is a kit comprising a first compound as disclosed herein and an oral sample collection device. In some embodiments, a first compound can be present in an oral sample collection device. In some embodiments, a first compound can comprise a polypeptide. In some embodiments, a polypeptide can comprise at least about 70% sequence identity to a polypeptide recited in Table 1, Table 7, or a salt of any of these, or any combination thereof, as determined by BLAST. In some embodiments, a treatment can prevent or delay heart failure developing in a subject.

Disclosed herein is a method comprising determining a probability score for a subject developing heart failure, a method comprising: (a) contacting a device comprising a sensor with a bodily fluid of a subject; (b) detecting a level of a biomarker in a bodily fluid of a subject using a device; wherein a detection at least in part occurs within a body of a subject, and wherein a bodily fluid is not processed prior to detection; (c) comparing a level of a biomarker with a reference level to determine a probability. In some embodiments, a subject does not currently have or has not been diagnosed with heart failure. In some embodiments, a subject has not been diagnosed with heart failure. In some embodiments, a subject can be assigned a probability score of developing heart failure. In some embodiments, a subject can be assigned a probability score of developing heart failure. In some embodiments, a probability score can comprise a low probability, a medium probability, a high probability, or a very high probability. In some embodiments, a method can further comprise administering a treatment to a subject, wherein a choice of treatment can be selected at least in part based on a probability score. In some embodiments, a reference level can comprise a range of reference levels. In some embodiments, a range of reference levels can comprise data from a range of reference samples. In some embodiments, a sensor can comprise an antibody or a functional fragment thereof. In some embodiments, a sensor can comprise a fluorophore, a chromophore, fluorescence-resonance energy transfer (FRET) donor, a FRET acceptor, or any combination thereof. In some embodiments, a biomarker can comprise a polypeptide. In some embodiments, a polypeptide does not comprise a natriuretic peptide. In some embodiments, a polypeptide can comprise at least about 70% sequence identity to a polypeptide recited in Table 1, Table 7, a salt of any of these, or any combination thereof, as determined by BLAST. In some embodiments, a biomarker can comprise a microbe. In some embodiments, a method further can comprise determining a microbiome status of a subject. In some embodiments, a method further can comprise correlating a microbiome status with known databases to determine a probability score for a subject developing heart failure. In some embodiments, a biological sample can comprise blood. In some embodiments, a biological sample can comprise saliva. In some embodiments, a biological sample can be obtained using an oral sample collection device. In some embodiments, a device can comprise a wireless transmitter. In some embodiments, a wireless transmitter can comprise a Bluetooth transmitter, an RF transmitter, a cellular signal transmitter, a Wi-fi transmitter, or any combination thereof. In some embodiments, a device can comprise a wireless receiver. In some embodiments, a wireless receiver can comprise a Bluetooth receiver, an RF receiver, a cellular signal receiver, a Wi-fi receiver, or any combination thereof. In some embodiments, an oral sample collection device can comprise an oral swab. In some embodiments, a method can further comprise administering a treatment to a subject. In some embodiments, a choice of treatment administered can be at least partially determined by a level of a biomarker detected in a bodily fluid of a subject. In some embodiments, a method can further comprise selecting a treatment from a database prior to an administering. In some embodiments, a database can be at least transiently stored on a computer readable memory. In some embodiments, a database can comprise a treatment formulary of medicaments or interventions. In some embodiments, a treatment can comprise a medicament. In some embodiments, a medicament can comprise a drug or biologic that is licensed or approved for a condition by the United States Federal Drug Agency (USFDA) anytime as of or after Apr. 1, 2020. In some embodiments, a drug or a biologic is not licensed or approved by the USFDA for heart failure anytime as of or after Apr. 1, 2020. In some embodiments, a medicament can comprise a drug or biologic that is not licensed or approved by the USFDA for any condition anytime as of or after Apr. 1, 2020. In some embodiments, a medicament can comprise a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator, cardioxyl, omecamtiv mecarbil, relaxin, serelaxin, staroxime, bucindolol, a phosphodiesterase 5 inhibitor, a vasopressin inhibitor, levosimendan, a sodium-glucose cotransporter-2 (SGLT2) inhibitor, an If channel blocker, an alpha blocker, a beta blocker, a beta receptor blocker, an ACE inhibitor, a stereoisomer of any of these, or a salt of any of these, or any combination thereof. In some embodiments, a beta receptor blocker or salt thereof, wherein a beta receptor blocker or salt thereof comprise at least one stereocenter in an S-configuration. In some embodiments, a beta receptor blocker can comprise a long acting beta blocker. In some embodiments, a beta receptor blocker can comprise a short acting beta blocker. In some embodiments, a long acting beta blocker or a short acting beta blocker can comprise pindolol, oxprenolol, atenolol, acebutolol, bisoprolol, metoprolol, nadolol, nebivolol, propranolol, a stereoisomer of any of these, a polymorph of any of these, a diastereomer of any of these, a salt of any of these, or any combination thereof. In some embodiments, a long acting or short acting beta blockers comprise S-pindolol, S-oxprenolol, S-atenolol, S-acebutolol, S-bisoprolol, S-metoprolol, S-nadolol, S-nebivolol, S-propranolol, a stereoisomer of any of these, a polymorph of any of these, a diastereomer of any of these, a salt of any of these, or any combination thereof. In some embodiments, a statin or salt thereof, wherein a statin or salt thereof can comprise atorvastatin, fluvastatin, lovastatin, pravastatin, rosuvastatin, simvastatin, pitavastatin, a salt of any of these, or any combination thereof. In some embodiments, a blood thinner or salt thereof, wherein a blood thinner or salt thereof can comprise apixaban, dabigatran, edoxaban, fondaparinux, heparin, rivaroxaban, warfarin, a salt of any of these, or any combination thereof. In some embodiments, a phosphodiesterase 5 inhibitor or salt thereof, wherein a phosphodiesterase 5 inhibitor can comprise amrinone, milrinone, avanafil, lodenafil, mirodenafil, sildenafil, tadalafil, vardenafil, udenafil, zaprinast, benzaminenafil, carvedilol, a salt of any of these, or any combination thereof. In some embodiments, a vasopressin inhibitor of salt thereof, wherein a vasopressin inhibitor can comprise conivaptan, relcovaptan, nelivaptan, lixivaptan, mozavaptan, satavaptan, tolvaptan, demeclocycline, lithium, a salt of any of these, or any combination thereof. In some embodiments, a SGLT2 inhibitor or salt thereof, wherein a SGLT2 inhibitor can comprise dapagliflozin, empagliflozin, canagliflozin, sotagliflozin, ertugliflozin, ipragliflozin, luseogliflozin, remogliflozin etabonate, sergliflozin etabonate, tofogliflozin a stereoisomer of any of these, a salt of any of these, or any combination thereof. In some embodiments, an aldosterone antagonist, or salt thereof, wherein an aldosterone antagonist or salt thereof can comprise spironolactone, eplerenone, finerenone, canrenoate, a stereoisomer of any of these, a salt of any of these, or any combination thereof. In some embodiments, an aldosterone synthesis inhibitor or a salt thereof, wherein an aldosterone synthesis inhibitor or salt thereof can comprise fadrozol, FAD 286, LCI699, a salt of any of these, or any combination thereof. In some embodiments, an angiotensin receptor antagonist or a salt thereof, wherein an angiotensin receptor antagonist or salt thereof can comprise a sartan, candesartan, irbesartan, valsartan, telmisartan, eprosartan, Olmesartan, azilsartan, fimasartan, sacubitril/valsartan, losartan, EXP 3174, amlodipine, a stereoisomer of any of these, a salt of any of these, or any combination thereof. In some embodiments, an ACE inhibitor, wherein an ACE inhibitor can comprise benazepril, captopril, enalapril, fosinopril, lisinopril, moexipril, perindopril, quinapril, ramipril, trandolapril, or any combination thereof. In some embodiments, an alpha blocker, wherein an alpha blocker can comprise phenoxybenzamine, phentolamine, tolazoline, trazodone, alfuzosin, doxazosin, prazosin, tamsulosin, terazosin, silodosin, atipamezole, idazoxan, mirtazapine, yohimbine, or any combination thereof. In some embodiments, a guanylate cyclase stimulator, wherein a guanylate cyclase stimulator can comprise a guanylate cyclase activator, adempas, riociguat, a salt of any of these, or any combination thereof. In some embodiments, an inotrope, wherein an inotrope can comprise a cardiac inotrope or a salt thereof. In some embodiments, a cardiac inotrope or a salt thereof, wherein a cardiac inotrope can comprise a positive inotrope or a salt thereof. In some embodiments, a positive cardiac inotrope or a salt thereof, wherein a positive cardiac inotrope or a salt thereof can comprise a cardiotonic drug, a cardiotonic agent, a cardiostimulatory drug, a cardiostimulatory agent, any salt thereof, or any combination thereof. In some embodiments, a positive cardiac inotrope or a salt thereof, wherein a positive cardiac inotrope or a salt thereof can comprise a cardiac glycoside or a salt thereof. In some embodiments, a cardiac glycoside or a salt thereof, wherein a cardiac glycoside or a salt thereof can comprise a cardenolide, a bufadienolide, a salt of either of these, or any combination thereof. In some embodiments, a cardenolide, wherein a cardenolide can comprise a convallotoxin, an antiarin, a strophanthin, a digoxin, a digitoxin, an oleandrin, an adonitoxin, a salt of any of these, or any combination thereof. In some embodiments, a bufadienolide, wherein a bufadienolide can comprise a scillarenin, a proscillaridine A, a daigremontianin, a hellebore, a salt of any of these, or any combination thereof. In some embodiments, a cardiac inotrope or a salt thereof, wherein a cardiac inotrope can comprise a myosin activator or a salt thereof. In some embodiments, a myosin activator can comprise an omecamtiv mecarbil or a salt thereof. In some embodiments, a cardiac inotrope or a salt thereof, wherein a cardiac inotrope can comprise a negative cardiac inotrope, or a salt thereof. In some embodiments, a negative cardiac inotrope, wherein a negative cardiac inotrope can comprise a beta-blocker, a calcium-channel blocker, an anti-arrhythmic medicine, a salt of any of these, or any combination thereof. In some embodiments, an intervention can comprise exercise, a selective diet, meditation, or any combination thereof. In some embodiments, a diet can comprise a supplement. In some embodiments, a supplement can comprise fish oil. In some embodiments, a method further can comprise monitoring a subject. In some embodiments, a monitoring can comprise monitoring a disease onset, disease progression, disease regression, or any combination thereof. In some embodiments, a method further can comprise monitoring an effectiveness of a treatment. In some embodiments, a monitoring can comprise measuring heart rate, blood pressure, EKG readings, or any combination thereof over a time period. In some embodiments, a treatment can prevent or delay heart failure developing in a subject.

A system comprising: a computer processor, a computer readable memory operatively coupled to a computer processor, wherein a computer readable memory at least transiently stores: a database that can comprise a treatment formulary of medicaments or interventions, and a plurality of biomarkers predictive of a probability of developing heart failure within a time period of from about 1 week to about 5 years; and an algorithm that, when executed by a computer processor, selects a treatment from a treatment formulary based on a biomarker selected from a plurality of compounds. In some embodiments, a system further can comprise a wireless transmitter or a wireless receiver. In some embodiments, a system can be configured for wireless communication to a device. In some embodiments, a system can be configured for wired communication to a device. In some embodiments, a device can be an oral sample collection device. In some embodiments, an oral sample collection device can comprise a compound, and wherein an oral sample collection device can be configured to contact a compound with a biomarker present in saliva when saliva is input into an oral sample collection device. In some embodiments, an oral sample collection device can comprise a wireless transmitter. In some embodiments, a wireless transmitter can comprise a Bluetooth transmitter, an RF transmitter, a cellular signal transmitter, a Wi-fi transmitter, or any combination thereof. In some embodiments, an oral sample collection device can comprise a wireless receiver. In some embodiments, a wireless receiver can comprise a Bluetooth receiver, an RF transmitter, a cellular signal receiver, a Wi-fi receiver, or any combination thereof. In some embodiments, an oral sample collection device can comprise an oral swab. In some embodiments, a system can be configured to access a database via a wireless transmitter or a wireless receiver, wherein a database can be stored on a server. In some embodiments, a server can comprise a cloud-based server.

INCORPORATION BY REFERENCE

All publications, databases, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 demonstrates the evaluation results in batches A0 (FIG. 3A), A1 (FIG. 3B), and A2 (FIG. 3C). TP=True Positives (sensitivity), TN=True Negatives (specificity), FP=False Positives, and FN=False Negatives.

FIG. 4 demonstrates the evaluation results in batches A1 (FIG. 4A), A2 (FIG. 4B), and A3 (FIG. 4C). TP=True Positives (sensitivity), TN=True Negatives (specificity), FP=False Positives, and FN=False Negatives.

FIG. 5 demonstrates the linear regression with the predicted risk level shown in the top right for biomarker S10A7, whose risk prediction spans from 1.7147 upwards. A high level of 5.3052 is found on the prediction line. FIG. 5A shows low amounts of the biomarker and the associated risk prediction, while

FIG. 6 demonstrates the linear regression with the predicted risk level shown in the top right for biomarker KI211A, whose risk prediction spans from 2.0754 upwards. A high level of 5.0651 is found on the prediction line. FIG. 6A shows low amounts of the biomarker and the associated risk prediction, while

FIG. 7 demonstrates the linear regression with the predicted risk level shown in the top right for biomarker CALM3, whose risk prediction spans from 3.4098 downwards. A low level of 0.0278 is found on the prediction line. FIG. 7A shows low amounts of the biomarker and the associated risk prediction, while

FIG. 8 demonstrates the linear regression with the predicted risk level shown in the top right for biomarker ACBP, whose risk prediction spans from 1.1196 upwards. A high level of 5.0024 is found on the prediction line. FIG. 8A shows low amounts of the biomarker and the associated risk prediction, while

FIG. 9 demonstrates the linear regression with the predicted risk level shown in the top right for biomarker AMPN, whose risk prediction spans from 2.1770 upwards. A high level of 4.0624 is found on the prediction line. FIG. 9A shows low amounts of the biomarker and the associated risk prediction, while

FIG. 10 demonstrates the linear regression with the predicted risk level shown in the top right for biomarker IGA2, whose risk prediction spans from 1.7369 upwards. A high level of 5.0222 is found on the prediction line. FIG. 10A shows low amounts of the biomarker and the associated risk prediction, while

FIG. 11 demonstrates the linear regression with the predicted risk level shown in the top right for biomarker AMD, whose risk prediction spans from 3.1035 downwards. A low level of 0.0004 is found on the prediction line. FIG. 11A shows low amounts of the biomarker and the associated risk prediction, while

FIG. 13 depicts different example of biosensors. FIG. 13A depicts an electronic biosensor that can be installed onto multiple platforms such as skin or clothing. FIG. 13B depicts an electronic biosensor installed onto a swab for use to detect disease. The swab also has electronics to transmit data to a software. FIG. 13C depicts an electronic biosensor installed into or onto a phone casing or other relevant usable device for use to detect diseases. The device also has electronics to transmit data to a software application.

FIG. 16 displays a selection of biomarkers and the mean ablation and PCI detection concentrations from serum samples, unstimulated whole saliva samples, gingival swabs, and sublingual swabs.

FIG. 17 depicts different ways in which a detection can occur and a risk value shown to a subject or healthcare professional.

DETAILED DESCRIPTION OF THE INVENTION

Figure 1A:
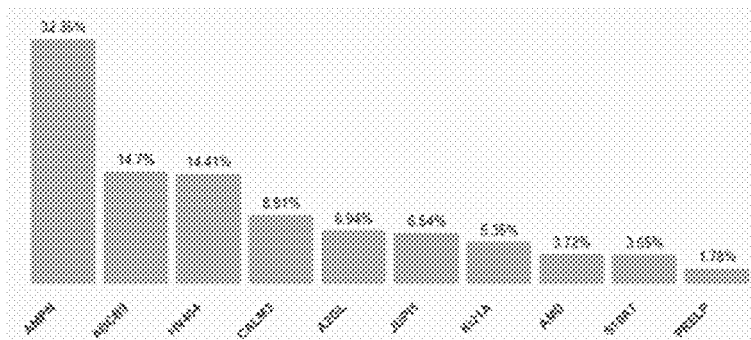
FIG. 1 demonstrates the field importance of selected biomarkers tested in batches A0 (FIG. 1A), A1 (FIG. 1B), and A2 (FIG. 1C).

Disclosed herein in some embodiments, are methods and compositions for detecting compounds that identify a probability of developing heart failure. In some embodiments, a method can comprise contacting a first compound with a second compound present in a biological sample from a subject that does not currently have or has not been diagnosed with heart failure, wherein a second compound when present in a biological sample at an increased level or a decreased level, relative to a level of a second compound in a reference sample, is indicative of developing heart failure within a time period.

In some embodiments, a method can comprise contacting a device comprising a sensor with a bodily fluid of a subject; detecting a biomarker in a bodily fluid of a subject using a device; wherein a detection at least in part occurs within a body of a subject, and wherein a bodily fluid is not processed prior to detection. In some embodiments, a sensor can comprise an antibody or a functional fragment thereof. The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, e.g., the limitations of the measurement system. For example, "about" can mean plus or minus 10%, per the practice in the art. Alternatively, "about" can mean a range of plus or minus 20%, plus or minus 10%, plus or minus 5%, or plus or minus 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed. Also, where ranges and/or subranges of values are provided, the ranges and/or subranges can include the endpoints of the ranges and/or subranges.

The term "substantially" as used herein can refer to a value approaching 100% of a given value. For example, a compound that is "substantially localized" in an organ can indicate that about 90% by weight of a compound, salt, or metabolite is present in an organ relative to a total amount of a compound, salt, or metabolite. In some embodiments, the term can refer to an amount that can be at least about 90%, 91%, 92%, 93%, 94%, 95%, 96%, 97%, 98%, 99%, 99.9%, or 99.99% of a total amount. In some embodiments, the term can refer to an amount that can be about 100% of a total amount.

The term "compound" can encompass a salt, a free base, a conjugate base, or a conjugate acid of a compound. A "first compound" can comprise a detection compound. A "second compound" can comprise one or more compounds present in a biological sample from a subject that does not currently have heart failure or that has not been diagnosed with heart failure.

The term "subject", "patient" or "individual" as used herein can encompass a mammal and a non-mammal. In some embodiments, a mammal can be any member of the Mammalian class, including but not limited to a human, a non-human primate such as a chimpanzee, an ape or other monkey species; a farm animal such as cattle, a horse, a sheep, a goat, a swine; a domestic animal such as a rabbit, a dog (or a canine), and a cat (or a feline); a laboratory animal including a rodent, such as a rat, a mouse and a guinea pig, and the like. A non-mammal can include a bird, a fish and the like. In some embodiments, a subject can be a mammal. In some embodiments, a subject can be a human. In some embodiments, a human can be an adult. In some embodiments, a human can be a child. In some embodiments, a human can be age 0-17 years old. In some embodiments, a human can be age 18-130 years old. In some embodiments, a subject can be a male. In some embodiments, a subject can be a female. In some embodiments, a subject can be diagnosed with, or can be suspected of having, a condition or disease. In some embodiments, a disease or condition can be cancer. In some embodiments, a disease or condition can be cardiac wasting. A subject can be a patient. A subject can be an individual. In some embodiments, a subject, patient or individual can be used interchangeably.

In some embodiments, "treat," "treating", "treatment," "ameliorate" or "ameliorating" and other grammatical equivalents can include prophylaxis. "Treat", "treating", "treatment", "ameliorate" or "ameliorating" and other grammatical equivalents can further include achieving a therapeutic benefit and/or a prophylactic benefit. In some embodiments, a therapeutic benefit can mean eradication of an underlying disease being treated. In some embodiments, a therapeutic benefit can be achieved with an eradication of one or more physiological symptoms associated with an underlying disease such that an improvement can be observed in a subject notwithstanding that, in some embodiments, a subject can still be afflicted with an underlying disease.

Disclosed herein in some embodiments, are methods of detecting a compound in a sample from a subject. In some embodiments, disclosed herein, a sample can comprise a sample from a subject. In some embodiments, a sample can comprise a second compound as disclosed herein. In some embodiments, a second compound as disclosed herein can be detected in a sample using methods disclosed herein.

In some embodiments, a subject can comprise a patient. In some embodiments, a patient can be in need thereof. In some embodiments, a subject can have a disease, have a high probability of having a disease, be at risk of having a disease, or be suspected of being at risk of having a disease.

In some embodiments, a sample can comprise a reference sample. In some embodiments, a reference level can be obtained from a reference sample. In some embodiments, a reference level can comprise a range. In some embodiments, a level can be compared to one or more reference levels. In some embodiments, multiple different reference levels can correlate with different probabilities of developing a disease. In some embodiments, a reference value can be obtained from a reference sample. In some embodiments, different reference levels can be obtained from different reference samples. In some embodiments, a reference sample can be from a biological sample from a second subject. In some embodiments, a second subject can be at least partially healthy. In some embodiments, a second subject does not currently have or has not been diagnosed with a heart disease. In some embodiments, a second subject does not currently have or has not been diagnosed with heart failure. In some embodiments, a second subject has not been hospitalized in the past twelve months. In some embodiments, a second subject can have heart failure but have not yet had an acute event. In some embodiments, an acute event can comprise an unplanned hospitalization, a hospital admission for at least 24 hours, being administered a diuretic intravenously in a clinic or a combination thereof. In some embodiments, a second subject can have a disease condition as disclosed herein.

In some embodiments, a sample can comprise a bodily fluid. In some embodiments, a bodily fluid can comprise amniotic fluid, amniotic sac, aqueous humor, bile, blood, blood plasma, breast milk, cerebrospinal fluid (CSF), cerebrospinal fluid rhinorrhea, chyle, chyme, endolymph, extracellular fluid, exudate, gastric acid, hemolacria, hemolymph, interstitial fluid, lymph, mucus, pericardial fluid, perilymph, peritoneal fluid, perspiration, phlegm, pus, rheum, saliva, semen, sweat, synovial fluid, tears, transcellular fluid, transudate, urine, vaginal lubricant, vitreous body, vomit, or any combination thereof. In some embodiments, a bodily fluid is not processed prior to detection. In some embodiments, a bodily fluid can be processed prior to detection. In some embodiments, a sample can be collected using a sample collection device.

In some embodiments, disclosed herein a subject can have a disease. In some embodiments, a subject can have a high probability of developing a disease. In some embodiments, a subject can be at risk of developing a disease. In some embodiments, a subject does not have a disease. In some embodiments, a subject has an early stage of a disease. In some embodiments, a subject has not been diagnosed with a disease. In some embodiments, a subject can be determined to be at risk of developing a disease using a method as disclosed herein. In some embodiments, a subject can be determined to have a probability of developing a disease using a method as disclosed herein. In some embodiments, a subject can be substantially healthy.

In some embodiments, disclosed herein a second subject can have a disease. In some embodiments, a second subject can be at risk of developing a disease. In some embodiments, a second subject can have a probability of developing a disease. In some embodiments, a second subject does not have a disease. In some embodiments, a second subject has an early stage of a disease. In some embodiments, a second subject has not been diagnosed with a disease. In some embodiments, a second subject can be substantially healthy. In some embodiments, a second subject can have a low probability of developing heart disease over a time period.

In some embodiments, a treatment administered to a subject with a low probability, a medium probability, a high probability, or a very high probability can comprise an intervention, a statin, an antihypertensive, an antiplatelet agent, a hypoglycemic agent, antiarrhythmic agent, an anti-inflammatory agent, an ACE inhibitor, an ARB, an ARNI, an SGLT2 inhibitor, a statin, an antihypertensive agent, an MRA, a Beta blocker, an ivabradine, a ranolazine, a trimetazidine, a pacemaker, an ICD, a CRT device, a CCM device, a guanylate cyclase stimulator, a guanylate cyclase activator, a myosin activator, a serelaxin, a hospital admission, a surgical intervention, an analog of any of these, a salt of any of these, or any combination thereof. In some embodiments, a guanylate cyclase stimulator can comprise a soluble guanylate cyclase stimulator or a salt thereof. In some embodiments, a guanylate cyclase activator can comprise a soluble guanylate cyclase activator or a salt thereof.

In some embodiments, a treatment administered to a subject with a low probability can comprise monitoring as described herein. In some embodiments, a treatment administered to a subject with a low probability can comprise an intervention as described herein.

In some embodiments, a treatment administered to a subject with a medium probability can comprise a statin, an antihypertensive, an antiplatelet agent, a hypoglycemic agent, antiarrhythmic agent, an anti-inflammatory agent, or any combination thereof.

In some embodiments, a treatment administered to a subject with a high probability can comprise an ACE inhibitor, an ARB, an ARNI, an SGLT2 inhibitor, a statin, an antihypertensive agent, an MRA, a Beta blocker, an ivabradine, a ranolazine, a trimetazidine, a pacemaker, an ICD, a CRT device, a CCM device, a guanylate cyclase stimulator, a guanylate cyclase activator, a myosin activator, a serelaxin, an analog of any of these, a salt of any of these, or any combination thereof.

In some embodiments, a treatment administered to a subject with a very high probability can comprise a hospital admission, a surgical intervention, an ACE inhibitor, an ARB, an ARNI, an SGLT2 inhibitor, a statin, an antihypertensive agent, an MRA, a Beta blocker, an ivabradine, a ranolazine, a trimetazidine, a pacemaker, an ICD, a CRT device, a CCM device, a guanylate cyclase stimulator, a guanylate cyclase activator, a myosin activator, a serelaxin, an analog of any of these, a salt of any of these, or any combination thereof.

In some embodiments, a disease can comprise a heart disease. In some embodiments, a heart disease can comprise heart failure. In some embodiments, a second subject can have a non-heart failure disease condition. In some embodiments, a non-heart failure disease condition can comprise a cardiac disease. In some embodiments, a cardiac disease can comprise heart failure. In some embodiments, a non-heart failure disease condition can comprise cancer.

In some embodiments, a subject can have a terminal illness. In some embodiments, a subject can have elevated plasma levels of a natriuretic peptide, as compared to a healthy subject. In some embodiments, a subject can have elevated plasma levels of a troponin, as compared to a healthy subject. In some embodiments, a troponin can comprise troponin I or troponin T. In some embodiments, a subject can have elevated plasma levels of aldosterone, as compared to a healthy subject. In some embodiments, a subject can have Chronic Obstructive Pulmonary Disease (COPD). In some embodiments, a subject can have COPD exacerbations. In some embodiments, a subject can be considered to be in need of palliative and/or hospice care. In some embodiments, palliative care can be at home or in institutional care structures.

In some embodiments, disclosed herein, are methods comprising a detection of a compound. In some embodiments, a method of detection can comprise using a sensor. In some embodiments, a sensor can comprise a first compound or detection compound. In some embodiments, a detection of a compound can comprise contacting a first compound with a second compound. In some embodiments, a second compound can comprise one or more compounds present in a biological sample from a subject that does not currently have heart failure or that has not been diagnosed with heart failure. In some embodiments, a detection can comprise contacting a second compound with a third compound. In some embodiments, a detection can comprise detecting a binding of a first compound with a second compound. In some embodiments, a detection can comprise detecting a binding of a second compound with a third compound. In some embodiments, a detection can comprise measuring a level of a second compound. In some embodiments, a detection can comprise quantifying a level of a second compound. In some embodiments, a detection can comprise determining a concentration of a compound. In some embodiments, a detection can comprise comparing a level of a second compound to a reference level. In some embodiments, a sample as disclosed herein can comprise a second compound. In some embodiments, a sensor can comprise a fluorophore, a chromophore, a fluorescence-resonance energy transfer (FRET) donor, a FRET acceptor, a pH sensor, or any combination thereof. In some embodiments, a fluorophore can be stimulated after contacting with a second compound. In some embodiments, a sensor can be contacted with a bodily fluid as disclosed herein. In some embodiments, a bodily fluid can be derived from a subject as disclosed herein. In some embodiments, a second compound can comprise a pH level. In some embodiments, a second compound can comprise a hydrogen ion.

In some embodiments, a second compound can comprise a detector. In some embodiments, a detector can comprise a microchannel plate (MCP) assembly, a fast decay phosphor, an electron multiplier, a detection plate, or any combination thereof. In some embodiments, a fast decay phosphor, an electron multiplier, a detection plate, or any combination thereof can be part of a mass spectrometer. In some embodiments, a method of detection can comprise mass spectrometry. In some embodiments, a method of detection can comprise ionizing a plurality of molecules, atoms, or a combination thereof, separation of molecules, atoms, or a combination thereof, detection of separated molecules, atoms, or a combination thereof, calculation of a mass of an atom or molecule; or any combination thereof.

In some embodiments, a second compound can comprise a biomarker. In some embodiments, a second compound can comprise a peptide or salt thereof. In some embodiments, a biomarker can comprise a polypeptide or salt thereof. In some embodiments, a polypeptide does not comprise a natriuretic peptide or salt thereof. In some embodiments, a polypeptide can comprise a natriuretic peptide or salt thereof. In some embodiments, a polypeptide can comprise at least about 70% sequence identity to a polypeptide recited in Table 1, Table 7 or a salt of any of these, as determined by Basic Local Alignment Search Tool (BLAST). In some embodiments, a polypeptide can comprise at least about 70% sequence identity to AMPN, AMD, CALM3, KI21A, ACBP, IGA2, a salt of any of these, or any combination thereof.

TABLE 1

Biomarker

- B-type natriuretic peptide (BNP)
- N-terminal-proBNP
- Atrial natriuretic peptide
- Galectin-3
- Neutrophil gelatinase associated lipocalin (NGAL)
- mid-regional pro-adrenomedullin (MR-ProADM)
- ST2
- Galectin-3
- NT-proBNP
- BNP
- MR-proANP
- Troponin T
- troponin I
- myosin light-chain I
- heart-type fatty-acid protein
- CKMB
- Myeloperoxidase
- uric acid
- oxidized low-density lipoproteins
- urinary biopyrrins
- urinary and plasma isoprostanes
- plasma malodialdehyde
- Renin
- angiotensin II
- aldosterone
- Norepinephrine
- Chromogranin A
- MR-proADM
- Arginine vasopressin
- copeptin
- ET-1
- big proET-1
- C-reactive protein
- TNF-α, soluble TNF receptors
- Fas
- Interleukins (1, 6 and 18)
- osteoprotegerin
- adiponectin
- Matrix metalloproteinases
- collagen propeptides
- GDF-15
- VEGFR-1
- KLK1
- S10A7
- IGHA2
- CAMP
- quiescin Q6
- Creatinine
- BUN
- eGFR
- cystatin C
- β-trace protein
- NGAL
- KIM-1
- NAG
- liver-type fatty acid binding protein
- IL-18
- Hemoglobin
- RDW
- ferritin
- transferrin sat
- albumin In some embodiments, a biomarker can comprise low density lipoprotein (LDL) cholesterol or a salt thereof. In some embodiments, a biomarker can comprise an inflammation biomarker, an oxidative stress biomarker, a metabolic biomarker or any combination thereof. In some embodiments, an inflammation biomarker can comprise C-reactive protein, interleukin 6, Fibrinogen, monocyte chemotactic protein-1, tumor necrosis factor alpha, any salt thereof, or any combination thereof. In some embodiments, an oxidative stress biomarker can comprise an isoprostane or a salt thereof. In some embodiments, a metabolic biomarker can comprise lipoprotein (a), low-density lipoproteins, high density lipoprotein, ApoB 100, Lipoprotein-associated phospholipase A2, homocysteine, vitamin D, fibroblast growth factor 23, adiponectin, glycated hemoglobin, haptoglobin, a salt of any of these, or any combination thereof. In some embodiments, a biomarker can comprise a natriuretic peptide. In some embodiments, a natriuretic peptide can comprise a circulating natriuretic peptide. In some embodiments, a natriuretic peptide can comprise atrial natriuretic peptide (ANP), brain-type natriuretic peptide (BNP), mid-regional pro-ANP (MR-proANP), neural endopeptidase (neprilysin), a salt of any of these, or any combination thereof. In some embodiments, a biomarker can comprise a peptide, a nucleic acid, or a combination thereof. In some embodiments a biomarker can comprise KLK1, S10A7, IGHA2, CAMP, or any combination thereof. In some embodiments, a biomarker can comprise a liver enzyme. In some embodiments, a biomarker can comprise a genetic biomarker. In some embodiments, a biomarker can comprise an epigenetic biomarker.

In some embodiments, a biomarker can comprise a microbe. In some embodiments, a method can further comprise determining a microbiome status of a subject.

In some embodiments, a biomarker can comprise a nucleic acid. In some embodiments, a nucleic acid can comprise RNA. In some embodiments, RNA can comprise a microRNA (miRNA). In some embodiments, a miRNA can comprise miR423-5p, miR320a, or miR22. In some embodiments, a nucleic acid can comprise DNA.

In some embodiments, a compound can comprise a plurality of compounds. In some embodiments, a compound can comprise a peptide or a salt thereof. In some embodiments, a peptide can comprise a polypeptide, a protein, a salt of any of these, or any combination thereof. In some embodiments, a polypeptide can comprise an antibody or a functional fragment thereof. In some embodiments, an antibody can bind to an analyte. In some embodiments, a first compound can comprise a fluorophore. In some embodiments, a first compound can comprise an array. In some embodiments, an array can change conductivity when contacted with a second compound. In some embodiments, a first compound can comprise an oligonucleotide array. In some embodiments, a first compound can comprise an electrode and a counter-electrode. In some embodiments, a detection can comprise a second compound contacting an electrode and counter-electrode. In some embodiments, a second compound contacting an electrode and counter-electrode can complete a circuit between an electrode and a counter-electrode.

In some embodiments, a second compound can comprise a substance that is not at least substantially present in a subject with heart failure. In some embodiments, a second compound can be at least substantially present in a subject with heart failure. In some embodiments, a second compound can be present at a decreased level in a biological sample from a subject, relative to a level of a second compound in a biological sample from a second subject. In some embodiments, a second compound can be present at an increased level in a biological sample from a subject, relative to a level of a second compound in a biological sample from a second subject. In some embodiments, a second compound can be present at a decreased level in a biological sample from a subject, relative to a level of a second compound in a biological sample from a second subject. In some embodiments, an increased level of a second compound can be indicative of an increased probability of a subject developing a disease condition as disclosed herein. In some embodiments, a decreased level of a second compound can be indicative of an increased probability of a subject developing a disease condition as disclosed herein. In some embodiments, a relative level of a second compound can be compared to a reference sample. In some embodiments, a level of a second compound can be detected at multiple time points in a time period to monitor a level of a second compound over time. In some embodiments, a measurement can be repeated over time in response to a detection of a measurement.

In some embodiments, a second compound can be enriched after contacting with a first compound. In some embodiments, a second compound can be enriched after contacting with a first compound relative to a concentration of a second compound present in a biological sample. In some embodiments, a second compound can be enriched in a sample collection device as described herein. In some embodiments, a detection can comprise enriching a second compound. In some embodiments, a detection can comprise amplifying a second compound. In some embodiments, a detection can comprise a polymerase chain reaction. In some embodiments, after a contacting of a first compound with a second compound occurs, a second compound can be washed. In some embodiments, non-binding substances, compounds, contaminants, or impurities can be washed away. In some embodiments, after a contacting of a first compound with a second compound occurs, a second compound can be flushed away from a first compound.

In some embodiments, a detection can occur while a first compound is at least partially inside a subject. In some embodiments, a sensor can be at least partially inside a subject during detection. In some embodiments, a device as disclosed herein can be at least partially inside a subject during detection. In some embodiments, a detection can occur on a sample derived from a subject. In some embodiments, a sample can be collected on a device prior to a detection.

In some embodiments, an increased level of a second compound can be indicative of a presence of a disease condition as disclosed herein. In some embodiments, a decreased level of a second compound can be indicative of a presence of a disease condition as disclosed herein. In some embodiments, an increased level can relative to a reference level. In some embodiments, a decreased level can be relative to a reference level.

In some embodiments, a detection of an increased or decreased level of a second compound can be used at least in part to determine if a subject should be administered a treatment as disclosed herein. In some embodiments, a level can be determined. In some embodiments, a level can determine a probability of developing a disease. In some embodiments, a probability can comprise a likelihood of developing a disease. In some embodiments, a level of a second compound can determine a type of treatment to be administered.

In some embodiments, a second subject can be from a subset of a group who went on to develop heart failure. In some embodiments, a subset can be from a group who did not originally have heart failure. In some embodiments, a second compound can be present at an increased level in a biological sample from a subject, relative to a level of a second compound in a biological sample from a second subject, wherein a second subject is from a subset of a group who went on to develop heart failure, wherein a subset is from a group who did not originally have heart failure.

In some embodiments, a second compound can comprise a polypeptide. In some embodiments, a polypeptide does not comprise a natriuretic peptide. In some embodiments, a polypeptide can comprise at least about 70% sequence identity to a polypeptide recited in Table 1, Table 7, a salt of any of these, or any combination thereof, as determined by BLAST. In some embodiments, a method can distinguish a first subject who would have developed heart failure without an administering over a time period from a second subject who would not have developed heart failure over a time period. In some embodiments, a method distinguishes a first subject from a second subject with an accuracy of at least about 90%.

As described herein, a measured value of a subject can be associated with a disease state of a subject as described herein. In some embodiments, an association between a measured value of a subject and a disease state can be indicative of a disease in a subject.

In some embodiments, a disease can comprise symptoms. In some embodiments, symptoms can comprise breathlessness, lethargy, reduced exercise tolerance, over congestive cardiac failure, increased mortality, or any combination thereof.

In some embodiments, a detection as described herein can be used to stratify a subject into a probability group. In some embodiments, a probability group can comprise imminent probability, short term probability, medium term probability or long term probability. In some embodiments, an imminent probability can comprise a probability of developing a disease within one month of a detection. In some embodiments, a short term probability can comprise developing a disease within one month to one year of a detection. In some embodiments, a medium term probability can comprise developing a disease within one year to ten years. In some embodiments, a long term probability can comprise developing a disease in more than about ten years. In some embodiments, a probability group can comprise low probability, medium probability, high probability, or very high probability. In some embodiments, a very high probability can comprise a probability of developing a disease within one month of a detection. In some embodiments, a high probability can comprise developing a disease within one month to one year of a detection. In some embodiments, a medium probability can comprise developing a disease within one year to ten years. In some embodiments, a low probability can comprise developing a disease in more than about ten years.

In some embodiments, disclosed herein, are compositions comprising a device. In some embodiments, disclosed herein, are methods comprising use of a device. In some embodiments, a method of detection can comprise a use of a device. In some embodiments, disclosed herein, a device can comprise a compound as disclosed herein. In some embodiments, a device can comprise a second compound as disclosed herein.

In some embodiments, a device can comprise a wireless transmitter. In some embodiments, a wireless transmitter can comprise a Bluetooth transmitter, an RF transmitter, a cellular signal transmitter, a Wi-fi transmitter, or any combination thereof. In some embodiments, a device can comprise a sample collection device. In some embodiments, a sample collection device can comprise an oral sample collection device. In some embodiments, an oral sample collection device can comprise an oral swab.

In some embodiments, a sample collection device can comprise a wireless receiver. In some embodiments, a wireless receiver can comprise a Bluetooth receiver, an RF receiver, a cellular signal receiver, a Wi-fi receiver, or any combination thereof. In some embodiments, a biological sample can be obtained using an oral sample collection device. In some embodiments, a device can comprise an oral sample collection device. In some embodiments, an oral sample collection device can comprise a first compound. In some embodiments, a device can be configured to perform a contacting when a saliva is input into an oral sample collection device. In some embodiments, an oral sample collection device can comprise a wireless transmitter. In some embodiments, an oral sample collection device can comprise an oral swab. In some embodiments, a method can comprise using a computer processor to execute an algorithm. In some embodiments, a method can comprise selecting a treatment from a database with the aid of a computer processor executing an algorithm. In some embodiments, a method comprising selecting a treatment from a database with the aid of a computer processor executing an algorithm can be performed prior to an administering. In some embodiments, a database can be at least transiently stored on a computer readable memory. In some embodiments, a database can comprise a treatment formulary of medicaments or interventions. In some embodiments, a database can comprise data. In some embodiments, data can comprise information regarding a plurality of second compounds. In some embodiments, data can be analyzed. In some embodiments, a data analysis can comprise sequential window acquisition of all theoretical mass spectra (SWATH-M), peptide query parameters (PQPs), or a combination thereof.

In some embodiments, an oral swab can comprise an oral swab. In some embodiments, an oral swab can comprise an electronic oral swab. In some embodiments, an electronic oral swab can be used for non-invasive disease detection. In some embodiments, a device can comprise a handle. In some embodiments, a swab can comprise a sampling head. In some embodiments, a sampling head can be releasably attachable to a handle. In some embodiments, a sampling head can be sized for insertion into a mouth. In some embodiments, a sampling head can comprise an enclosure. In some embodiments, an enclosure can be made from a biocompatible material. In some embodiments, a sampling head can be contacted with a subject's mouth and saliva. In some embodiments, a sampling head can comprise a biosensor. In some embodiments, a biosensor can be housed within an enclosure. In some embodiments, a biosensor can comprise a transducer, a biological element, a reagent or a combination thereof. In some embodiments, a biosensor can be configured to generate a biosensor signal. In some embodiments, a transduce can convert a detection signal to an electrical signal. In some embodiments, an electrical signal can be transmitted by a device. In some embodiments, an electrical signal can be processed by a computer processor. In some embodiments, an electrical signal can be processed by a system comprising a processor, a computer readable medium, or a combination thereof. In some embodiments, a system can relay a signal, transmit a signal, store a signal, receive a signal, process a signal, or any combination thereof. In some embodiments, a signal can comprise information. In some embodiments, information can be analyzed. In some embodiments, a signal can comprise data. In some embodiments, a signal comprise a test result. In some embodiments, a signal comprise a level of a second compound as described herein.

In some embodiments, a biosensor signal can be proportional to a concentration level of an analyte in saliva within a predetermined measuring range in response to an interaction between the biological element or reagent and the analyte.

In some embodiments, a sampling head can comprise an opening through an enclosure for fluid communication of saliva to a biosensor.

In some embodiments, a device can comprise a wireless transmitter coupled to a biosensor, configured to wirelessly transmit signal data corresponding to a biosensor signal, to a computing device comprising a processor. In some embodiments, a sampling head can comprise a wireless transmitter. In some embodiments, a wireless transmitter can comprise a passive near field communication (NFC) device. In some embodiments, a transmitter can be a small transmitter. In some embodiments, a device does not require its own power source. In some embodiments, a device can be powered by an electromagnetic field. In some embodiments, an electromagnetic field can be produced by an active NFC component when it comes into range. In some embodiments, a device can be powered by a mobile phone with NFC turned on. In some embodiments, a transmission frequency for data across NFC can comprise 13.56 megahertz. In some embodiments, data can be transmitted at either 106, 212, or 424 kilobits per second. In some embodiments, read/write mode can be activated. In some embodiments, read/write mode can comprise a one-way wireless data transmission when the mobile phone is linked with a sampling head to read signal data from a sampling head. In some embodiments, NFC can have a range of about 10 cm. In some embodiments, Bluetooth connections can transmit data up to 10 meters or more from a sampling head if a Bluetooth RF transceiver is provided as a wireless transmitter. In some embodiments, Bluetooth can require pairing. In some embodiments, pairing can take a few seconds to establish. In some embodiments, a handle can comprise a wireless transmitter. In some embodiments, an electrical connection can be provided between a handle and a sampling head to transmit a biosensor signal from a biosensor to a wireless transmitter. In some embodiments, a wireless transmitter can transmit a signal data via Near Field Communication (NFC) or Bluetooth to a computing device.

In some embodiments, an oral swab can further comprise a resilient spring member configured to provide a snap-fit connection with a handle. In some embodiments, a resilient spring member enables detachment of a sampling head from a handle. In some embodiments, a resilient spring member can be resiliently deformable.

In some embodiments, a resilient spring member can comprise a spring arm having a locking tip to releasably engage with a receptacle in a handle to provide visual confirmation of correct engagement. In some embodiments, a user can see a locking tip. In some embodiments, a locking tip can have a contrasting color fully within a receptacle. In some embodiments, a locking tip and receptacle can be shaped and sized to provide an audible confirmation in response to correct engagement. In some embodiments, an audible confirmation can comprise a click sound.

In some embodiments, a resilient spring member can comprise a curved section. In some embodiments, a curved section can assist with easier deflection of a resilient spring member along its longitudinal axis when it inserted into a hollow section of a handle and a locking tip abuts against an upper inner surface of a hollow section. In some embodiments, a curved section can project in a direction opposite to a protruding direction of a locking tip. In some embodiments, a locking tip can have an angled peripheral wall to prevent it from catching against a peripheral opening edge of a hollow section. In some embodiments, dimensions of a curved section can be tuned to provide a desired amount of deflection required to conveniently insert a resilient spring member within a hollow section with minimal force, and for a locking tip to removably mate with a receptacle.

In some embodiments, a locking tip comprising a visual aid can prevent upside down insertion of a sampling head to a handle and can therefore prevent accidental detachment from incorrect engagement. In some embodiments, a locking tip can allow a subject to use a digit to apply a finger force to depress a locking tip initiating disengagement of a sampling head from a handle. In some embodiments, a digit can comprise a thumb or index finger. In some embodiments, a user can also point a sampling head at a downward angle. In some embodiments, gravity can assist to cause a sampling head to become fully disengaged and fall directly into a rubbish bin. In some embodiments, a subject does not need to touch saliva or a used sampling head which improves hygiene and convenience from a single step disengagement process.

In some embodiments, use of a resilient spring member can prevent a sampling head unintentionally disengaging from a handle because a spring or resiliency provides a secure engagement force. In some embodiments, a finger force can be required to fully depress a locking tip below an outer wall thickness of a handle, accidentally touching a locking tip will not cause accidental detachment of a sampling head from a handle.

In some embodiments, a handle can comprise a slanted portion located between a first planar portion, arranged parallel to a second planar portion. In some embodiments, a slanted portion can provide a vertical offset between two parallel planar portions for enabling a sampling head to contact saliva at a side of a mouth with minimal obstruction by teeth. In some embodiments, a shape of a handle can also be ergonomic which can provide greater comfort in using a swab in a patient's mouth compared to a handle that is completely straight.

In some embodiments, a handle can be tubular. In some embodiments, a first planar portion can include a hollow portion configured to receive a resilient spring member. In some embodiments, a first planar portion can have a length shorter than a length of a second planar portion. In some embodiments, an oral swab can be center-balanced when a sampling head is attached to a handle. In some embodiments, a weight balancing can make it easier for users to manipulate a swab in their mouth to collect saliva, especially for elderly users who may have reduced dexterity or unsteady hands.

In some embodiments, a height of a locking tip can be a predetermined height such that when a locking tip is engaged with a receptacle, an upper surface of a first planar portion can be flush with an upper surface of a locking tip.

In some embodiments, a toothbrush can comprise a resilient spring member configured to provide a snap-fit connection with a handle. In some embodiments, a resilient spring member can enable detachment of a sampling head from a handle. In some embodiments, a resilient spring member can be resiliently deformable.

In some embodiments, a second planar portion can comprise a bristled portion along an upper surface. In some embodiments, a second planar portion can be in a shape of a diamond. In some embodiments, a tip of a second planar portion can be narrowed to enable easier access to posterior teeth especially. In some embodiments, narrowing a tip of a second planar portion can provide easier access to posterior teeth for a subject with a smaller oral cavity.

In some embodiments, a handle can be tubular. In some embodiments, a first planar portion can include a hollow portion configured to receive a resilient spring member. In some embodiments, a first planar portion can comprise a length shorter than a length of a second planar portion.

In some embodiments, a slanted portion of a handle can comprise a narrowed neck which may provide convenience when inserted into a mouth and teeth are brushed as it is slimmer in this region. In some embodiments, a slanted portion may be approximately 45 degrees relative to a planar portion. In some embodiments, a toothbrush can be angled or contra-angled to reach back teeth and difficult to clean areas. In some embodiments, a handle can be made from a rigid material or semi-rigid material. In some embodiments, a semi-rigid material can enable a handle to have some flexibility. In some embodiments, flexibility can be advantageous to reduce gum injury caused by excessive brushing force. In some embodiments, a handle can comprise a slip prevention feature. In some embodiments, a slip prevention feature can at least partially help avoid a toothbrush slipping away during brushing. In some embodiments, a slip prevention feature can include a deformable material or a high friction surface finish.

In some embodiments, rather than having a separate toothbrush and oral swab, an electronic toothbrush can require less storage space and can conveniently enable a user to perform a swab before or after brushing teeth without having to switch hands. In some embodiments, requiring less storage space can be particularly useful if a subject is travelling or otherwise away from home and luggage capacity is limited. In some embodiments, a sampling head can be replaced after each use. In some embodiments, a handle with a bristled portion can be used approximately for 6 to 16 weeks before replacement. In some embodiments, an electronic toothbrush can eliminate a need for a user to have a separate conventional toothbrush.

In some embodiments, a sampling head can be attached to a handle. In some embodiments, an outer surface of a sampling head can be flush with an outer surface of a handle. In some embodiments, a sampling head and handle can have rounded sides. In some embodiments, distal ends of a sampling head and handle can be chamfered or have rounded corners. In some embodiments, rounded sides and chamfered corners reduce a severity of impact damage in an event an oral swab is dropped onto a hard surface such as a tiled bathroom floor.

In some embodiments, a sample head can have an identify authentication feature stored in a storage device, for example, non-volatile memory or an RFID tag. In some embodiments, a wireless transmitter can be configured to transmit identification data from an identify authentication feature to authenticate a sampling head with a personal health application executed by a processor of a computing device. In some embodiments, an identification data may be a 160 bit value.

In some embodiments, data being collected from a subject can be medical data. In some embodiments, medical data can be considered highly sensitive and confidential. In some embodiments, identification data can be encrypted and a computing device or a remote server can have a cryptographic key to decrypt an encrypted identification data for authenticating a sampling head. In some embodiments, a cryptographic key can comprise a string of data used by a cryptographic algorithm to transform cipher text into plain text, for authentication. In some embodiments, cipher text can comprise encrypted identification data. In some embodiments, an encryption may be a non-federated cryptographic protocol that can be used to provide end-to-end encryption. In some embodiments, encryption can comprise a Double Ratchet algorithm, prekeys, a triple Diffie-Hellman (3-DH) handshake, or any combination thereof. In some embodiments, encryption can use Curve25519, AES-256, HMAC-SHA256 or any combination thereof as primitives.

In some embodiments, a personal health application can comprise an access control module. In some embodiments, an access control module can be configured to detect whether a sampling head is authenticated by analyzing a transmitted identification data. In some embodiments, if a sampling head cannot be authenticated, a personal health application does not process signal data. In some embodiments, not processing data can prevent data corruption of a personal health application which may have accumulated a large amount of historical user data from previous swabs. In some embodiments, a swab can be part of a batch of swabs that have been recalled due to a potential safety concern identified. In some embodiments, blocking receipt of signal data, a user can be notified by a message displayed on a personal health application that there may be a recall in place and then to return any remaining swabs to a place of purchase for refund or change.

In some embodiments, a mobile computing device can comprise one or more microprocessors. In some embodiments, a microprocessor can comprise a CPU. In some embodiments, a microprocessor can retrieve data and/or instructions from memory and execute retrieved instructions in a conventional manner. In some embodiments, memory can include persistent memory, volatile memory, or a combination. In some embodiments, persistent memory can comprise magnetic and/or optical disks, ROM, and PROM, or any combination thereof. In some embodiments, volatile memory can comprise RAM. In some embodiments, a CPU can be embodied as a System on chip (SoC) comprising a CPU, GPU, LTE modem, display processor, and video processor. In some embodiments, an LTE modem can comprise a Cat. 9 LTE modem.

In some embodiments, a CPU can be interfaced to, or otherwise operably associated with, a communications interface, one or more user input/output (I/O) interfaces, and local storage, which may comprise a combination of volatile and non-volatile storage. In some embodiments, non-volatile storage may include solid-state non-volatile memory, such as read only memory (ROM) flash memory, or the like. In some embodiments, volatile storage may include random access memory (RAM). In some embodiments, RAM can be LPDDR4, LPDDR4X or LPDDR5 RAM with a capacity of 32 GB to 256 GB. In some embodiments, a CPU and a memory can be connected to one another through a conventional interconnect. In some embodiments, a conventional interconnect can comprise a bus. In some embodiments, a CPU and a memory can be further connected to a touchscreen display.

In some embodiments, storage can contain program instructions and transient data relating to the operation of device. In some embodiments, a storage can contain programs and data content relevant to a normal operation of a device. In some embodiments, a storage can also include program instructions which, when executed by a processor can instruct a device to perform operations as disclosed herein. In some embodiments, a device can include additional peripheral interfaces. In some embodiments, a peripheral interface can comprise an interface to high-capacity non-volatile storage, such as a hard disk drive, optical drive, or any combination thereof. In some embodiments, programs can include operating system programs and data, as well as other executable application software generally unrelated to the present invention.

In some embodiments, an operating system can comprise logic implemented by a CPU of a device that can provide services used by other logic implemented in a device. In some embodiments, services can include management of computer resources. In some embodiments, computer resources can comprise file systems, peripheral device support, networking services, and computer process management. In some embodiments, a subject does not directly use an operating system but rather uses logic that in turn uses the operating system to perform various tasks. In some embodiments, an operating system can be used in a mobile computing device. In some embodiments, an operating system can be used in an Android mobile operating system produced by Google, Inc., an iOS operating system produced by Apple Computer, or a Windows 7 mobile operating system produced by Microsoft Corp. In some embodiments, applications can define a behavior performed by a device. In some embodiments, an application can be pre-installed before acquisition of a device by an end user. In some embodiments, applications can be installed by a user of a device.

In some embodiments, a number of software components of a device can be stored in memory. In some embodiments, an operating system and applications can comprise part of one or more computer processes executing within a CPU from a memory. In some embodiments, part of one or more computer processes can also be implemented using digital logic circuitry.

In some embodiments, a storage device can maintain a known program and data content relevant to a normal operation of a device. In some embodiments, a storage device can contain operating system programs and data. In some embodiments, executable application software can be necessary for intended functions of a device. In some embodiments, a storage device can also contain program instructions which, when executed by a processor, can instruct a device to perform operations relating to an embodiment of a present invention. In some embodiments, during operation, instructions and data held on a storage device can be transferred to volatile memory for execution on demand.

In some embodiments, a processor can also be operably associated with a communications interface in a conventional manner. In some embodiments, a communications interface can facilitate access to a data communications network such as an internet or home network.

In some embodiments, when in use a volatile storage can contain a corresponding body of program instructions transferred from a storage device or via communications interface and configured to perform processing and other operations embodying features of a present invention.

In some embodiments, a device can comprise an electronic toothbrush for non-invasive disease detection. In some embodiments, an electronic toothbrush can comprise a handle. In some embodiments, a handle can have a first end comprising a bristled portion, and an opposite second end. In some embodiments, a bristled portion can comprise a plurality of soft bristles or firm bristles. In some embodiments, bristles of a bristled portion can be concentrated closely to clean each tooth of potentially carcinogenic materials. In some embodiments, bristles can be arranged spatially. In some embodiments, outer edge peripheral bristles can be longer and softer than inner located bristles. In some embodiments, bristles can be curved rather than straight. In some embodiments, curved bristles can follow curvature of teeth. In some embodiments, curved bristles can safely reach in between teeth and into sulcular areas. In some embodiments, bristles can be made from a biocompatible thermoplastic material. In some embodiments, a biocompatible thermoplastic material can comprise nylon.

In some embodiments, a toothbrush can comprise a sampling head releasably attachable to a handle at a second end of a handle and sized for insertion into a mouth. In some embodiments, a sampling head can comprise an enclosure made from a biocompatible material because it comes into contact with a person's mouth and saliva. In some embodiments, a sampling head can comprise a same or similar component as a head of an electronic oral swab.

In some embodiments, a handle can comprise a wireless transmitter. In some embodiments, an electrical connection can be provided between a handle and a sampling head to transmit a biosensor signal from a biosensor to a wireless transmitter. In some embodiments, a wireless transmitter may transmit a signal data via Near Field Communication (NFC) or Bluetooth to a computing device.

Disclosed herein in some embodiments, is a kit comprising a device as disclosed herein. In some embodiments, a kit can comprise a device. In some embodiments, a kit can comprise a packaging. In some embodiments, a kit can be at least partially sterile. In some embodiments, a kit can comprise instructions.

In some embodiments, a kit can comprise a first compound as disclosed herein, and an oral sample collection device. In some embodiments, a first compound can be present in an oral sample collection device. In some embodiments, a second compound can comprise a polypeptide. In some embodiments, a polypeptide can comprise at least about 70% sequence identity to a polypeptide recited in Table 1, Table 7, a salt of any of these, or any combination thereof, as determined by BLAST.

Disclosed herein in some embodiments, are methods comprising analyzing data from a detection. In some embodiments, a device can analyze data from a detection. Disclosed herein in some embodiments, is a method of using a machine learning model to determine a risk of a subject developing heart failure. In some embodiments, a method can comprise measuring a level of one or more compounds present in a biological sample from a subject that does not currently have heart failure or that has not been diagnosed with heart failure, wherein an increased or decreased level of the compound relative to a reference level is indicative of a risk of developing heart failure within a time period. In some embodiments, a method can further comprise clustering the level of the one or more compounds present in the biological sample using the machine learning model. In some embodiments, a method can further comprise identifying a cluster of the one or more compound present in the biological sample, wherein the cluster represents the plurality of biomarker levels associated with a risk of a subject developing heart failure. In some embodiments, a method can further comprise determining the risk of the subject developing heart failure within a time period. In some embodiments, a machine learning model clusters the level of the one or more compounds present in the biological sample using linear regression, a neural network, ensemble, or any combination thereof. In some embodiments, a machine learning model can increase the accuracy of prediction scores over time as more data is added to a database. In some embodiments, as more data is used to train a machine learning model, a level of one or more biomarkers can be more accurately associated with a specific disease risk, a specific treatment, or a combination thereof. In some embodiments, a machine learning model can provide a selection of a treatment that results in a lower chance of a subject developing heart failure. In some embodiments, a machine learning model can allow for precision medicine, a subject specific prescription, or a combination thereof in response to a specific reading of one or more biomarkers from a sample obtained from a subject that has not been diagnosed with or does not have heart failure. In some embodiments a method of using a machine learning model can comprise using a system comprising: a computer processor, a computer readable memory operatively coupled to a computer processor, wherein a computer readable memory at least transiently stores: a database that can comprise a treatment formulary of medicaments or interventions, and a plurality of biomarkers predictive of a probability of developing heart failure within a time period of from about 1 week to about 5 years; and an algorithm that, when executed by a computer processor, selects a treatment from a treatment formulary based on a biomarker selected from a plurality of compounds. In some embodiments, a system further can comprise a wireless transmitter or a wireless receiver. In some embodiments, a system can be configured for wireless communication to a device. In some embodiments, a system can be configured for wired communication to a device. In some embodiments, a device can be an oral sample collection device. In some embodiments, an oral sample collection device can comprise a compound, and wherein an oral sample collection device can be configured to contact a compound with a biomarker present in saliva when saliva is input into an oral sample collection device. In some embodiments, an oral sample collection device can comprise a wireless transmitter. In some embodiments, a wireless transmitter can comprise a Bluetooth transmitter, an RF transmitter, a cellular signal transmitter, a Wi-fi transmitter, or any combination thereof. In some embodiments, an oral sample collection device can comprise a wireless receiver. In some embodiments, a wireless receiver can comprise a Bluetooth receiver, an RF transmitter, a cellular signal receiver, a Wi-fi receiver, or any combination thereof. In some embodiments, an oral sample collection device can comprise an oral swab. In some embodiments, a system can be configured to access a database via a wireless transmitter or a wireless receiver, wherein a database can be stored on a server. In some embodiments, a server can comprise a cloud-based server. In some embodiments, an increased or decreased level of the compound relative to a reference level can be indicative of a risk of developing heart failure within a time period. In some embodiments, a method can further comprise determining a risk of a subject developing heart failure within a time period based on an increased or decreased level of one or more compounds. In some embodiments, a method can further comprise administering a treatment for a heart failure to a subject based on a risk score. In some embodiments, one or more compounds can comprise one or more biomarkers.

In some embodiments, a method can distinguish a first subject who would have developed heart failure without an administering over a time period from a second subject who would not have developed heart failure over a time period.

In some embodiments, a method can distinguish a first subject from a second subject with an accuracy of at least about 90%.

Also disclosed herein in some embodiments, is a method of monitoring a disease in a subject. In some embodiments, monitoring a disease can comprise measuring a biomarker in a subject. In some embodiments, measurements and comparisons can be performed repeatedly. In some embodiments, monitoring can be used to determine a prognosis for a patient. In some embodiments, monitoring can be used to detect disease onset in a patient. In some embodiments, monitoring can comprise measuring progression of a disease over time. In some embodiments, monitoring can comprise measuring heart rate, blood pressure, EKG readings, or any combination thereof over a time period as disclosed herein. In some embodiments, a treatment strategy can be changed in response to changes detected during monitoring.

In some embodiments, monitoring can be used to determine efficacy of a treatment. In some embodiments, determining an efficacy of a treatment can comprise making one or more measurements over a time period. In some embodiments, one or more measurements can be compared to previously recorded measurements, a reference value, or a combination thereof. In some embodiments, a value of a recorded measurement can decrease over time. In some embodiments, a value of a recorded measurement can increase over time. In some embodiments, a measurement value not decreasing over a time period can be used to determine at least in part if a treatment is effective. In some embodiments, a measurement value not increasing over a time period can be used to determine at least in part if a treatment is effective. In some embodiments, a measurement value not staying constant over a time period can be used to determine at least in part if a treatment is effective. In some embodiments, a decrease or increase in a measurement value over a time period can be used to determine whether to continue, modify, change, or cease treatment.

In some embodiments, a time period can comprise about 1 day, about 2 days, about 3 days, about 4 days, about 5 days, about 6 days, about 7 days, about two weeks, about three weeks, about one month, about two months, about three months, about four months, about five months, about six months, about seven months, about eight months, about nine months, about ten months, about eleven months, about one year, about two years, or more than about two years after a first treatment.

In some embodiments, a detection of a measurement can be used to determine a prognosis for a disease. In some embodiments, detection of a measurement can be comprised with a further test. In some embodiments, a further test can comprise a cardiac test. In some embodiments, a further test can comprise measurement of a biomarker.

In some embodiments, a method of monitoring can comprise monitoring a wasting of muscle mass in a subject. In some embodiments, a muscle mass can comprise cardiac muscle mass. In some embodiments, cardiac muscle mass can comprise ventricular muscle mass. In some embodiments, ventricular muscle mass can comprise left ventricular muscle mass. In some embodiments, monitoring wasting of muscle mass can comprise recording a measurement in a subject, comparing a measurement to a reference level, and repeating the previous steps.

In some embodiments, a method can further comprise correlating a microbiome status with a known database to determine a probability score for a subject developing heart failure.

In some embodiments, a subject as disclosed herein can be a patient in need thereof. In some embodiments, a subject as disclosed herein can be administered a therapy or treatment. In some embodiments, a decision to administer a treatment to a subject can at least be in part based on a detection of a second compound as disclosed herein. In some embodiments, disclosed herein, a method can comprise administering a treatment to a subject. In some embodiments, a treatment can be selected from a database prior to administering. In some embodiments, a treatment can be administered to a subject diagnosed with a disease as disclosed herein. In some embodiments, a treatment can be administered to a subject that does not yet have a disease. In some embodiments, a treatment can be administered prophylactically. In some embodiments, monitoring can determine a success of a prophylactic to prevent disease onset over a time period.

In some embodiments, a treatment can ameliorate at least one symptom of a disease or condition. In some embodiments, administering can prevent an occurrence of a disease as disclosed herein over a time period. In some embodiments, administering can slow a development of a disease. In some embodiments, administering can delay an onset of a disease. In some embodiments, a treatment can reduce a frequency of incidence of a symptom of a disease or condition over a time period. In some embodiments, a symptom of a disease or condition can comprise a hospitalization, cardiac arrest, death, or a combination thereof. In some embodiments, a treatment can further prevent an occurrence of a disease as disclosed herein over a period of time that is longer than a time period of a treatment.

In some embodiments, a time period can comprise about zero days to about one day, about one day to one week, about one week to about two weeks, about two weeks to about four weeks, about four weeks to about two months, about two months to about six months, about six months to about one year, about one year to about eighteen months, about eighteen months to about two years, about two years to about three years, about three years to about four years, about four years to about five years, about five years to about six years, about six years to about seven years, about seven years to about eight years, about eight years to about nine years, about nine years to about ten years, about ten years to about twenty years, about twenty years to about thirty years, about thirty years to about forty years, about forty years to about one hundred years, or any combination thereof. In some embodiments, a time period can comprise about zero months to about three months, about three months to about eighteen month, about one week to about eighteen months, about one week to about two years, about one week to about three years, about one week to about four years, about one week to about five years, about one week to about four years, about one week to about five years, about one week to about six years, about one week to about seven years, about one week to about eight years, about one week to about nine years, about one week to about ten years, about one week to about twenty years, about one week to about thirty years, about one week to about forty years, about one week to about fifty years, about one week to about sixty years, or any combination thereof.

In some embodiments, a treatment can comprise cardioversion, defibrillation, a medicament or any combination thereof. In some embodiments, cardioversion can comprise electrical cardioversion, chemical cardioversion, or a combination thereof.

In some embodiments, a medicament can comprise a drug, or a salt, polymorph, solvate, isomer, stereoisomer, prodrug, or metabolite thereof. A drug can be licensed or approved by a regulatory agency. In some embodiments, a medicament may not be licensed or approved by a regulatory agency.

In some embodiments, a medicament can comprise a drug or biologic. In some embodiments, a medicament can comprise a drug or biologic that is licensed or approved for a condition by the United States Federal Drug Agency (USFDA) anytime as of or after Apr. 1, 2020.

In some embodiments, a medicament can comprise a drug or a biologic that was not licensed or approved by the USFDA for heart failure anytime as of or after Apr. 1, 2020.

In some embodiments, a medicament can comprise a drug or biologic that was not licensed or approved by the USFDA for any condition anytime as of or after Apr. 1, 2020.

In some embodiments, a medicament can comprise a statin, an anti-inflammatory, a blood thinner, an antioxidant, a polypeptide, an alpha blocker, a beta blocker, a beta receptor blocker, an ACE inhibitor, an aldosterone antagonist, a mineralocorticoid receptor antagonist, an aldosterone synthesis inhibitor, a myosin activator, cardioxyl, omecamtiv mecarbil, relaxin, serelaxin, staroxime, bucindolol, a phosphodiesterase 5 inhibitor, a vasopressin inhibitor, levosimendan, a sodium-glucose cotransporter-2 (SGLT2) inhibitor, an If channel blocker, a stereoisomer of any of these, a salt of any of these, or any combination thereof.

In some embodiments a drug can comprise an inotrope or a salt thereof. In some embodiments, an inotrope can comprise a cardiac inotrope or a salt thereof. In some embodiments, a cardiac inotrope can comprise a positive inotrope or a salt thereof. In some embodiments, a positive inotrope can comprise a cardiotonic drug, a cardiotonic agent, a cardiostimulatory drug, a cardiostimulatory agent, any salt thereof, or any combination thereof. In some embodiments, a positive cardiac inotrope can strengthen a force of a heartbeat. In some embodiments, a cardiac inotrope can comprise a negative cardiac inotrope, or a salt thereof. In some embodiments, a negative cardiac inotrope or a salt thereof can weaken a force of a heartbeat. In some embodiments, a cardiostimulatory drug can comprise a cardiotonic drug. In some embodiments, a cardiostimulatory drug can enhance cardiac function. In some embodiments, a cardiostimulatory drug can enhance cardiac function by increasing heart rate (chronotropy), myocardial contractility (inotropy), increasing cardiac output, increasing arterial pressure, or any combination thereof. In some embodiments, a drug can increase electrical conduction (dromotropy) within the heart. In some embodiments, a drug can augment relaxation (lusitropy). In some embodiments, a drug can produce systemic vasodilation. In some embodiments, a drug can produce vasoconstriction. In some embodiments, a mechanism of producing vasoconstriction can be different from a cardiac mechanism.

In some embodiments, a positive inotrope or a salt thereof can comprise a cardiac glycoside or a salt thereof. In some embodiments, a cardiac glycoside can comprise a cardenolide, a bufadienolide, a salt of either of these, or any combination thereof. In some embodiments, a cardenolide can comprise a convallotoxin, an antiarin, a strophanthin, a digoxin, a digitoxin, an oleandrin, an adonitoxin, a salt of any of these, or any combination thereof. In some embodiments, a bufadienolide can comprise a scillarenin, a proscillaridine A, a daigremontianin, a hellebore, a salt of any of these, or any combination thereof. In some embodiments, a positive inotrope can comprise a myosin activator or a salt thereof. In some embodiments, a myosin activator can comprise an omecamtiv mecarbil or a salt thereof.

In some embodiments, a negative cardiac inotrope can comprise a beta-blocker, a calcium-channel blocker, an anti-arrhythmic medicine, or any combination thereof.

In some embodiments, a guanylate cyclase stimulator can comprise adempas, riociguat, or a combination thereof.

In some embodiments, a beta receptor blocker or salt thereof can comprise a long-acting beta blocker. In some embodiments, a beta receptor blocker or salt thereof can comprise a short-acting beta blocker. In some embodiments, a short acting beta blocker can comprise pindolol, oxprenolol, atenolol, acebutolol, bisoprolol, carvedilol, metoprolol, nadolol, nebivolol, propranolol, a stereoisomer of any of these, a polymorph of any of these, a diastereomer of any of these, a salt of any of these, or any combination thereof.

In some embodiments, a beta receptor blocker or salt thereof can comprise at least one stereocenter in an S-configuration. In some embodiments, a beta receptor blocker can comprise S-pindolol, S-oxprenolol, S-atenolol, S-acebutolol, S-bisoprolol, S-carvedilol, S-metoprolol, S-nadolol, S-nebivolol, S-propranolol, a stereoisomer of any of these, a polymorph of any of these, a diastereomer of any of these, a salt of any of these.

In some embodiments, a statin or salt thereof can comprise atorvastatin, fluvastatin, lovastatin, pravastatin, rosuvastatin, simvastatin, pitavastatin, a salt of any of these, or any combination thereof.

In some embodiments, a blood thinner or salt thereof, can comprise apixaban, dabigatran, edoxaban, fondaparinux, heparin, rivaroxaban, warfarin, or a salt of any of these.

In some embodiments, a phosphodiesterase 5 inhibitor can comprise amrinone, milrinone, avanafil, lodenafil, mirodenafil, sildenafil, tadalafil, vardenafil, udenafil, zaprinast, benzaminenafil, carvedilol, a stereoisomer of any of these, a salt of any of these, or any combination thereof. In some embodiments, a vasopressin inhibitor can comprise tolvaptan, a stereoisomer of any of these, a salt of any of these, or any combination thereof.

In some embodiments, a vasopressin inhibitor of salt thereof can comprise conivaptan, relcovaptan, nelivaptan, lixivaptan, mozavaptan, satavaptan, tolvaptan, demeclocycline, lithium, a salt of any of these, or any combination thereof.

In some embodiments, a SGLT2 inhibitor can comprise dapagliflozin, empagliflozin, canagliflozin, sotagliflozin, ertugliflozin, ipragliflozin, luseogliflozin, remogliflozin etabonate, sergliflozin etabonate, tofogliflozin a stereoisomer of any of these, a salt of any of these, or any combination thereof.

In some embodiments, an aldosterone antagonist or salt thereof can comprise spironolactone, eplerenone, finerenone, canrenoate, a stereoisomer of any of these, a salt of any of these, or any combination thereof.

In some embodiments, an aldosterone synthesis inhibitor or a salt thereof, can comprise fadrozol, FAD 286, LCI699, a salt of any of these, or any combination thereof.

In some embodiments, an angiotensin receptor antagonist or a salt thereof, can comprise a sartan, candesartan, irbesartan, valsartan, telmisartan, eprosartan, Olmesartan, azilsartan, fimasartan, sacubitril/valsartan, losartan, EXP 3174, a stereoisomer of any of these, a salt of any of these, or any combination thereof.

In some embodiments, a mineralocorticoid receptor antagonist can comprise eplerenone, spironolactone, finerenone, canrenoate, aldactone, a stereoisomer of any of these, a salt of any of these, or any combination thereof.

In some embodiments, an aldosterone synthesis inhibitor can comprise fadrozol, FAD 286, LCI699, a stereoisomer of any of these, a salt of any of these, or any combination thereof.

In some embodiments, an angiotensin receptor antagonist or a salt thereof can comprise a sartan, candesartan, irbesartan, valsartan, telmisartan, eprosartan, olmesartan, azilsartan, fimasartan, sacubitril/valsartan, losartan, EXP 3174, amlodipine, a stereoisomer of any of these, or a salt of any of these.

In some embodiments, an If channel blocker or a salt thereof can comprise ivabradine, zatebradine, cilobradine, ZD7288, alinidine, or a salt of any of these.

In some embodiments, an ACE inhibitor can comprise benazepril, captopril, enalapril, fosinopril, lisinopril, moexipril, omapatrilat, perindopril, quinapril, ramipril, trandolapril, or any combination thereof.

In some embodiments, an alpha blocker can comprise phenoxybenzamine, phentolamine, tolazoline, trazodone, alfuzosin, doxazosin, prazosin, tamsulosin, terazosin, silodosin, atipamezole, idazoxan, mirtazapine, yohimbine, or any combination thereof.

A medicament can be administered orally, rectally, or parenterally, in formulations containing conventionally acceptable carriers, adjuvants, and vehicles as desired. The term "parenteral" as used herein can include subcutaneous, intravenous, intramuscular, or intrasternal injection and infusion techniques. In some embodiments, administration can include injection or infusion, including intra-arterial, intracardiac, intracerebroventricular, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration. In some exemplary embodiments, a route of administration can be via an injection such as an intramuscular, intravenous, subcutaneous, or intraperitoneal injection.

In some embodiments, a medicament can be present as a pharmaceutical composition in a form suitable for administration. In some embodiments, solid dosage forms for oral administration can include capsules, tablets, caplets, pills, troches, lozenges, powders, and granules. In some embodiments, a capsule can comprise a core material comprising a nutritive protein or salt thereof or composition and a shell wall that encapsulates a core material. In some embodiments, a core material can comprise at least one of a solid, a liquid, and an emulsion. In some embodiments, a shell wall material can comprise a soft gelatin, a hard gelatin, a polymer, or any combination thereof. In some embodiments, a suitable polymer can comprise cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate; vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac); or any combination thereof. In some embodiments, at least one polymer can function as a taste-masking agent.

In some embodiments, tablets, pills, and the like can be compressed, multiply compressed, multiply layered, and/or coated. In some embodiments, a coating can be single or multiple. In some embodiments, a coating material can comprise a saccharide, a polysaccharide, a glycoprotein, a salt of any of these, or any combination thereof. In some embodiments, a coating material can be extracted from at least one of a plant, a fungus, a microbe, or any combination thereof. In some embodiments, a coating material can comprise a corn starch, a wheat starch, a potato starch, a tapioca starch, a cellulose, a hemicellulose, a dextran, a maltodextrin, a cyclodextrin, an inulin, a pectin, a mannan, a gum arabic, a locust bean gum, a mesquite gum, a guar gum, a gum karaya, a gum ghatti, a tragacanth gum, a funori, a carrageenan, an agar, an alginate, a chitosan, a gellan gum, a salt of any of these, or any combination thereof. In some embodiments, a coating material can comprise a protein or a salt thereof. In some embodiments, a coating material can comprise a fat, a saccharide, an oil, or a combination thereof. In some embodiments, a fat or an oil can be high temperature melting. In some embodiments, a fat or oil can be hydrogenated or partially hydrogenated. In some embodiments, a fat or oil can be derived from a plant. In some embodiments, a fat or oil can comprise at least one of glycerides, free fatty acids, and fatty acid esters. In some embodiments, a coating material can comprise at least one edible wax. In some embodiments, an edible wax can be derived from animals, insects, or plants. In some embodiments, an edible wax can include beeswax, lanolin, bayberry wax, carnauba wax, rice bran wax, or a combination thereof. In some embodiments, tablets and pills can additionally be prepared with enteric coatings.

In some embodiments, a medicament can comprise a liquid formulation. In some embodiments, a liquid formulation can comprise a syrup (for example, an oral formulation), an intravenous formulation, an intranasal formulation, an ocular formulation (e.g. for treating an eye infection), an otic formulation (e.g. for treating an ear infection), an ointment, a cream, or an aerosol. In some embodiments, a combination of various formulations can be administered. In some embodiments, a tablet, pill, and the like can be formulated for an extended release profile.

In some embodiments, a medicament can be administered in a composition for topical administration. In some embodiments, an active agent can be formulated for direct application to a target area. In some embodiments, forms chiefly conditioned for topical application can take a form, for example, of creams, milks, gels, powders, dispersion or microemulsions, lotions thickened to a greater or lesser extent, impregnated pads, ointments or sticks, aerosol formulations (e.g. sprays or foams), hydrogel, soaps, detergents, lotions or cakes of soap. In some embodiments, forms can comprise wound dressings, coated bandages or other polymer coverings, ointments, creams, lotions, pastes, jellies, sprays, and aerosols. In some embodiments, a medicament disclosed herein can be delivered via patches or bandages for dermal administration. In some embodiments, a medicament can be formulated to be part of an adhesive polymer, such as polyacrylate or acrylate/vinyl acetate copolymer. In some embodiments, for long-term applications it might be desirable to use microporous and/or breathable backing laminates, so hydration or maceration of a skin can be minimized. In some embodiments, a backing layer can be any appropriate thickness that will provide a desired protective and support functions. In some embodiments, a suitable thickness can comprise about 1 to about 1000 microns or about 10 to about 300 microns. In some embodiments, a topical administration can be in a form of a nail coating or lacquer. In some embodiments, a medicament can be formulated in a solution for topical administration that contains ethyl acetate (NF), isopropyl alcohol (USP), and butyl monoester of poly[methylvinyl ether/maleic acid] in isopropyl alcohol.

In some embodiments, a medicament can comprise drops. In some embodiments, drops can comprise eye drops, nose drops, or a combination thereof. In some embodiments, drops can be formulated with a medicament in an aqueous or non-aqueous base also comprising one or more dispersing agents, solubilizing agents or suspending agents. In some embodiments, liquid sprays can be pumped or can be conveniently delivered from pressurized packs. In some embodiments, drops can be delivered via a simple eye dropper-capped bottle, via a plastic bottle adapted to deliver liquid contents drop-wise, or via a specially shaped closure.

In some embodiments, ointments and creams can, for example, be formulated with an aqueous or oily base with an addition of suitable thickening and/or gelling agents. In some embodiments, lotions can be formulated with an aqueous or oily base and will in general also contain one or more emulsifying agents, stabilizing agents, dispersing agents, suspending agents, thickening agents, or coloring agents.

In some embodiments, aerosol can be employed to administer a medicament to a respiratory tract. In some embodiments, administration by inhalation or insufflation, a composition may take the form of a dry powder, for example, a powder mix of a therapeutic agent and a suitable powder base such as lactose or starch. In some embodiments, a medicament can also be administered in an aqueous solution when administered in an aerosol or inhaled form. In some embodiments, an inhalable formulation can be an inhalable respiratory formulation. In some embodiments, other aerosol pharmaceutical formulations can comprise, for example, a physiologically acceptable buffered saline solution containing from about 0.001 mg/ml to about 100 mg/ml for example from about 0.1 to about 100 mg/ml, such as 0.5-50 mg/ml, 0.5-20 mg/ml, 0.5-10 mg/ml, 0.5-5 mg/ml or 1-5 mg/ml of a medicament specific for an indication or disease to be treated.

In some embodiments, administration of a medicament to a subject can be used to at least partially ameliorate a condition as described herein. In some embodiments, administration of a medicament can be performed for a treatment duration of at least about at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days consecutive or nonconsecutive days. In some embodiments, a treatment duration can be from about 1 to about 30 days, from about 2 to about 30 days, from about 3 to about 30 days, from about 4 to about 30 days, from about 5 to about 30 days, from about 6 to about 30 days, from about 7 to about 30 days, from about 8 to about 30 days, from about 9 to about 30 days, from about 10 to about 30 days, from about 11 to about 30 days, from about 12 to about 30 days, from about 13 to about 30 days, from about 14 to about 30 days, from about 15 to about 30 days, from about 16 to about 30 days, from about 17 to about 30 days, from about 18 to about 30 days, from about 19 to about 30 days, from about 20 to about 30 days, from about 21 to about 30 days, from about 22 to about 30 days, from about 23 to about 30 days, from about 24 to about 30 days, from about 25 to about 30 days, from about 26 to about 30 days, from about 27 to about 30 days, from about 28 to about 30 days, or from about 29 to about 30 days.

In some embodiments, administration of a medicament can be performed at least 1, 2, 3, 4, 5, 6, 7, 8, 9, 10, 11, 12, 13, 14, 15, 16, 17, 18, 19, 20, 21, 22, 23, or 24 times a day. In some embodiments, administration of a medicament can be performed at least 1, 2, 3, 4, 5, 6, 7, 8, 9, 10, 11, 12, 13, 14, 15, 16, 17, 18, 19, 20, or 21 times a week. In some embodiments, administration of a medicament can be performed at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 times a month.

In some embodiments, a treatment can comprise administering a medical device to a subject. In some embodiments, a medical device can comprise a cardioverter defibrillator, a pacemaker, or any combination thereof. In some embodiments, a medical device can be contacted with a ventricle. In some embodiments, a medical device can constrict to assist a ventricle contracting.

In some embodiments, a cardioverter defibrillator can comprise an implantable cardioverter defibrillator. In some embodiments, a cardioverter defibrillator can comprise a wearable cardioverter defibrillator. In some embodiments, a cardioverter defibrillator can be applied or held in proximity to a subject's skin.

In some embodiments, a medicament can be a metabolism-modifying agent. In some embodiments, a metabolism-modifying agent can include elamipretide, trimetazidine, perhexiline, etomoxir, dichloroacetate, coenzyme Q10, ubiquinol, nicotinamide riboside, metformin, resveratrol, pterostilbene, rapamycin, a salt of any of these, or any combination thereof.

In some embodiments, a method can comprise determining a probability score for a subject developing heart failure.

In some embodiments, a treatment can comprise an intervention. In some embodiments, an intervention can comprise exercise, a selective diet, meditation, instructions to see a cardiologist, instructions to see a therapist, stress reduction measures, weight loss, physical exercise, lifestyle intervention, instructions to dispense a medicament, instructions to receive an ultrasound, or any combination thereof. In some embodiments, a diet can comprise a reduced salt consumption, a reduced alcohol consumption, a reduced calorie consumption, an increased vegetable consumption, or any combination thereof. In some embodiments, a diet can comprise a supplement. In some embodiments, a supplement can comprise fish oil.

Disclosed herein in some embodiments, are compositions comprising a system. Disclosed herein in some embodiments, are methods comprising a system. In some embodiments, a system can comprise a computer processor, a computer readable memory operatively coupled to a computer processor, a database, an algorithm, or any combination thereof. In some embodiments, a computer readable memory can at least transiently store a database that can comprise a treatment formulary of medicaments or interventions, a plurality of biomarkers predictive of a probability of developing heart failure within a time period as disclosed herein, or any combination thereof. In some embodiments, an algorithm, when executed by a computer processor, can select a treatment from a treatment formulary based on a biomarker selected from a plurality of compounds. In some embodiments, a system can further comprise a wireless transmitter or a wireless receiver. In some embodiments, a system can be configured for wireless communication to a device. In some embodiments, a system can be configured for wired communication to a device.

In some embodiments, a system can comprise an oral sample collection device comprising a compound, and wherein an oral sample collection device can be configured to contact a compound with a biomarker present in saliva when saliva is input into an oral sample collection device.

In some embodiments, a system can be configured to access a database via a wireless transmitter or a wireless receiver, wherein a database can be stored on a server. In some embodiments, a server can comprise a cloud-based server.

EXAMPLES

Example 1: Method of Detection

A healthcare practitioner takes an oral swab from a patient using a device. A first compound in the sensor of the device is contacted with a second compound in the saliva of the patient. The second compound binds to a first compound in the device and the binding is detected. The level of binding is quantitatively detected. The data from the detection is transmitted wirelessly to a computer processor, where it is added to a dataset in a readable storage medium. An algorithm executed by the computer processor determines the relative level of the second compound compared to a reference value from a subject who has developed heart failure and a reference value from a subject who is substantially healthy. The recorded value is found to be at an increased level relative to the value from the reference value from the subject who is healthy, and to be closer in value to the reference sample from the subject who has heart failure. The data is processed by an algorithm to stratify the subject into a short term probability group. A healthcare practitioner determines that an appropriate prophylactic treatment should be administered to the subject and schedules a series of repeat follow up measurements to monitor the subject for any indications of heart failure onset.

Example 2: Device

A device for detection comprising an electronic oral swab for non-invasive disease detection, comprising: a handle; and a sampling head releasably attachable to the handle and sized for insertion into a mouth, the sampling head including: an enclosure made from a biocompatible material; a biosensor housed within the enclosure, the biosensor comprising a transducer and a biological element or reagent, the biosensor configured to generate a biosensor signal proportional to a concentration level of an analyte in saliva within a predetermined measuring range in response to an interaction between the biological element or reagent and the analyte; and an opening through the enclosure for fluid communication of saliva to the biosensor; a wireless transmitter coupled to the biosensor, configured to wirelessly transmit signal data corresponding to the biosensor signal, to a computing device comprising a processor.

Example 3: Toothbrush for Monitoring and Detecting a Disease

A toothbrush comprising bristles and a device for detection comprising an electronic oral swab for non-invasive disease detection, comprising: a handle; and a sampling head releasably attachable to the handle and sized for insertion into a mouth, the sampling head including: an enclosure made from a biocompatible material; a biosensor housed within the enclosure, the biosensor comprising a transducer and a biological element or reagent, the biosensor configured to generate a biosensor signal proportional to a concentration level of an analyte in saliva within a predetermined measuring range in response to an interaction between the biological element or reagent and the analyte; and an opening through the enclosure for fluid communication of saliva to the biosensor; a wireless transmitter coupled to the biosensor, configured to wirelessly transmit signal data corresponding to the biosensor signal, to a computing device comprising a processor.

Example 4: Method of Using a Toothbrush to Detect Heart Failure

A subject uses a toothbrush as described in example 3 to clean their teeth. During use of a device saliva contacts a biosensor in the device. The biosensor can comprise a biological element or reagent, the biosensor configured to generate a biosensor signal proportional to a concentration level of an analyte in saliva within a predetermined measuring range in response to an interaction between the biological element or reagent and the analyte. A transducer converts the biosensor signal to an electrical recording of a measurement. The signal is passed wirelessly via Bluetooth to a second device, which can be a cell phone or tablet. The second device can comprise a processor which executes an algorithm to compare the analyte level to one or more reference levels. When a level of an analyte in the saliva of a subject surpasses or falls below a reference level, a positive result is generated. The positive result is communicated to the subject through a user interface on an application of the second device. The result can also be communicated to a healthcare practitioner either automatically, or manually by a subject sharing the result. The positive result can be indicative of a subject having a probability of developing heart failure. The concentration of the analyte detected can determine a probability level of a subject developing heart failure, with different probability levels comprising very high probability, high probability, medium probability, or low probability. Alternatively, probability factors can comprise imminent probability, short-term probability, medium-term probability, or long-term probability. Upon receiving a positive result from a second device, a healthcare practitioner can prescribe a treatment to ameliorate or prevent the heart failure in the subject. Such treatments can comprise continued monitoring for a low probability subject, an intervention such as diet and exercise for a medium probability subject, or a medicament for a high probability subject. While preferred embodiments of the present invention have been shown and disclosed herein, it will be obvious to those skilled in the art that such embodiments are provided by way of example only. Numerous variations, changes, and substitutions will now occur to those skilled in the art without departing from the invention. It should be understood that various alternatives to the embodiments of the invention disclosed herein may be employed in practicing the invention. It is intended that the following claims define the scope of the invention and that methods and structures within the scope of these claims and their equivalents be covered thereby.

Example 5: Study of Subjects to Determine Predictive Markers of Heart Failure

5.1 Recruitment of Subjects

Twenty subjects with a background of cardiovascular illness and risk factors were recruited. Each subject underwent assessment including medical history, medication history, clinical evaluation by a heart failure expert and collection of saliva by the following method:

5.1.1 Collection and Storage of Human Saliva for Proteomic Studies

Saliva is a highly valid biological fluid that can be used for diagnostic applications.

Various number of components can be identified in saliva, which provides real-time data on the patient's condition. The substances found in saliva include but are not limited to DNA, RNA, proteins, metabolites, and microbiota from both oral and gastrointestinal origin.

Clinical proteomics can be used as a method-of-choice for the screening of biomarkers used for early discovery and early diagnostics.

5.1.2 Reagents and Equipment

Saliva Sample (collected in a 50 mL Falcon tube)
Protease inhibitor (EDTA-free Protease Inhibitor Cocktail)
Micropipette and tips
5×1.2 mL barcoded cryovials
Ice bucket and ice for chilling tubes
50.0 mL Falcon tubes
Data Elements to Track
Sample ID. [collection site]
Date & Time Saliva Collected [collection site]
Exact Volume of Saliva Collected from the participant [laboratory]
Number of Aliquots and Aliquot volume [laboratory]

5.1.3 Procedure

Participants were required to brush their teeth after their last meal before saliva collection. Prior to the saliva collection, participants were advised not to eat or drink 1 h before sample collection. Drinking water was allowed. Where possible, all saliva samples were collected between 10:00 a.m. and 12:00 p.m., to minimize any inter-individual variation of saliva composition associated with circadian rhythms. Participants were asked to sit in a comfortable position and to rinse their mouths with water to remove potential food residue.

The collection tube was removed from the freezer and the cocktail in the tube allowed to start to partially thaw. The cocktail was not allowed to heat up to room temperature. A fridge temperature of around 4° C. was ideal. The collection tubes were pre-labelled. The SampleID on the tube and ParticipantID were noted and capture on the "PI questionnaire" document. Participants received a general oral inspection to ensure their mouth contained no food residues, had general good oral hygiene, and did not have gingivitis or any bleeding of the gums. The participant tilted their heads down, to allow saliva to pool in their mouth for 1 min, before drooling into a 50 mL Falcon tube.

The participant ideally drooled 2.5 mL of saliva into the tube, which already contained 2.5 mL of inhibitor. It was therefore aimed for the inhibitor and saliva combined to reach the 5 mL mark on the tube, however 50 mL tubes are not accurate to a 1 mL increment. A saliva volume of 1 mL to 4 mL was therefore acceptable. The saliva and inhibitor combined could therefore measure 3.5 mL (not indicated on tube) to 6.5 mL (not indicated on tube).

Once saliva was collected, the tube was shaken vigorously for 5 seconds until no frozen remnants of the inhibitor cocktail were visible. The sample was not returned to the freezer until the cocktail had thawed and been allowed to properly mix with the saliva. It was expected that the frozen cocktail would rapidly thaw and mix with the saliva once combined. The collection tubes were returned to the supplied freezer immediately after sample collection. The collected samples were collected and sent to the laboratory for analysis.

The thawed samples were received and placed in a centrifuge. The speed was set to 4,000 G and spun for 90 seconds. 1 mL aliquots of the saliva supernatant component were made, making sure to avoid the pellet at the bottom after centrifuging. One 1 mL aliquot of each sample was batched at 4° C. for the next testing cycle in no longer than 4 hours to avoid an additional freeze-thaw cycle of these samples. The rest of the samples were stored at −80° C. until further analysis.

Where freezing was not possible, samples were placed on ice or refrigerated immediately at 4° C. and maintained at this temperature for no longer than necessary (ideally less than 4 hours) before freezing at −80° C. to minimize degradation and to prevent bacterial growth.

Optional Preservative and Denaturing Cocktail—Only for Long Term Storage Samples:

A working concentration of EDTA-free Protease Inhibitor Cocktail was prepared using 1 tablet per 10 ml extraction solution. The tablet was pushed through the foil packaging using the base of a thumb (not fingernail) to prevent the breakage of tablets. One EDTA-free Protease Inhibitor Cocktail tablet was sufficient for the inhibition of the proteolytic activity in 10 ml extraction solution. Alternatively, a stock solution (7× conc.) was prepared.

Stock Solution (7× Conc.)

One EDTA-free Protease Inhibitor Cocktail tablet was dissolved in 1.5 ml dist. water or in 1.5 ml 100 mM phosphate buffer, pH 7.0. The stock solution could be stored at 2 to 8° C. for 1 to 2 weeks, or at least 12 weeks at −15 to −25° C.

5.1.4 References

1. Mitulović G. Proteomics of the Salivary Fluid 2017. Available from: www.intechopen.com/books/salivary-glands-new-approaches-in-diagnostics-and-treatment/proteomics-of-the-salivary-fluid.
2. Pappa E, Vastardis H, Mermelekas G, Gerasimidi-Vazeou A, Zoidakis J, Vougas K. Saliva Proteomics Analysis Offers Insights on Type 1 Diabetes Pathology in a Pediatric Population. Frontiers in physiology. 2018; 9:444.
3. Bhattarai K R, Kim H-R, Chae H-J. Compliance with Saliva Collection Protocol in Healthy Volunteers: Strategies for Managing Risk and Errors. International Journal of Medical Sciences. 2018; 15(8):823-31.

5.2 Patient Disease Status

Fifteen of the twenty participants were considered at risk of heart failure within the next five years and five were considered to be free of such risk of heart failure (controls). The 15 at risk patients were found to have distinctly different levels of certain biomarkers compared to the controls.

5.2.1 Recruitment of Patients

Twenty participants were recruited with a background of cardiovascular illness and risk factors. Each participant underwent assessment including medical history, medication history, clinical evaluation by a heart failure expert and collection of saliva by the method described in Example sections 5.1-5.3.

5.2.2 Physical and Medical Assessment

Physical assessment were evaluated based on participants' overall physique, such as their proportional weight and height, physical mobility, their regular diet and physical activities level. The participants were segmented with a grading method; 3—Unhealthy, 2—Average, 1—Fit.

Most participants are living with multiple medical conditions, due to health issues developed earlier in life. The level of health issues was considered, with a grading method for segmentation. The grading was defined as; 3—Significant, 2—Insignificant, 1—None

5.2.3 Medication

Each participants' current medication treatments are significantly factored as evidence of heart failure development risk level. Participants were found to be treated with significant number of cardiac related medications, including:

Metformin Hydrochloride
Empagliflozin
Linagliptin
Sitagliptin
Felodipine
Candesartan Cilexetil
Perindopril Erbumine (Coversil)
Indapamide (Diuretic)
Ramipril
Nebivolol
Entresto
Bisoprolol Fumarate
Diltiazem
Olmesartan
Felodipine
Karvezide (Irbesartan; Hydrochlorothiazide)
Mizart (Telmisartan)
Amlodipine
Metoprolol
Atenolol
Nicorandil
Apixiban
Duo Plidogrel
Aspirin (Spren)
Diltiazem Hydrochloride (Cartia), Aspirin
Clopidogrel
Rosuvastatin
Atorvastat The drug treatment types were segmented as:

| | |
|---|---|
| Heart Failure | 35% |
| Type 2 Diabetes | 20% |
| Hypertension | 70% |
| Angina | 15% |
| Blood Clot | 20% |
| Cholesterol | 40% |

5.2.4 Risk Level Assessment

The early risk of heart failure review was conducted by an expert cardiologist with the segmented information assembled as presented in Table 2.

TABLE 2

| | Profile | | Biomarkers | Number of | Cardiologist | |
|---|---|---|---|---|---|---|
| Participant ID | Physical Assessment | Medical Conditions | Overall Risk Level | Cardiac Medications | Assessment Risk Level | Overall Risk Level |
| 192 | 2 | 3 | H | 2 | 4 | H |
| 153 | 3 | 3 | H | 5 | 4 | H |
| 198 | 3 | 3 | H | 4 | 4 | H |
| 189 | 3 | 3 | H | 3 | 4 | H |
| 183 | 3 | 3 | H | 1 | 4 | H |
| 171 | 2 | 3 | H | 2 | 3 | M |
| 164 | 2 | 3 | H | 6 | 3 | M |
| 157 | 2 | 3 | H | 3 | 3 | M |
| 163 | 2 | 3 | H | 4 | 3 | M |
| 166 | 2 | 3 | H | 0 | 2 | M |
| 162 | 2 | 3 | H | 3 | 2 | M |
| 200 | 2 | 3 | H | 2 | 2 | M |
| 169 | 2 | 3 | H | 2 | 2 | M |
| 172 | 2 | 1 | L | 0 | 1 | L |
| 187 | 2 | 1 | L | 0 | 1 | L |
| 151 | 1 | 1 | L | 0 | 1 | L |
| 152 | 1 | 1 | L | 0 | 1 | L |
| 165 | 1 | 1 | L | 0 | 1 | L |
| 197 | 2 | 1 | H | 1 | 1 | M |
| 195 | 1 | 2 | H | 1 | 1 | M |

The summary of the participants' heart failure risk level were identified as follows:

High risk of heart failure occurring within 6 months (#5)

Medium risk of heart failure, not likely within 6 months, but likely within 10 years (#10)

Low risk of heart failure within 10 years (Controls #5)

High levels of biomarker readings were identified with the medium and high-risk participants, correlating to the risk factors as expected. While the participants may not have been diagnosed with heart failure, the drug treatments and physical attributes were shown to be evident to minimize further heart failure development.

5.2.5 Profiles

Participants were identified as either having no risk of heart failure (1), low risk (2), medium risk (3), or high risk (4), given their profile, type of ongoing drug treatments and overall biomarker readings.

Most significant was participant 192 who was taking the heart failure specific medication Entresto (but not for heart failure) and with multiple historic and current health issues, including multiple operations undertaken. At the age of 70, she had a relatively thin physical body structure. Her primary physical activity was general walking daily. Since retirement, she had been a relatively active social worker. There were extensive historical health conditions including atrial fibrillation, high cholesterol, under active thyroid, acute acid reflux, hiatus hernia and urinal difficulties. She had also been a tobacco smoker for the majority of the early years of her life. There had been extensive operations through the years, including multiple caesarean, fistula, hysterectomy, gall bladder removal, breast reduction and skin tightening operations. Additionally, she was an insomnia sufferer with both cataracts removed. Currently, amongst multiple vitamin supplements, she was undertaking 5 prescribed medications, which included Rosuvastatin and, most significantly, the specific heart failure drug treatment Entresto even though she had never had or been diagnosed with heart failure. She was placed on Entresto as an alternative to an ACE inhibitor because of the risk of cough. She maintained a relatively balanced diet. [Cardiologist Assessment score 4].

Participant 153 at age 65 was taking 9 prescribed medications which included 5 cardiac related medications: Empagliflozin, Amlodipine, Metoprolol, Spren (Aspren) and Atorvastatin. The retiree had overweight physical features and undertook few physical activities apart from weekly general walks in the neighborhood and caring for grandchildren. Significant heart damage was expected, due to multiple heart attacks—first event in 2018 and the second in 2020. A stent operation was received after her first heart attack. Additionally, arthritis and hypertension were diagnosed with treatments since over 5 years ago, with sleep apnea diagnosis within the same period. Most recently, Type 2 diabetes was diagnosed within the past 6 months. Hospitalization was required for the multiple heart attacks and Type 2 diabetes diagnosis. The current diet was consistent within the diabetic dietician suggestions. [Cardiologist Assessment score 4].

Participant 198 was a lung cancer patient at 80 years of age. At the time of the study he was prescribed with 9 medications which included 4 cardiac related drugs; Telmisartan (Mizart), Nicorandil, Clopidogrel and Rosuvastatin. Participant was at a relatively average physique with lethargic mobility. Hypertension, angina, blood clots and high cholesterol was diagnosed earlier in life with continuous drug treatments, amongst lung cancer medical treatments currently being received. [Cardiologist Assessment score 4].

Participant 189 is a non-English speaking 70-year-old, retired European immigrant living in Australia. Her diagnosed health conditions include Type 2 Diabetes, Hypertension and high cholesterol. Currently, her prescribed medications include Empagliflozin, Linagliptin and Atorvastat. She is with frail physical feature, little physical activities and minimal in consideration for her diet. [Cardiologist Assessment score 4].

Participant 183 at age 72 had an overweight physique, and was an upper-class retiree with hypertension. The participant was a recipient of the prescribed medication Karvezide at the time of the study. It appeared there was a lack of regular physical activities apart from the household regularities with an average level of controlled diet. [Cardiologist Assessment score 4].

Medium Risk Participants

The participants identified as medium risk had substantial health issues with moderate physical conditions and their respective biomarker reading levels. Thus, the risk of heart failure was reduced with substantial level of physical activities and the effective medications.

Participant 171 was an obese, social worker at the age of 66. She was diagnosed with Type 2 diabetes earlier in life with multiple health related conditions, including spinal problems and multiple joint operations in her shoulders and knee. Her 5 prescribed medications included Metformin and Candesartan, with known diagnosis of hypertension and vascular disease. Other prescribed drugs were primarily for the pain caused by the spinal condition. Regular physical activities included caring for grandchildren and gardening. Efforts were made to sustain a balanced diet, however, her food consumption remained high in sugar content. [Cardiologist Assessment score 3].

Participant 164 was an obese, full-time 74-year-old owner of a small bookstore. Hypertension was diagnosed in her 20s after her first pregnancy. Over 25 years ago, a stent operation was received after a mild heart attack. Most recently, a heart valve replacement operation was received 2 years ago. She had been taking aspirin for the past 20 years due to heart issues. The medications she had been prescribed at the time of the study included Perindopril erbumine, Indapamide, Nebivolol, Apixiban, Diltiazem Hydrochloride and Rosuvastatin. At the time of the study, other health issues included low levels of cholesterol, joints and ligaments issues, slow metabolism and sleep disorders. Regular activities included physical work at the bookstore (heavy boxes), caring for the grandchildren, caring for the acre of garden and walking the dog several times a week. She also regularly attended live musical events which included dancing. A relatively strict diet was maintained to minimize escalation of her health conditions. [Cardiologist Assessment score 3].

Participant 157 was 61 years of age, working full-time from home, with a healthy physique appearance. Diagnosis early in life included hypertension, blood clot and high cholesterol, with a heart attack episode resulting in an operation to insert 8 stents. At the time of the study, the prescribed medications included Diltiazem, Duo Plidogrel, and Rosuvastatin. Physical activities included golf, and a strenuous diet was maintained by the participant to minimize risks of further heart issues development. [Cardiologist Assessment score 3].

Participant 163 is a 68-year-old, clerical officer working from home, often also a pet caretaker. Participant was a sufferer from Type 2 Diabetes, hypertension and high cholesterol health conditions. Her prescribed medications included Empagliflozin, Sitagliptin, Amlodipine and Rosuvastatin. She had average physique and diet. Her other regular activities included supporting local new immigrants to the community and religious activities. [Cardiologist Assessment score 3].

Participant 166 was a 55-year-old full time executive working in a high stress level environment. While he was not taking any prescribed medication at the time of the study, he had been diagnosed with fatty liver disease. At an average body physique, his cholesterol level had also been historically high with a relatively balanced diet. There was only minimal physical activity maintained with general walking. [Cardiologist Assessment score 2].

Participant 162 was a 55-year-old full time working technological engineer, with an obese physique. Hypertension, angina and cholesterol issues were identified earlier in life. His prescribed medications included Perindopril erbumine, Felodipine and Atenolol. There's been a lack of physical activities in most recent times, with a "fast food at times" and high level of carbohydrates diet. He is also currently suffering from sleep apnea. [Cardiologist Assessment score 2].

Participant 200 was a 50 year-old working from home with a healthy physique appearance. However, he had a "hole in heart" and valve surgery in the early years of life. At the time of the study he had been prescribed with medication for hypertension and heart failure medications, Ramipril and Bisoprolol fumarate. Although having suffered from health issues, he remained very active with competitive tennis and regular daily 5 km walks. Care was taken in dietary control to minimize escalation of his health conditions. [Cardiologist Assessment score 2].

Participant 169 was an overweight 65 year-old retiree with hypertension, high cholesterol, angina and thyroid health issues. His prescribed medications included Olmesartan and Rosuvastatin. The only physical activity was primarily walking in the neighborhood while having a relatively relaxed diet which included occasional fast food and alcohol. He was an active tobacco smoker in the early years of life. [Cardiologist Assessment score 2].

Participant 197 was an overweight 55 year old working from home. He had a history of diabetes issues and had been prescribed Perindopril erbumine for hypertension. His only physical activity was general walking and caring for a number of various pets at home. [Cardiologist Assessment score 1].

Participant 195 was a 49 year old, OHS assessment executive, often on multiple warehouse sites—often "on his feet". He had an athletic physique, and often exercised at the gym. While being relatively active, he was prescribed with Perindopril erbumine for hypertension. His diet was well controlled without any fast food with the family being highly health conscious. [Cardiologist Assessment score 1].

Low Risk Controls

The Low risk of heart failure (controls) were considered based on the physical and health conditions that had precisely correlated with low biomarker readings. There were no known health issues reported nor any prescribed medications administered.

Participant 172 was a 52-year-old executive working from home with an athletic physique. His physical activities included competitive tennis with a well-controlled balanced diet. [Cardiologist Assessment score 1].

Participant 187 was an active 43-year-old who was minimally above a healthy cholesterol threshold. There were no other historical or current health issues at the time of the study. [Cardiologist Assessment score 1].

Participant 151 was an active 55-year-old nursing professional, whom at the time of the study was providing private nursing care. She maintained regular annual medical checks, including cardiology tests, with no issues found in any results, apart from cholesterol levels being marginally close to healthy threshold levels. [Cardiologist Assessment score 1].

Participant 152 at 52 years of age, was a working nurse with in-depth health consciousness and a high level of physical activities including roller skating. There were no medications prescribed or any health issues. [Cardiologist Assessment score 1].

Participant 165 was a 61-year-old university professor, who maintained a highly active lifestyle, including swimming and tennis, and a balanced diet. There were no prescriptive medications nor any health issues. [Cardiologist Assessment score 1].

Assessment of Participants

Of the 20 participants, 15 were considered at risk of heart failure within the next 5 years (and 5 of these within the ensuing 6 months) and 5 were considered to be free of such risk of heart failure (controls). The 15 at risk patients were found to have distinctly different levels of certain biomarkers compared to the controls.

Participant 171 was at the age of 66 with prescribed medications for Type 2 Diabetes, and hypertension, in addition to significant pain killers for her spinal condition. Her assessment was at high risk (3).

Participant 164 was a 74-year-old currently prescribed with medication for hypertension, blood clot and high cholesterol. A stent operation was received after a mild heart attack with heart valve replacement operation received 2 years ago. She was assessed as high risk (3).

Participant 198 was a lung cancer patient at 80 years of age, with prescribed medications for Hypertension, Angina, Blood Clot and High Cholesterol, amongst lung cancer medical treatments currently being received. He was assessed as being very high risk (4).

Participant 192 was 70 years old, on heart failure medication, and did little physical activity. She was a tobacco smoker for most of her life. She was assessed as being very high risk (4).

Participant 153 at age 65 was taking prescribed medications for Type 2 diabetes, Hypertension, Angina, Blood Clot and High Cholesterol at the time of the study. Significant heart damage was expected from multiple heart attacks and a stent operation she received. She was assessed as being very high risk (4).

Participant 189 was a 70-year-old retiree with diagnosed health conditions; Type 2 Diabetes, Hypertension and high cholesterol. She had frail physical features with little physical activities and minimal in consideration for her diet. She was assessed as being very high risk (4).

Participant 187 was an active 43-year-old with minimally above threshold cholesterol. There were no other historical or current health issues. No medications were prescribed. She was assessed as being low risk (1).

Participant 172 was an athletic 52-year-old with an active lifestyle. At the time of the study he had recently begun taking light doses of prescribed medication as a preventative measure to manage cholesterol levels. There were no historical or current health issues. He was assessed as being low risk (1).

Participant 152 was a 52-year-old clinical nurse with high level of physical activities including roller skating. No medications were prescribed. She was assessed as being low risk (1)

TABLE 3

| | | | | Biomarker | | | | | | |
|---|---|---|---|---|---|---|---|---|---|---|
| | | | | S10A7 | KI21A | CALM3 | ACBP | AMPN | IGA2 | AMD |
| | At | Vascular | | | | Biomarker correlation | | | | |
| Participant | Risk | Disease | Age | + | − | + | + | − | − | − |
| 171 | Y | Y | 66 | 315,890 | 572 | 5,014 | 14,195 | 15 | 170,954 | 493 |
| 164 | Y | N | 74 | 130,289 | 246 | 4,958 | 13,311 | 11 | 83,988 | 481 |
| 198 | Y | Y | 80 | 52,070 | 303 | 641 | 16,973 | 24 | 47,631 | 460 |
| 192 | Y | N | 70 | 42,931 | 266 | 12,410 | 7,945 | 20 | 53,029 | 422 |
| 153 | Y | Y | 65 | 35,050 | 115 | 271 | 8,904 | 2 | 122,416 | 592 |
| 189 | Y | Y | 70 | 26,239 | 3,091 | 328 | 4,529 | 29 | 54,973 | 458 |
| 187 | N | N | 43 | 1,494 | 7,368 | 123 | 1,518 | 57 | 215,497 | 1,193 |
| 172 | N | N | 52 | 1,107 | 9,361 | 91 | 796 | 83 | 520,432 | 1,264 |
| 152 | N | N | 52 | 889 | 8,274 | 160 | 1,127 | 78 | 310,992 | 2,075 |

Participants in Table 3 consistently correlated to their assessed risk across each of the biomarkers listed as examples, namely S10A7, KL21A, CALM3, ACBP, AMPN, IGA2 and AMD. Highlighted biomarker values indicate where the value is one standard deviation above or below the mean of the control group. The + or − sign indicates whether the specific marker is positively (+) or negatively (−) correlated. In other words, a positive correlated biomarker needs to be one standard deviation above the mean of the control group to be highlighted. The highlight indicates risk for that marker. For example: Participant 171 has a reading of 315,890 for S10A7. Controls have a mean value of 1,036. One standard deviation (68%) above the mean is 1,036× 1.68=1,740. Therefore 315,890 is greater than 1,740. The mean, range, min and max for the control and 'at risk' groups are shown below for the "at risk" group in Table 4, and for the control group in Table 5.

TABLE 4

| AT RISK GROUP | Expression of biomarker (Participant Count = 15) | | | |
|---|---|---|---|---|
| Age | 64 | 30 | 50 | 80 |
| AMPN | 20 | 36 | 2 | 38 |
| AMD | 639 | 589 | 422 | 1,011 |
| CALM3 | 1,977 | 12,273 | 137 | 12,410 |
| KI21A | 1,674 | 6,237 | 109 | 6,346 |
| ACBP | 7,225 | 15,257 | 1,716 | 16,973 |
| IGA2 | 101,997 | 123,323 | 47,631 | 170,954 |
| S10A7 | 45,230 | 313,839 | 2,051 | 315,890 |

TABLE 5

| CONTROL GROUP | Expression of biomarker (Participant Count = 5) | | | |
|---|---|---|---|---|
| Age | 50 | 12 | 43 | 55 |
| AMPN | 76 | 142 | 10 | 152 |
| AMD | 1,363 | 1,068 | 1,007 | 2,075 |
| CALM3 | 108 | 109 | 51 | 160 |
| KI21A | 7,223 | 4,061 | 5,300 | 9,361 |
| ACBP | 1,437 | 1,156 | 796 | 1,952 |
| IGA2 | 258,704 | 438,110 | 82,322 | 520,432 |
| S10A7 | 1,036 | 759 | 735 | 1,494 |

Table 6 lists the differential expression of the control vs 'at risk' for each biomarker. The ANOVA p value is also listed for the respective biomarkers.

TABLE 6

| Protein | Differential expressed | Anova p value |
|---|---|---|
| AMPN | 3.3 | 0.010 |
| AMD | 2.1 | 0.000 |
| CALM3 | 7.3 | 0.006 |
| KI21A | 10.0 | 0.003 |
| ACBP | 4.3 | 0.000 |
| IGA2 | 2.3 | 0.004 |
| S10A7 | 15.0 | 0.001 |

Table 7 lists all the significant biomarkers that had significance to the 20 samples that had been tested using a Mass spectrometry SWATCH method.

TABLE 7

| Uniprot ID | Abbrev. name | Control average | AtRisk average | Control vs Risk delta | Anova p-value | ProteinName | GO |
|---|---|---|---|---|---|---|---|
| P31151 | S10A7 | 1,006,380 | 15,111,224 | 15.02 | 0.001 | Protein S100-A7 (Psoriasin) (S100 calcium-binding protein A7) | azurophil granule lumen [GO: 0035578]; collagen-containing extracellular matrix [GO: 0062023]; cytoplasm [GO: 0005737]; cytosol [GO: 0005829]; endoplasmic reticulum [GO: 0005783]; extracellular region [GO: 0005576]; extracellular space [GO: 0005615]; focal adhesion |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0005925]; nucleus [GO: 0005634]; calcium ion binding [GO: 0005509]; calcium-dependent protein binding [GO: 0048306]; RAGE receptor binding [GO: 0050786]; zinc ion binding [GO: 0008270]; angiogenesis [GO: 0001525]; antimicrobial humoral immune response mediated by antimicrobial peptide [GO: 0061844]; antimicrobial humoral response [GO: 0019730]; defense response to Gram-negative bacterium [GO: 0050829]; epidermis development [GO: 0008544]; innate immune response [GO: 0045087]; keratinocyte differentiation [GO: 0030216]; neutrophil degranulation [GO: 0043312]; positive regulation of ERK1 and ERK2 cascade [GO: 0070374]; positive regulation of granulocyte chemotaxis [GO: 0071624]; positive regulation of monocyte chemotaxis [GO: 0090026]; positive regulation of T cell chemotaxis [GO: 0010820]; response to lipopolysaccharide [GO: 0032496]; response to reactive oxygen species [GO: 0000302]; sequestering of metal ion [GO: 0051238] |
| A0M8Q6 | IGLC7 | 97,679 | 1,339,761 | 13.72 | 0.014 | Immunoglobulin lambda constant 7 (Ig lambda-7 chain C region) | external side of plasma membrane [GO: 0009897]; extracellular region [GO: 0005576]; immunoglobulin complex, circulating [GO: 0042571]; plasma membrane [GO: 0005886]; antigen binding [GO: 0003823]; immunoglobulin receptor binding [GO: 0034987]; B cell receptor signaling pathway [GO: 0050853]; complement activation [GO: 0006956]; complement activation, classical pathway |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0006958]; defense response to bacterium [GO: 0042742]; Fc-epsilon receptor signaling pathway [GO: 0038095]; Fc-gamma receptor signaling pathway involved in phagocytosis [GO: 0038096]; innate immune response [GO: 0045087]; leukocyte migration [GO: 0050900]; negative regulation of inflammatory response to antigenic stimulus [GO: 0002862]; opsonization [GO: 0008228]; peptide cross-linking [GO: 0018149]; phagocytosis, engulfment [GO: 0006911]; phagocytosis, recognition [GO: 0006910]; positive regulation of B cell activation [GO: 0050871]; receptor-mediated endocytosis [GO: 0006898]; regulation of complement activation [GO: 0030449]; regulation of immune response [GO: 0050776] |
| Q9NP78 | ABCB9 | 259,205 | 2,886,652 | 11.14 | 0.000 | ATP-binding cassette sub-family B member 9 (ATP-binding cassette transporter 9) (ABC transporter 9 protein) (hABCB9) (TAP-like protein) (TAPL) | integral component of endoplasmic reticulum membrane [GO: 0030176]; integral component of membrane [GO: 0016021]; intracellular membrane-bounded organelle [GO: 0043231]; lysosomal membrane [GO: 0005765]; lysosome [GO: 0005764]; MHC class I peptide loading complex [GO: 0042824]; ABC-type peptide antigen transporter activity [GO: 0015433]; ABC-type peptide transporter activity [GO: 0015440]; ATP binding [GO: 0005524]; ATPase activity [GO: 0016887]; ATPase-coupled transmembrane transporter activity [GO: 0042626]; protein homodimerization activity [GO: 0042803]; TAP1 binding [GO: 0046978]; transmembrane |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | transporter activity [GO: 0022857]; antigen processing and presentation of endogenous peptide antigen via MHC class I [GO: 0019885]; peptide transport [GO: 0015833]; protein transport [GO: 0015031]; transmembrane transport [GO: 0055085] |
| P03973 | SLPI | 4,688,764 | 448,243 | 10.46 | 0.023 | Antileukoproteinase (ALP) (BLPI) (HUSI-1) (Mucus proteinase inhibitor) (MPI) (Protease inhibitor WAP4) (Secretory leukocyte protease inhibitor) (Seminal proteinase inhibitor) (WAP four-disulfide core domain protein 4) | collagen-containing extracellular matrix [GO: 0062023]; extracellular exosome [GO: 0070062]; extracellular region [GO: 0005576]; extracellular space [GO: 0005615]; Golgi apparatus [GO: 0005794]; specific granule lumen [GO: 0035580]; DNA binding [GO: 0003677]; endopeptidase inhibitor activity [GO: 0004866]; enzyme binding [GO: 0019899]; mRNA binding [GO: 0003729]; serine-type endopeptidase inhibitor activity [GO: 0004867]; antibacterial humoral response [GO: 0019731]; immune response [GO: 0006955]; innate immune response [GO: 0045087]; modulation of process of other organism [GO: 0035821]; negative regulation of protein binding [GO: 0032091]; negative regulation of viral genome replication [GO: 0045071]; neutrophil degranulation [GO: 0043312]; response to lipopolysaccharide [GO: 0032496] |
| Q7Z4S6 | KI21A | 7,062,544 | 706,251 | 10.00 | 0.003 | Kinesin-like protein KIF21A (Kinesin-like protein KIF2) (Renal carcinoma antigen NY-REN-62) | cytosol [GO: 0005829]; kinesin complex [GO: 0005871]; microtubule [GO: 0005874]; plasma membrane [GO: 0005886]; ATP binding [GO: 0005524]; ATP-dependent microtubule motor activity [GO: 1990939]; ATPase activity [GO: 0016887]; microtubule binding [GO: 0008017]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | microtubule motor activity [GO: 0003777]; microtubule-based movement [GO: 0007018] |
| Q7Z7M9 | GALT5 | 171,663 | 17,606 | 9.75 | 0.009 | Polypeptide N-acetylgalactosaminyltransferase 5 (EC 2.4.1.41) (Polypeptide GalNAc transferase 5) (GalNAc-T5) (pp-GaNTase 5) (Protein-UDP acetylgalactosaminyltransferase 5) (UDP-GalNAc:polypeptide N-acetylgalactosaminyltransferase 5) | Golgi apparatus [GO: 0005794]; Golgi membrane [GO: 0000139]; integral component of membrane [GO: 0016021]; carbohydrate binding [GO: 0030246]; metal ion binding [GO: 0046872]; polypeptide N-acetylgalactosaminyltransferase activity [GO: 0004653]; glycosaminoglycan biosynthetic process [GO: 0006024]; O-glycan processing [GO: 0016266] |
| P0DP2 | CALM3 | 100,657 | 731,788 | 7.27 | 0.006 | Calmodulin-3 | calcium channel complex [GO: 0034704]; catalytic complex [GO: 1902494]; centrosome [GO: 0005813]; cytoplasm [GO: 0005737]; growth cone [GO: 0030426]; mitochondrial membrane [GO: 0031966]; myelin sheath [GO: 0043209]; nucleus [GO: 0005634]; plasma membrane [GO: 0005886]; protein-containing complex [GO: 0032991]; sarcomere [GO: 0030017]; spindle microtubule [GO: 0005876]; spindle pole [GO: 0000922]; synaptic vesicle membrane [GO: 0030672]; vesicle [GO: 0031982]; voltage-gated potassium channel complex [GO: 0008076]; adenylate cyclase activator activity [GO: 0010856]; adenylate cyclase binding [GO: 0008179]; calcium ion binding [GO: 0005509]; calcium-dependent protein binding [GO: 0048306]; disordered domain specific binding [GO: 0097718]; enzyme regulator activity [GO: 0030234]; ion channel binding [GO: 0044325]; N-terminal myristoylation domain binding [GO: 0031997]; nitric-oxide synthase binding |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0050998]; nitric-oxide synthase regulator activity [GO: 0030235]; phosphatidylinositol 3-kinase binding [GO: 0043548]; protein domain specific binding [GO: 0019904]; protein kinase binding [GO: 0019901]; protein phosphatase activator activity [GO: 0072542]; protein serine/threonine kinase activator activity [GO: 0043539]; titin binding [GO: 0031432]; type 3 metabotropic glutamate receptor binding [GO: 0031800]; activation of adenylate cyclase activity [GO: 0007190]; detection of calcium ion [GO: 0005513]; establishment of protein localization to mitochondrial membrane [GO: 0090151]; G protein-coupled receptor signaling pathway [GO: 0007186]; G2/M transition of mitotic cell cycle [GO: 0000086]; negative regulation of high voltage-gated calcium channel activity [GO:1901842]; negative regulation of peptidyl-threonine phosphorylation [GO: 0010801]; negative regulation of ryanodine-sensitive calcium-release channel activity [GO: 0060315]; positive regulation of cyclic-nucleotide phosphodiesterase activity [GO: 0051343]; positive regulation of DNA binding [GO: 0043388]; positive regulation of nitric-oxide synthase activity [GO: 0051000]; positive regulation of peptidyl-threonine phosphorylation [GO: 0010800]; positive regulation of phosphoprotein phosphatase activity [GO: 0032516]; positive regulation of protein autophosphorylation [GO: 0031954]; positive regulation of protein dephosphorylation [GO: 0035307]; positive |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | regulation of protein serine/threonine kinase activity [GO: 0071902]; positive regulation of ryanodine-sensitive calcium-release channel activity [GO: 0060316]; regulation of cardiac muscle cell action potential [GO: 0098901]; regulation of cardiac muscle contraction [GO: 0055117]; regulation of cardiac muscle contraction by regulation of the release of sequestered calcium ion [GO: 0010881]; regulation of cell communication by electrical coupling involved in cardiac conduction [GO:1901844]; regulation of cytokinesis [GO: 0032465]; regulation of heart rate [GO: 0002027]; regulation of release of sequestered calcium ion into cytosol by sarcoplasmic reticulum [GO: 0010880]; regulation of synaptic vesicle endocytosis |
| Q9NZT1 | CALL5 | 292,820 | 1,902,352 | 6.50 | 0.003 | Calmodulin-like protein 5 (Calmodulin-like skin protein) | [GO: 1900242]; regulation of synaptic vesicle exocytosis [GO:2000300]; response to amphetamine [GO: 0001975]; response to calcium ion [GO: 0051592]; response to corticosterone [GO: 0051412]; substantia nigra development [GO: 0021762] extracellular region [GO: 0005576]; ficolin-1-rich granule lumen [GO: 1904813]; calcium ion binding [GO: 0005509]; enzyme regulator activity [GO: 0030234]; epidermis development [GO: 0008544]; neutrophil degranulation [GO: 0043312]; signal transduction [GO: 0007165] |

TABLE 7-continued

| Uniprot ID | Abbrev. name | Control average | AtRisk average | Control vs Risk delta | Anova p-value | ProteinName | GO |
|---|---|---|---|---|---|---|---|
| O95969 | SG1D2 | 36,661 | 191,255 | 5.22 | 0.005 | Secretoglobin family 1D member 2 (Lipophilin-B) | extracellular space [GO: 0005615] |
| P31949 | S10AB | 270,030 | 1,385,546 | 5.13 | 0.011 | Protein S100-A11 (Calgizzarin) (Metastatic lymph node gene 70 protein) (MLN 70) (Protein S100-C) (S100 calcium-binding protein A11) [Cleaved into: Protein S100-A11, N-terminally processed] | extracellular space [GO: 0005615]; nucleus [GO: 0005634]; ruffle [GO: 0001726]; secretory granule lumen [GO: 0034774]; cadherin binding involved in cell-cell adhesion [GO: 0098641]; calcium ion binding [GO: 0005509]; calcium-dependent protein binding [GO: 0048306]; protein homodimerization activity [GO: 0042803]; S100 protein binding [GO: 0044548]; negative regulation of cell population proliferation [GO: 0008285]; negative regulation of DNA replication [GO: 0008156]; neutrophil degranulation [GO: 0043312]; positive regulation of smooth muscle cell migration [GO: 0014911]; signal transduction [GO: 0007165] |
| P46783 | RS10 | 22,761 | 115,695 | 5.08 | 0.011 | 40S ribosomal protein S10 (Small ribosomal subunit protein eS10) | cytosol [GO: 0005829]; cytosolic small ribosomal subunit [GO: 0022627]; focal adhesion [GO: 0005925]; membrane [GO: 0016020]; nucleolus [GO: 0005730]; nucleoplasm [GO: 0005654]; ribosome [GO: 0005840]; RNA binding [GO: 0003723]; structural constituent of ribosome [GO: 0003735]; nuclear-transcribed mRNA catabolic process, nonsense-mediated decay [GO: 0000184]; ribosomal small subunit assembly [GO: 0000028]; SRP-dependent cotranslational protein targeting to membrane [GO: 0006614]; translation |

TABLE 7-continued

| Uniprot ID | Abbrev. name | Control average | AtRisk average | Control vs Risk delta | Anova p-value | ProteinName | GO |
|---|---|---|---|---|---|---|---|
| Q9UGY1 | NOL12 | 60,052 | 289,076 | 4.81 | 0.040 | Nucleolar protein 12 | [GO: 0006412]; translational initiation [GO: 0006413]; viral transcription [GO: 0019083] nucleolus [GO: 0005730]; identical protein binding [GO: 0042802]; RNA binding [GO: 0003723]; rRNA binding [GO: 0019843] |
| P62841 | RS15 | 15,821 | 72,972 | 4.61 | 0.017 | 40S ribosomal protein S15 (RIG protein) (Small ribosomal subunit protein uS19) | cytosol [GO: 0005829]; cytosolic small ribosomal subunit [GO: 0022627]; focal adhesion [GO: 0005925]; membrane [GO: 0016020]; nucleoplasm [GO: 0005654]; nucleus [GO: 0005634]; DNA binding [GO: 0003677]; RNA binding [GO: 0003723]; structural constituent of ribosome [GO: 0003735]; nuclear-transcribed mRNA catabolic process, nonsense-mediated decay [GO: 0000184]; osteoblast differentiation [GO: 0001649]; ribosomal small subunit assembly [GO: 0000028]; ribosomal small subunit biogenesis [GO: 0042274]; ribosomal small subunit export from nucleus [GO: 0000056]; rRNA processing [GO: 0006364]; SRP-dependent cotranslational protein targeting to membrane [GO: 0006614]; translation [GO: 0006412]; translational initiation [GO: 0006413]; viral transcription [GO: 0019083] |
| P01601 | KVD16 | 411,929 | 93,276 | 4.42 | 0.021 | Immunoglobulin kappa variable 1D-16 (Ig kappa chain V-I region HK146) (Ig kappa chain V-I region HK189) | extracellular region [GO: 0005576]; extracellular space [GO: 0005615]; immunoglobulin complex [GO: 0019814]; plasma membrane [GO: 0005886]; antigen binding [GO: 0003823]; complement activation [GO: 0006956]; complement activation, classical pathway [GO: 0006958]; Fc-epsilon receptor signaling pathway [GO: 0038095]; Fc-gamma receptor |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | signaling pathway involved in phagocytosis [GO: 0038096]; immune response [GO: 0006955]; leukocyte migration [GO: 0050900]; negative regulation of inflammatory response to antigenic stimulus [GO: 0002862]; opsonization [GO: 0008228]; peptide cross-linking [GO: 0018149]; receptor-mediated endocytosis [GO: 0006898]; regulation of complement activation [GO: 0030449]; regulation of immune response [GO: 0050776] |
| P02812 | PRB2 | 60,289,539 | 13,760,720 | 4.38 | 0.033 | Basic salivary proline-rich protein 2 (Salivary proline-rich protein) (Con1 glycoprotein) [Cleaved into: Basic proline-rich peptide IB-1; Basic proline-rich peptide P-E (IB-9); Basic proline-rich peptide IB-7; Basic proline-rich peptide IB-8c (Basic peptide P-F); Basic proline-rich peptide IB-4] | extracellular region [GO: 0005576] |
| P07108 | ACBP | 1,366,139 | 5,811,090 | 4.25 | 0.000 | Acyl-CoA-binding protein (ACBP) (Diazepam-binding inhibitor) (DBI) (Endozepine) (EP) | endoplasmic reticulum lumen [GO: 0005788]; extracellular exosome [GO: 0070062]; Golgi apparatus [GO: 0005794]; perinuclear endoplasmic reticulum [GO: 0097038]; protein-lipid complex [GO: 0032994]; benzodiazepine receptor binding [GO: 0030156]; identical protein binding [GO: 0042802]; lipid binding [GO: 0008289]; long-chain fatty acyl-CoA binding [GO: 0036042]; acyl-CoA metabolic process [GO: 0006637]; negative regulation of protein lipidation [GO:1903060]; phosphatidylcholine acyl-chain remodeling [GO: 0036151]; positive regulation of CoA-transferase activity [GO: 1905920]; positive regulation of phospholipid transport [GO:2001140] |

TABLE 7-continued

| Uniprot ID | Abbrev. name | Control average | AtRisk average | Control vs Risk delta | Anova p-value | ProteinName | GO |
|---|---|---|---|---|---|---|---|
| P27482 | CALL3 | 1,153,513 | 4,638,566 | 4.02 | 0.009 | Calmodulin-like protein 3 (CaM-like protein) (CLP) (Calmodulin-related protein NB-1) | extracellular exosome [GO: 0070062]; calcium ion binding [GO: 0005509]; enzyme regulator activity [GO: 0030234] |
| Q9NZH0 | GPC5B | 113,392 | 28,524 | 3.98 | 0.026 | G-protein coupled receptor family C group 5 member B (A-69G12.1) (Retinoic acid-induced gene 2 protein) (RAIG-2) | cell surface [GO: 0009986]; cytoplasmic vesicle membrane [GO: 0030659]; cytosol [GO: 0005829]; extracellular exosome [GO: 0070062]; extracellular space [GO: 0005615]; integral component of membrane [GO: 0016021]; intracellular membrane-bounded organelle [GO: 0043231]; nucleolus [GO: 0005730]; nucleoplasm [GO: 0005654]; plasma membrane [GO: 0005886]; receptor complex [GO: 0043235]; G protein-coupled receptor activity [GO: 0004930]; G protein-coupled receptor binding [GO: 0001664]; protein kinase activator activity [GO: 0030295]; protein kinase binding [GO: 0019901]; positive regulation of canonical Wnt signaling pathway [GO: 0090263]; positive regulation of I-kappaB kinase/NF-kappaB signaling [GO: 0043123]; positive regulation of inflammatory response [GO: 0050729]; positive regulation of macrophage cytokine production [GO: 0060907]; positive regulation of neuron differentiation [GO: 0045666]; positive regulation of protein tyrosine kinase activity [GO: 0061098] |
| Q6P5S2 | LEG1H | 29,932,578 | 7,884,593 | 3.80 | 0.010 | Protein LEG1 homolog | extracellular exosome [GO: 0070062]; extracellular space [GO: 0005615]; multicellular organism development [GO: 0007275] |

TABLE 7-continued

| Uniprot ID | Abbrev. name | Control average | AtRisk average | Control vs Risk delta | Anova p-value | ProteinName | GO |
|---|---|---|---|---|---|---|---|
| Q8IX01 | SUGP2 | 10,789 | 2,852 | 3.78 | 0.026 | SURP and G-patch domain-containing protein 2 (Arginine/serine-rich-splicing factor 14) (Splicing factor, arginine/serine-rich 14) | nuclear body [GO: 0016604]; nucleoplasm [GO: 0005654]; RNA binding [GO: 0003723]; mRNA processing [GO: 0006397]; RNA splicing [GO: 0008380] |
| P28325 | CYTD | 18,634,465 | 66,975,938 | 3.59 | 0.009 | Cystatin-D (Cystatin-5) | extracellular exosome [GO: 0070062]; extracellular region [GO: 0005576]; extracellular space [GO: 0005615]; cysteine-type endopeptidase inhibitor activity [GO: 0004869] |
| P23083 | HV102 | 3,094,358 | 874,755 | 3.54 | 0.001 | Immunoglobulin heavy variable 1-2 (Ig heavy chain V-I region ND) (Ig heavy chain V-I region V35) | external side of plasma membrane [GO: 0009897]; extracellular region [GO: 0005576]; immunoglobulin complex, circulating [GO: 0042571]; plasma membrane [GO: 0005886]; antigen binding [GO: 0003823]; immunoglobulin receptor binding [GO: 0034987]; B cell receptor signaling pathway [GO: 0050853]; complement activation [GO: 0006956]; complement activation, classical pathway [GO: 0006958]; defense response to bacterium [GO: 0042742]; Fc-epsilon receptor signaling pathway [GO: 0038095]; Fc-gamma receptor signaling pathway involved in phagocytosis [GO: 0038096]; immune response [GO: 0006955]; innate immune response [GO: 0045087]; leukocyte migration [GO: 0050900]; negative regulation of inflammatory response to antigenic stimulus [GO: 0002862]; opsonization [GO: 0008228]; peptide cross-linking [GO: 0018149]; phagocytosis, engulfment [GO: 0006911]; phagocytosis, recognition [GO: 0006910]; positive regulation of B cell activation [GO: 0050871]; |

TABLE 7-continued

| Uniprot ID | Abbrev. name | Control average | AtRisk average | Control vs Risk delta | Anova p-value | ProteinName | GO |
|---|---|---|---|---|---|---|---|
| P01591 | IGJ | 254,949,858 | 72,868,065 | 3.50 | 0.001 | Immunoglobulin J chain (Joining chain of multimeric IgA and IgM) | receptor-mediated endocytosis [GO: 0006898]; regulation of complement activation [GO: 0030449]; regulation of immune response [GO: 0050776] blood microparticle [GO: 0072562]; dimeric IgA immunoglobulin complex [GO: 0071750]; extracellular exosome [GO: 0070062]; extracellular region [GO: 0005576]; extracellular space [GO: 0005615]; monomeric IgA immunoglobulin complex [GO: 0071748]; pentameric IgM immunoglobulin complex [GO: 0071756]; secretory dimeric IgA immunoglobulin complex [GO: 0071752]; secretory IgA immunoglobulin complex [GO: 0071751]; antigen binding [GO: 0003823]; IgA binding [GO: 0019862]; immunoglobulin receptor binding [GO: 0034987]; protein homodimerization activity [GO: 0042803]; protein-macromolecule adaptor activity [GO: 0030674]; adaptive immune response [GO: 0002250]; antibacterial humoral response [GO: 0019731]; glomerular filtration [GO: 0003094]; humoral immune response [GO: 0006959]; immune response [GO: 0006955]; innate immune response [GO: 0045087]; leukocyte migration [GO: 0050900]; positive regulation of respiratory burst [GO: 0060267]; protein-containing complex assembly [GO: 0065003]; receptor-mediated endocytosis [GO: 0006898]; retina homeostasis [GO: 0001895] |
| Q15942 | ZYX | 2,143,957 | 617,222 | 3.47 | 0.014 | Zyxin (Zyxin-2) | actin cytoskeleton [GO: 0015629]; adherens junction [GO: 0005912]; cytoplasm [GO: 0005737]; cytosol [GO: 0005829]; focal |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | adhesion [GO: 0005925]; nucleus [GO: 0005634]; phagocytic vesicle [GO: 0045335]; plasma membrane [GO: 0005886]; stress fiber [GO: 0001725]; metal ion binding [GO: 0046872]; RNA binding [GO: 0003723]; cell-cell signaling [GO: 0007267]; cell-matrix adhesion [GO: 0007160]; cellular response to interferon-gamma [GO: 0071346]; integrin-mediated signaling pathway [GO: 0007229]; regulation of inflammatory response [GO: 0050727]; signal transduction [GO: 0007165]; stress fiber assembly [GO: 0043149]; transforming growth factor beta receptor signaling pathway [GO: 0007179]; viral process [GO: 0016032] |
| P31025 | LCN1 | 30,330,854 | 105,334,304 | 3.47 | 0.033 | Lipocalin-1 (Tear lipocalin) (Tlc) (Tear prealbumin) (TP) (von Ebner gland protein) (VEG protein) | extracellular region [GO: 0005576]; extracellular space [GO: 0005615]; chloride ion binding [GO: 0031404]; cysteine-type endopeptidase inhibitor activity [GO: 0004869]; signaling receptor binding [GO: 0005102]; small molecule binding [GO: 0036094]; zinc ion binding [GO: 0008270]; long-chain fatty acid transport [GO: 0015909]; proteolysis [GO: 0006508]; response to stimulus [GO: 0050896]; retina homeostasis [GO: 0001895]; sensory perception of taste [GO: 0050909] |
| Q04941 | PLP2 | 139,383 | 40,439 | 3.45 | 0.028 | Proteolipid protein 2 (Differentiation-dependent protein A4) (Intestinal membrane A4 protein) | endoplasmic reticulum [GO: 0005783]; endoplasmic reticulum membrane [GO: 0005789]; integral component of membrane [GO: 0016021]; membrane [GO: 0016020]; plasma membrane [GO: 0005886]; chemokine binding [GO: 0019956]; ion transmembrane transporter activity [GO: 0015075]; |

TABLE 7-continued

| Uniprot ID | Abbrev. name | Control average | AtRisk average | Control vs Risk delta | Anova p-value | ProteinName | GO |
|---|---|---|---|---|---|---|---|
| A0A075B6K4 | LV310 | 1,306,454 | 385,001 | 3.39 | 0.013 | Immunoglobulin lambda variable 3-10 | chemotaxis [GO: 0006935]; cytokine-mediated signaling pathway [GO: 0019221]; ion transport [GO: 0006811] extracellular space [GO: 0005615]; immunoglobulin complex [GO: 0019814]; plasma membrane [GO: 0005886]; adaptive immune response [GO: 0002250]; immune response [GO: 0006955] |
| P15144 | AMPN | 56,159 | 16,886 | 3.33 | 0.010 | Aminopeptidase N (AP-N) (hAPN) (EC 3.4.11.2) (Alanyl aminopeptidase) (Aminopeptidase M) (AP-M) (Microsomal aminopeptidase) (Myeloid plasma membrane glycoprotein CD13) (gp150) (CD antigen CD13) | cytoplasm [GO: 0005737]; endoplasmic reticulum-Golgi intermediate compartment [GO: 0005793]; extracellular exosome [GO: 0070062]; extracellular space [GO: 0005615]; integral component of membrane [GO: 0016021]; lysosomal membrane [GO: 0005765]; plasma membrane [GO: 0005886]; secretory granule membrane [GO: 0030667]; aminopeptidase activity [GO: 0004177]; metalloaminopeptidase activity [GO: 0070006]; metallopeptidase activity [GO: 0008237]; peptide binding [GO: 0042277]; signaling receptor activity [GO: 0038023]; virus receptor activity [GO: 0001618]; zinc ion binding [GO: 0008270]; angiogenesis [GO: 0001525]; cell differentiation [GO: 0030154]; neutrophil degranulation [GO: 0043312]; peptide catabolic process [GO: 0043171]; proteolysis [GO: 0006508]; regulation of blood pressure [GO: 0008217]; signal transduction [GO: 0007165] |

TABLE 7-continued

| Uniprot ID | Abbrev. name | Control average | AtRisk average | Control vs Risk delta | Anova p-value | ProteinName | GO |
|---|---|---|---|---|---|---|---|
| Q8NES3 | LFNG | 212,321 | 65,302 | 3.25 | 0.050 | Beta-1,3-N-acetylglucosaminyltransferase lunatic fringe (EC 2.4.1.222) (O-fucosylpeptide 3-beta-N-acetylglucosaminyltransferase) | extracellular region [GO: 0005576]; extracellular vesicle [GO:1903561]; Golgi membrane [GO: 0000139]; integral component of Golgi membrane [GO: 0030173]; acetylglucosaminyltransferase activity [GO: 0008375]; metal ion binding [GO: 0046872]; O-fucosylpeptide 3-beta-N-acetylglucosaminyltransferase activity [GO: 0033829]; animal organ morphogenesis [GO: 0009887]; marginal zone B cell differentiation [GO: 0002315]; negative regulation of Notch signaling pathway involved in somitogenesis [GO:1902367]; regulation of Notch signaling pathway [GO: 0008593]; regulation of somitogenesis [GO: 0014807]; somitogenesis [GO: 0001756]; T cell differentiation [GO: 0030217] |
| P01717 | LV325 | 299,219 | 93,280 | 3.21 | 0.004 | Immunoglobulin lambda variable 3-25 (Ig lambda chain V-IV region Hil) | blood microparticle [GO: 0072562]; extracellular region [GO: 0005576]; extracellular space [GO: 0005615]; immunoglobulin complex [GO: 0019814]; plasma membrane [GO: 0005886]; antigen binding [GO: 0003823]; complement activation [GO: 0006956]; complement activation, classical pathway [GO: 0006958]; Fc-epsilon receptor signaling pathway [GO: 0038095]; Fc-gamma receptor signaling pathway involved in phagocytosis [GO: 0038096]; immune response [GO: 0006955]; leukocyte migration [GO: 0050900]; negative regulation of inflammatory response to antigenic stimulus [GO: 0002862]; opsonization [GO: 0008228]; peptide cross-linking [GO: 0018149]; |

TABLE 7-continued

| Uniprot ID | Abbrev. name | Control average | AtRisk average | Control vs Risk delta | Anova p-value | ProteinName | GO |
|---|---|---|---|---|---|---|---|
| P16885 | PLCG2 | 53,680 | 171,703 | 3.20 | 0.038 | 1-phosphatidylinositol 4,5-bisphosphate phosphodiesterase gamma-2 (EC 3.1.4.11) (Phosphoinositide phospholipase C-gamma-2) (Phospholipase C-IV) (PLC-IV) (Phospholipase C-gamma-2) (PLC-gamma-2) | receptor-mediated endocytosis [GO: 0006898]; regulation of complement activation [GO: 0030449]; regulation of immune response [GO: 0050776] cytosol [GO: 0005829]; extracellular exosome [GO: 0070062]; plasma membrane [GO: 0005886]; phosphatidylinositol phospholipase C activity [GO: 0004435]; phosphorylation-dependent protein binding [GO: 0140031]; phosphotyrosine residue binding [GO: 0001784]; activation of store-operated calcium channel activity [GO: 0032237]; B cell differentiation [GO: 0030183]; B cell receptor signaling pathway [GO: 0050853]; calcium-mediated signaling [GO: 0019722]; Fc-epsilon receptor signaling pathway [GO: 0038095]; Fc-gamma receptor signaling pathway involved in phagocytosis [GO: 0038096]; follicular B cell differentiation [GO: 0002316]; inositol phosphate metabolic process [GO: 0043647]; inositol trisphosphate biosynthetic process [GO: 0032959]; negative regulation of inflammatory response to antigenic stimulus [GO: 0002862]; negative regulation of programmed cell death [GO: 0043069]; phosphatidylinositol biosynthetic process [GO: 0006661]; phospholipid catabolic process [GO: 0009395]; platelet activation [GO: 0030168]; positive regulation of epithelial cell migration [GO: 0010634]; positive regulation of receptor internalization [GO: 0002092]; positive regulation of type I interferon production [GO: 0032481]; release of sequestered calcium ion into cytosol [GO: 0051209]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | response to lipopolysaccharide [GO: 0032496]; stimulatory C-type lectin receptor signaling pathway [GO: 0002223]; T cell receptor signaling pathway [GO: 0050852]; Wnt signaling pathway [GO: 0016055] |
| Q9HC84 | MUC5B | 1,033,569,305 | 324,735,024 | 3.18 | 0.047 | Mucin-5B (MUC-5B) (Cervical mucin) (High molecular weight salivary mucin MG1) (Mucin-5 subtype B, tracheobronchial) (Sublingual gland mucin) | extracellular exosome [GO: 0070062]; extracellular matrix [GO: 0031012]; extracellular space [GO: 0005615]; Golgi lumen [GO: 0005796]; intracellular membrane-bounded organelle [GO: 0043231]; plasma membrane [GO: 0005886]; O-glycan processing [GO: 0016266]; stimulatory C-type lectin receptor signaling pathway [GO: 0002223] |
| Q96FQ6 | S10AG | 648,580 | 203,832 | 3.18 | 0.017 | Protein S100-A16 (Aging-associated gene 13 protein) (Protein S100-F) (S100 calcium-binding protein A16) | cytoplasm [GO: 0005737]; cytosol [GO: 0005829]; extracellular exosome [GO: 0070062]; extracellular space [GO: 0005615]; nucleolus [GO: 0005730]; nucleus [GO: 0005634]; plasma membrane [GO: 0005886]; calcium ion binding [GO: 0005509]; calcium-dependent protein binding [GO: 0048306]; protein homodimerization activity [GO: 0042803]; RNA binding [GO: 0003723]; response to calcium ion [GO: 0051592] |
| Q86V81 | THOC4 | 975,961 | 309,405 | 3.15 | 0.033 | THO complex subunit 4 (Tho4) (Ally of AML-1 and LEF-1) (Aly/REF export factor) (Transcriptional coactivator Aly/REF) (bZIP-enhancing factor BEF) | catalytic step 2 spliceosome [GO: 0071013]; cytoplasm [GO: 0005737]; cytosol [GO: 0005829]; extracellular exosome [GO: 0070062]; membrane [GO: 0016020]; nuclear speck [GO: 0016607]; nucleoplasm [GO: 0005654]; nucleus [GO: 0005634]; transcription export complex [GO: 0000346]; C5-methylcytidine-containing RNA binding [GO: 0062153]; RNA binding [GO: 0003723]; mRNA 3'-end |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | processing [GO: 0031124]; mRNA export from nucleus [GO: 0006406]; mRNA splicing, via spliceosome [GO: 0000398]; osteoblast differentiation [GO: 0001649]; positive regulation of DNA-templated transcription, elongation [GO: 0032786]; regulation of DNA recombination [GO: 0000018]; replication fork processing [GO: 0031297]; RNA export from nucleus [GO: 0006405]; viral mRNA export from host cell nucleus [GO: 0046784]; viral process [GO: 0016032] |
| A0A0J9 YXX1 | HV5X1 | 6,754,962 | 2,142,836 | 3.15 | 0.001 | Immunoglobulin heavy variable 5-10-1 | external side of plasma membrane [GO: 0009897]; immunoglobulin complex, circulating [GO: 0042571]; antigen binding [GO: 0003823]; immunoglobulin receptor binding [GO: 0034987]; B cell receptor signaling pathway [GO: 0050853]; complement activation, classical pathway [GO: 0006958]; defense response to bacterium [GO: 0042742]; innate immune response [GO: 0045087]; phagocytosis, engulfment [GO: 0006911]; phagocytosis, recognition [GO: 0006910]; positive regulation of B cell activation [GO: 0050871] |
| P01714 | LV319 | 1,442,287 | 462,857 | 3.12 | 0.001 | Immunoglobulin lambda variable 3-19 (Ig lambda chain V-III region SH) | extracellular exosome [GO: 0070062]; extracellular region [GO: 0005576]; extracellular space [GO: 0005615]; immunoglobulin complex [GO: 0019814]; plasma membrane [GO: 0005886]; antigen binding [GO: 0003823]; complement activation [GO: 0006956]; complement activation, classical pathway [GO: 0006958]; Fc-epsilon receptor signaling pathway [GO: 0038095]; Fc- |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | gamma receptor signaling pathway involved in phagocytosis [GO: 0038096]; immune response [GO: 0006955]; leukocyte migration [GO: 0050900]; negative regulation of inflammatory response to antigenic stimulus [GO: 0002862]; opsonization [GO: 0008228]; peptide cross-linking [GO: 0018149]; receptor-mediated endocytosis [GO: 0006898]; regulation of complement activation [GO: 0030449]; regulation of immune response [GO: 0050776] |
| Q8TAA3 | PSMA8 | 21,481 | 66,929 | 3.12 | 0.003 | Proteasome subunit alpha-type 8 (Proteasome alpha 4 subunit) (Alpha4s) (Proteasome subunit alpha-type 7-like) | cytoplasm [GO: 0005737]; cytosol [GO: 0005829]; extracellular exosome [GO: 0070062]; nucleus [GO: 0005634]; proteasome core complex [GO: 0005839]; proteasome core complex, alpha-subunit complex [GO: 0019773]; spermatoproteasome complex [GO: 1990111]; endopeptidase activity [GO: 0004175]; anaphase-promoting complex-dependent catabolic process [GO: 0031145]; antigen processing and presentation of exogenous peptide antigen via MHC class I, TAP-dependent [GO: 0002479]; cell differentiation [GO: 0030154]; Fc-epsilon receptor signaling pathway [GO: 0038095]; interleukin-1-mediated signaling pathway [GO: 0070498]; MAPK cascade [GO: 0000165]; meiotic cell cycle [GO: 0051321]; negative regulation of canonical Wnt signaling pathway [GO: 0090090]; negative regulation of G2/M transition of mitotic cell cycle [GO: 0010972]; NIK/NF-kappaB signaling [GO: 0038061]; positive regulation of canonical Wnt signaling pathway [GO: 0090263]; post-translational protein |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | modification [GO: 0043687]; pre-replicative complex assembly [GO: 0036388]; proteasomal protein catabolic process [GO: 0010498]; proteasomal ubiquitin-independent protein catabolic process [GO: 0010499]; proteasome-mediated ubiquitin-dependent protein catabolic process [GO: 0043161]; protein deubiquitination [GO: 0016579]; protein polyubiquitination [GO: 0000209]; regulation of cellular amino acid metabolic process [GO: 0006521]; regulation of hematopoietic stem cell differentiation [GO: 1902036]; regulation of meiosis I [GO: 0060631]; regulation of mitotic cell cycle phase transition [GO:1901990]; regulation of mRNA stability [GO: 0043488]; regulation of transcription from RNA polymerase II promoter in response to hypoxia [GO: 0061418]; SCF-dependent proteasomal ubiquitin-dependent protein catabolic process [GO: 0031146]; spermatogenesis [GO: 0007283]; stimulatory C-type lectin receptor signaling pathway [GO: 0002223]; T cell receptor signaling pathway [GO: 0050852]; transmembrane transport [GO: 0055085]; tumor necrosis factor-mediated signaling pathway [GO: 0033209]; Wnt signaling pathway, planar cell polarity pathway [GO: 0060071] |
| P78380 | OLR1 | 14,019 | 43,676 | 3.12 | 0.009 | Oxidized low-density lipoprotein receptor 1 (Ox-LDL receptor 1) (C-type lectin domain family 8 member A) (Lectin-like oxidized LDL receptor 1) (LOX-1) (Lectin-like oxLDL receptor 1) (hLOX-1) (Lectin-type oxidized | extracellular region [GO: 0005576]; integral component of plasma membrane [GO: 0005887]; intracellular membrane-bounded organelle [GO: 0043231]; membrane |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | LDL receptor 1) [Cleaved into: Oxidized low-density lipoprotein receptor 1, soluble form] | [GO: 0016020]; membrane raft [GO: 0045121]; nucleoplasm [GO: 0005654]; plasma membrane [GO: 0005886]; receptor complex [GO: 0043235]; specific granule membrane [GO: 0035579]; tertiary granule membrane [GO: 0070821]; carbohydrate binding [GO: 0030246]; identical protein binding [GO: 0042802]; low-density lipoprotein particle receptor activity [GO: 0005041]; blood circulation [GO: 0008015]; cell death [GO: 0008219]; inflammatory response [GO: 0006954]; leukocyte cell-cell adhesion [GO: 0007159]; leukocyte migration [GO: 0050900]; lipoprotein metabolic process [GO: 0042157]; neutrophil degranulation [GO: 0043312]; proteolysis [GO: 0006508] |
| Q13177 | PAK2 | 146,112 | 47,302 | 3.09 | 0.027 | Serine/threonine-protein kinase PAK 2 (EC 2.7.11.1) (Gamma-PAK) (PAK65) (S6/H4 kinase) (p21-activated kinase 2) (PAK-2) (p58) [Cleaved into: PAK-2p27 (p27); PAK-2p34 (p34) (C-t-PAK2)] | cell-cell junction [GO: 0005911]; cytoplasm [GO: 0005737]; cytosol [GO: 0005829]; glutamatergic synapse [GO: 0098978]; nucleus [GO: 0005634]; perinuclear region of cytoplasm [GO: 0048471]; plasma membrane [GO: 0005886]; postsynaptic density [GO: 0014069]; ATP binding [GO: 0005524]; cadherin binding [GO: 0045296]; identical protein binding [GO: 0042802]; protein kinase activity [GO: 0004672]; protein kinase binding [GO: 0019901]; protein serine kinase activity [GO: 0106310]; protein serine/threonine kinase activity [GO: 0004674]; protein threonine kinase activity [GO: 0106311]; protein tyrosine kinase activator activity [GO: 0030296]; small GTPase binding [GO: 0031267]; activation of protein kinase activity |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0032147]; adherens junction assembly [GO: 0034333]; apoptotic process [GO: 0006915]; bicellular tight junction assembly [GO: 0070830]; cellular response to organic cyclic compound [GO: 0071407]; dendritic spine development [GO: 0060996]; Fc-epsilon receptor signaling pathway [GO: 0038095]; interleukin-12-mediated signaling pathway [GO: 0035722]; negative regulation of apoptotic process [GO: 0043066]; negative regulation of cysteine-type endopeptidase activity involved in execution phase of apoptosis [GO:2001271]; negative regulation of protein kinase activity [GO: 0006469]; negative regulation of stress fiber assembly [GO: 0051497]; peptidyl-serine phosphorylation [GO: 0018105]; phosphorylation [GO: 0016310]; positive regulation of extrinsic apoptotic signaling pathway [GO: 2001238]; positive regulation of peptidyl-tyrosine phosphorylation [GO: 0050731]; protein autophosphorylation [GO: 0046777]; protein localization to cell-cell junction [GO: 0150105]; protein phosphorylation [GO: 0006468]; regulation of axonogenesis [GO: 0050770]; regulation of cytoskeleton organization [GO: 0051493]; regulation of defense response to virus by virus [GO: 0050690]; regulation of growth [GO: 0040008]; signal transduction [GO: 0007165]; stimulatory C-type lectin receptor signaling pathway [GO: 0002223]; stress- |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | activated protein kinase signaling cascade [GO: 0031098]; T cell costimulation [GO: 0031295]; T cell receptor signaling pathway [GO: 0050852]; vascular endothelial growth factor receptor signaling pathway [GO: 0048010] |
| O60885 | BRD4 | 124,580 | 42,461 | 2.93 | 0.010 | Bromodomain-containing protein 4 (Protein HUNK1) | chromosome [GO: 0005694]; condensed nuclear chromosome [GO: 0000794]; nucleoplasm [GO: 0005654]; nucleus [GO: 0005634]; chromatin binding [GO: 0003682]; enzyme binding [GO: 0019899]; lysine-acetylated histone binding [GO: 0070577]; P-TEFb complex binding [GO: 0106140]; p53 binding [GO: 0002039]; RNA polymerase II C-terminal domain binding [GO: 0099122]; RNA polymerase II CTD heptapeptide repeat kinase activity [GO: 0008353]; transcription coactivator activity [GO: 0003713]; transcription coregulator activity [GO: 0003712]; cellular response to DNA damage stimulus [GO: 0006974]; chromatin organization [GO: 0006325]; chromatin remodeling [GO: 0006338]; negative regulation by host of viral transcription [GO: 0043922]; negative regulation of DNA damage checkpoint [GO:2000002]; positive regulation of G2/M transition of mitotic cell cycle [GO: 0010971]; positive regulation of histone H3-K36 trimethylation [GO: 2001255]; positive regulation of I-kappaB kinase/NF-kappaB signaling [GO: 0043123]; positive regulation of transcription by RNA polymerase II [GO: 0045944]; positive regulation of transcription elongation from RNA |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | polymerase II promoter [GO: 0032968]; positive regulation of transcription, DNA-templated [GO: 0045893]; regulation of inflammatory response [GO: 0050727]; regulation of phosphorylation of RNA polymerase II C-terminal domain [GO:1901407]; regulation of transcription involved in G1/S transition of mitotic cell cycle [GO: 0000083]; viral process [GO: 0016032] |
| P19957 | ELAF | 67,483 | 196,903 | 2.92 | 0.041 | Elafin (Elastase-specific inhibitor) (ESI) (Peptidase inhibitor 3) (PI-3) (Protease inhibitor WAP3) (Skin-derived antileukoproteinase) (SKALP) (WAP four-disulfide core domain protein 14) | cornified envelope [GO: 0001533]; cytosol [GO: 0005829]; extracellular matrix [GO: 0031012]; extracellular region [GO: 0005576]; extracellular space [GO: 0005615]; endopeptidase inhibitor activity [GO: 0004866]; serine-type endopeptidase inhibitor activity [GO: 0004867]; structural constituent of skin epidermis [GO: 0030280]; antibacterial humoral response [GO: 0019731]; antimicrobial humoral response [GO: 0019730]; copulation [GO: 0007620]; cornification [GO: 0070268]; innate immune response [GO: 0045087]; peptide cross-linking [GO: 0018149] |
| Q9BRL6 | SRSF8 | 51,306 | 141,319 | 2.75 | 0.022 | Serine/arginine-rich splicing factor 8 (Pre-mRNA-splicing factor SRP46) (Splicing factor SRp46) (Splicing factor, arginine/serine-rich 2B) | cytoplasm [GO: 0005737]; cytosol [GO: 0005829]; nuclear speck [GO: 0016607]; nucleoplasm [GO: 0005654]; RNA binding [GO: 0003723]; mRNA splicing, via spliceosome [GO: 0000398] |
| P61626 | LYSC | 823,035,736 | 300,657,309 | 2.74 | 0.035 | Lysozyme C (EC 3.2.1.17) (1,4-beta-N-acetylmuramidase C) | azurophil granule lumen [GO: 0035578]; extracellular exosome [GO: 0070062]; extracellular region [GO: 0005576]; extracellular space [GO: 0005615]; specific granule lumen [GO: 0035580]; tertiary granule lumen [GO:1904724]; identical protein |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | binding [GO: 0042802]; lysozyme activity [GO: 0003796]; amyloid fibril formation [GO:1990000]; antimicrobial humoral response [GO: 0019730]; cytolysis [GO: 0019835]; defense response to bacterium [GO: 0042742]; defense response to Gram-negative bacterium [GO: 0050829]; defense response to Gram-positive bacterium [GO: 0050830]; inflammatory response [GO: 0006954]; killing of cells of other organism [GO: 0031640]; neutrophil degranulation [GO: 0043312]; retina homeostasis [GO: 0001895] |
| P54108 | CRIS3 | 35,993,306 | 13,156,769 | 2.74 | 0.002 | Cysteine-rich secretory protein 3 (CRISP-3) (Specific granule protein of 28 kDa) (SGP28) | extracellular matrix [GO: 0031012]; extracellular region [GO: 0005576]; extracellular space [GO: 0005615]; specific granule [GO: 0042581]; specific granule lumen [GO: 0035580]; tertiary granule lumen [GO: 1904724]; defense response [GO: 0006952]; innate immune response [GO: 0045087]; neutrophil degranulation [GO: 0043312] |
| P00492 | HPRT | 323,998 | 118,436 | 2.74 | 0.020 | Hypoxanthine-guanine phosphoribosyltransferase (HGPRT) (HGPRTase) (EC 2.4.2.8) | cytoplasm [GO: 0005737]; cytosol [GO: 0005829]; extracellular exosome [GO: 0070062]; guanine phosphoribosyltransferase activity [GO: 0052657]; hypoxanthine phosphoribosyltransferase activity [GO: 0004422]; identical protein binding [GO: 0042802]; magnesium ion binding [GO: 0000287]; nucleotide binding [GO: 0000166]; adenine salvage [GO: 0006168]; central nervous system neuron development [GO: 0021954]; cerebral cortex neuron differentiation [GO: 0021895]; dendrite morphogenesis [GO: 0048813]; dopamine metabolic process [GO: 0042417]; GMP catabolic process |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0046038]; GMP salvage [GO: 0032263]; grooming behavior [GO: 0007625]; guanine salvage [GO: 0006178]; hypoxanthine metabolic process [GO: 0046100]; hypoxanthine salvage [GO: 0043103]; IMP metabolic process [GO: 0046040]; IMP salvage [GO: 0032264]; locomotory behavior [GO: 0007626]; lymphocyte proliferation [GO: 0046651]; positive regulation of dopamine metabolic process [GO: 0045964]; protein homotetramerization [GO: 0051289]; purine nucleotide biosynthetic process [GO: 0006164]; purine ribonucleoside salvage [GO: 0006166]; purine-containing compound salvage [GO: 0043101]; response to amphetamine [GO: 0001975]; striatum development [GO: 0021756]; T cell mediated cytotoxicity [GO: 0001913] |
| Q9UBH0 | I36RA | 95,212 | 260,231 | 2.73 | 0.000 | Interleukin-36 receptor antagonist protein (IL-36Ra) (FIL1 delta) (IL-1-related protein 3) (IL-1RP3) (Interleukin-1 HY1) (IL-1HY1) (Interleukin-1 delta) (IL-1 delta) (Interleukin-1 family member 5) (IL-1F5) (Interleukin-1 receptor antagonist homolog 1) (IL-1ra homolog 1) (Interleukin-1-like protein 1) (IL-1L1) | cytoplasm [GO: 0005737]; extracellular region [GO: 0005576]; extracellular space [GO: 0005615]; cytokine activity [GO: 0005125]; interleukin-1 receptor antagonist activity [GO: 0005152]; interleukin-1 receptor binding [GO: 0005149]; antifungal humoral response [GO: 0019732]; cellular response to lipopolysaccharide [GO: 0071222]; cytokine-mediated signaling pathway [GO: 0019221]; inflammatory response [GO: 0006954]; inflammatory response to antigenic stimulus [GO: 0002437]; innate immune response [GO: 0045087]; negative regulation of cytokine-mediated signaling pathway [GO: 0001960]; negative regulation of interferon-gamma production [GO: 0032689]; negative regulation of |

TABLE 7-continued

| Uniprot ID | Abbrev. name | Control average | AtRisk average | Control vs Risk delta | Anova p-value | ProteinName | GO |
|---|---|---|---|---|---|---|---|
| Q9BWS9 | CHID1 | 27,186 | 9,956 | 2.73 | 0.022 | Chitinase domain-containing protein 1 (Stabilin-1-interacting chitinase-like protein) (SI-CLP) | interleukin-17 production [GO: 0032700]; negative regulation of interleukin-6 production [GO: 0032715] extracellular exosome [GO: 0070062]; extracellular region [GO: 0005576]; extracellular space [GO: 0005615]; late endosome [GO: 0005770]; lysosomal lumen [GO: 0043202]; lysosome [GO: 0005764]; membrane [GO: 0016020]; nucleus [GO: 0005634]; trans-Golgi network [GO: 0005802]; chitin binding [GO: 0008061]; oligosaccharide binding [GO: 0070492]; carbohydrate metabolic process [GO: 0005975]; innate immune response [GO: 0045087]; negative regulation of cytokine production involved in inflammatory response [GO: 1900016]; platelet degranulation [GO: 0002576] |
| P46776 | RL27A | 13,307 | 36,313 | 2.73 | 0.034 | 60S ribosomal protein L27a (Large ribosomal subunit protein uL15) | cytosol [GO: 0005829]; cytosolic large ribosomal subunit [GO: 0022625]; endoplasmic reticulum [GO: 0005783]; membrane [GO: 0016020]; RNA binding [GO: 0003723]; structural constituent of ribosome [GO: 0003735]; nuclear-transcribed mRNA catabolic process, nonsense-mediated decay [GO: 0000184]; rRNA processing [GO: 0006364]; SRP-dependent cotranslational protein targeting to membrane [GO: 0006614]; translation [GO: 0006412]; translational initiation [GO: 0006413]; viral transcription [GO: 0019083] |
| Q13630 | FCL | 37,272 | 100,529 | 2.70 | 0.022 | GDP-L-fucose synthase (EC 1.1.1.271) (GDP-4-keto-6-deoxy-D-mannose-3,5-epimerase-4-reductase) (Protein FX) (Red cell NADP(H)-binding protein) (Short- | cytosol [GO: 0005829]; extracellular exosome [GO: 0070062]; electron transfer activity [GO: 0009055]; GDP-4-dehydro-D-rhamnose reductase activity [GO: 0042356]; GDP-L- |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | chain dehydrogenase/reductase family 4E member 1) | fucose synthase activity [GO: 0050577]; GDP-mannose 3,5-epimerase activity [GO: 0047918]; identical protein binding [GO: 0042802]; 'de novo' GDP-L-fucose biosynthetic process [GO: 0042351]; GDP-mannose metabolic process [GO: 0019673]; leukocyte cell-cell adhesion [GO: 0007159]; positive regulation of endothelial cell migration [GO: 0010595]; positive regulation of endothelial cell-matrix adhesion via fibronectin [GO:1904906] |
| O00231 | PSD11 | 35,871 | 96,056 | 2.68 | 0.002 | 26S proteasome non-ATPase regulatory subunit 11 (26S proteasome regulatory subunit RPN6) (26S proteasome regulatory subunit S9) (26S proteasome regulatory subunit p44.5) | cytosol [GO: 0005829]; extracellular region [GO: 0005576]; ficolin-1-rich granule lumen [GO:1904813]; membrane [GO: 0016020]; nucleoplasm [GO: 0005654]; nucleus [GO: 0005634]; proteasome accessory complex [GO: 0022624]; proteasome complex [GO: 0000502]; proteasome regulatory particle, lid subcomplex [GO: 0008541]; secretory granule lumen [GO: 0034774]; structural molecule activity [GO: 0005198]; anaphase-promoting complex-dependent catabolic process [GO: 0031145]; antigen processing and presentation of exogenous peptide antigen via MHC class I, TAP-dependent [GO: 0002479]; Fc-epsilon receptor signaling pathway [GO: 0038095]; interleukin-1-mediated signaling pathway [GO: 0070498]; MAPK cascade [GO: 0000165]; negative regulation of canonical Wnt signaling pathway [GO: 0090090]; negative regulation of G2/M transition of mitotic cell cycle [GO: 0010972]; neutrophil degranulation [GO: 0043312]; NIK/NF-kappaB signaling [GO: 0038061]; positive |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | regulation of canonical Wnt signaling pathway [GO: 0090263]; post-translational protein modification [GO: 0043687]; pre-replicative complex assembly [GO: 0036388]; proteasome assembly [GO: 0043248]; proteasome-mediated ubiquitin-dependent protein catabolic process [GO: 0043161]; protein deubiquitination [GO: 0016579]; protein polyubiquitination [GO: 0000209]; regulation of cellular amino acid metabolic process [GO: 0006521]; regulation of hematopoietic stem cell differentiation [GO:1902036]; regulation of mitotic cell cycle phase transition [GO:1901990]; regulation of mRNA stability [GO: 0043488]; regulation of transcription from RNA polymerase II promoter in response to hypoxia [GO: 0061418]; SCF-dependent proteasomal ubiquitin-dependent protein catabolic process [GO: 0031146]; stem cell differentiation [GO: 0048863]; stimulatory C-type lectin receptor signaling pathway [GO: 0002223]; T cell receptor signaling pathway [GO: 0050852]; transmembrane transport [GO: 0055085]; tumor necrosis factor-mediated signaling pathway [GO: 0033209]; ubiquitin-dependent protein catabolic process [GO: 0006511]; Wnt signaling pathway, planar cell polarity pathway [GO: 0060071] |
| P06331 | HV434 | 532,600 | 200,507 | 2.66 | 0.040 | Immunoglobulin heavy variable 4-34 (Ig heavy chain V-II region ARH-77) | external side of plasma membrane [GO: 0009897]; extracellular region [GO: 0005576]; immunoglobulin complex, circulating [GO: 0042571]; plasma membrane [GO: 0005886]; antigen |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | binding [GO: 0003823]; immunoglobulin receptor binding [GO: 0034987]; B cell receptor signaling pathway [GO: 0050853]; complement activation [GO: 0006956]; complement activation, classical pathway [GO: 0006958]; defense response to bacterium [GO: 0042742]; Fc-epsilon receptor signaling pathway [GO: 0038095]; Fc-gamma receptor signaling pathway involved in phagocytosis [GO: 0038096]; immune response [GO: 0006955]; innate immune response [GO: 0045087]; leukocyte migration [GO: 0050900]; negative regulation of inflammatory response to antigenic stimulus [GO: 0002862]; opsonization [GO: 0008228]; peptide cross-linking [GO: 0018149]; phagocytosis, engulfment [GO: 0006911]; phagocytosis, recognition [GO: 0006910]; positive regulation of B cell activation [GO: 0050871]; receptor-mediated endocytosis [GO: 0006898]; regulation of complement activation [GO: 0030449]; regulation of immune response [GO: 0050776] |
| P62993 | GRB2 | 56,510 | 148,197 | 2.62 | 0.031 | Growth factor receptor-bound protein 2 (Adapter protein GRB2) (Protein Ash) (SH2/SH3 adapter GRB2) | cell-cell junction [GO: 0005911]; COP9 signalosome [GO: 0008180]; cytoplasm [GO: 0005737]; cytosol [GO: 0005829]; endosome [GO: 0005768]; extracellular exosome [GO: 0070062]; Golgi apparatus [GO: 0005794]; Grb2-EGFR complex [GO: 0070436]; nucleolus [GO: 0005730]; nucleoplasm [GO: 0005654]; nucleus [GO: 0005634]; plasma membrane [GO: 0005886]; vesicle |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | membrane [GO: 0012506]; ephrin receptor binding [GO: 0046875]; epidermal growth factor receptor binding [GO: 0005154]; identical protein binding [GO: 0042802]; insulin receptor substrate binding [GO: 0043560]; neurotrophin TRKA receptor binding [GO: 0005168]; phosphotyrosine residue binding [GO: 0001784]; protein kinase binding [GO: 0019901]; protein phosphatase binding [GO: 0019903]; protein-containing complex binding [GO: 0044877]; protein-macromolecule adaptor activity [GO: 0030674]; RNA binding [GO: 0003723]; SH3 domain binding [GO: 0017124]; actin cytoskeleton reorganization [GO: 0031532]; aging [GO: 0007568]; anatomical structure formation involved in morphogenesis [GO: 0048646]; axon guidance [GO: 0007411]; branching involved in labyrinthine layer morphogenesis [GO: 0060670]; cellular response to ionizing radiation [GO: 0071479]; cytokine-mediated signaling pathway [GO: 0019221]; entry of bacterium into host cell [GO: 0035635]; epidermal growth factor receptor signaling pathway [GO: 0007173]; ERBB2 signaling pathway [GO: 0038128]; Fc-epsilon receptor signaling pathway [GO: 0038095]; Fc-gamma receptor signaling pathway involved in phagocytosis [GO: 0038096]; fibroblast growth factor receptor signaling pathway [GO: 0008543]; insulin receptor signaling pathway [GO: 0008286]; interleukin-15-mediated signaling |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | pathway [GO: 0035723]; leukocyte migration [GO: 0050900]; MAPK cascade [GO: 0000165]; membrane organization [GO: 0061024]; negative regulation of epidermal growth factor receptor signaling pathway [GO: 0042059]; neurotrophin TRK receptor signaling pathway [GO: 0048011]; positive regulation of actin filament polymerization [GO: 0030838]; positive regulation of protein kinase B signaling [GO: 0051897]; positive regulation of Ras protein signal transduction [GO: 0046579]; positive regulation of reactive oxygen species metabolic process [GO:2000379]; Ras protein signal transduction [GO: 0007265]; receptor internalization [GO: 0031623]; regulation of MAPK cascade [GO: 0043408]; signal transduction in response to DNA damage [GO: 0042770]; T cell costimulation [GO: 0031295]; viral process [GO: 0016032] |
| P08493 | MGP | 307,281 | 799,600 | 2.60 | 0.003 | Matrix Gla protein (MGP) (Cell growth-inhibiting gene 36 protein) | collagen-containing extracellular matrix [GO: 0062023]; extracellular exosome [GO: 0070062]; extracellular matrix [GO: 0031012]; calcium ion binding [GO: 0005509]; extracellular matrix structural constituent [GO: 0005201]; structural constituent of bone [GO: 0008147]; cartilage condensation [GO: 0001502]; cell differentiation [GO: 0030154]; ossification [GO: 0001503]; regulation of bone mineralization [GO: 0030500] |
| Q6FI13 | H2A2A | 6,598,218 | 17,134,253 | 2.60 | 0.016 | Histone H2A type 2-A (H2A-clustered histone 18) (H2A-clustered histone 19) (Histone H2A.2) (Histone H2A/o) | extracellular exosome [GO: 0070062]; nucleosome [GO: 0000786]; nucleus [GO: 0005634]; DNA binding [GO: 0003677]; protein |

TABLE 7-continued

| Uniprot ID | Abbrev. name | Control average | AtRisk average | Control vs Risk delta | Anova p-value | ProteinName | GO |
|---|---|---|---|---|---|---|---|
| Q9H173 | SIL1 | 26,005 | 67,153 | 2.58 | 0.007 | Nucleotide exchange factor SIL1 (BIP-associated protein) (BAP) | heterodimerization activity [GO: 0046982]; chromatin silencing [GO: 0006342] endoplasmic reticulum [GO: 0005783]; endoplasmic reticulum lumen [GO: 0005788]; extracellular space [GO: 0005615]; adenyl-nucleotide exchange factor activity [GO: 0000774]; unfolded protein binding [GO: 0051082]; cotranslational protein targeting to membrane [GO: 0006613]; intracellular protein transport [GO: 0006886]; protein folding [GO: 0006457] |
| P02808 | STAT | 31,783,683 | 82,053,253 | 2.58 | 0.047 | Statherin | extracellular region [GO: 0005576]; extracellular matrix constituent, lubricant activity [GO: 0030197]; hydroxyapatite binding [GO: 0046848]; structural constituent of tooth enamel [GO: 0030345]; biomineral tissue development [GO: 0031214]; defense response to bacterium [GO: 0042742]; negative regulation of bone mineralization [GO: 0030502]; ossification [GO: 0001503]; saliva secretion [GO: 0046541] |
| P08758 | ANXA5 | 366,465 | 940,764 | 2.57 | 0.014 | Annexin A5 (Anchorin CII) (Annexin V) (Annexin-5) (Calphobindin I) (CBP-I) (Endonexin II) (Lipocortin V) (Placental anticoagulant protein 4) (PP4) (Placental anticoagulant protein I) (PAP-I) (Thromboplastin inhibitor) (Vascular anticoagulant-alpha) (VAC-alpha) | collagen-containing extracellular matrix [GO: 0062023]; cytoplasm [GO: 0005737]; cytosol [GO: 0005829]; extracellular exosome [GO: 0070062]; extracellular region [GO: 0005576]; focal adhesion [GO: 0005925]; membrane [GO: 0016020]; calcium ion binding [GO: 0005509]; calcium-dependent phospholipid binding [GO: 0005544]; phospholipase inhibitor activity [GO: 0004859]; phospholipid binding [GO: 0005543]; blood coagulation [GO: 0007596]; negative regulation of apoptotic process [GO: 0043066]; negative regulation of coagulation [GO: 0050819]; platelet |

TABLE 7-continued

| Uniprot ID | Abbrev. name | Control average | AtRisk average | Control vs Risk delta | Anova p-value | ProteinName | GO |
|---|---|---|---|---|---|---|---|
| P0DOX | IGE | 1,178,375 | 460,789 | 2.56 | 0.005 | Immunoglobulin epsilon heavy chain (Immunoglobulin epsilon heavy chain ND) | degranulation [GO: 0002576]; signal transduction [GO: 0007165] extracellular region [GO: 0005576]; immunoglobulin complex [GO: 0019814]; plasma membrane [GO: 0005886]; adaptive immune response [GO: 0002250] |
| P42126 | ECI1 | 117,742 | 46,141 | 2.55 | 0.011 | Enoyl-CoA delta isomerase 1, mitochondrial (EC 5.3.3.8) (3,2-trans-enoyl-CoA isomerase) (Delta(3),Delta(2)-enoyl-CoA isomerase) (D3,D2-enoyl-CoA isomerase) (Dodecenoyl-CoA isomerase) | mitochondrial matrix [GO: 0005759]; mitochondrion [GO: 0005739]; dodecenoyl-CoA delta-isomerase activity [GO: 0004165]; enoyl-CoA hydratase activity [GO: 0004300]; intramolecular oxidoreductase activity, transposing C=C bonds [GO: 0016863]; fatty acid beta-oxidation [GO: 0006635] |
| P50749 | RASF2 | 25,756 | 64,961 | 2.52 | 0.030 | Ras association domain-containing protein 2 | condensed chromosome kinetochore [GO: 0000777]; cytoplasm [GO: 0005737]; cytosol [GO: 0005829]; Golgi apparatus [GO: 0005794]; kinetochore [GO: 0000776]; nucleoplasm [GO: 0005654]; nucleus [GO: 0005634]; plasma membrane [GO: 0005886]; protein-containing complex [GO: 0032991]; protein kinase activity [GO: 0004672]; bone remodeling [GO: 0046849]; cell cycle [GO: 0007049]; epidermal growth factor receptor signaling pathway via I-kappaB kinase/NF-kappaB cascade [GO: 0038168]; homeostasis of number of cells [GO: 0048872]; negative regulation of NIK/NF-kappaB signaling [GO:1901223]; negative regulation of peptidyl-serine phosphorylation [GO: 0033137]; ossification [GO: 0001503]; positive regulation of apoptotic process [GO: 0043065]; positive regulation of JNK cascade [GO: 0046330]; positive regulation of protein |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | autophosphorylation [GO: 0031954]; positive regulation of protein kinase activity [GO: 0045860]; protein stabilization [GO: 0050821]; regulation of NIK/NF-kappaB signaling [GO:1901222]; regulation of osteoblast differentiation [GO: 0045667]; regulation of osteoclast differentiation [GO: 0045670]; signal transduction [GO: 0007165]; skeletal system development [GO: 0001501] |
| Q9ULW8 | PADI3 | 251,948 | 100,865 | 2.50 | 0.021 | Protein-arginine deiminase type-3 (EC 3.5.3.15) (Peptidylarginine deiminase III) (Protein-arginine deiminase type III) | cytoplasm [GO: 0005737]; cytosol [GO: 0005829]; nucleus [GO: 0005634]; calcium ion binding [GO: 0005509]; identical protein binding [GO: 0042802]; protein-arginine deiminase activity [GO: 0004668]; chromatin organization [GO: 0006325]; histone citrullination [GO: 0036414]; protein citrullination [GO: 0018101] |
| A0A075B6R2 | HV404 | 850,039 | 341,302 | 2.49 | 0.024 | Immunoglobulin heavy variable 4-4 | external side of plasma membrane [GO: 0009897]; immunoglobulin complex, circulating [GO: 0042571]; antigen binding [GO: 0003823]; immunoglobulin receptor binding [GO: 0034987]; B cell receptor signaling pathway [GO: 0050853]; complement activation, classical pathway [GO: 0006958]; defense response to bacterium [GO: 0042742]; innate immune response [GO: 0045087]; phagocytosis, engulfment [GO: 0006911]; phagocytosis, recognition [GO: 0006910]; positive regulation of B cell activation [GO: 0050871] |
| P04080 | CYTB | 23,329,698 | 57,505,633 | 2.46 | 0.023 | Cystatin-B (CPI-B) (Liver thiol proteinase inhibitor) (Stefin-B) | collagen-containing extracellular matrix [GO: 0062023]; cytoplasm [GO: 0005737]; cytosol [GO: 0005829]; extracellular exosome [GO: 0070062]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | extracellular region [GO: 0005576]; extracellular space [GO: 0005615]; ficolin-1-rich granule lumen [GO:1904813]; nucleolus [GO: 0005730]; nucleus [GO: 0005634]; secretory granule lumen [GO: 0034774]; tertiary granule lumen [GO:1904724]; cysteine-type endopeptidase inhibitor activity [GO: 0004869]; endopeptidase inhibitor activity [GO: 0004866]; protease binding [GO: 0002020]; RNA binding [GO: 0003723]; adult locomotory behavior [GO: 0008344]; negative regulation of peptidase activity [GO: 0010466]; negative regulation of proteolysis [GO: 0045861]; neutrophil degranulation [GO: 0043312] |
| A0A087WSY4 | HV432 | 849,577 | 345,920 | 2.46 | 0.028 | Immunoglobulin heavy variable 4-30-2 | external side of plasma membrane [GO: 0009897]; immunoglobulin complex, circulating [GO: 0042571]; antigen binding [GO: 0003823]; immunoglobulin receptor binding [GO: 0034987]; B cell receptor signaling pathway [GO: 0050853]; complement activation, classical pathway [GO: 0006958]; defense response to bacterium [GO: 0042742]; innate immune response [GO: 0045087]; phagocytosis, engulfment [GO: 0006911]; phagocytosis, recognition [GO: 0006910]; positive regulation of B cell activation [GO: 0050871] |
| P62851 | RS25 | 176,989 | 432,017 | 2.44 | 0.009 | 40S ribosomal protein S25 (Small ribosomal subunit protein eS25) | cytosol [GO: 0005829]; cytosolic small ribosomal subunit [GO: 0022627]; extracellular exosome [GO: 0070062]; nucleolus [GO: 0005730]; nucleoplasm [GO: 0005654]; nucleus [GO: 0005634]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | postsynaptic density [GO: 0014069]; ribosome [GO: 0005840]; small ribosomal subunit [GO: 0015935]; RNA binding [GO: 0003723]; structural constituent of ribosome [GO: 0003735]; nuclear-transcribed mRNA catabolic process, nonsense-mediated decay [GO: 0000184]; ribosomal small subunit biogenesis [GO: 0042274]; rRNA processing [GO: 0006364]; SRP-dependent cotranslational protein targeting to membrane [GO: 0006614]; translation [GO: 0006412]; translational initiation [GO: 0006413]; viral transcription [GO: 0019083] |
| P07477 | TRY1 | 792,519 | 326,267 | 2.43 | 0.006 | Trypsin-1 (EC 3.4.21.4) (Beta-trypsin) (Cationic trypsinogen) (Serine protease 1) (Trypsin I) [Cleaved into: Alpha-trypsin chain 1; Alpha-trypsin chain 2] | blood microparticle [GO: 0072562]; collagen-containing extracellular matrix [GO: 0062023]; extracellular region [GO: 0005576]; extracellular space [GO: 0005615]; metal ion binding [GO: 0046872]; serine-type endopeptidase activity [GO: 0004252]; cobalamin metabolic process [GO: 0009235]; digestion [GO: 0007586]; extracellular matrix disassembly [GO: 0022617]; proteolysis [GO: 0006508] |
| P05546 | HEP2 | 788,214 | 326,072 | 2.42 | 0.018 | Heparin cofactor 2 (Heparin cofactor II) (HC-II) (Protease inhibitor leuserpin-2) (HLS2) (Serpin D1) | endoplasmic reticulum lumen [GO: 0005788]; extracellular exosome [GO: 0070062]; extracellular region [GO: 0005576]; extracellular space [GO: 0005615]; endopeptidase inhibitor activity [GO: 0004866]; heparin binding [GO: 0008201]; serine-type endopeptidase inhibitor activity [GO: 0004867]; blood coagulation [GO: 0007596]; cellular protein metabolic process [GO: 0044267]; chemotaxis [GO: 0006935]; negative regulation of endopeptidase activity |

TABLE 7-continued

| Uniprot ID | Abbrev. name | Control average | AtRisk average | Control vs Risk delta | Anova p-value | ProteinName | GO |
|---|---|---|---|---|---|---|---|
| P10599 | THIO | 9,900,240 | 23,762,367 | 2.40 | 0.002 | Thioredoxin (Trx) (ATL-derived factor) (ADF) (Surface-associated sulphydryl protein) (SASP) (allergen Hom s Trx) | [GO: 0010951]; post-translational protein modification [GO: 0043687] cytoplasm [GO: 0005737]; cytosol [GO: 0005829]; extracellular exosome [GO: 0070062]; extracellular region [GO: 0005576]; nucleoplasm [GO: 0005654]; nucleus [GO: 0005634]; peptide disulfide oxidoreductase activity [GO: 0015037]; protein disulfide oxidoreductase activity [GO: 0015035]; protein homodimerization activity [GO: 0042803]; protein-disulfide reductase activity [GO: 0047134]; RNA binding [GO: 0003723]; activation of protein kinase B activity [GO: 0032148]; cell redox homeostasis [GO: 0045454]; cellular oxidant detoxification [GO: 0098869]; glycerol ether metabolic process [GO: 0006662]; negative regulation of hydrogen peroxide-induced cell death [GO:1903206]; negative regulation of protein export from nucleus [GO: 0046826]; negative regulation of transcription by RNA polymerase II [GO: 0000122]; positive regulation of DNA binding [GO: 0043388]; positive regulation of peptidyl-cysteine S-nitrosylation [GO: 2000170]; positive regulation of peptidyl-serine phosphorylation [GO: 0033138]; positive regulation of protein kinase B signaling [GO: 0051897]; purinergic nucleotide receptor signaling pathway [GO: 0035590]; response to nitric oxide [GO: 0071731]; response to radiation [GO: 0009314] |
| Q6IBSO | TWF2 | 172,789 | 72,008 | 2.40 | 0.035 | Twinfilin-2 (A6-related protein) (hA6RP) (Protein tyrosine kinase 9-like) (Twinfilin-1-like protein) | actin filament [GO: 0005884]; cytoplasm [GO: 0005737]; extracellular exosome [GO: 0070062]; filopodium [GO: 0030175]; growth cone [GO: 0030426]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | lamellipodium [GO: 0030027]; myofibril [GO: 0030016]; perinuclear region of cytoplasm [GO: 0048471]; stereocilium [GO: 0032420]; actin filament binding [GO: 0051015]; actin monomer binding [GO: 0003785]; ATP binding [GO: 0005524]; cadherin binding [GO: 0045296]; phosphatidylinositol-4,5-bisphosphate binding [GO: 0005546]; protein kinase C binding [GO: 0005080]; RNA binding [GO: 0003723]; actin filament depolymerization [GO: 0030042]; barbed-end actin filament capping [GO: 0051016]; cell projection organization [GO: 0030030]; cellular response to growth factor stimulus [GO: 0071363]; cellular response to retinoic acid [GO: 0071300]; negative regulation of actin filament polymerization [GO: 0030837]; positive regulation of axon extension [GO: 0045773]; positive regulation of lamellipodium assembly [GO: 0010592]; positive regulation of neuron projection development [GO: 0010976]; regulation of actin cytoskeleton organization [GO: 0032956]; regulation of lamellipodium assembly [GO: 0010591]; regulation of microvillus length [GO: 0032532]; sequestering of actin monomers [GO: 0042989] |
| O43852 | CALU | 15,110 | 36,213 | 2.40 | 0.033 | Calumenin (Crocalbin) (IEF SSP 9302) | endoplasmic reticulum [GO: 0005783]; endoplasmic reticulum lumen [GO: 0005788]; endoplasmic reticulum membrane [GO: 0005789]; extracellular region [GO: 0005576]; Golgi apparatus |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0005794]; melanosome [GO: 0042470]; membrane [GO: 0016020]; sarcoplasmic reticulum lumen [GO: 0033018]; calcium ion binding [GO: 0005509]; cellular protein metabolic process [GO: 0044267]; post-translational protein modification [GO: 0043687] |
| Q01105 | SET | 34,044 | 81,229 | 2.39 | 0.029 | Protein SET (HLA-DR-associated protein II) (Inhibitor of granzyme A-activated DNase) (IGAAD) (PHAPII) (Phosphatase 2A inhibitor I2PP2A) (I-2PP2A) (Template-activating factor I) (TAF-I) | chromatin [GO: 0000785]; cytoplasm [GO: 0005737]; cytosol [GO: 0005829]; endoplasmic reticulum [GO: 0005783]; lipid droplet [GO: 0005811]; nucleoplasm [GO: 0005654]; nucleus [GO: 0005634]; perinuclear region of cytoplasm [GO: 0048471]; protein-containing complex [GO: 0032991]; chromatin binding [GO: 0003682]; DNA binding [GO: 0003677]; histone binding [GO: 0042393]; protein phosphatase inhibitor activity [GO: 0004864]; protein phosphatase regulator activity [GO: 0019888]; DNA replication [GO: 0006260]; mitotic chromosome condensation [GO: 0007076]; negative regulation of histone acetylation [GO: 0035067]; negative regulation of neuron apoptotic process [GO: 0043524]; negative regulation of transcription, DNA-templated [GO: 0045892]; nucleosome assembly [GO: 0006334]; nucleosome disassembly [GO: 0006337]; regulation of mRNA stability [GO: 0043488]; viral process [GO: 0016032] |
| B3EWG6 | FM25G | 848,646 | 2,006,327 | 2.36 | 0.020 | Protein FAM25G | |
| Q15185 | TEBP | 48,241 | 113,159 | 2.35 | 0.037 | Prostaglandin E synthase 3 (EC 5.3.99.3) (Cytosolic prostaglandin E2 synthase) (cPGES) (Hsp90 co-chaperone) | chaperone complex [GO: 0101031]; chromosome, telomeric region [GO: 0000781]; cytosol [GO: 0005829]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | (Progesterone receptor complex p23) (Telomerase-binding protein p23) | nucleoplasm [GO: 0005654]; nucleus [GO: 0005634]; protein-containing complex [GO: 0032991]; telomerase holoenzyme complex [GO: 0005697]; chaperone binding [GO: 0051087]; DNA polymerase binding [GO: 0070182]; Hsp90 protein binding [GO: 0051879]; prostaglandin-E synthase activity [GO: 0050220]; telomerase activity [GO: 0003720]; unfolded protein binding [GO: 0051082]; chaperone cofactor-dependent protein refolding [GO: 0051085]; chaperone-mediated protein complex assembly [GO: 0051131]; cyclooxygenase pathway [GO: 0019371]; positive regulation of phosphorylation [GO: 0042327]; positive regulation of telomerase activity [GO: 0051973]; prostaglandin biosynthetic process [GO: 0001516]; protein folding [GO: 0006457]; protein stabilization [GO: 0050821]; regulation of cellular response to heat [GO: 1900034]; signal transduction [GO: 0007165]; telomerase holoenzyme complex assembly [GO:1905323]; telomere maintenance [GO: 0000723]; telomere maintenance via telomerase [GO: 0007004]; xenobiotic metabolic process [GO: 0006805] |
| Q9TNN7 | 1C05 | 86,715 | 37,058 | 2.34 | 0.031 | Merged into P10321. | |
| Q5EBL8 | PDZ11 | 82,727 | 35,866 | 2.31 | 0.049 | PDZ domain-containing protein 11 (ATPase-interacting PDZ protein) (Plasma membrane calcium ATPase-interacting single-PDZ protein) (PMCA-interacting single-PDZ protein) | adherens junction [GO: 0005912]; basolateral plasma membrane [GO: 0016323]; cell-cell junction [GO: 0005911]; cytosol [GO: 0005829]; extracellular region [GO: 0005576]; pore complex [GO: 0046930]; presynapse [GO: 0098793]; synapse [GO: 0045202]; protein C-terminus binding |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0008022]; antimicrobial humoral response [GO: 0019730]; biotin metabolic process [GO: 0006768]; ion transmembrane transport [GO: 0034220]; maintenance of epithelial cell apical/basal polarity [GO: 0045199]; neurotransmitter secretion [GO: 0007269]; pantothenate metabolic process [GO: 0015939]; pore complex assembly [GO: 0046931]; protein localization to basolateral plasma membrane [GO: 1903361]; transmembrane transport [GO: 0055085] |
| A0A0C4DH25 | KVD20 | 18,689,830 | 8,124,027 | 2.30 | 0.003 | Immunoglobulin kappa variable 3D-20 | extracellular region [GO: 0005576]; extracellular space [GO: 0005615]; immunoglobulin complex [GO: 0019814]; plasma membrane [GO: 0005886]; complement activation [GO: 0006956]; complement activation, classical pathway [GO: 0006958]; Fc-epsilon receptor signaling pathway [GO: 0038095]; Fc-gamma receptor signaling pathway involved in phagocytosis [GO: 0038096]; immune response [GO: 0006955]; leukocyte migration [GO: 0050900]; negative regulation of inflammatory response to antigenic stimulus [GO: 0002862]; opsonization [GO: 0008228]; peptide cross-linking [GO: 0018149]; receptor-mediated endocytosis [GO: 0006898]; regulation of complement activation [GO: 0030449]; regulation of immune response [GO: 0050776] |
| P0DJI8 | SAA1 | 788,909 | 1,812,419 | 2.30 | 0.016 | Serum amyloid A-1 protein (SAA) [Cleaved into: Amyloid protein A (Amyloid fibril protein AA); Serum amyloid protein A(2-104); | cytoplasmic microtubule [GO: 0005881]; endocytic vesicle lumen [GO: 0071682]; extracellular exosome |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | Serum amyloid protein A(3-104); Serum amyloid protein A(2-103); Serum amyloid protein A(2-102); Serum amyloid protein A(4-101)] | [GO: 0070062]; extracellular region [GO: 0005576]; high-density lipoprotein particle [GO: 0034364]; G protein-coupled receptor binding [GO: 0001664]; heparin binding [GO: 0008201]; activation of MAPK activity [GO: 0000187]; acute-phase response [GO: 0006953]; amyloid fibril formation [GO:1990000]; cytokine-mediated signaling pathway [GO: 0019221]; G protein-coupled receptor signaling pathway [GO: 0007186]; innate immune response [GO: 0045087]; lymphocyte chemotaxis [GO: 0048247]; macrophage chemotaxis [GO: 0048246]; negative regulation of inflammatory response [GO: 0050728]; neutrophil chemotaxis [GO: 0030593]; platelet activation [GO: 0030168]; positive regulation of cell adhesion [GO: 0045785]; positive regulation of cytokine production [GO: 0001819]; positive regulation of cytosolic calcium ion concentration [GO: 0007204]; positive regulation of interleukin-1 production [GO: 0032732]; receptor-mediated endocytosis [GO: 0006898]; regulation of protein secretion [GO: 0050708] |
| P04433 | KV311 | 13,090,866 | 5,711,696 | 2.29 | 0.002 | Immunoglobulin kappa variable 3-11 (Ig kappa chain V-III region VG) | blood microparticle [GO: 0072562]; extracellular exosome [GO: 0070062]; extracellular region [GO: 0005576]; extracellular space [GO: 0005615]; immunoglobulin complex [GO: 0019814]; plasma membrane [GO: 0005886]; antigen binding [GO: 0003823]; complement activation [GO: 0006956]; complement activation, classical pathway [GO: 0006958]; Fc-epsilon receptor |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | signaling pathway [GO: 0038095]; Fc-gamma receptor signaling pathway involved in phagocytosis [GO: 0038096]; immune response [GO: 0006955]; leukocyte migration [GO: 0050900]; negative regulation of inflammatory response to antigenic stimulus [GO: 0002862]; opsonization [GO: 0008228]; peptide cross-linking [GO: 0018149]; receptor-mediated endocytosis [GO: 0006898]; regulation of complement activation [GO: 0030449]; regulation of immune response [GO: 0050776] |
| Q9HOU4 | RAB1B | 312,439 | 714,602 | 2.29 | 0.004 | Ras-related protein Rab-1B | cytosol [GO: 0005829]; endomembrane system [GO: 0012505]; endoplasmic reticulum membrane [GO: 0005789]; endoplasmic reticulum-Golgi intermediate compartment membrane [GO: 0033116]; extracellular exosome [GO: 0070062]; Golgi apparatus [GO: 0005794]; Golgi membrane [GO: 0000139]; perinuclear region of cytoplasm [GO: 0048471]; phagophore assembly site membrane [GO: 0034045]; transport vesicle [GO: 0030133]; GTP binding [GO: 0005525]; GTPase activity [GO: 0003924]; autophagosome assembly [GO: 0000045]; COPII vesicle coating [GO: 0048208]; endoplasmic reticulum to Golgi vesicle-mediated transport [GO: 0006888]; intracellular protein transport [GO: 0006886]; positive regulation of glycoprotein metabolic process [GO:1903020]; post-translational protein modification [GO: 0043687]; regulation of autophagosome |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | assembly [GO:2000785]; retrograde vesicle-mediated transport, Golgi to endoplasmic reticulum [GO: 0006890]; virion assembly [GO: 0019068] |
| P0DOX2 | IGA2 | 216,137,561 | 94,850,425 | 2.28 | 0.004 | Immunoglobulin alpha-2 heavy chain (Immunoglobulin alpha-2 heavy chain BUT) | extracellular region [GO: 0005576]; immunoglobulin complex [GO: 0019814]; plasma membrane [GO: 0005886]; adaptive immune response [GO: 0002250] |
| P80748 | LV321 | 479,593 | 210,897 | 2.27 | 0.020 | Immunoglobulin lambda variable 3-21 (Ig lambda chain V-III region LOI) (Ig lambda chain V-V region DEL) (Ig lambda chain V-VII region MOT) | blood microparticle [GO: 0072562]; extracellular exosome [GO: 0070062]; extracellular region [GO: 0005576]; extracellular space [GO: 0005615]; immunoglobulin complex [GO: 0019814]; plasma membrane [GO: 0005886]; antigen binding [GO: 0003823]; complement activation [GO: 0006956]; complement activation, classical pathway [GO: 0006958]; Fc-epsilon receptor signaling pathway [GO: 0038095]; Fc-gamma receptor signaling pathway involved in phagocytosis [GO: 0038096]; immune response [GO: 0006955]; leukocyte migration [GO: 0050900]; negative regulation of inflammatory response to antigenic stimulus [GO: 0002862]; opsonization [GO: 0008228]; peptide cross-linking [GO: 0018149]; receptor-mediated endocytosis [GO: 0006898]; regulation of complement activation [GO: 0030449]; regulation of immune response [GO: 0050776] |
| Q9ULZ3 | ASC | 125,033 | 283,431 | 2.27 | 0.007 | Apoptosis-associated speck-like protein containing a CARD (hASC) (Caspase recruitment domain-containing protein 5) (PYD and CARD domain-containing protein) (Target of | AIM2 inflammasome complex [GO: 0097169]; azurophil granule lumen [GO: 0035578]; cytoplasm [GO: 0005737]; cytosol [GO: 0005829]; endoplasmic reticulum [GO: 0005783]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | methylation-induced silencing 1) | extracellular region [GO: 0005576]; Golgi membrane [GO: 0000139]; IkappaB kinase complex [GO: 0008385]; mitochondrion [GO: 0005739]; neuronal cell body [GO: 0043025]; NLRP1 inflammasome complex [GO: 0072558]; NLRP3 inflammasome complex [GO: 0072559]; nucleolus [GO: 0005730]; nucleoplasm [GO: 0005654]; nucleus [GO: 0005634]; protein-containing complex [GO: 0032991]; secretory granule lumen [GO: 0034774]; BMP receptor binding [GO: 0070700]; cysteine-type endopeptidase activator activity involved in apoptotic process [GO: 0008656]; cysteine-type endopeptidase activity involved in apoptotic process [GO: 0097153]; enzyme binding [GO: 0019899]; identical protein binding [GO: 0042802]; interleukin-6 receptor binding [GO: 0005138]; ion channel binding [GO: 0044325]; myosin I binding [GO: 0017024]; protease binding [GO: 0002020]; protein dimerization activity [GO: 0046983]; protein homodimerization activity [GO: 0042803]; Pyrin domain binding [GO: 0032090]; tropomyosin binding [GO: 0005523]; activation of cysteine-type endopeptidase activity [GO: 0097202]; activation of cysteine-type endopeptidase activity involved in apoptotic process [GO: 0006919]; activation of innate immune response [GO: 0002218]; apoptotic process [GO: 0006915]; cellular response to interleukin-1 [GO: 0071347]; cellular response to lipopolysaccharide [GO: 0071222]; cellular response to tumor necrosis factor [GO: 0071356]; defense |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | response to Gram-negative bacterium [GO: 0050829]; defense response to virus [GO: 0051607]; inflammatory response [GO: 0006954]; innate immune response [GO: 0045087]; intrinsic apoptotic signaling pathway by p53 class mediator [GO: 0072332]; intrinsic apoptotic signaling pathway in response to DNA damage by p53 class mediator [GO: 0042771]; macropinocytosis [GO: 0044351]; myeloid dendritic cell activation [GO: 0001773]; myeloid dendritic cell activation involved in immune response [GO: 0002277]; negative regulation of cytokine production involved in inflammatory response [GO:1900016]; negative regulation of I-kappaB kinase/NF-kappaB signaling [GO: 0043124]; negative regulation of interferon-beta production [GO: 0032688]; negative regulation of NF-kappaB transcription factor activity [GO: 0032088]; negative regulation of protein serine/threonine kinase activity [GO: 0071901]; neutrophil degranulation [GO: 0043312]; positive regulation of actin filament polymerization [GO: 0030838]; positive regulation of activated T cell proliferation [GO: 0042104]; positive regulation of adaptive immune response [GO: 0002821]; positive regulation of antigen processing and presentation of peptide antigen via MHC class II [GO: 0002588]; positive regulation of apoptotic process [GO: 0043065]; positive regulation of chemokine production [GO: 0032722]; positive regulation of cysteine-type endopeptidase activity [GO:2001056]; positive regulation of |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | cysteine-type endopeptidase activity involved in apoptotic process [GO: 0043280]; positive regulation of defense response to virus by host [GO: 0002230]; positive regulation of DNA-binding transcription factor activity [GO: 0051091]; positive regulation of ERK1 and ERK2 cascade [GO: 0070374]; positive regulation of extrinsic apoptotic signaling pathway [GO:2001238]; positive regulation of interferon-gamma production [GO: 0032729]; positive regulation of interleukin-1 beta production [GO: 0032731]; positive regulation of interleukin-10 production [GO: 0032733]; positive regulation of interleukin-6 production [GO: 0032755]; positive regulation of interleukin-8 production [GO: 0032757]; positive regulation of JNK cascade [GO: 0046330]; positive regulation of NF-kappaB transcription factor activity [GO: 0051092]; positive regulation of phagocytosis [GO: 0050766]; positive regulation of release of cytochrome c from mitochondria [GO: 0090200]; positive regulation of T cell activation [GO: 0050870]; positive regulation of T cell migration [GO:2000406]; positive regulation of tumor necrosis factor production [GO: 0032760]; protein homooligomerization [GO: 0051260]; purinergic nucleotide receptor signaling pathway [GO: 0035590]; regulation of autophagy [GO: 0010506]; regulation of GTPase activity [GO: 0043087]; regulation of inflammatory response |

TABLE 7-continued

| Uniprot ID | Abbrev. name | Control average | AtRisk average | Control vs Risk delta | Anova p-value | ProteinName | GO |
|---|---|---|---|---|---|---|---|
| P05362 | ICAM1 | 20,061 | 45,436 | 2.26 | 0.034 | Intercellular adhesion molecule 1 (ICAM-1) (Major group rhinovirus receptor) (CD antigen CD54) | [GO: 0050727]; regulation of intrinsic apoptotic signaling pathway [GO:2001242]; regulation of protein stability [GO: 0031647]; regulation of tumor necrosis factor-mediated signaling pathway [GO: 0010803]; signal transduction [GO: 0007165]; tumor necrosis factor-mediated signaling pathway [GO: 0033209] cell surface [GO: 0009986]; collagen-containing extracellular matrix [GO: 0062023]; external side of plasma membrane [GO: 0009897]; extracellular exosome [GO: 0070062]; extracellular space [GO: 0005615]; focal adhesion [GO: 0005925]; immunological synapse [GO: 0001772]; integral component of plasma membrane [GO: 0005887]; membrane [GO: 0016020]; membrane raft [GO: 0045121]; plasma membrane [GO: 0005886]; integrin binding [GO: 0005178]; signaling receptor activity [GO: 0038023]; transmembrane signaling receptor activity [GO: 0004888]; virus receptor activity [GO: 0001618]; acute inflammatory response to antigenic stimulus [GO: 0002438]; adhesion of symbiont to host [GO: 0044406]; cell adhesion [GO: 0007155]; cell adhesion mediated by integrin [GO: 0033627]; cell aging [GO: 0007569]; cellular response to alkaloid [GO: 0071312]; cellular response to amyloid-beta [GO:1904646]; cellular response to dexamethasone stimulus [GO: 0071549]; cellular response to glucose stimulus [GO: 0071333]; cellular response to hypoxia [GO: 0071456]; cellular response to interleukin-1 |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0071347]; cellular response to interleukin-6 [GO: 0071354]; cellular response to leukemia inhibitory factor [GO:1990830]; cellular response to lipopolysaccharide [GO: 0071222]; cellular response to nutrient levels [GO: 0031669]; cellular response to tumor necrosis factor [GO: 0071356]; cytokine-mediated signaling pathway [GO: 0019221]; establishment of endothelial barrier [GO: 0061028]; establishment of endothelial intestinal barrier [GO: 0090557]; establishment of Sertoli cell barrier [GO: 0097368]; extracellular matrix organization [GO: 0030198]; heterophilic cell-cell adhesion via plasma membrane cell adhesion molecules [GO: 0007157]; interferon-gamma-mediated signaling pathway [GO: 0060333]; leukocyte cell-cell adhesion [GO: 0007159]; leukocyte migration [GO: 0050900]; membrane to membrane docking [GO: 0022614]; negative regulation of calcium ion transport [GO: 0051926]; negative regulation of endothelial cell apoptotic process [GO:2000352]; negative regulation of extrinsic apoptotic signaling pathway via death domain receptors [GO:1902042]; ovarian follicle development [GO: 0001541]; positive regulation of actin filament polymerization [GO: 0030838]; positive regulation of cellular extravasation [GO: 0002693]; positive regulation of ERK1 and ERK2 cascade [GO: 0070374]; positive regulation of GTPase activity [GO: 0043547]; positive regulation of |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | leukocyte adhesion to vascular endothelial cell [GO:1904996]; positive regulation of NF-kappaB transcription factor activity [GO: 0051092]; positive regulation of nitric oxide biosynthetic process [GO: 0045429]; positive regulation of peptidyl-tyrosine phosphorylation [GO: 0050731]; positive regulation of vasoconstriction [GO: 0045907]; receptor-mediated virion attachment to host cell [GO: 0046813]; regulation of cell shape [GO: 0008360]; regulation of immune response [GO: 0050776]; regulation of leukocyte mediated cytotoxicity [GO: 0001910]; regulation of ruffle assembly [GO:1900027]; response to amino acid [GO: 0043200]; response to amphetamine [GO: 0001975]; response to copper ion [GO: 0046688]; response to drug [GO: 0042493]; response to ethanol [GO: 0045471]; response to gonadotropin [GO: 0034698]; response to insulin [GO: 0032868]; response to ionizing radiation [GO: 0010212]; response to sulfur dioxide [GO: 0010477]; sensory perception of sound [GO: 0007605]; T cell activation via T cell receptor contact with antigen bound to MHC molecule on antigen presenting cell [GO: 0002291]; T cell antigen processing and presentation [GO: 0002457]; T cell extravasation [GO: 0072683] |
| Q6UWP8 | SBSN | 1,193,666 | 2,695,523 | 2.26 | 0.023 | Suprabasin | extracellular exosome [GO: 0070062] |
| P61254 | RL26 | 56,705 | 126,610 | 2.23 | 0.020 | 60S ribosomal protein L26 (Large ribosomal subunit protein uL24) | cytoplasm [GO: 0005737]; cytosol [GO: 0005829]; cytosolic large ribosomal subunit [GO: 0022625]; cytosolic ribosome |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0022626]; extracellular exosome [GO: 0070062]; membrane [GO: 0016020]; nucleolus [GO: 0005730]; nucleoplasm [GO: 0005654]; ribonucleoprotein complex [GO: 1990904]; mRNA 5'-UTR binding [GO: 0048027]; RNA binding [GO: 0003723]; structural constituent of ribosome [GO: 0003735]; cellular response to gamma radiation [GO: 0071480]; cellular response to UV [GO: 0034644]; cytoplasmic translation [GO: 0002181]; DNA damage response, signal transduction by p53 class mediator resulting in cell cycle arrest [GO: 0006977]; nuclear-transcribed mRNA catabolic process, nonsense-mediated decay [GO: 0000184]; positive regulation of DNA damage response, signal transduction by p53 class mediator resulting in transcription of p21 class mediator [GO:1902164]; positive regulation of intrinsic apoptotic signaling pathway in response to DNA damage by p53 class mediator [GO: 1902167]; positive regulation of translation [GO: 0045727]; regulation of translation involved in cellular response to UV [GO: 1904803]; ribosomal large subunit biogenesis [GO: 0042273]; rRNA processing [GO: 0006364]; SRP-dependent cotranslational protein targeting to membrane [GO: 0006614]; translation [GO: 0006412]; translational initiation [GO: 0006413]; viral transcription [GO: 0019083] |
| Q14624 | ITIH4 | 719,434 | 1,598,075 | 2.22 | 0.013 | Inter-alpha-trypsin inhibitor heavy chain H4 (ITI heavy chain H4) (ITI-HC4) (Inter-alpha-inhibitor heavy chain 4) | blood microparticle [GO: 0072562]; collagen-containing extracellular matrix [GO: 0062023]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | (Inter-alpha-trypsin inhibitor family heavy chain-related protein) (IHRP) (Plasma kallikrein sensitive glycoprotein 120) (Gp120) (PK-120) [Cleaved into: 70 kDa inter-alpha-trypsin inhibitor heavy chain H4; 35 kDa inter-alpha-trypsin inhibitor heavy chain H4] | extracellular exosome [GO: 0070062]; extracellular region [GO: 0005576]; platelet dense granule lumen [GO: 0031089]; endopeptidase inhibitor activity [GO: 0004866]; serine-type endopeptidase inhibitor activity [GO: 0004867]; acute-phase response [GO: 0006953]; hyaluronan metabolic process [GO: 0030212]; platelet degranulation [GO: 0002576]; response to cytokine [GO: 0034097] |
| P02750 | A2GL | 471,501 | 1,044,615 | 2.22 | 0.000 | Leucine-rich alpha-2-glycoprotein (LRG) | extracellular exosome [GO: 0070062]; extracellular region [GO: 0005576]; extracellular space [GO: 0005615]; ficolin-1-rich granule lumen [GO:1904813]; intracellular membrane-bounded organelle [GO: 0043231]; membrane [GO: 0016020]; specific granule lumen [GO: 0035580]; tertiary granule lumen [GO:1904724]; transforming growth factor beta receptor binding [GO: 0005160]; brown fat cell differentiation [GO: 0050873]; neutrophil degranulation [GO: 0043312]; positive regulation of angiogenesis [GO: 0045766]; positive regulation of endothelial cell proliferation [GO: 0001938]; positive regulation of transforming growth factor beta receptor signaling pathway [GO: 0030511]; response to bacterium [GO: 0009617] |
| P82979 | SARNP | 213,117 | 96,270 | 2.21 | 0.049 | SAP domain-containing ribonucleoprotein (Cytokine-induced protein of 29 kDa) (Nuclear protein Hcc-1) (Proliferation-associated cytokine-inducible protein CIP29) | cytoplasmic ribonucleoprotein granule [GO: 0036464]; nuclear speck [GO: 0016607]; nucleoplasm [GO: 0005654]; nucleus [GO: 0005634]; transcription export complex [GO: 0000346]; DNA binding [GO: 0003677]; RNA binding [GO: 0003723]; mRNA 3'-end |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | processing [GO: 0031124]; mRNA export from nucleus [GO: 0006406]; poly(A)+ mRNA export from nucleus [GO: 0016973]; regulation of translation [GO: 0006417]; RNA export from nucleus [GO: 0006405] |
| P61086 | UBE2K | 22,994 | 50,294 | 2.19 | 0.025 | Ubiquitin-conjugating enzyme E2 K (EC 2.3.2.23) (E2 ubiquitin-conjugating enzyme K) (Huntingtin-interacting protein 2) (HIP-2) (Ubiquitin carrier protein) (Ubiquitin-conjugating enzyme E2-25 kDa) (Ubiquitin-conjugating enzyme E2(25K)) (Ubiquitin-conjugating enzyme E2-25K) (Ubiquitin-protein ligase) | cytosol [GO: 0005829]; filopodium tip [GO: 0032433]; nucleus [GO: 0005634]; ATP binding [GO: 0005524]; ubiquitin conjugating enzyme activity [GO: 0061631]; ubiquitin protein ligase binding [GO: 0031625]; ubiquitin-protein transferase activity [GO: 0004842]; ubiquitin-ubiquitin ligase activity [GO: 0034450]; cellular response to interferon-beta [GO: 0035458]; free ubiquitin chain polymerization [GO: 0010994]; intrinsic apoptotic signaling pathway in response to endoplasmic reticulum stress [GO: 0070059]; positive regulation of peptidyl-threonine phosphorylation [GO: 0010800]; positive regulation of tumor necrosis factor-mediated signaling pathway [GO: 1903265]; positive regulation of type I interferon-mediated signaling pathway [GO: 0060340]; proteasome-mediated ubiquitin-dependent protein catabolic process [GO: 0043161]; protein K48-linked ubiquitination [GO: 0070936]; protein polyubiquitination [GO: 0000209]; protein ubiquitination [GO: 0016567]; regulation of proteasomal ubiquitin-dependent protein catabolic process [GO: 0032434]; ubiquitin-dependent protein catabolic process [GO: 0006511] |
| P01040 | CYTA | 446,666 | 968,059 | 2.17 | 0.024 | Cystatin-A (Cystatin-AS) (Stefin-A) [Cleaved into: Cystatin-A, N-terminally processed] | cornified envelope [GO: 0001533]; cytoplasm [GO: 0005737]; cytosol [GO: 0005829]; extracellular space [GO: 0005615]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | nucleoplasm [GO: 0005654]; cysteine-type endopeptidase inhibitor activity [GO: 0004869]; protease binding [GO: 0002020]; cell-cell adhesion [GO: 0098609]; cornification [GO: 0070268]; keratinocyte differentiation [GO: 0030216]; negative regulation of peptidase activity [GO: 0010466]; negative regulation of proteolysis [GO: 0045861]; peptide cross-linking [GO: 0018149] |
| Q9NVG8 | TBC13 | 43,672 | 20,263 | 2.16 | 0.024 | TBC1 domain family member 13 | cytosol [GO: 0005829]; membrane [GO: 0016020]; GTPase activator activity [GO: 0005096]; small GTPase binding [GO: 0031267]; activation of GTPase activity [GO: 0090630]; intracellular protein transport [GO: 0006886] |
| P68363 | TBA1B | 474,945 | 221,191 | 2.15 | 0.039 | Tubulin alpha-1B chain (Alpha-tubulin ubiquitous) (Tubulin K-alpha-1) (Tubulin alpha-ubiquitous chain) [Cleaved into: Detyrosinated tubulin alpha-1B chain] | cytoplasm [GO: 0005737]; cytoplasmic microtubule [GO: 0005881]; membrane raft [GO: 0045121]; microtubule [GO: 0005874]; microtubule cytoskeleton [GO: 0015630]; double-stranded RNA binding [GO: 0003725]; GTP binding [GO: 0005525]; GTPase activity [GO: 0003924]; structural constituent of cytoskeleton [GO: 0005200]; structural molecule activity [GO: 0005198]; ubiquitin protein ligase binding [GO: 0031625]; cell division [GO: 0051301]; cellular response to interleukin-4 [GO: 0071353]; cytoskeleton-dependent intracellular transport [GO: 0030705]; |
| P19021 | AMD | 1,321,341 | 618,430 | 2.14 | 0.000 | Peptidyl-glycine alpha-amidating monooxygenase (PAM) [Includes: Peptidylglycine alpha-hydroxylating monooxygenase (PHM) | microtubule cytoskeleton organization [GO: 0000226]; microtubule-based process [GO: 0007017]; mitotic cell cycle |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | (EC 1.14.17.3); Peptidyl-alpha-hydroxyglycine alpha-amidating lyase (EC 4.3.2.5) (Peptidylamidoglycolate lyase) (PAL)] | [GO: 0000278] cell surface [GO: 0009986]; extracellular exosome [GO: 0070062]; extracellular region [GO: 0005576]; integral component of membrane [GO: 0016021]; membrane [GO: 0016020]; neuron projection [GO: 0043005]; perikaryon [GO: 0043204]; perinuclear region of cytoplasm [GO: 0048471]; plasma membrane [GO: 0005886]; secretory granule membrane [GO: 0030667]; trans-Golgi network [GO: 0005802]; transport vesicle membrane [GO: 0030658]; calcium ion binding [GO: 0005509]; copper ion binding [GO: 0005507]; identical protein binding [GO: 0042802]; L-ascorbic acid binding [GO: 0031418]; peptidylamidoglycolate lyase activity [GO: 0004598]; peptidylglycine monooxygenase activity [GO: 0004504]; protein kinase binding [GO: 0019901]; zinc ion binding [GO: 0008270]; central nervous system development [GO: 0007417]; fatty acid primary amide biosynthetic process [GO: 0062112]; heart development [GO: 0007507]; lactation [GO: 0007595]; limb development [GO: 0060173]; long-chain fatty acid metabolic process [GO: 0001676]; maternal process involved in female pregnancy [GO: 0060135]; odontogenesis [GO: 0042476]; ovulation cycle process [GO: 0022602]; peptide amidation [GO: 0001519]; protein amidation [GO: 0018032]; regulation of actin cytoskeleton |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | organization [GO: 0032956]; regulation of protein secretion [GO: 0050708]; regulation of transcription by RNA polymerase II [GO: 0006357]; response to copper ion [GO: 0046688]; response to drug [GO: 0042493]; response to estradiol [GO: 0032355]; response to glucocorticoid |
| O00244 | ATOX1 | 12,336 | 26,304 | 2.13 | 0.034 | Copper transport protein ATOX1 (Metal transport protein ATX1) | [GO: 0051384]; response to hypoxia [GO: 0001666]; response to pH [GO: 0009268]; response to zinc ion [GO: 0010043]; toxin metabolic process [GO: 0009404] cytosol [GO: 0005829]; copper chaperone activity [GO: 0016531]; copper ion binding [GO: 0005507]; copper-dependent protein binding [GO: 0032767]; cuprous ion binding [GO:1903136]; metallochaperone activity [GO: 0016530]; cellular copper ion homeostasis [GO: 0006878]; copper ion transport [GO: 0006825]; response to oxidative stress [GO: 0006979] |
| P31948 | STIP1 | 183,292 | 86,306 | 2.12 | 0.044 | Stress-induced-phosphoprotein 1 (STI1) (Hsc70/Hsp90-organizing protein) (Hop) (Renal carcinoma antigen NY-REN-11) (Transformation-sensitive protein IEF SSP 3521) | chaperone complex [GO: 0101031]; cytosol [GO: 0005829]; Golgi apparatus [GO: 0005794]; nucleus [GO: 0005634]; protein-containing complex [GO: 0032991]; chaperone binding [GO: 0051087]; Hsp70 protein binding [GO: 0030544]; Hsp90 protein binding [GO: 0051879]; protein C-terminus binding [GO: 0008022]; RNA binding [GO: 0003723]; cellular response to interleukin-7 [GO: 0098761] |
| P32969 | RL9 | 57,192 | 119,396 | 2.09 | 0.000 | 60S ribosomal protein L9 (Large ribosomal subunit protein uL6) | cytosol [GO: 0005829]; cytosolic large ribosomal subunit [GO: 0022625]; focal adhesion [GO: 0005925]; membrane [GO: 0016020]; nucleus [GO: 0005634]; ribosome [GO: 0005840]; RNA |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | binding [GO: 0003723]; rRNA binding [GO: 0019843]; structural constituent of ribosome [GO: 0003735]; cytoplasmic translation [GO: 0002181]; nuclear-transcribed mRNA catabolic process, nonsense-mediated decay [GO: 0000184]; rRNA processing [GO: 0006364]; SRP-dependent cotranslational protein targeting to membrane [GO: 0006614]; translation [GO: 0006412]; translational initiation [GO: 0006413]; viral transcription [GO: 0019083] |
| P13716 | HEM2 | 220,656 | 108,388 | 2.04 | 0.024 | Delta-aminolevulinic acid dehydratase (ALADH) (EC 4.2.1.24) (Porphobilinogen synthase) | cytosol [GO: 0005829]; extracellular exosome [GO: 0070062]; extracellular region [GO: 0005576]; ficolin-1-rich granule lumen [GO: 1904813]; nucleus [GO: 0005634]; secretory granule lumen [GO: 0034774]; catalytic activity [GO: 0003824]; identical protein binding [GO: 0042802]; porphobilinogen synthase activity [GO: 0004655]; proteasome core complex binding [GO:1904854]; zinc ion binding [GO: 0008270]; cellular response to interleukin-4 [GO: 0071353]; cellular response to lead ion [GO: 0071284]; heme biosynthetic process [GO: 0006783]; negative regulation of proteasomal protein catabolic process [GO: 1901799]; neutrophil degranulation [GO: 0043312]; protein homooligomerization [GO: 0051260]; protoporphyrinogen IX biosynthetic process [GO: 0006782]; response to activity [GO: 0014823]; response to aluminum ion [GO: 0010044]; response to amino acid [GO: 0043200]; response to arsenic-containing substance [GO: 0046685]; response to cadmium ion [GO: 0046686]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | response to cobalt ion [GO: 0032025]; response to drug [GO: 0042493]; response to ethanol [GO: 0045471]; response to fatty acid [GO: 0070542]; response to glucocorticoid [GO: 0051384]; response to herbicide [GO: 0009635]; response to hypoxia [GO: 0001666]; response to ionizing radiation [GO: 0010212]; response to iron ion [GO: 0010039]; response to lipopolysaccharide [GO: 0032496]; response to mercury ion [GO: 0046689]; response to methylmercury [GO: 0051597]; response to oxidative stress [GO: 0006979]; response to platinum ion [GO: 0070541]; response to selenium ion [GO: 0010269]; response to vitamin B1 [GO: 0010266]; response to vitamin E [GO: 0033197]; response to zinc ion [GO: 0010043] |
| O75071 | EFC14 | 22,803 | 46,304 | 2.03 | 0.036 | EF-hand calcium-binding domain-containing protein 14 | calcium ion binding [GO: 0005509] |
| O95793 | STAU1 | 51,349 | 25,481 | 2.02 | 0.047 | Double-stranded RNA-binding protein Staufen homolog 1 | cell body [GO: 0044297]; cytoplasm [GO: 0005737]; cytoplasmic ribonucleoprotein granule [GO: 0036464]; cytoplasmic stress granule [GO: 0010494]; cytosol [GO: 0005829]; dendrite [GO: 0030425]; endoplasmic reticulum [GO: 0005783]; extracellular exosome [GO: 0070062]; glutamatergic synapse [GO: 0098978]; membrane [GO: 0016020]; microtubule associated complex [GO: 0005875]; neuronal cell body [GO: 0043025]; plasma membrane [GO: 0005886]; rough endoplasmic reticulum [GO: 0005791]; double-stranded RNA binding [GO: 0003725]; protein phosphatase 1 binding [GO: 0008157]; RNA |

TABLE 7-continued

| Uniprot ID | Abbrev. name | Control average | AtRisk average | Control vs Risk delta | Anova p-value | ProteinName | GO |
|---|---|---|---|---|---|---|---|
| O1551 | ARPC5 | 462,740 | 929,606 | 2.01 | 0.009 | Actin-related protein 2/3 complex subunit 5 (Arp2/3 complex 16 kDa subunit) (p16-ARC) | binding [GO: 0003723]; cellular response to oxidative stress [GO: 0034599]; modification of postsynaptic structure [GO: 0099010]; positive regulation by virus of viral protein levels in host cell [GO: 0046726]; positive regulation of long-term synaptic potentiation [GO: 1900273]; positive regulation of viral genome replication [GO: 0045070]; viral process [GO: 0016032] actin cytoskeleton [GO: 0015629]; Arp2/3 protein complex [GO: 0005885]; cytoplasm [GO: 0005737]; cytosol [GO: 0005829]; endosome [GO: 0005768]; extracellular exosome [GO: 0070062]; extracellular region [GO: 0005576]; ficolin-1-rich granule lumen [GO: 1904813]; focal adhesion [GO: 0005925]; growth cone [GO: 0030426]; lamellipodium [GO: 0030027]; nucleus [GO: 0005634]; secretory granule lumen [GO: 0034774]; site of double-strand break [GO: 0035861]; actin binding [GO: 0003779]; structural constituent of cytoskeleton [GO: 0005200]; actin cytoskeleton organization [GO: 0030036]; actin filament network formation [GO: 0051639]; Arp2/3 complex-mediated actin nucleation [GO: 0034314]; cell migration [GO: 0016477]; ephrin receptor signaling pathway [GO: 0048013]; Fc-gamma receptor signaling pathway involved in phagocytosis [GO: 0038096]; lamellipodium organization [GO: 0097581]; maintenance of cell polarity [GO: 0030011]; membrane organization [GO: 0061024]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | microtubule organizing center localization [GO: 0061842]; neutrophil degranulation [GO: 0043312]; orbitofrontal cortex development [GO: 0021769]; smooth muscle cell migration [GO: 0014909] |
| O75531 | BAF | 25,077 | 50,325 | 2.01 | 0.021 | Barrier-to-autointegration factor (Breakpoint cluster region protein 1) [Cleaved into: Barrier-to-autointegration factor, N-terminally processed] | condensed chromosome [GO: 0000793]; cytoplasm [GO: 0005737]; cytosol [GO: 0005829]; nuclear envelope [GO: 0005635]; nucleoplasm [GO: 0005654]; nucleus [GO: 0005634]; DNA binding [GO: 0003677]; enzyme binding [GO: 0019899]; identical protein binding [GO: 0042802]; LEM domain binding [GO: 0097726]; protein C-terminus binding [GO: 0008022]; protein homodimerization activity [GO: 0042803]; protein N-terminus binding [GO: 0047485]; chromosome condensation [GO: 0030261]; chromosome segregation [GO: 0007059]; DNA integration [GO: 0015074]; establishment of integrated proviral latency [GO: 0075713]; mitotic nuclear envelope reassembly [GO: 0007084]; negative regulation of viral genome replication [GO: 0045071]; nuclear transport [GO: 0051169]; response to virus [GO: 0009615] |
| P01019 | ANGT | 51,445 | 102,940 | 2.00 | 0.037 | Angiotensinogen (Serpin A8) [Cleaved into: Angiotensin-1 (Angiotensin 1-10) (Angiotensin I) (Ang I); Angiotensin-2 (Angiotensin 1-8) (Angiotensin II) (Ang II); Angiotensin-3 (Angiotensin 2-8) (Angiotensin III) (Ang III) (Des-Asp[1]-angiotensin II); Angiotensin-4 (Angiotensin 3-8) (Angiotensin IV) (Ang IV); Angiotensin 1-9; Angiotensin 1-7; | blood microparticle [GO: 0072562]; collagen-containing extracellular matrix [GO: 0062023]; cytosol [GO: 0005829]; extracellular exosome [GO: 0070062]; extracellular region [GO: 0005576]; extracellular space [GO: 0005615]; growth factor activity [GO: 0008083]; hormone activity [GO: 0005179]; receptor ligand activity [GO: 0048018]; serine- |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | Angiotensin 1-5; Angiotensin 1-4] | type endopeptidase inhibitor activity [GO: 0004867]; sodium channel regulator activity [GO: 0017080]; superoxide-generating NADPH oxidase activator activity [GO: 0016176]; type 1 angiotensin receptor binding [GO: 0031702]; type 2 angiotensin receptor binding [GO: 0031703]; activation of MAPK activity [GO: 0000187]; angiotensin-activated signaling pathway [GO: 0038166]; blood vessel remodeling [GO: 0001974]; cell-cell signaling [GO: 0007267]; G protein-coupled receptor signaling pathway [GO: 0007186]; G protein-coupled receptor signaling pathway coupled to cGMP nucleotide second messenger [GO: 0007199]; kidney development [GO: 0001822]; low-density lipoprotein particle remodeling [GO: 0034374]; maintenance of blood vessel diameter homeostasis by renin-angiotensin [GO: 0002034]; negative regulation of endopeptidase activity [GO: 0010951]; negative regulation of gene expression [GO: 0010629]; negative regulation of MAP kinase activity [GO: 0043407]; negative regulation of neurotrophin TRK receptor signaling pathway [GO: 0051387]; negative regulation of sodium ion transmembrane transporter activity [GO:2000650]; nitric oxide mediated signal transduction [GO: 0007263]; phospholipase C-activating G protein-coupled receptor signaling pathway [GO: 0007200]; positive regulation of activation of Janus kinase activity [GO: 0010536]; positive regulation of branching involved in ureteric bud |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | morphogenesis [GO: 0090190]; positive regulation of cardiac muscle hypertrophy [GO: 0010613]; positive regulation of cellular protein metabolic process [GO: 0032270]; positive regulation of cholesterol esterification [GO: 0010873]; positive regulation of cytokine production [GO: 0001819]; positive regulation of endothelial cell migration [GO: 0010595]; positive regulation of epidermal growth factor receptor signaling pathway [GO: 0045742]; positive regulation of extrinsic apoptotic signaling pathway [GO:2001238]; positive regulation of fibroblast proliferation [GO: 0048146]; positive regulation of gap junction assembly [GO: 1903598]; positive regulation of inflammatory response [GO: 0050729]; positive regulation of macrophage derived foam cell differentiation [GO: 0010744]; positive regulation of membrane hyperpolarization [GO: 1902632]; positive regulation of NAD(P)H oxidase activity [GO: 0033864]; positive regulation of NF-kappaB transcription factor activity [GO: 0051092]; positive regulation of peptidyl-tyrosine phosphorylation [GO: 0050731]; positive regulation of phosphatidylinositol 3-kinase signaling [GO: 0014068]; positive regulation of protein tyrosine kinase activity [GO: 0061098]; positive regulation of reactive oxygen species metabolic process [GO:2000379]; positive regulation of transcription, DNA-templated [GO: 0045893]; regulation of blood pressure [GO: 0008217]; regulation of blood |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | volume by renin-angiotensin [GO: 0002016]; regulation of cardiac conduction [GO: 1903779]; regulation of cell growth [GO: 0001558]; regulation of cell population proliferation [GO: 0042127]; regulation of extracellular matrix assembly [GO:1901201]; regulation of metabolic process [GO: 0019222]; regulation of renal output by angiotensin [GO: 0002019]; regulation of renal sodium excretion [GO: 0035813]; regulation of vasoconstriction [GO: 0019229]; renal system process [GO: 0003014]; renin-angiotensin regulation of aldosterone production [GO: 0002018]; response to muscle activity involved in regulation of muscle adaptation [GO: 0014873]; vasoconstriction [GO: 0042310] |
| Q9Y5L4 | TIM13 | 95,356 | 190,669 | 2.00 | 0.003 | Mitochondrial import inner membrane translocase subunit Tim13 | fibrillar center [GO: 0001650]; mitochondrial inner membrane [GO: 0005743]; mitochondrial intermembrane space protein transporter complex [GO: 0042719]; mitochondrion [GO: 0005739]; zinc ion binding [GO: 0008270]; chaperone-mediated protein transport [GO: 0072321]; protein insertion into mitochondrial inner membrane [GO: 0045039]; protein targeting to mitochondrion [GO: 0006626]; sensory perception of sound [GO: 0007605] |
| Q9Y3C8 | UFC1 | 100,021 | 50,044 | 2.00 | 0.036 | Ubiquitin-fold modifier-conjugating enzyme 1 (Ufm1-conjugating enzyme 1) | extracellular exosome [GO: 0070062]; UFM1 conjugating enzyme activity [GO: 0061657]; UFM1 transferase activity [GO: 0071568]; brain development [GO: 0007420]; protein K69-linked ufmylation [GO: 1990592]; protein ufmylation |

TABLE 7-continued

| Uniprot ID | Abbrev. name | Control average | AtRisk average | Control vs Risk delta | Anova p-value | ProteinName | GO |
|---|---|---|---|---|---|---|---|
| Q24JP5 | T132A | 141,239 | 71,196 | 1.98 | 0.020 | Transmembrane protein 132A (HSPA5-binding protein 1) | [GO: 0071569]; response to endoplasmic reticulum stress [GO: 0034976]; reticulophagy [GO: 0061709] endoplasmic reticulum [GO: 0005783]; endoplasmic reticulum lumen [GO: 0005788]; endoplasmic reticulum membrane [GO: 0005789]; extracellular exosome [GO: 0070062]; Golgi apparatus [GO: 0005794]; Golgi membrane [GO: 0000139]; integral component of membrane [GO: 0016021]; cellular protein metabolic process [GO: 0044267]; post-translational protein modification [GO: 0043687] |
| Q9Y3Q8 | T22D4 | 29,167 | 57,158 | 1.96 | 0.047 | TSC22 domain family protein 4 (TSC22-related-inducible leucine zipper protein 2) (Tsc-22-like protein THG-1) | nucleus [GO: 0005634]; negative regulation of transcription, DNA-templated [GO: 0045892]; regulation of transcription by RNA polymerase II [GO: 0006357]; response to osmotic stress [GO: 0006970] |
| O60235 | TM11D | 626,942 | 1,224,393 | 1.95 | 0.028 | Transmembrane protease serine 11D (EC 3.4.21.-) (Airway trypsin-like protease) [Cleaved into: Transmembrane protease serine 11D non-catalytic chain; Transmembrane protease serine 11D catalytic chain] | extracellular exosome [GO: 0070062]; extracellular region [GO: 0005576]; integral component of plasma membrane [GO: 0005887]; peptidase activity [GO: 0008233]; serine-type endopeptidase activity [GO: 0004252]; proteolysis [GO: 0006508]; respiratory gaseous exchange by respiratory system [GO: 0007585] |
| P11586 | C1TC | 79,459 | 40,698 | 1.95 | 0.046 | C-1-tetrahydrofolate synthase, cytoplasmic (C1-THF synthase) [Cleaved into: C-1-tetrahydrofolate synthase, cytoplasmic, N-terminally processed] [Includes: Methylenetetrahydrofolate dehydrogenase (EC 1.5.1.5); Methenyltetrahydrofolate cyclohydrolase (EC 3.5.4.9); Formyltetrahydrofolate synthetase (EC 6.3.4.3)] | cytosol [GO: 0005829]; extracellular exosome [GO: 0070062]; membrane [GO: 0016020]; mitochondrion [GO: 0005739]; ATP binding [GO: 0005524]; formate-tetrahydrofolate ligase activity [GO: 0004329]; methenyltetrahydrofolate cyclohydrolase activity [GO: 0004477]; methylenetetrahydrofolate dehydrogenase (NAD+) activity [GO: 0004487]; methylenetetrahydrofolate dehydrogenase |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | (NADP+) activity [GO: 0004488]; methylenetetrahydrofolate dehydrogenase [NAD(P)+] activity [GO: 0004486]; 10-formyltetrahydrofolate biosynthetic process [GO: 0009257]; embryonic neurocranium morphogenesis [GO: 0048702]; embryonic viscerocranium morphogenesis [GO: 0048703]; folic acid metabolic process [GO: 0046655]; heart development [GO: 0007507]; histidine biosynthetic process [GO: 0000105]; methionine biosynthetic process [GO: 0009086]; methionine metabolic process [GO: 0006555]; neural tube closure [GO: 0001843]; one-carbon metabolic process [GO: 0006730]; purine nucleotide biosynthetic process [GO: 0006164]; serine family amino acid biosynthetic process [GO: 0009070]; serine family amino acid metabolic process [GO: 0009069]; somite development [GO: 0061053]; tetrahydrofolate interconversion [GO: 0035999] |
| Q15814 | TBCC | 93,935 | 48,145 | 1.95 | 0.026 | Tubulin-specific chaperone C (Tubulin-folding cofactor C) (CFC) | cytoplasm [GO: 0005737]; cytoskeleton [GO: 0005856]; cytosol [GO: 0005829]; microtubule [GO: 0005874]; photoreceptor connecting cilium [GO: 0032391]; chaperone binding [GO: 0051087]; GTPase activity [GO: 0003924]; tubulin binding [GO: 0015631]; cell morphogenesis [GO: 0000902]; post-chaperonin tubulin folding pathway [GO: 0007023]; protein folding [GO: 0006457]; tubulin complex assembly [GO: 0007021] |
| P07919 | QCR6 | 110,633 | 214,983 | 1.94 | 0.045 | Cytochrome b-c1 complex subunit 6, mitochondrial (Complex III subunit 6) (Complex III subunit | mitochondrial inner membrane [GO: 0005743]; mitochondrial respirasome |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | VIII) (Cytochrome c1 non-heme 11 kDa protein) (Mitochondrial hinge protein) (Ubiquinol-cytochrome c reductase complex 11 kDa protein) | [GO: 0005746]; mitochondrial respiratory chain complex III [GO: 0005750]; mitochondrion [GO: 0005739]; ubiquinol-cytochrome-c reductase activity [GO: 0008121]; aerobic respiration [GO: 0009060]; mitochondrial electron transport, ubiquinol to cytochrome c [GO: 0006122]; oxidative phosphorylation [GO: 0006119] |
| P02790 | HEMO | 2,258,007 | 4,369,070 | 1.93 | 0.027 | Hemopexin (Beta-1B-glycoprotein) | blood microparticle [GO: 0072562]; collagen-containing extracellular matrix [GO: 0062023]; endocytic vesicle lumen [GO: 0071682]; extracellular exosome [GO: 0070062]; extracellular region [GO: 0005576]; extracellular space [GO: 0005615]; heme transmembrane transporter activity [GO: 0015232]; metal ion binding [GO: 0046872]; cellular iron ion homeostasis [GO: 0006879]; heme metabolic process [GO: 0042168]; heme transport [GO: 0015886]; hemoglobin metabolic process [GO: 0020027]; positive regulation of humoral immune response mediated by circulating immunoglobulin [GO: 0002925]; positive regulation of immunoglobulin production [GO: 0002639]; positive regulation of interferon-gamma-mediated signaling pathway [GO: 0060335]; positive regulation of tyrosine phosphorylation of STAT protein [GO: 0042531]; receptor-mediated endocytosis [GO: 0006898]; viral process [GO: 0016032] |
| Q9NPA8 | ENY2 | 28,926 | 55,945 | 1.93 | 0.040 | Transcription and mRNA export factor ENY2 (Enhancer of yellow 2 transcription factor homolog) | DUBm complex [GO: 0071819]; mitochondrion [GO: 0005739]; nuclear pore nuclear basket [GO: 0044615]; nucleoplasm |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0005654]; SAGA complex [GO: 0000124]; transcription export complex 2 [GO: 0070390]; chromatin binding [GO: 0003682]; nuclear receptor coactivator activity [GO: 0030374]; transcription coactivator activity [GO: 0003713]; histone deubiquitination [GO: 0016578]; negative regulation of insulin secretion involved in cellular response to glucose stimulus [GO: 0061179]; poly(A)+ mRNA export from nucleus [GO: 0016973]; positive regulation of transcription, DNA-templated [GO: 0045893]; regulation of transcription by RNA polymerase II [GO: 0006357]; transcription elongation from RNA polymerase II promoter [GO: 0006368] |
| P25311 | ZA2G | 33,074,828 | 63,955,674 | 1.93 | 0.047 | Zinc-alpha-2-glycoprotein (Zn-alpha-2-GP) (Zn-alpha-2-glycoprotein) | collagen-containing extracellular matrix [GO: 0062023]; external side of plasma membrane [GO: 0009897]; extracellular exosome [GO: 0070062]; extracellular region [GO: 0005576]; extracellular space [GO: 0005615]; nucleus [GO: 0005634]; protein transmembrane transporter activity [GO: 0008320]; ribonuclease activity [GO: 0004540]; antigen processing and presentation of endogenous peptide antigen via MHC class Ib [GO: 0002476]; cell adhesion [GO: 0007155]; detection of chemical stimulus involved in sensory perception of bitter taste [GO: 0001580]; negative regulation of cell population proliferation [GO: 0008285]; retina homeostasis [GO: 0001895]; transmembrane transport [GO: 0055085] |

TABLE 7-continued

| Uniprot ID | Abbrev. name | Control average | AtRisk average | Control vs Risk delta | Anova p-value | ProteinName | GO |
|---|---|---|---|---|---|---|---|
| O60506 | HNRPQ | 214,821 | 413,769 | 1.93 | 0.029 | Heterogeneous nuclear ribonucleoprotein Q (hnRNP Q) (Glycine- and tyrosine-rich RNA-binding protein) (GRY-RBP) (NS1-associated protein 1) (Synaptotagmin-binding, cytoplasmic RNA-interacting protein) | catalytic step 2 spliceosome [GO: 0071013]; CRD-mediated mRNA stability complex [GO: 0070937]; endoplasmic reticulum [GO: 0005783]; GAIT complex [GO: 0097452]; histone pre-mRNA 3'end processing complex [GO: 0071204]; membrane [GO: 0016020]; nucleoplasm [GO: 0005654]; nucleus [GO: 0005634]; ribonucleoprotein complex [GO: 1990904]; mRNA 5'-UTR binding [GO: 0048027]; mRNA binding [GO: 0003729]; RNA binding [GO: 0003723]; cellular response to interferon-gamma [GO: 0071346]; CRD-mediated mRNA stabilization [GO: 0070934]; mRNA splicing, via spliceosome [GO: 0000398]; negative regulation of translation [GO: 0017148]; osteoblast differentiation [GO: 0001649]; RNA processing [GO: 0006396]; RNA splicing [GO: 0008380]; viral process [GO: 0016032] |
| P51993 | FUT6 | 93,932 | 48,948 | 1.92 | 0.017 | 4-galactosyl-N-acetylglucosaminide 3-alpha-L-fucosyltransferase FUT6 (EC 2.4.1.152) (Fucosyltransferase 6) (Fucosyltransferase VI) (Fuc-TVI) (FucT-VI) (Galactoside 3-L-fucosyltransferase) | extracellular exosome [GO: 0070062]; extracellular region [GO: 0005576]; Golgi apparatus [GO: 0005794]; Golgi cisterna membrane [GO: 0032580]; Golgi membrane [GO: 0000139]; integral component of membrane [GO: 0016021]; 4-galactosyl-N-acetylglucosaminide 3-alpha-L-fucosyltransferase activity [GO: 0017083]; alpha-(1->3)-fucosyltransferase activity [GO: 0046920]; fucosyltransferase activity [GO: 0008417]; ceramide metabolic process [GO: 0006672]; fucosylation [GO: 0036065]; L-fucose catabolic process [GO: 0042355]; N-glycan fucosylation [GO: 0036071]; oligosaccharide |

TABLE 7-continued

| Uniprot ID | Abbrev. name | Control average | AtRisk average | Control vs Risk delta | Anova p-value | ProteinName | GO |
|---|---|---|---|---|---|---|---|
| P0DOY2 | IGLC2 | 36,285,258 | 18,916,758 | 1.92 | 0.023 | Immunoglobulin lambda constant 2 (Ig lambda chain C region Kern) (Ig lambda chain C region NIG-64) (Ig lambda chain C region SH) (Ig lambda chain C region X) (Ig lambda-2 chain C region) | biosynthetic process [GO: 0009312]; protein glycosylation [GO: 0006486] blood microparticle [GO: 0072562]; external side of plasma membrane [GO: 0009897]; extracellular exosome [GO: 0070062]; extracellular region [GO: 0005576]; extracellular space [GO: 0005615]; immunoglobulin complex, circulating [GO: 0042571]; plasma membrane [GO: 0005886]; antigen binding [GO: 0003823]; immunoglobulin receptor binding [GO: 0034987]; B cell receptor signaling pathway [GO: 0050853]; complement activation [GO: 0006956]; complement activation, classical pathway [GO: 0006958]; defense response to bacterium [GO: 0042742]; Fc-epsilon receptor signaling pathway [GO: 0038095]; Fc-gamma receptor signaling pathway involved in phagocytosis [GO: 0038096]; innate immune response [GO: 0045087]; leukocyte migration [GO: 0050900]; negative regulation of inflammatory response to antigenic stimulus [GO: 0002862]; opsonization [GO: 0008228]; peptide cross-linking [GO: 0018149]; phagocytosis, engulfment [GO: 0006911]; phagocytosis, recognition [GO: 0006910]; positive regulation of B cell activation [GO: 0050871]; receptor-mediated endocytosis [GO: 0006898]; regulation of complement activation [GO: 0030449]; regulation of immune response [GO: 0050776] |
| Q12805 | FBLN3 | 96,101 | 50,162 | 1.92 | 0.048 | EGF-containing fibulin-like extracellular matrix protein 1 (Extracellular protein S1-5) (Fibrillin- | collagen-containing extracellular matrix [GO: 0062023]; extracellular exosome |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | like protein) (Fibulin-3) (FIBL-3) | [GO: 0070062]; extracellular matrix [GO: 0031012]; extracellular region [GO: 0005576]; extracellular space [GO: 0005615]; calcium ion binding [GO: 0005509]; epidermal growth factor receptor binding [GO: 0005154]; epidermal growth factor-activated receptor activity [GO: 0005006]; growth factor activity [GO: 0008083]; camera-type eye development [GO: 0043010]; embryonic eye morphogenesis [GO: 0048048]; epidermal growth factor receptor signaling pathway [GO: 0007173]; negative regulation of chondrocyte differentiation [GO: 0032331]; peptidyl-tyrosine phosphorylation [GO: 0018108]; post-embryonic eye morphogenesis [GO: 0048050]; regulation of transcription, DNA-templated [GO: 0006355]; visual perception [GO: 0007601] |
| P37802 | TAGL2 | 1,329,364 | 2,543,935 | 1.91 | 0.004 | Transgelin-2 (Epididymis tissue protein Li 7e) (SM22-alpha homolog) | cytosol [GO: 0005829]; extracellular exosome [GO: 0070062]; extracellular region [GO: 0005576]; vesicle [GO: 0031982]; cadherin binding [GO: 0045296]; epithelial cell differentiation [GO: 0030855]; platelet degranulation [GO: 0002576] |
| P04196 | HRG | 497,512 | 942,991 | 1.90 | 0.024 | Histidine-rich glycoprotein (Histidine-proline-rich glycoprotein) (HPRG) | blood microparticle [GO: 0072562]; cell surface [GO: 0009986]; collagen-containing extracellular matrix [GO: 0062023]; endolysosome [GO: 0036019]; extracellular exosome [GO: 0070062]; extracellular region [GO: 0005576]; plasma membrane [GO: 0005886]; platelet alpha granule lumen [GO: 0031093]; cysteine-type endopeptidase inhibitor activity |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0004869]; endopeptidase inhibitor activity [GO: 0004866]; heme binding [GO: 0020037]; heparan sulfate proteoglycan binding [GO: 0043395]; heparin binding [GO: 0008201]; immunoglobulin binding [GO: 0019865]; metal ion binding [GO: 0046872]; serine-type endopeptidase inhibitor activity [GO: 0004867]; signaling receptor binding [GO: 0005102]; zinc ion binding [GO: 0008270]; angiogenesis [GO: 0001525]; antimicrobial humoral immune response mediated by antimicrobial peptide [GO: 0061844]; chemotaxis [GO: 0006935]; cytolysis by host of symbiont cells [GO: 0051838]; defense response to fungus [GO: 0050832]; fibrinolysis [GO: 0042730]; heme transport [GO: 0015886]; negative regulation of angiogenesis [GO: 0016525]; negative regulation of blood vessel endothelial cell migration [GO: 0043537]; negative regulation of cell adhesion [GO: 0007162]; negative regulation of cell adhesion mediated by integrin [GO: 0033629]; negative regulation of cell growth [GO: 0030308]; negative regulation of cell population proliferation [GO: 0008285]; negative regulation of endopeptidase activity [GO: 0010951]; negative regulation of endothelial cell chemotaxis [GO:2001027]; negative regulation of fibrinolysis [GO: 0051918]; negative regulation of lamellipodium assembly [GO: 0010593]; negative regulation of vascular endothelial |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | growth factor signaling pathway [GO: 1900747]; platelet activation [GO: 0030168]; platelet degranulation [GO: 0002576]; positive regulation of apoptotic process [GO: 0043065]; positive regulation of blood vessel remodeling [GO:2000504]; positive regulation of focal adhesion assembly [GO: 0051894]; positive regulation of immune response to tumor cell [GO: 0002839]; regulation of actin cytoskeleton organization [GO: 0032956]; regulation of blood coagulation [GO: 0030193]; regulation of gene expression [GO: 0010468]; regulation of peptidyl-tyrosine phosphorylation [GO: 0050730]; regulation of platelet activation [GO: 0010543]; regulation of protein-containing complex assembly [GO: 0043254] |
| P17050 | NAGAB | 30,226 | 57,000 | 1.89 | 0.033 | Alpha-N-acetylgalactosaminidase (EC 3.2.1.49) (Alpha-galactosidase B) | cytoplasm [GO: 0005737]; extracellular exosome [GO: 0070062]; lysosome [GO: 0005764]; alpha-galactosidase activity [GO: 0004557]; alpha-N-acetylgalactosaminidase activity [GO: 0008456]; protein homodimerization activity [GO: 0042803]; carbohydrate catabolic process [GO: 0016052]; glycolipid catabolic process [GO: 0019377]; glycoside catabolic process [GO: 0016139]; glycosylceramide catabolic process [GO: 0046477]; oligosaccharide metabolic process [GO: 0009311] |
| P35813 | PPM1A | 31,211 | 16,721 | 1.87 | 0.020 | Protein phosphatase 1A (EC 3.1.3.16) (Protein phosphatase 2C isoform alpha) (PP2C-alpha) (Protein phosphatase IA) | cytosol [GO: 0005829]; membrane [GO: 0016020]; nucleoplasm [GO: 0005654]; nucleus [GO: 0005634]; plasma membrane [GO: 0005886]; calmodulin-dependent |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | protein phosphatase activity [GO: 0033192]; magnesium ion binding [GO: 0000287]; manganese ion binding [GO: 0030145]; protein serine phosphatase activity [GO: 0106306]; protein serine/threonine phosphatase activity [GO: 0004722]; protein threonine phosphatase activity [GO: 0106307]; R-SMAD binding [GO: 0070412]; cell cycle arrest [GO: 0007050]; cellular response to transforming growth factor beta stimulus [GO: 0071560]; dephosphorylation [GO: 0016311]; N-terminal protein myristoylation [GO: 0006499]; negative regulation of BMP signaling pathway [GO: 0030514]; negative regulation of I-kappaB kinase/NF-kappaB signaling [GO: 0043124]; negative regulation of NIK/NF-kappaB signaling [GO:1901223]; negative regulation of SMAD protein complex assembly [GO: 0010991]; negative regulation of transcription by RNA polymerase II [GO: 0000122]; negative regulation of transforming growth factor beta receptor signaling pathway [GO: 0030512]; peptidyl-threonine dephosphorylation [GO: 0035970]; positive regulation of canonical Wnt signaling pathway [GO: 0090263]; positive regulation of I-kappaB kinase/NF-kappaB signaling [GO: 0043123]; positive regulation of protein export from nucleus [GO: 0046827]; positive regulation of transcription, DNA-templated [GO: 0045893]; protein dephosphorylation [GO: 0006470] |

TABLE 7-continued

| Uniprot ID | Abbrev. name | Control average | AtRisk average | Control vs Risk delta | Anova p-value | ProteinName | GO |
|---|---|---|---|---|---|---|---|
| Q14254 | FLOT2 | 95,775 | 176,637 | 1.84 | 0.015 | Flotillin-2 (Epidermal surface antigen) (ESA) (Membrane component chromosome 17 surface marker 1) | adherens junction [GO: 0005912]; basolateral plasma membrane [GO: 0016323]; caveola [GO: 0005901]; cell-cell contact zone [GO: 0044291]; cytoplasmic vesicle [GO: 0031410]; endocytic vesicle [GO: 0030139]; endosome [GO: 0005768]; extracellular exosome [GO: 0070062]; flotillin complex [GO: 0016600]; focal adhesion [GO: 0005925]; intracellular membrane-bounded organelle [GO: 0043231]; lamellipodium [GO: 0030027]; membrane [GO: 0016020]; perinuclear region of cytoplasm [GO: 0048471]; plasma membrane [GO: 0005886]; uropod [GO: 0001931]; vesicle [GO: 0031982]; cell adhesion [GO: 0007155]; epidermis development [GO: 0008544]; membrane raft assembly [GO: 0001765]; negative regulation of amyloid precursor protein catabolic process [GO: 1902992]; negative regulation of gene expression [GO: 0010629]; positive regulation of establishment of T cell polarity [GO:1903905]; positive regulation of NF-kappaB transcription factor activity [GO: 0051092]; protein localization to plasma membrane [GO: 0072659]; protein localization to plasma membrane raft [GO: 0044860]; protein stabilization [GO: 0050821]; regulation of myoblast differentiation [GO: 0045661]; regulation of necroptotic process [GO: 0060544] |
| P16870 | CBPE | 1,719,295 | 935,148 | 1.84 | 0.035 | Carboxypeptidase E (CPE) (EC 3.4.17.10) (Carboxypeptidase H) (CPH) (Enkephalin convertase) | extracellular exosome [GO: 0070062]; extracellular space [GO: 0005615]; Golgi apparatus |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | (Prohormone-processing carboxypeptidase) | [GO: 0005794]; nucleus [GO: 0005634]; plasma membrane [GO: 0005886]; transport vesicle membrane [GO: 0030658]; carboxypeptidase activity [GO: 0004180]; cell adhesion molecule binding [GO: 0050839]; metallocarboxypeptidase activity [GO: 0004181]; neurexin family protein binding [GO: 0042043]; zinc ion binding [GO: 0008270]; cardiac left ventricle morphogenesis [GO: 0003214]; cellular protein modification process [GO: 0006464]; neuropeptide signaling pathway [GO: 0007218]; peptide metabolic process [GO: 0006518]; protein localization to membrane [GO: 0072657]; protein processing [GO: 0016485]; Wnt signaling pathway [GO: 0016055] |
| P09958 | FURIN | 1,220,714 | 667,143 | 1.83 | 0.013 | Furin (EC 3.4.21.75) (Dibasic-processing enzyme) (Paired basic amino acid residue-cleaving enzyme) (PACE) | cell surface [GO: 0009986]; endoplasmic reticulum [GO: 0005783]; endosome membrane [GO: 0010008]; extracellular exosome [GO: 0070062]; extracellular region [GO: 0005576]; Golgi lumen [GO: 0005796]; Golgi membrane [GO: 0000139]; integral component of Golgi membrane [GO: 0030173]; membrane [GO: 0016020]; membrane raft [GO: 0045121]; plasma membrane [GO: 0005886]; trans-Golgi network [GO: 0005802]; trans-Golgi network transport vesicle [GO: 0030140]; endopeptidase activity [GO: 0004175]; metal ion binding [GO: 0046872]; nerve growth factor binding [GO: 0048406]; peptidase activity [GO: 0008233]; peptide binding [GO: 0042277]; protease binding [GO: 0002020]; serine-type endopeptidase activity [GO: 0004252]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | serine-type endopeptidase inhibitor activity [GO: 0004867]; amyloid fibril formation [GO:1990000]; blastocyst formation [GO: 0001825]; collagen catabolic process [GO: 0030574]; cornification [GO: 0070268]; dibasic protein processing [GO: 0090472]; extracellular matrix disassembly [GO: 0022617]; extracellular matrix organization [GO: 0030198]; negative regulation of inflammatory response to antigenic stimulus [GO: 0002862]; negative regulation of low-density lipoprotein particle receptor catabolic process [GO: 0032804]; negative regulation of transforming growth factor beta1 production [GO: 0032911]; nerve growth factor processing [GO: 0032455]; nerve growth factor production [GO: 0032902]; peptide biosynthetic process [GO: 0043043]; peptide hormone processing [GO: 0016486]; positive regulation of membrane protein ectodomain proteolysis [GO: 0051044]; positive regulation of transforming growth factor beta1 activation [GO: 1901394]; protein processing [GO: 0016485]; regulation of cholesterol transport [GO: 0032374]; regulation of endopeptidase activity [GO: 0052548]; regulation of lipoprotein lipase activity [GO: 0051004]; regulation of protein catabolic process [GO: 0042176]; regulation of signal transduction [GO: 0009966]; secretion by cell [GO: 0032940]; signal peptide processing [GO: 0006465]; transforming growth factor beta receptor |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | signaling pathway [GO: 0007179]; viral life cycle [GO: 0019058]; viral protein processing [GO: 0019082]; zymogen activation [GO: 0031638]; zymogen inhibition [GO: 0097341] |
| P16152 | CBR1 | 442,719 | 801,903 | 1.81 | 0.030 | Carbonyl reductase [NADPH] 1 (EC 1.1.1.184) (15-hydroxyprostaglandin dehydrogenase [NADP(+)]) (EC 1.1.1.196) (EC 1.1.1.197) (20-beta-hydroxysteroid dehydrogenase) (NADPH-dependent carbonyl reductase 1) (Prostaglandin 9-ketoreductase) (PG-9-KR) (Prostaglandin-E(2) 9-reductase) (EC 1.1.1.189) (Short chain dehydrogenase/reductase family 21C member 1) | cytosol [GO: 0005829]; extracellular exosome [GO: 0070062]; extracellular vesicle [GO:1903561]; 15-hydroxyprostaglandin dehydrogenase (NADP+) activity [GO: 0047021]; 15-hydroxyprostaglandin-D dehydrogenase (NADP+) activity [GO: 0047020]; carbonyl reductase (NADPH) activity [GO: 0004090]; oxidoreductase activity, acting on NAD(P)H, quinone or similar compound as acceptor [GO: 0016655]; prostaglandin-E2 9-reductase activity [GO: 0050221]; cyclooxygenase pathway [GO: 0019371]; drug metabolic process [GO: 0017144]; epithelial cell differentiation [GO: 0030855]; vitamin K metabolic process [GO: 0042373] |
| P47755 | CAZA2 | 502,909 | 277,691 | 1.81 | 0.010 | F-actin-capping protein subunit alpha-2 (CapZ alpha-2) | actin cytoskeleton [GO: 0015629]; brush border [GO: 0005903]; cortical cytoskeleton [GO: 0030863]; cytosol [GO: 0005829]; extracellular exosome [GO: 0070062]; extracellular region [GO: 0005576]; F-actin capping protein complex [GO: 0008290]; membrane [GO: 0016020]; actin filament binding [GO: 0051015]; actin cytoskeleton organization [GO: 0030036]; antigen processing and presentation of exogenous peptide antigen via MHC class II [GO: 0019886]; barbed-end actin filament capping [GO: 0051016]; blood coagulation [GO: 0007596]; endoplasmic reticulum to Golgi vesicle-mediated transport |

TABLE 7-continued

| Uniprot ID | Abbrev. name | Control average | AtRisk average | Control vs Risk delta | Anova p-value | ProteinName | GO |
|---|---|---|---|---|---|---|---|
| P58499 | FAM3B | 1,715,875 | 949,144 | 1.81 | 0.014 | Protein FAM3B (Cytokine-like protein 2-21) (Pancreatic-derived factor) (PANDER) | [GO: 0006888]; innate immune response [GO: 0045087]; protein-containing complex assembly [GO: 0065003] extracellular exosome [GO: 0070062]; extracellular region [GO: 0005576]; extracellular space [GO: 0005615]; cytokine activity [GO: 0005125]; apoptotic process [GO: 0006915]; glucose homeostasis [GO: 0042593]; insulin secretion [GO: 0030073] |
| Q86VP6 | CAND1 | 45,823 | 82,739 | 1.81 | 0.032 | Cullin-associated NEDD8-dissociated protein 1 (Cullin-associated and neddylation-dissociated protein 1) (TBP-interacting protein of 120 kDa A) (TBP-interacting protein 120A) (p120 CAND1) | cullin-RING ubiquitin ligase complex [GO: 0031461]; cytoplasm [GO: 0005737]; cytosol [GO: 0005829]; extracellular exosome [GO: 0070062]; extracellular region [GO: 0005576]; ficolin-1-rich granule lumen [GO:1904813]; Golgi apparatus [GO: 0005794]; membrane [GO: 0016020]; nucleoplasm [GO: 0005654]; nucleus [GO: 0005634]; secretory granule lumen [GO: 0034774]; ubiquitin ligase complex [GO: 0000151]; TBP-class protein binding [GO: 0017025]; cell differentiation [GO: 0030154]; cellular iron ion homeostasis [GO: 0006879]; negative regulation of catalytic activity [GO: 0043086]; neutrophil degranulation [GO: 0043312]; positive regulation of RNA polymerase II transcription preinitiation complex assembly [GO: 0045899]; post-translational protein modification [GO: 0043687]; protein ubiquitination [GO: 0016567]; SCF complex assembly [GO: 0010265] |
| Q9Y6R7 | FCGBP | 4,509,992 | 2,501,142 | 1.80 | 0.019 | IgGFc-binding protein (Fcgamma-binding protein antigen) (FcgammaBP) | extracellular exosome [GO: 0070062]; extracellular matrix [GO: 0031012]; extracellular space [GO: 0005615] |

TABLE 7-continued

| Uniprot ID | Abbrev. name | Control average | AtRisk average | Control vs Risk delta | Anova p-value | ProteinName | GO |
|---|---|---|---|---|---|---|---|
| A0A0B 4J1X5 | HV374 | 937,879 | 1,664,922 | 1.78 | 0.041 | Immunoglobulin heavy variable 3-74 | external side of plasma membrane [GO: 0009897]; immunoglobulin complex, circulating [GO: 0042571]; antigen binding [GO: 0003823]; immunoglobulin receptor binding [GO: 0034987]; B cell receptor signaling pathway [GO: 0050853]; complement activation, classical pathway [GO: 0006958]; defense response to bacterium [GO: 0042742]; innate immune response [GO: 0045087]; phagocytosis, engulfment [GO: 0006911]; phagocytosis, recognition [GO: 0006910]; positive regulation of B cell activation [GO: 0050871] |
| Q00169 | PIPNA | 61,311 | 107,714 | 1.76 | 0.019 | Phosphatidylinositol transfer protein alpha isoform (PI-TP-alpha) (PtdIns transfer protein alpha) (PtdInsTP alpha) | cytoplasm [GO: 0005737]; cytosol [GO: 0005829]; extracellular exosome [GO: 0070062]; nucleus [GO: 0005634]; phosphatidylcholine binding [GO: 0031210]; phosphatidylcholine transfer activity [GO: 0120019]; phosphatidylcholine transporter activity [GO: 0008525]; phosphatidylglycerol binding [GO:1901611]; phosphatidylinositol binding [GO: 0035091]; phosphatidylinositol transfer activity [GO: 0008526]; interleukin-12-mediated signaling pathway [GO: 0035722]; lipid metabolic process [GO: 0006629]; phospholipid transport [GO: 0015914]; visual perception [GO: 0007601] |
| P10606 | COX5B | 174,615 | 306,423 | 1.75 | 0.046 | Cytochrome c oxidase subunit 5B, mitochondrial (Cytochrome c oxidase polypeptide Vb) | mitochondrial inner membrane [GO: 0005743]; mitochondrion [GO: 0005739]; cytochrome-c oxidase activity [GO: 0004129]; metal ion binding [GO: 0046872]; mitochondrial electron transport, cytochrome c to oxygen [GO: 0006123]; respiratory gaseous exchange by |

TABLE 7-continued

| Uniprot ID | Abbrev. name | Control average | AtRisk average | Control vs Risk delta | Anova p-value | ProteinName | GO |
|---|---|---|---|---|---|---|---|
| Q9BX68 | HINT2 | 6,406 | 11,022 | 1.72 | 0.040 | Histidine triad nucleotide-binding protein 2, mitochondrial (HINT-2) (EC 3.-.-.-) (HINT-3) (HIT-17kDa) (PKCI-1-related HIT protein) | respiratory system [GO: 0007585] cytoplasm [GO: 0005737]; mitochondrion [GO: 0005739]; hydrolase activity [GO: 0016787]; nucleotide binding [GO: 0000166]; apoptotic process [GO: 0006915]; lipid catabolic process [GO: 0016042]; negative regulation of peptidyl-lysine acetylation [GO: 2000757]; steroid biosynthetic process [GO: 0006694] |
| P08195 | 4F2 | 14,621 | 24,934 | 1.71 | 0.023 | 4F2 cell-surface antigen heavy chain (4F2hc) (4F2 heavy chain antigen) (Lymphocyte activation antigen 4F2 large subunit) (Solute carrier family 3 member 2) (CD antigen CD98) | amino acid transport complex [GO:1990184]; apical plasma membrane [GO: 0016324]; basal plasma membrane [GO: 0009925]; basolateral plasma membrane [GO: 0016323]; cell junction [GO: 0030054]; cell surface [GO: 0009986]; extracellular exosome [GO: 0070062]; integral component of membrane [GO: 0016021]; lysosomal membrane [GO: 0005765]; melanosome [GO: 0042470]; membrane [GO: 0016020]; nucleoplasm [GO: 0005654]; plasma membrane [GO: 0005886]; aromatic amino acid transmembrane transporter activity [GO: 0015173]; cadherin binding [GO: 0045296]; calcium:sodium antiporter activity [GO: 0005432]; catalytic activity [GO: 0003824]; double-stranded RNA binding [GO: 0003725]; L-alanine transmembrane transporter activity [GO: 0015180]; L-leucine transmembrane transporter activity [GO: 0015190]; neutral amino acid transmembrane transporter activity [GO: 0015175]; RNA binding [GO: 0003723]; amino acid transport [GO: 0006865]; calcium |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | ion transport [GO: 0006816]; carbohydrate metabolic process [GO: 0005975]; L-alanine import across plasma membrane [GO: 1904273]; L-alpha-amino acid transmembrane transport [GO: 1902475]; L-leucine import across plasma membrane [GO: 1903801]; leucine import across plasma membrane [GO: 0098713]; leukocyte migration [GO: 0050900]; phenylalanine transport [GO: 0015823]; response to exogenous dsRNA [GO: 0043330]; tryptophan transport [GO: 0015827] |
| P46782 | RS5 | 370,214 | 629,678 | 1.70 | 0.043 | 40S ribosomal protein S5 (Small ribosomal subunit protein uS7) [Cleaved into: 40S ribosomal protein S5, N-terminally processed] | cytosol [GO: 0005829]; cytosolic small ribosomal subunit [GO: 0022627]; extracellular exosome [GO: 0070062]; focal adhesion [GO: 0005925]; membrane [GO: 0016020]; nucleoplasm [GO: 0005654]; ribonucleoprotein complex [GO:1990904]; ribosome [GO: 0005840]; mRNA binding [GO: 0003729]; RNA binding [GO: 0003723]; rRNA binding [GO: 0019843]; structural constituent of ribosome [GO: 0003735]; nuclear-transcribed mRNA catabolic process, nonsense-mediated decay [GO: 0000184]; regulation of translational fidelity [GO: 0006450]; ribosomal small subunit assembly [GO: 0000028]; SRP-dependent cotranslational protein targeting to membrane [GO: 0006614]; translation [GO: 0006412]; translational initiation [GO: 0006413]; viral transcription [GO: 0019083] |
| P30101 | PDIA3 | 11,140,398 | 6,609,725 | 1.69 | 0.023 | Protein disulfide-isomerase A3 (EC 5.3.4.1) (58 kDa glucose-regulated protein) (58 kDa | cell surface [GO: 0009986]; endoplasmic reticulum [GO: 0005783]; endoplasmic reticulum |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | microsomal protein) (p58) (Disulfide isomerase ER-60) (Endoplasmic reticulum resident protein 57) (ER protein 57) (ERp57) (Endoplasmic reticulum resident protein 60) (ER protein 60) (ERp60) | lumen [GO: 0005788]; extracellular exosome [GO: 0070062]; extracellular space [GO: 0005615]; focal adhesion [GO: 0005925]; melanosome [GO: 0042470]; MHC class I peptide loading complex [GO: 0042824]; nucleus [GO: 0005634]; phagocytic vesicle [GO: 0045335]; recycling endosome membrane [GO: 0055038]; cysteine-type endopeptidase activity [GO: 0004197]; disulfide oxidoreductase activity [GO: 0015036]; identical protein binding [GO: 0042802]; peptide disulfide oxidoreductase activity [GO: 0015037]; phospholipase C activity [GO: 0004629]; protein disulfide isomerase activity [GO: 0003756]; RNA binding [GO: 0003723]; antigen processing and presentation of exogenous peptide antigen via MHC class I, TAP-dependent [GO: 0002479]; antigen processing and presentation of peptide antigen via MHC class I [GO: 0002474]; cellular response to interleukin-7 [GO: 0098761]; positive regulation of extrinsic apoptotic signaling pathway [GO:2001238]; protein folding [GO: 0006457]; protein folding in endoplasmic reticulum [GO: 0034975]; response to endoplasmic reticulum stress [GO: 0034976] |
| P00441 | SODC | 626,977 | 1,051,120 | 1.68 | 0.010 | Superoxide dismutase [Cu-Zn] (EC 1.15.1.1) (Superoxide dismutase 1) (hSod1) | axon cytoplasm [GO:1904115]; cytoplasm [GO: 0005737]; cytoplasmic vesicle [GO: 0031410]; cytosol [GO: 0005829]; dendrite cytoplasm [GO: 0032839]; dense core granule [GO: 0031045]; extracellular exosome [GO: 0070062]; extracellular region [GO: 0005576]; extracellular space [GO: 0005615]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | lysosome [GO: 0005764]; mitochondrial intermembrane space [GO: 0005758]; mitochondrial matrix [GO: 0005759]; mitochondrion [GO: 0005739]; neuronal cell body [GO: 0043025]; nucleoplasm [GO: 0005654]; nucleus [GO: 0005634]; peroxisome [GO: 0005777]; protein-containing complex [GO: 0032991]; chaperone binding [GO: 0051087]; copper ion binding [GO: 0005507]; identical protein binding [GO: 0042802]; protein phosphatase 2B binding [GO: 0030346]; small GTPase binding [GO: 0031267]; superoxide dismutase activity [GO: 0004784]; zinc ion binding [GO: 0008270]; activation of MAPK activity [GO: 0000187]; anterograde axonal transport [GO: 0008089]; auditory receptor cell stereocilium organization [GO: 0060088]; cell aging [GO: 0007569]; cellular iron ion homeostasis [GO: 0006879]; cellular response to ATP [GO: 0071318]; cellular response to cadmium ion [GO: 0071276]; cellular response to oxidative stress [GO: 0034599]; cellular response to potassium ion [GO: 0035865]; embryo implantation [GO: 0007566]; glutathione metabolic process [GO: 0006749]; heart contraction [GO: 0060047]; hydrogen peroxide biosynthetic process [GO: 0050665]; interleukin-12-mediated signaling pathway [GO: 0035722]; locomotory behavior [GO: 0007626]; muscle cell cellular homeostasis [GO: 0046716]; myeloid cell homeostasis [GO: 0002262]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | negative regulation of cholesterol biosynthetic process [GO: 0045541]; negative regulation of inflammatory response [GO: 0050728]; negative regulation of neuron apoptotic process [GO: 0043524]; neurofilament cytoskeleton organization [GO: 0060052]; ovarian follicle development [GO: 0001541]; peripheral nervous system myelin maintenance [GO: 0032287]; placenta development [GO: 0001890]; platelet degranulation [GO: 0002576]; positive regulation of apoptotic process [GO: 0043065]; positive regulation of catalytic activity [GO: 0043085]; positive regulation of cytokine production [GO: 0001819]; positive regulation of oxidative stress-induced intrinsic apoptotic signaling pathway [GO: 1902177]; positive regulation of phagocytosis [GO: 0050766]; positive regulation of superoxide anion generation [GO: 0032930]; reactive oxygen species metabolic process [GO: 0072593]; regulation of blood pressure [GO: 0008217]; regulation of GTPase activity [GO: 0043087]; regulation of mitochondrial membrane potential [GO: 0051881]; regulation of multicellular organism growth [GO: 0040014]; regulation of organ growth [GO: 0046620]; regulation of protein kinase activity [GO: 0045859]; regulation of T cell differentiation in thymus [GO: 0033081]; relaxation of vascular associated smooth muscle [GO: 0060087]; removal of superoxide radicals [GO: 0019430]; response to amphetamine [GO: 0001975]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | response to antibiotic [GO: 0046677]; response to antipsychotic drug [GO: 0097332]; response to axon injury [GO: 0048678]; response to carbon monoxide [GO: 0034465]; response to copper ion [GO: 0046688]; response to drug [GO: 0042493]; response to ethanol [GO: 0045471]; response to heat [GO: 0009408]; response to hydrogen peroxide [GO: 0042542]; response to nutrient levels [GO: 0031667]; response to organic substance [GO: 0010033]; response to superoxide [GO: 0000303]; retina homeostasis [GO: 0001895]; retrograde axonal transport [GO: 0008090]; sensory perception of sound [GO: 0007605]; spermatogenesis [GO: 0007283]; superoxide anion generation [GO: 0042554]; superoxide metabolic process [GO: 0006801]; thymus development [GO: 0048538]; transmission of nerve impulse [GO: 0019226] |
| P61916 | NPC2 | 605,322 | 1,004,339 | 1.66 | 0.025 | NPC intracellular cholesterol transporter 2 (Epididymal secretory protein E1) (Human epididymis-specific protein 1) (He1) (Niemann-Pick disease type C2 protein) | azurophil granule lumen [GO: 0035578]; endoplasmic reticulum [GO: 0005783]; extracellular exosome [GO: 0070062]; extracellular region [GO: 0005576]; extracellular space [GO: 0005615]; lysosomal lumen [GO: 0043202]; lysosome [GO: 0005764]; cholesterol binding [GO: 0015485]; cholesterol transfer activity [GO: 0120020]; enzyme binding [GO: 0019899]; sterol binding [GO: 0032934]; cholesterol efflux [GO: 0033344]; cholesterol homeostasis [GO: 0042632]; cholesterol metabolic process [GO: 0008203]; cholesterol transport |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0030301]; glycolipid transport [GO: 0046836]; intracellular cholesterol transport [GO: 0032367]; intracellular sterol transport [GO: 0032366]; low-density lipoprotein particle clearance [GO: 0034383]; neutrophil degranulation [GO: 0043312]; phospholipid transport [GO: 0015914]; regulation of isoprenoid metabolic process [GO: 0019747]; response to virus [GO: 0009615]; sterol transport [GO: 0015918] |
| P52815 | RM12 | 93,185 | 153,865 | 1.65 | 0.011 | 39S ribosomal protein L12, mitochondrial (L12mt) (MRP-L12) (5c5-2) (Mitochondrial large ribosomal subunit protein bL12m) | mitochondrial inner membrane [GO: 0005743]; mitochondrial large ribosomal subunit [GO: 0005762]; mitochondrion [GO: 0005739]; RNA binding [GO: 0003723]; structural constituent of ribosome [GO: 0003735]; mitochondrial transcription [GO: 0006390]; mitochondrial translational elongation [GO: 0070125]; mitochondrial translational termination [GO: 0070126]; positive regulation of transcription, DNA-templated [GO: 0045893] |
| P10321 | 1C07 | 124,488 | 204,279 | 1.64 | 0.038 | HLA class I histocompatibility antigen, C alpha chain (HLA-C) (HLA-Cw) (Human leukocyte antigen C) | cell surface [GO: 0009986]; early endosome membrane [GO: 0031901]; endoplasmic reticulum [GO: 0005783]; ER to Golgi transport vesicle membrane [GO: 0012507]; extracellular exosome [GO: 0070062]; Golgi apparatus [GO: 0005794]; Golgi membrane [GO: 0000139]; integral component of lumenal side of endoplasmic reticulum membrane [GO: 0071556]; integral component of plasma membrane [GO: 0005887]; membrane [GO: 0016020]; MHC |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | class I protein complex [GO: 0042612]; phagocytic vesicle membrane [GO: 0030670]; plasma membrane [GO: 0005886]; recycling endosome membrane [GO: 0055038]; secretory granule membrane [GO: 0030667]; peptide antigen binding [GO: 0042605]; TAP binding [GO: 0046977]; adaptive immune response [GO: 0002250]; antigen processing and presentation of endogenous peptide antigen via MHC class I via ER pathway, TAP-independent [GO: 0002486]; antigen processing and presentation of exogenous peptide antigen via MHC class I, TAP-dependent [GO: 0002479]; antigen processing and presentation of exogenous peptide antigen via MHC class I, TAP-independent [GO: 0002480]; antigen processing and presentation of peptide antigen via MHC class I [GO: 0002474]; immune response [GO: 0006955]; interferon-gamma-mediated signaling pathway [GO: 0060333]; neutrophil degranulation [GO: 0043312]; regulation of immune response [GO: 0050776]; type I interferon signaling pathway [GO: 0060337]; viral process [GO: 0016032] |
| O00468 | AGRIN | 60,836 | 38,787 | 1.57 | 0.025 | Agrin [Cleaved into: Agrin N-terminal 110 kDa subunit; Agrin C-terminal 110 kDa subunit; Agrin C-terminal 90 kDa fragment (C90); Agrin C-terminal 22 kDa fragment (C22)] | basement membrane [GO: 0005604]; collagen-containing extracellular matrix [GO: 0062023]; extracellular exosome [GO: 0070062]; extracellular region [GO: 0005576]; Golgi lumen [GO: 0005796]; integral component of membrane [GO: 0016021]; lysosomal lumen [GO: 0043202]; plasma membrane [GO: 0005886]; synapse |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0045202]; calcium ion binding [GO: 0005509]; chondroitin sulfate binding [GO: 0035374]; dystroglycan binding [GO: 0002162]; heparan sulfate proteoglycan binding [GO: 0043395]; laminin binding [GO: 0043236]; sialic acid binding [GO: 0033691]; structural constituent of cytoskeleton [GO: 0005200]; animal organ morphogenesis [GO: 0009887]; clustering of voltage-gated sodium channels [GO: 0045162]; extracellular matrix organization [GO: 0030198]; G protein-coupled acetylcholine receptor signaling pathway [GO: 0007213]; glycosaminoglycan biosynthetic process [GO: 0006024]; glycosaminoglycan catabolic process [GO: 0006027]; neuromuscular junction development [GO: 0007528]; positive regulation of filopodium assembly [GO: 0051491]; positive regulation of GTPase activity [GO: 0043547]; positive regulation of synaptic growth at neuromuscular junction [GO: 0045887]; positive regulation of transcription by RNA polymerase II [GO: 0045944]; receptor clustering [GO: 0043113]; retinoid metabolic process [GO: 0001523]; signal transduction [GO: 0007165]; synapse organization [GO: 0050808]; tissue development [GO: 0009888] |
| Q29963 | 1C06 | 42,543 | 65,799 | 1.55 | 0.044 | Merged into P10321. | |
| Q9HAT2 | SIAE | 122,586 | 79,650 | 1.54 | 0.015 | Sialate O-acetylesterase (EC 3.1.1.53) (H-Lse) (Sialic acid-specific 9-O-acetylesterase) | extracellular exosome [GO: 0070062]; extracellular space [GO: 0005615]; lysosome [GO: 0005764]; sialate 4-O-acetylesterase activity [GO: 0106331]; sialate 9-0-acetylesterase activity [GO: 0106330]; sialate O-acetylesterase activity [GO: 0001681]; carbohydrate |

TABLE 7-continued

| Uniprot ID | Abbrev. name | Control average | AtRisk average | Control vs Risk delta | Anova p-value | ProteinName | GO |
|---|---|---|---|---|---|---|---|
| Q7LBR1 | CHM1B | 38,770 | 59,139 | 1.53 | 0.028 | Charged multivesicular body protein 1b (CHMP1.5) (Chromatin-modifying protein 1b) (CHMP1b) (Vacuolar protein sorting-associated protein 46-2) (Vps46-2) (hVps46-2) | metabolic process [GO: 0005975]; regulation of immune system process [GO: 0002682] cytosol [GO: 0005829]; endosome membrane [GO: 0010008]; ESCRT III complex [GO: 0000815]; extracellular exosome [GO: 0070062]; late endosome membrane [GO: 0031902]; membrane coat [GO: 0030117]; midbody [GO: 0030496]; multivesicular body [GO: 0005771]; nucleoplasm [GO: 0005654]; identical protein binding [GO: 0042802]; protein domain specific binding [GO: 0019904]; cell division [GO: 0051301]; endosome transport via multivesicular body sorting pathway [GO: 0032509]; ESCRT III complex disassembly [GO:1904903]; establishment of protein localization [GO: 0045184]; late endosome to vacuole transport [GO: 0045324]; midbody abscission [GO: 0061952]; mitotic metaphase plate congression [GO: 0007080]; multivesicular body assembly [GO: 0036258]; nucleus organization [GO: 0006997]; protein transport [GO: 0015031]; regulation of centrosome duplication [GO: 0010824]; regulation of mitotic spindle assembly [GO: 1901673]; viral budding via host ESCRT complex [GO: 0039702] |
| P07996 | TSP1 | 2,297,854 | 1,536,784 | 1.50 | 0.003 | Thrombospondin-1 (Glycoprotein G) | cell surface [GO: 0009986]; collagen-containing extracellular matrix [GO: 0062023]; endoplasmic reticulum [GO: 0005783]; endoplasmic reticulum lumen [GO: 0005788]; external side of plasma membrane [GO: 0009897]; extracellular exosome [GO: 0070062]; extracellular matrix |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | [GO: 0031012]; extracellular region [GO: 0005576]; extracellular space [GO: 0005615]; fibrinogen complex [GO: 0005577]; platelet alpha granule [GO: 0031091]; platelet alpha granule lumen [GO: 0031093]; sarcoplasmic reticulum [GO: 0016529]; secretory granule [GO: 0030141]; calcium ion binding [GO: 0005509]; collagen V binding [GO: 0070052]; extracellular matrix structural constituent [GO: 0005201]; fibrinogen binding [GO: 0070051]; fibroblast growth factor binding [GO: 0017134]; fibronectin binding [GO: 0001968]; heparin binding [GO: 0008201]; identical protein binding [GO: 0042802]; integrin binding [GO: 0005178]; laminin binding [GO: 0043236]; low-density lipoprotein particle binding [GO: 0030169]; phosphatidylserine binding [GO: 0001786]; proteoglycan binding [GO: 0043394]; transforming growth factor beta binding [GO: 0050431]; activation of MAPK activity [GO: 0000187]; behavioral response to pain [GO: 0048266]; cell adhesion [GO: 0007155]; cell cycle arrest [GO: 0007050]; cell migration [GO: 0016477]; cellular response to growth factor stimulus [GO: 0071363]; cellular response to heat [GO: 0034605]; cellular response to tumor necrosis factor [GO: 0071356]; chronic inflammatory response [GO: 0002544]; engulfment of apoptotic cell [GO: 0043652]; extracellular matrix organization [GO: 0030198]; immune response [GO: 0006955]; inflammatory response [GO: 0006954]; |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | negative regulation of angiogenesis [GO: 0016525]; negative regulation of antigen processing and presentation of peptide or polysaccharide antigen via MHC class II [GO: 0002581]; negative regulation of apoptotic process [GO: 0043066]; negative regulation of blood vessel endothelial cell migration [GO: 0043537]; negative regulation of blood vessel endothelial cell proliferation involved in sprouting angiogenesis [GO: 1903588]; negative regulation of cell migration involved in sprouting angiogenesis [GO: 0090051]; negative regulation of cell-matrix adhesion [GO: 0001953]; negative regulation of cGMP-mediated signaling [GO: 0010754]; negative regulation of cysteine-type endopeptidase activity involved in apoptotic process [GO: 0043154]; negative regulation of dendritic cell antigen processing and presentation [GO: 0002605]; negative regulation of endothelial cell chemotaxis [GO:2001027]; negative regulation of endothelial cell migration [GO: 0010596]; negative regulation of endothelial cell proliferation [GO: 0001937]; negative regulation of extrinsic apoptotic signaling pathway [GO:2001237]; negative regulation of fibrinolysis [GO: 0051918]; negative regulation of fibroblast growth factor receptor signaling pathway [GO: 0040037]; negative regulation of focal adhesion assembly [GO: 0051895]; negative regulation of |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | interleukin-12 production [GO: 0032695]; negative regulation of long-chain fatty acid import across plasma membrane [GO: 0010748]; negative regulation of nitric oxide mediated signal transduction [GO: 0010751]; negative regulation of plasminogen activation [GO: 0010757]; negative regulation of sprouting angiogenesis [GO:1903671]; peptide cross-linking [GO: 0018149]; platelet degranulation [GO: 0002576]; positive regulation of angiogenesis [GO: 0045766]; positive regulation of blood coagulation [GO: 0030194]; positive regulation of blood vessel endothelial cell migration [GO: 0043536]; positive regulation of cell migration [GO: 0030335]; positive regulation of cell population proliferation [GO: 0008284]; positive regulation of chemotaxis [GO: 0050921]; positive regulation of endothelial cell apoptotic process [GO:2000353]; positive regulation of endothelial cell migration [GO: 0010595]; positive regulation of extrinsic apoptotic signaling pathway via death domain receptors [GO:1902043]; positive regulation of fibroblast migration [GO: 0010763]; positive regulation of macrophage activation [GO: 0043032]; positive regulation of macrophage chemotaxis [GO: 0010759]; positive regulation of phosphorylation [GO: 0042327]; positive regulation of protein kinase B signaling [GO: 0051897]; positive regulation of reactive oxygen species metabolic process [GO:2000379]; positive |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | regulation of smooth muscle cell proliferation [GO: 0048661]; positive regulation of transforming growth factor beta receptor signaling pathway [GO: 0030511]; positive regulation of transforming growth factor beta1 production [GO: 0032914]; positive regulation of translation [GO: 0045727]; positive regulation of tumor necrosis factor production [GO: 0032760]; regulation of megakaryocyte differentiation [GO: 0045652]; response to calcium ion [GO: 0051592]; response to drug [GO: 0042493]; response to endoplasmic reticulum stress [GO: 0034976]; response to glucose [GO: 0009749]; response to hypoxia [GO: 0001666]; response to magnesium ion [GO: 0032026]; response to mechanical stimulus [GO: 0009612]; response to progesterone [GO: 0032570]; response to testosterone [GO: 0033574]; response to unfolded protein [GO: 0006986]; sprouting angiogenesis [GO: 0002040] |
| P13688 | CEAM1 | 127,906 | 364,656 | 2.85 | 0.150 | Carcinoembryonic antigen-related cell adhesion molecule 1 (Biliary glycoprotein 1) (BGP-1) (CD antigen CD66a) | adherens junction [GO: 0005912]; apical plasma membrane [GO: 0016324]; basal plasma membrane [GO: 0009925]; cell junction [GO: 0030054]; cell surface [GO: 0009986]; cell-cell junction [GO: 0005911]; extracellular exosome [GO: 0070062]; integral component of membrane [GO: 0016021]; integral component of plasma membrane [GO: 0005887]; lateral plasma membrane [GO: 0016328]; membrane [GO: 0016020]; microvillus membrane [GO: 0031528]; plasma |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | membrane [GO: 0005886]; specific granule membrane [GO: 0035579]; tertiary granule membrane [GO: 0070821]; transport vesicle membrane [GO: 0030658]; actin binding [GO: 0003779]; bile acid transmembrane transporter activity [GO: 0015125]; calmodulin binding [GO: 0005516]; filamin binding [GO: 0031005]; identical protein binding [GO: 0042802]; kinase binding [GO: 0019900]; protein dimerization activity [GO: 0046983]; protein homodimerization activity [GO: 0042803]; protein phosphatase binding [GO: 0019903]; protein tyrosine kinase binding [GO:1990782]; angiogenesis [GO: 0001525]; bile acid and bile salt transport [GO: 0015721]; blood vessel development [GO: 0001568]; cell adhesion [GO: 0007155]; cell migration [GO: 0016477]; cell-cell adhesion via plasma-membrane adhesion molecules [GO: 0098742]; cellular response to insulin stimulus [GO: 0032869]; common myeloid progenitor cell proliferation [GO: 0035726]; granulocyte colony-stimulating factor signaling pathway [GO: 0038158]; homophilic cell adhesion via plasma membrane adhesion molecules [GO: 0007156]; insulin catabolic process [GO: 1901143]; insulin receptor internalization [GO: 0038016]; integrin-mediated signaling pathway [GO: 0007229]; leukocyte migration [GO: 0050900]; negative regulation of cytotoxic T cell degranulation [GO: 0043318]; negative regulation of fatty acid biosynthetic process [GO: 0045717]; negative regulation of |

TABLE 7-continued

| Uniprot ID | Abbrev. name | Control average | AtRisk average | Control vs Risk delta | Anova p-value | ProteinName | GO |
|---|---|---|---|---|---|---|---|
| | | | | | | | granulocyte differentiation [GO: 0030853]; negative regulation of hepatocyte proliferation [GO:2000346]; negative regulation of interleukin-1 production [GO: 0032692]; negative regulation of lipid biosynthetic process [GO: 0051055]; negative regulation of natural killer cell mediated cytotoxicity directed against tumor cell target [GO: 0002859]; negative regulation of platelet aggregation [GO: 0090331]; negative regulation of protein kinase activity [GO: 0006469]; negative regulation of T cell mediated cytotoxicity [GO: 0001915]; negative regulation of T cell receptor signaling pathway [GO: 0050860]; negative regulation of vascular permeability [GO: 0043116]; neutrophil degranulation [GO: 0043312]; positive regulation of vasculogenesis [GO:2001214]; regulation of blood vessel remodeling [GO: 0060312]; regulation of cell growth [GO: 0001558]; regulation of cell migration [GO: 0030334]; regulation of endothelial cell differentiation [GO: 0045601]; regulation of endothelial cell migration [GO: 0010594]; regulation of epidermal growth factor receptor signaling pathway [GO: 0042058]; regulation of ERK1 and ERK2 cascade [GO: 0070372]; regulation of homophilic cell adhesion [GO:1903385]; regulation of phosphatidylinositol 3-kinase signaling [GO: 0014066]; regulation of sprouting |

TABLE 7-continued

| Uniprot ID | Abbrev. name | Control average | AtRisk average | Control vs Risk delta | Anova p-value | ProteinName | GO |
|---|---|---|---|---|---|---|---|
| Q9UK76 | JUPI1 | 695,806 | 1,070,216 | 1.54 | 0.081 | Jupiter microtubule associated homolog 1 (Androgen-regulated protein 2) (Hematological and neurological expressed 1 protein) [Cleaved into: Jupiter microtubule associated homolog 1, N-terminally processed] | angiogenesis [GO: 1903670]; wound healing, spreading of cells [GO: 0044319] cytoplasm [GO: 0005737]; nuclear membrane [GO: 0031965]; nucleolus [GO: 0005730]; nucleoplasm [GO: 0005654] |
| P51888 | PRELP | 49,932 | 74,266 | 1.49 | 0.238 | Prolargin (Proline-arginine-rich end leucine-rich repeat protein) | collagen-containing extracellular matrix [GO: 0062023]; extracellular exosome [GO: 0070062]; extracellular matrix [GO: 0031012]; extracellular region [GO: 0005576]; extracellular space [GO: 0005615]; extracellular vesicle [GO:1903561]; Golgi lumen [GO: 0005796]; lysosomal lumen [GO: 0043202]; extracellular matrix structural constituent [GO: 0005201]; extracellular matrix structural constituent conferring compression resistance [GO: 0030021]; heparin binding [GO: 0008201]; cell aging [GO: 0007569]; keratan sulfate biosynthetic process [GO: 0018146]; eratan sulfate catabolic process [GO: 0042340]; skeletal system development [GO: 0001501] |

In Table 7 the quantification was measured in ng/ml, GO means Gene Ontology, and the GO number refers to the Gene Ontology number on Uniprot. The Uniprot ID identifies a unique gene/protein as listed in the Uniprot database (GO database).

Participants were identified with high risk of heart failure, while the biomarker readings were high. Surprisingly the participants did not have heart failure, due to the drug treatments. Risk of heart failure was maintained (prevented from escalating) with medications taken.

Participant 192 at age 70 was taking the heart failure specific medication Entresto at the time of the study, and had multiple historic and current health issues. Amongst other medications, she had been prescribed Rosuvastatin. She was assessed as a very high risk of developing heart failure within 6 months (4).

Participant 153 at age 65 was expected to have heart damage from historical heart issues, and was taking prescribed medications Empagliflozin, Amlodipine, Metoprolol, Aspirin (Spren) and Atorvastatin at the time of the study. Most recently, Type 2 diabetes was diagnosed within the past 6 months. Her assessment was to be at very high risk of developing heart failure within 6 months (4).

Participant 198 at 80 years of age was a lung cancer patient with historical heart issues. His prescribed medications at the time of the study included Mizart (Telmisartan), Nicorandil, Clopidogrel and Rosuvastatin. He was also receiving multiple lung cancer treatments currently. His assessment was to be at very high risk of developing heart failure within 6 months (4).

Participant 189 was a 70-year-old. Her prescribed medications included Empagliflozin, Linagliptin and Atorvastat. Her assessment was to be at very high risk of developing heart failure within 6 months (4).

Participant 163 was a 68-year-old taking prescribed medications Empagliflozin, Sitagliptin, Amlodipine and Rosuvastatin. Her assessment was at high risk for developing heart failure within 10 years (3).

Participant 183 was a 72 old with prescribed medication Karvezide. Her assessment was to be at very high risk of developing heart failure within 6 months (4).

Participant 171 at age 66 was prescribed with Metformin hydrochloride and Candesartan cilexetil and other painkiller prescribed drugs due to the pain caused by her spinal condition. Her assessment was at high risk for developing heart failure within 10 years (3).

Participant 164 at age 74 was prescribed with Perindopril erbumine, Indapamide, Nebivolol, Apixiban, Diltiazem Hydrochloride and Rosuvastatin. Her assessment was at high risk for developing heart failure within 10 years (3).

Participant 157 was 61 years of age with prescribed medications including Diltiazem, Duo Plidogrel, and Rosuvastatin. His assessment was at high risk for developing heart failure within 10 years (3).

Participant 162 was 55 years old with medications Perindopril erbumine, Felodipine and Atenolol. He was at medium risk (2).

Participant 200 was 50 years old prescribed with medications Ramipril and Bisoprolol fumarate. He was at medium risk (2).

Participant 169 was at 65 years of age with prescribed medications Olmesartan and Rosuvastatin. He was at medium risk (2).

Effective medication treatments can comprise a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator cardioxyl, an omecamtiv mecarbil, a relaxin, a serelaxin, a staroxime, bucindolol, a phosphodiesterase 5 inhibitor, a vasopressin inhibitor, a levosimendan, a sodium-glucose cotransporter-2 (SGLT2) inhibitor, an If channel blocker, an alpha blocker, a beta receptor blocker, a beta blocker, an ACE inhibitor, a stereoisomer of any of these, a salt of any of these, or any combination thereof. Effective treatments can also comprise a high level of physical activities and dietary controls to reduce further escalation in heart failure development.

Participant 164 was an obese, full-time 74-year-old owner of a small book store. Hypertension was diagnosed in her 20s after her first pregnancy. Over 25 years ago, a stent operation was received after a mild heart attack. Most recently, she received a heart valve replacement operation 2 years ago. She had been taking aspirin for the past 20 years due to heart issues. Her prescribed medications at the time of the study included Perindopril erbumine, Indapamide, Nebivolol, Apixiban, Diltiazem Hydrochloride and Rosuvastatin. At the time of the study, other health issues included low levels of cholesterol, joints and ligaments issues, slow metabolism and sleep disorders. A busy working life, with regular activities included physical work at the bookstore (heavy boxes), caring for her grandchildren, caring for the acre of garden and walking the dog several times a week. She also regularly attended live musical events which included dancing. A relatively strict diet was maintained to minimize escalation of her health conditions. She had been assessed to be at high risk for developing heart failure within 10 years (3)

Participant 157 was 61 years of age, working full-time from home, with a healthy physique appearance. Diagnosis early in life included hypertension, blood clot and high cholesterol, with a heart attack episode resulting in an operation to receive 8 stents. At the time of the study, the prescribed medications included Diltiazem, Duo Plidogrel, and Rosuvastatin. An avid golfer, a strenuous diet was maintained to minimize risks of further heart issues developing. His assessment was at high risk for developing heart failure within 10 years (3).

Participant 200 was 55 years old, working from home, with a healthy physique appearance. However, he had a "hole in heart" and valve surgery in the early years of life. At the time of the study he had been prescribed with medication for hypertension and heart failure medications, Ramipril and Bisoprolol fumarate. Although having suffered from the health issues, he remained very active with competitive tennis and regular daily 5 km walks. He took care with dietary control to minimize escalation to his health conditions. He was assessed to be at medium risk (2).

Example 6—Biomarkers (Analytes) Only Algorithms

A biomarker only algorithm was run in 6 different batches to verify a model could be built consistently on different random selection data and test sets as well as introducing variable model building approaches (various types such as ensembles, logistic regressions and deepnets). The consistency of evaluation results was compared. No accuracy variability between the 6 batches evaluation performance was observed. The conclusion was that the biomarkers provided accurate predictions of disease risk without the need for any other clinical features such as age, gender or condition descriptions.

Each batch was run independently of one another. Variable parts included:
  Random selected train/test dataset generated from the original raw data
  Random models built (ensemble, logistic regression, and deepnet)
  Roughly 100 models were built in every batch. The best ~10-15% of the algorithms were selected. The selection aimed to include at least one of each type of algorithm to increase stability and smooth out potential shortfalls of individual models.

The final multi model therefore consisted of different combinations of number and type.

Evaluation of the multi-model algorithm is done with its random selected testing pair. The testing dataset has not been introduced to the learning process until now. It therefore acts as a second test pass as the first test pass was performed during training with the training dataset. Since datasets are split randomly into 70/30% train/test datasets, each batch is trained and then tested on different selections. In other words, even the test sets differ between batches.

Figure 1B:
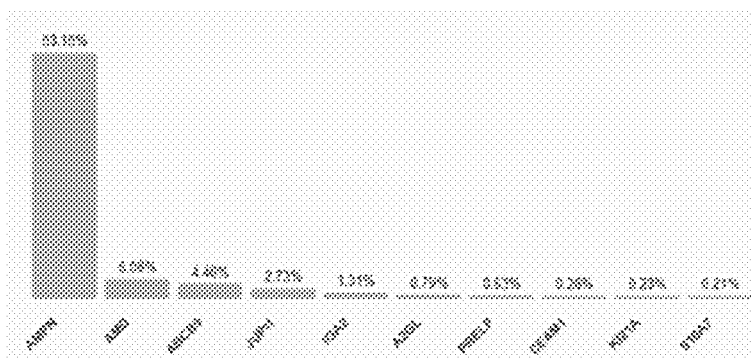
Figure 1C:
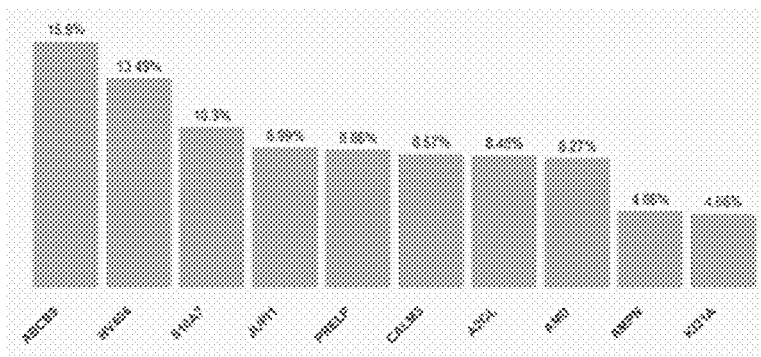

FIG. 1 demonstrates the field importance of selected biomarkers tested in batches A0 (FIG. 1A), A1 (FIG. 1B), and A2 (FIG. 1C).

Figure 2A:
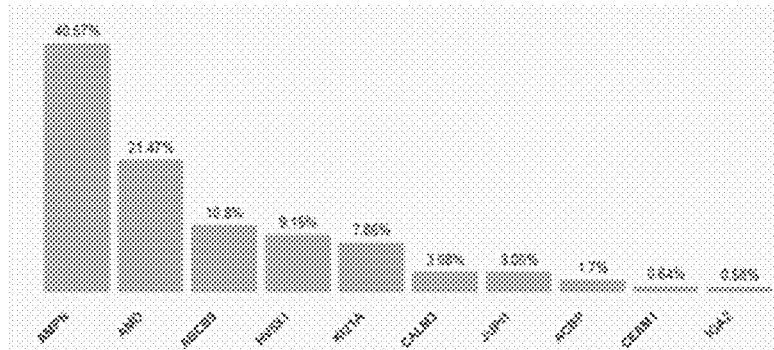
FIG. 2 demonstrates the field importance of selected biomarkers tested in batches A3 (FIG. 2A), A4 (FIG. 2B), and A5 (FIG. 2C).
Figure 2B:
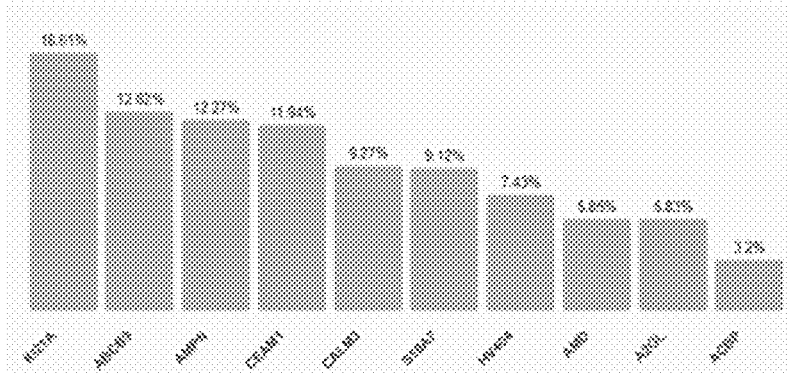
Figure 2C:
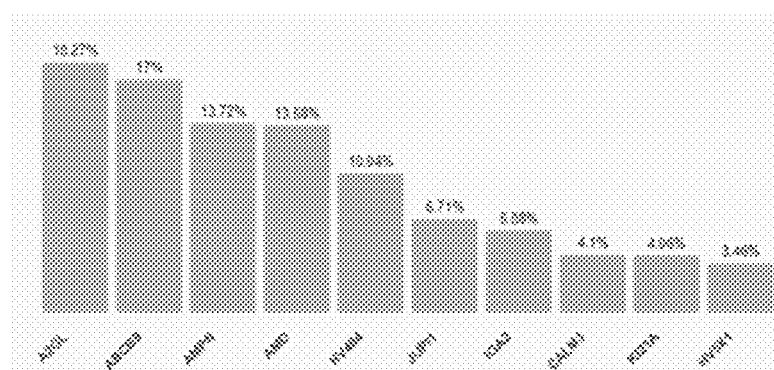

FIG. 2 demonstrates the field importance of selected biomarkers tested in batches A3 (FIG. 2A), A4 (FIG. 2B), and A5 (FIG. 2C).

Figures 3A, 3B, 3C:
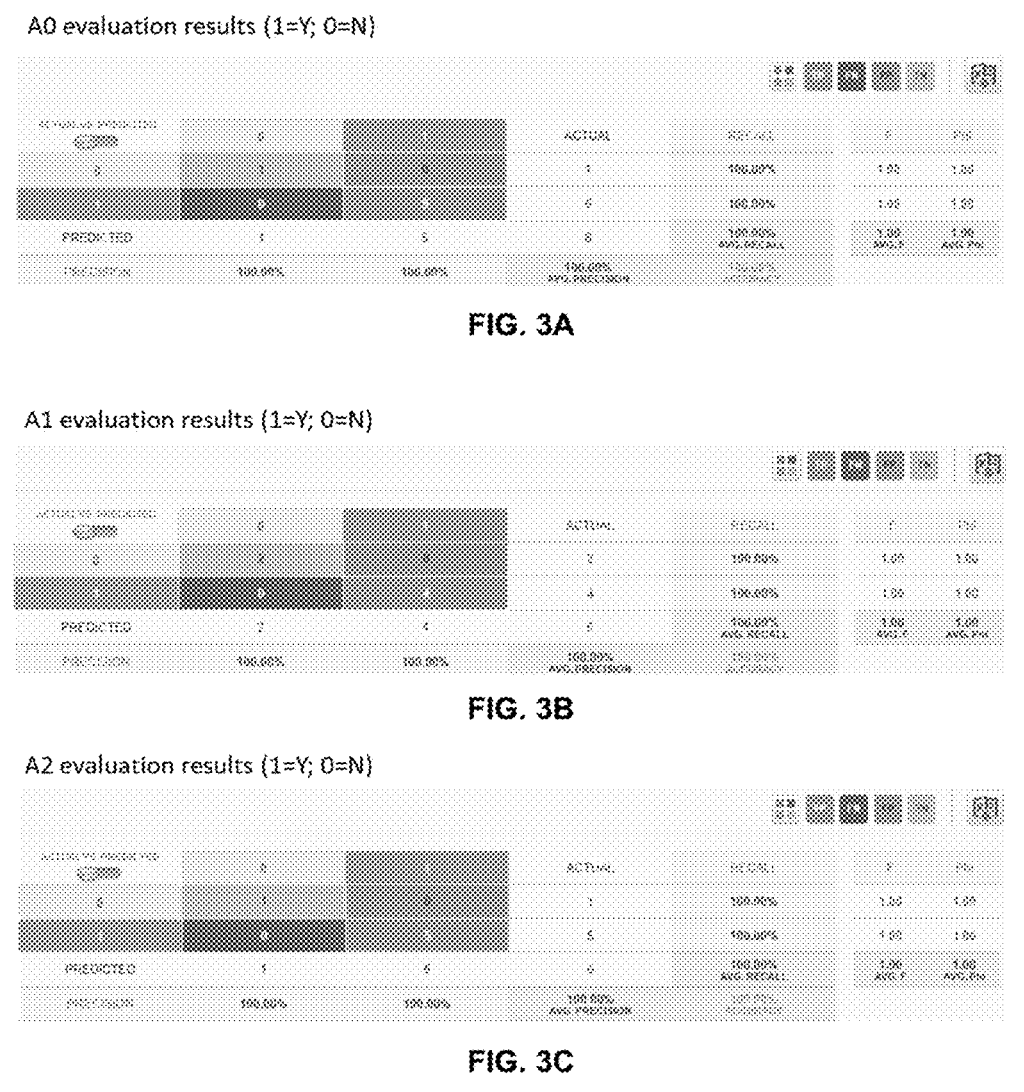

FIG. 3 demonstrates the evaluation results in batches A0 (FIG. 3A), A1 (FIG. 3B), and A2 (FIG. 3C). TP=True Positives (sensitivity), TN=True Negatives (specificity), FP=False Positives, and FN=False Negatives.

FIG. 4 demonstrates the evaluation results in batches A1 (FIG. 4A), A2 (FIG. 4B), and A3 (FIG. 4C). TP=True Positives (sensitivity), TN=True Negatives (specificity), FP=False Positives, and FN=False Negatives.

Figure 5A:
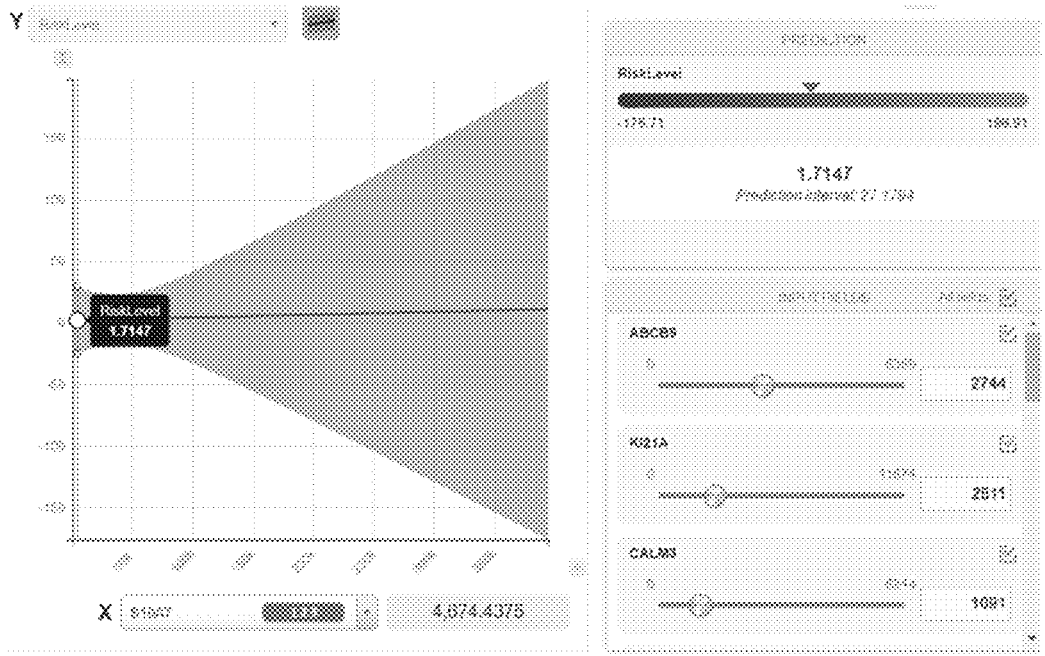
Figure 5B:
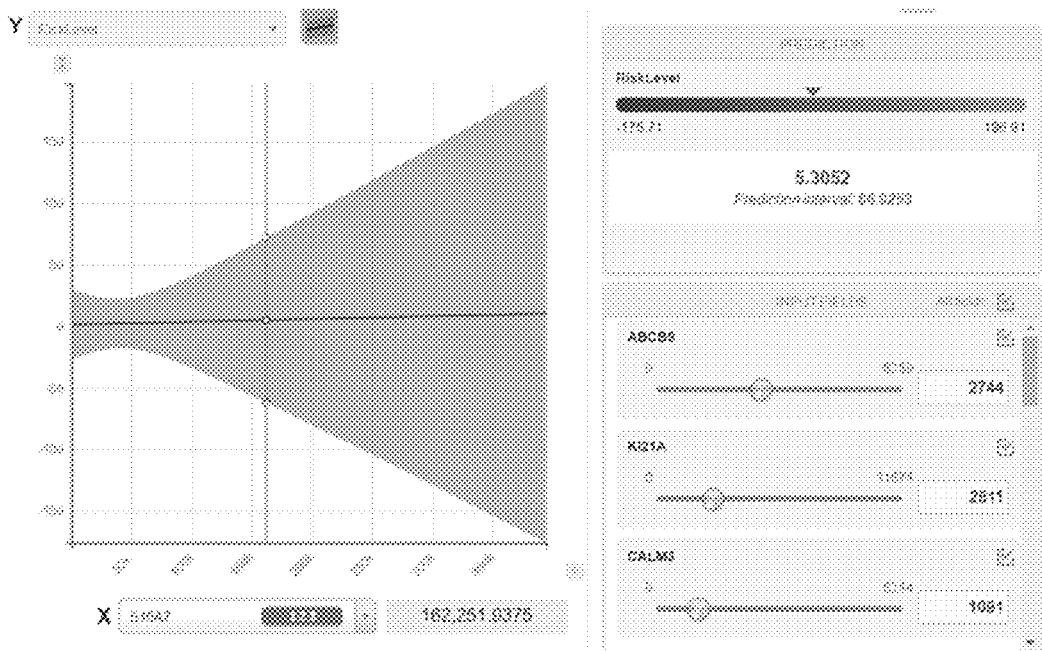
FIG. 5B shows high amounts of the biomarker and the associated risk prediction. Other methods of building algorithms were also used, e.g., logistic regression, decision tree and neural network (data not shown).

FIG. 5 demonstrates the linear regression with the predicted risk level shown in the top right for biomarker S10A7, whose risk prediction spans from 1.7147 upwards. A high level of 5.3052 is found on the prediction line. FIG. 5A shows low amounts of the biomarker and the associated risk prediction, while FIG. 5B shows high amounts of the biomarker and the associated risk prediction. Other methods of building algorithms were also used, e.g., logistic regression, decision tree and neural network (data not shown).

Figure 6A:
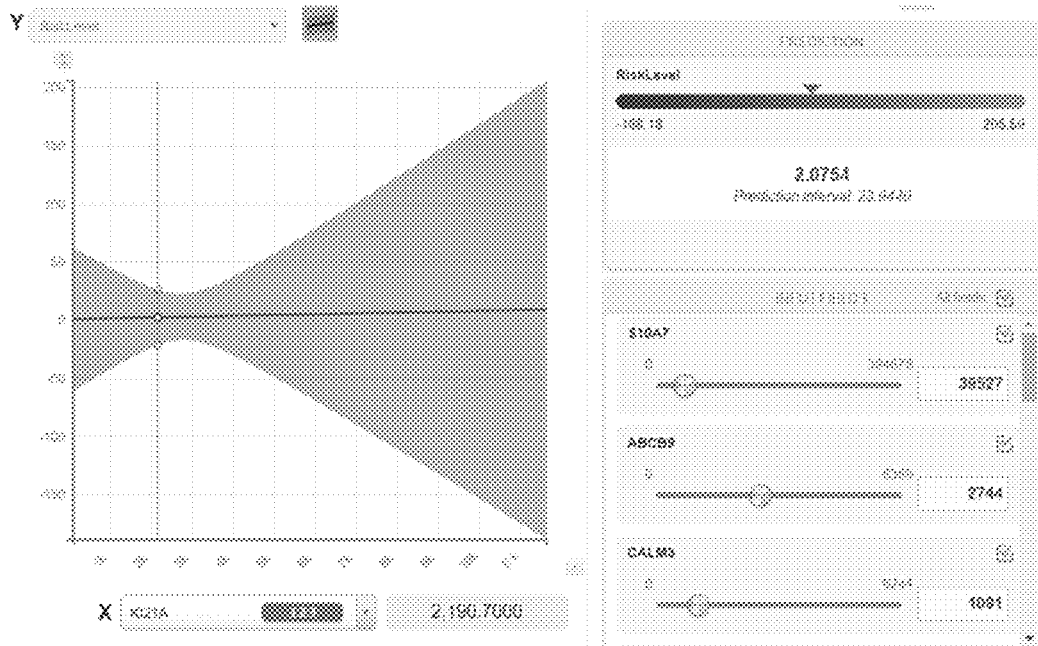
Figure 6B:
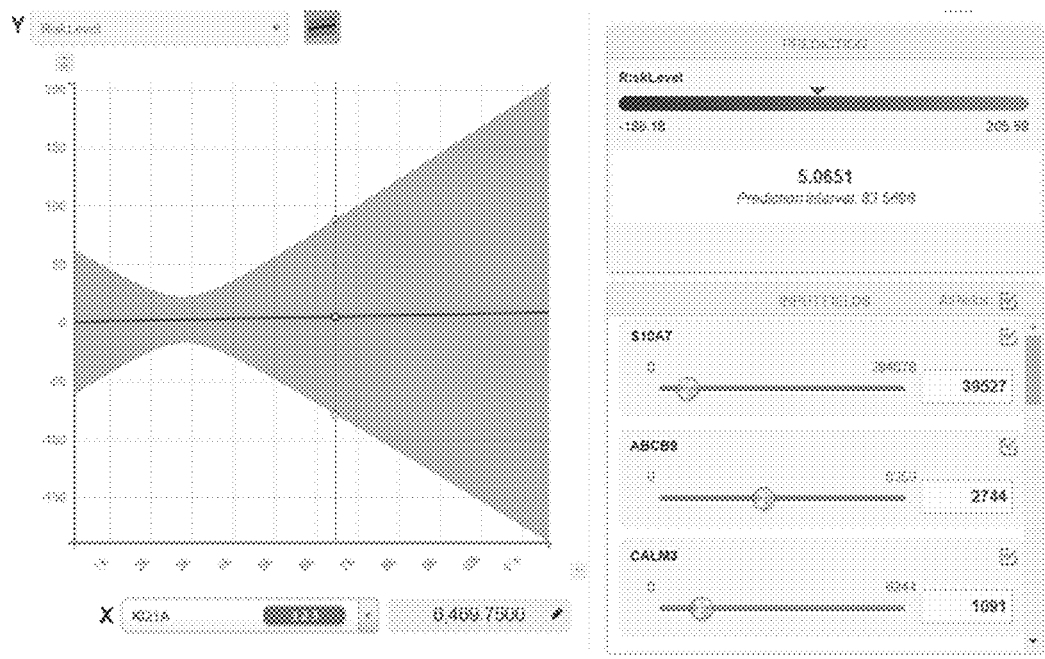
FIG. 6B shows high amounts of the biomarker and the associated risk prediction. Other methods of building algorithms were also used, e.g., logistic regression, decision tree and neural network (data not shown).

FIG. 6 demonstrates the linear regression with the predicted risk level shown in the top right for biomarker KI21A, whose risk prediction spans from 2.0754 upwards. A high level of 5.0651 is found on the prediction line. FIG. 6A shows low amounts of the biomarker and the associated risk prediction, while FIG. 6B shows high amounts of the biomarker and the associated risk prediction. Other methods of building algorithms were also used, e.g., logistic regression, decision tree and neural network (data not shown).

Figure 7A:
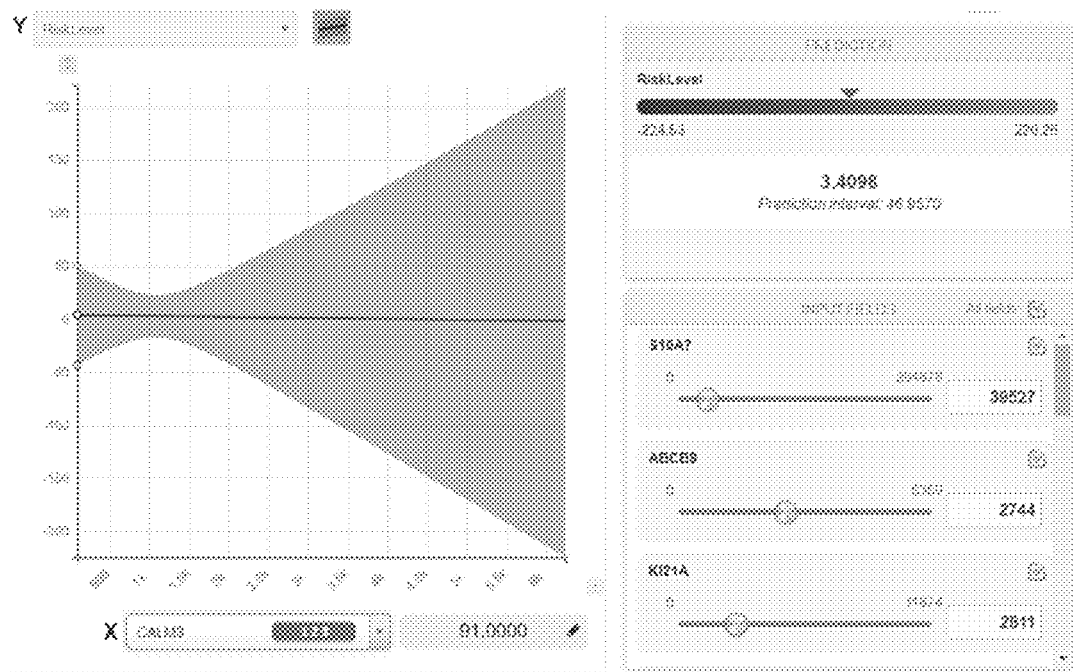
Figure 7B:
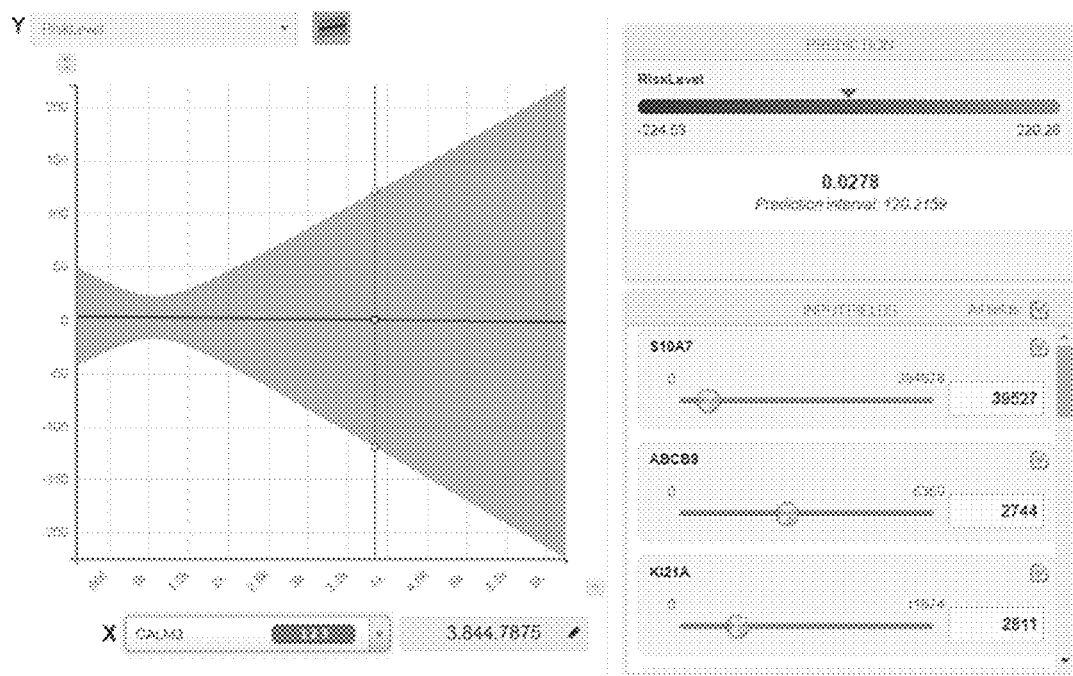
FIG. 7B shows high amounts of the biomarker and the associated risk prediction. Other methods of building algorithms were also used, e.g., logistic regression, decision tree and neural network (data not shown).

FIG. 7 demonstrates the linear regression with the predicted risk level shown in the top right for biomarker CALM3, whose risk prediction spans from 3.4098 downwards. A low level of 0.0278 is found on the prediction line. FIG. 7A shows low amounts of the biomarker and the associated risk prediction, while FIG. 7B shows high amounts of the biomarker and the associated risk prediction. Other methods of building algorithms were also used, e.g., logistic regression, decision tree and neural network (data not shown).

Figure 8A:
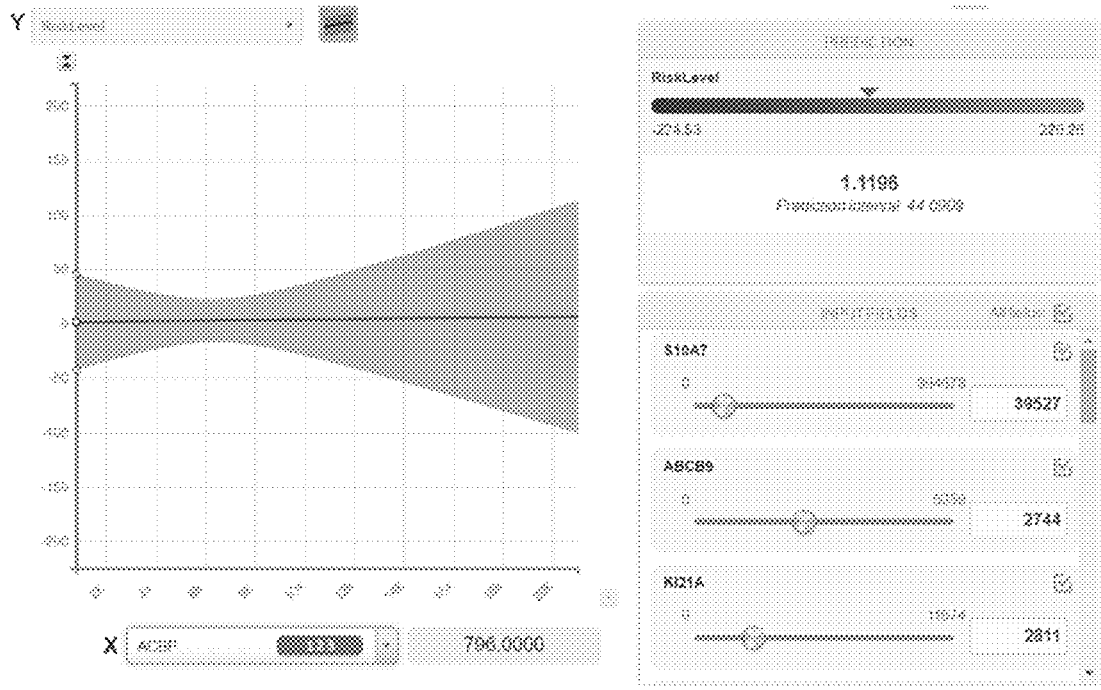
Figure 8B:
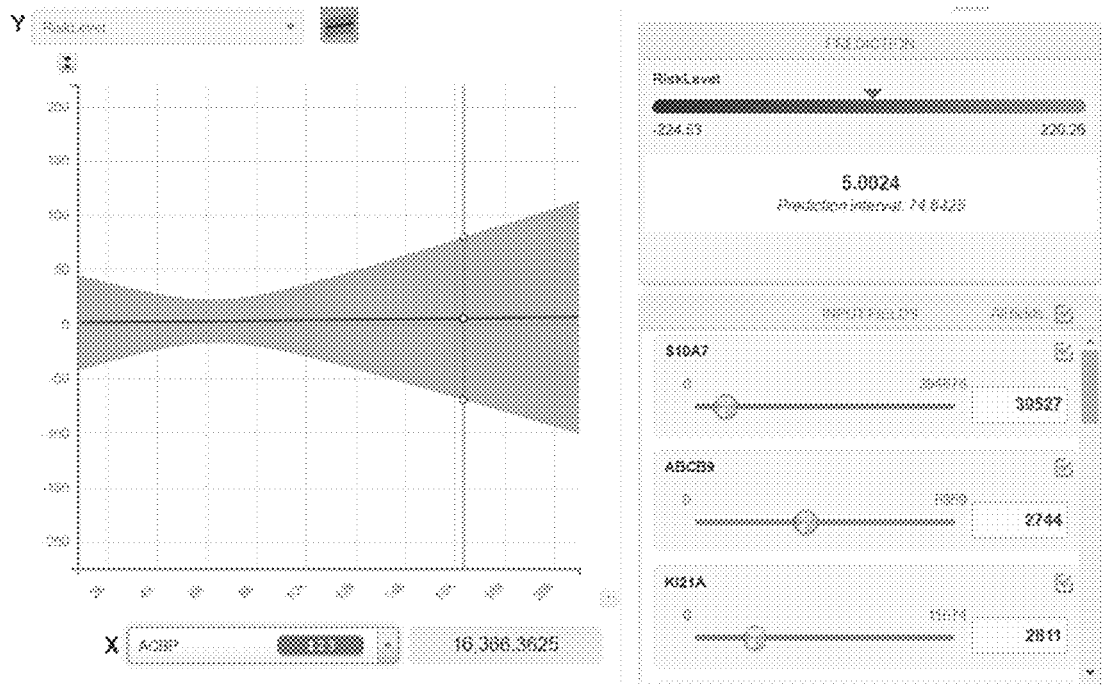
FIG. 8B shows high amounts of the biomarker and the associated risk prediction. Other methods of building algorithms were also used, e.g., logistic regression, decision tree and neural network (data not shown).

FIG. 8 demonstrates the linear regression with the predicted risk level shown in the top right for biomarker ACBP, whose risk prediction spans from 1.1196 upwards. A high level of 5.0024 is found on the prediction line. FIG. 8A shows low amounts of the biomarker and the associated risk prediction, while FIG. 8B shows high amounts of the biomarker and the associated risk prediction. Other methods of building algorithms were also used, e.g., logistic regression, decision tree and neural network (data not shown).

Figure 9A:
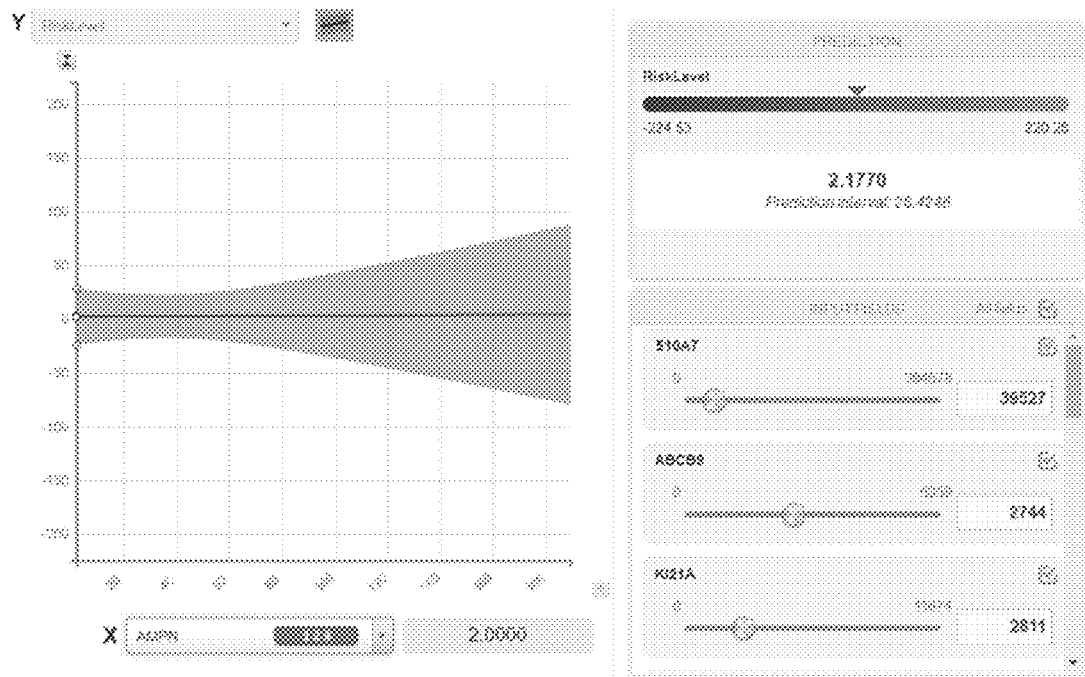
Figure 9B:
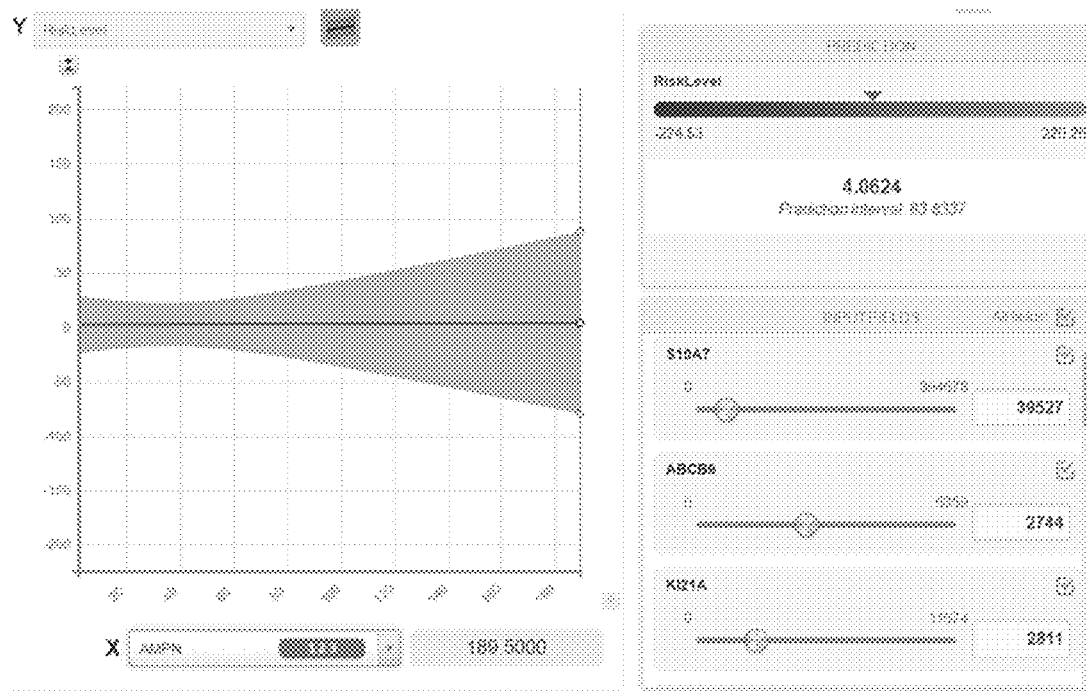
FIG. 9B shows high amounts of the biomarker and the associated risk prediction. Other methods of building algorithms were also used, e.g., logistic regression, decision tree and neural network (data not shown).

FIG. 9 demonstrates the linear regression with the predicted risk level shown in the top right for biomarker AMPN, whose risk prediction spans from 2.1770 upwards. A high level of 4.0624 is found on the prediction line. FIG. 9A shows low amounts of the biomarker and the associated risk prediction, while FIG. 9B shows high amounts of the biomarker and the associated risk prediction. Other methods of building algorithms were also used, e.g., logistic regression, decision tree and neural network (data not shown).

Figure 10A:
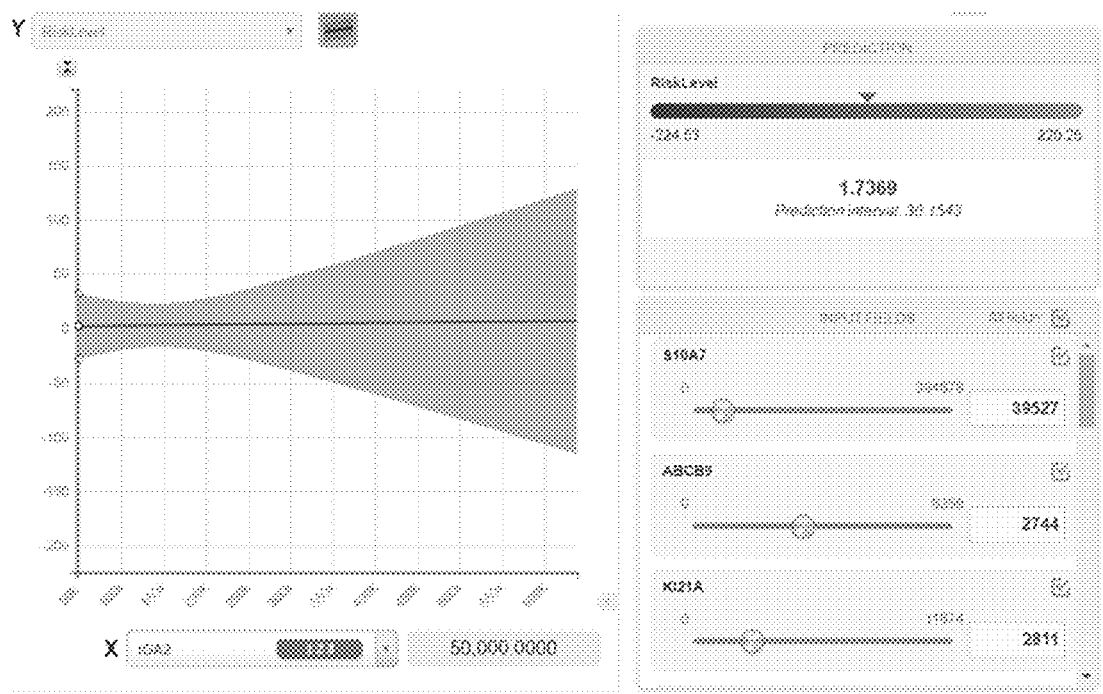
Figure 10B:
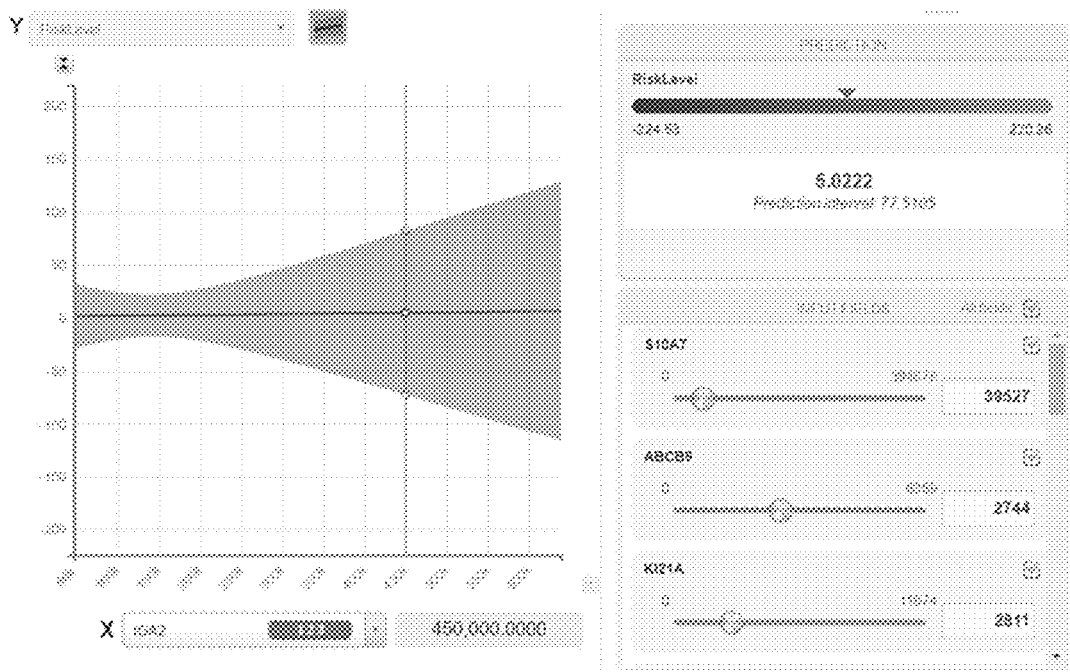
FIG. 10B shows high amounts of the biomarker and the associated risk prediction. Other methods of building algorithms were also used, e.g., logistic regression, decision tree and neural network (data not shown).

FIG. 10 demonstrates the linear regression with the predicted risk level shown in the top right for biomarker IGA2, whose risk prediction spans from 1.7369 upwards. A high level of 5.0222 is found on the prediction line. FIG. 10A shows low amounts of the biomarker and the associated risk prediction, while FIG. 10B shows high amounts of the biomarker and the associated risk prediction. Other methods of building algorithms were also used, e.g., logistic regression, decision tree and neural network (data not shown).

Figure 11A:
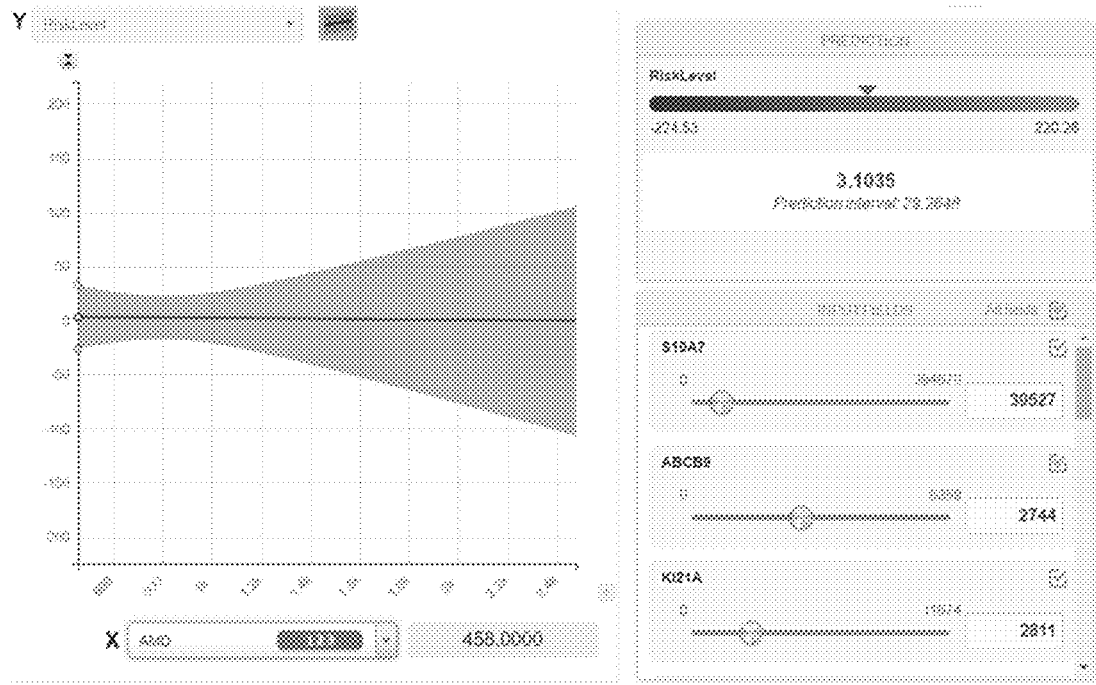
Figure 11B:
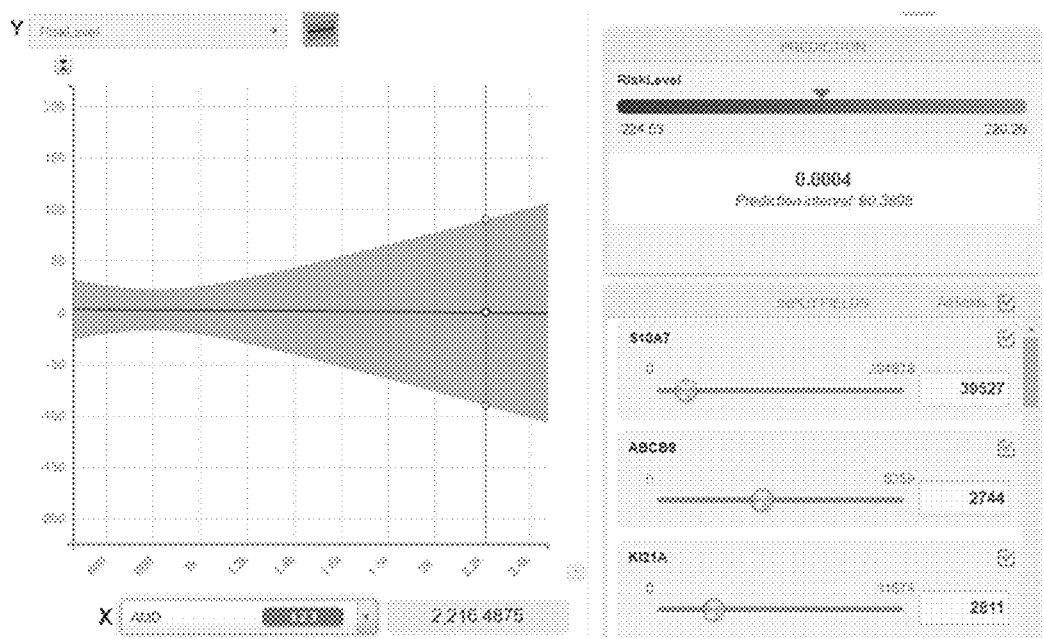
FIG. 11B shows high amounts of the biomarker and the associated risk prediction. Other methods of building algorithms were also used, e.g., logistic regression, decision tree and neural network (data not shown).

FIG. 11 demonstrates the linear regression with the predicted risk level shown in the top right for biomarker AMD, whose risk prediction spans from 3.1035 downwards. A low level of 0.0004 is found on the prediction line. FIG. 11A shows low amounts of the biomarker and the associated risk prediction, while FIG. 11B shows high amounts of the biomarker and the associated risk prediction. Other methods of building algorithms were also used, e.g., logistic regression, decision tree and neural network (data not shown).

Figure 12:
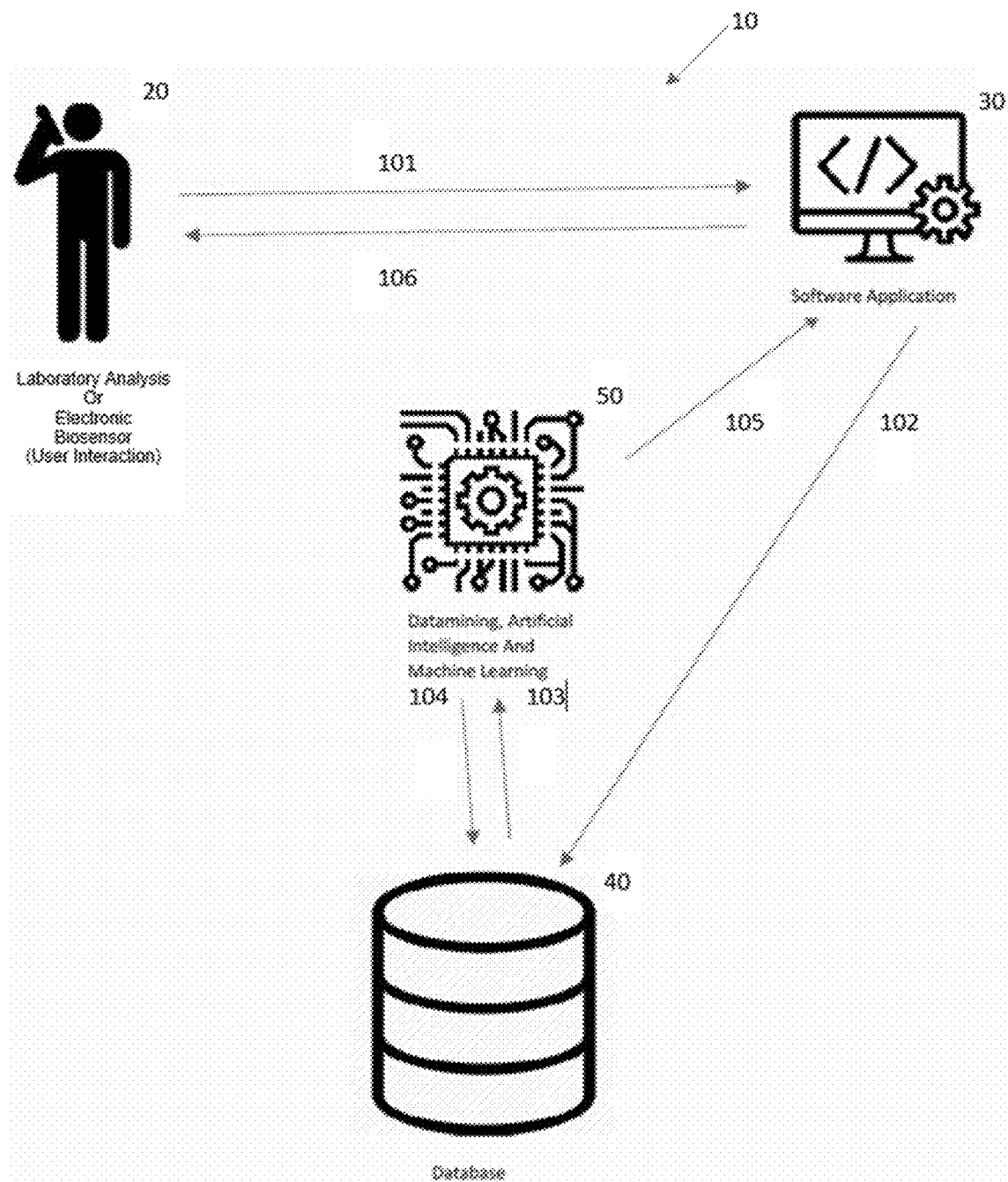
FIG. 12 shows a schematic diagram (10) of a sensor or lab analysis (20), a software application (3), a database (40), and data mining, artificial intelligence, and machine learning (50), and the interactions of data between them. 101 Data from a sensor is transmitted to a software application. 102 Data from the software is transmitted to a database. 103 data from the database is used for machine learning. 104 data that has been analyzed is transmitted to the database. 105 data from the machine learning is transmitted to a software application. 106 data from the software application is transmitted to the end user.

FIG. 12 shows a schematic diagram (10) of a sensor or lab analysis (20), a software application (3), a database (40), and data mining, artificial intelligence, and machine learning (50), and the interactions of data between them. 101 Data from a sensor is transmitted to a software application. 102 Data from the software is transmitted to a database. 103 data from the database is used for machine learning. 104 data that has been analyzed is transmitted to the database. 105 data from the machine learning is transmitted to a software application. 106 data from the software application is transmitted to the end user.

FIG. 13 depicts different example of biosensors. FIG. 13A depicts an electronic biosensor that an be installed onto multiple platforms such as skin or clothing. FIG. 13B depicts an electronic biosensor installed onto a swab for use to detect disease. The swab also has electronics to transmit data to a software. FIG. 13 depicts an electronic biosensor installed into or onto a phone casing or other relevant usable device for use to detect diseases. The device also has electronics to transmit data to a software application.

Figure 14:
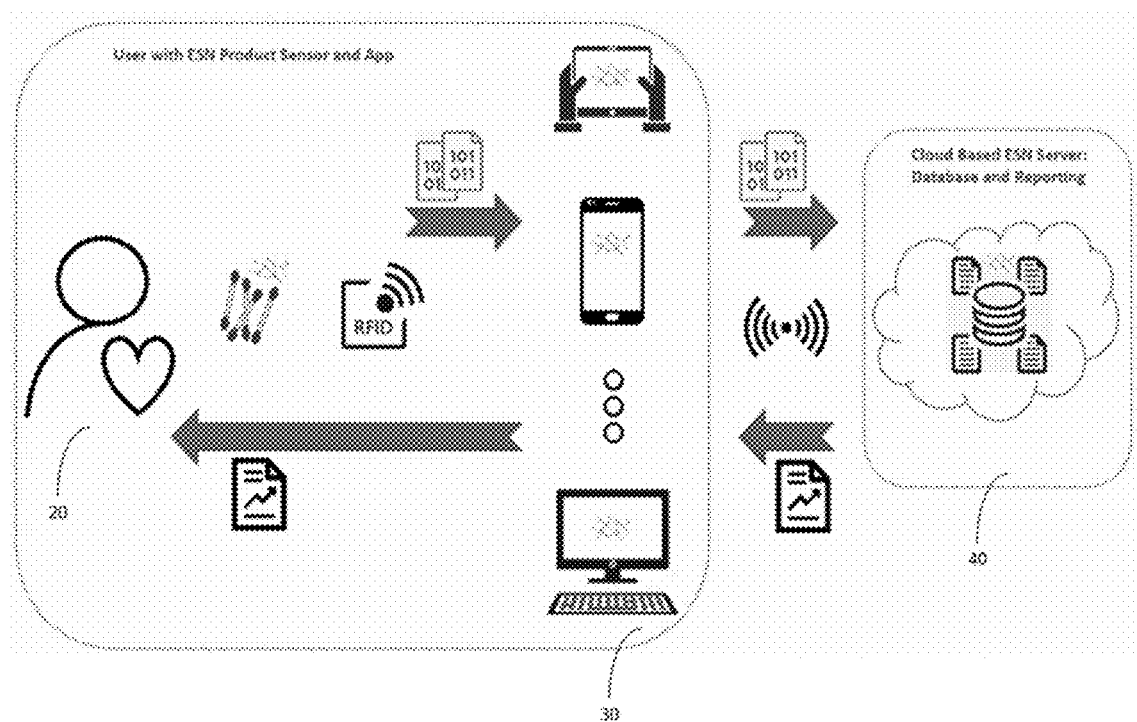
FIG. 14 depicts how data can be transmitted between a sensor or a user (20), a software (30), and a cloud based server with a database (40). Data can be transmitted between these different systems wirelessly, for example using RFID, Bluetooth, or Wi-Fi.

FIG. 14 depicts how data can be transmitted between a sensor or a user (20), a software (30), and a cloud based server with a database (40). Data can be transmitted between these different systems wirelessly, for example using RFID, Bluetooth, or Wifi.

Figure 15:
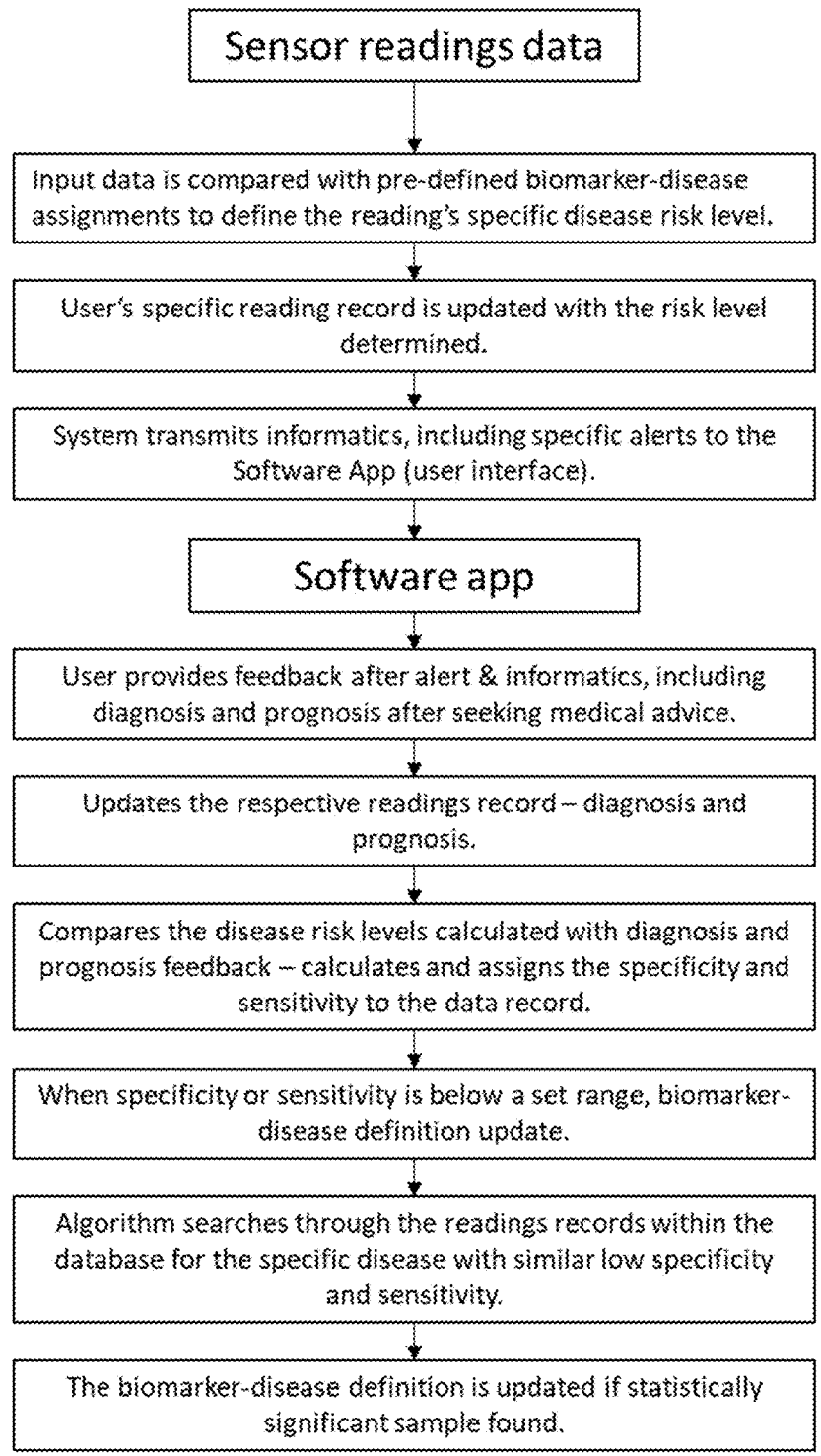
FIG. 15 depicts a flowchart showing how data can be transmitted from a sensor to a software app, with different steps of data input and processing. Input data can be compared with pre-defined biomarker-disease assignments to define the reading's specific disease risk level. A user's specific reading record can be updated with the risk level determined. A system can transmit informatics, including specific alerts to a software app (user interface). A user can provide feedback to a software app after an alert & informatics, including diagnosis and prognosis after seeking medical advice. A software app can update a respective readings record with a diagnosis and prognosis. A software app can compare a disease risk level calculated with diagnosis and prognosis feedback, and can calculate and assign specificity and sensitivity to the data record. When a specificity or sensitivity is below a set range, a biomarker-disease definition can be updated. An algorithm can search through a readings record within a database for a specific disease with similar low specificity and sensitivity. A biomarker-disease definition can be updated if a statistically significant sample is found.

FIG. 15 depicts a flowchart showing how data can be transmitted from a sensor to a software app, with different steps of data input and processing. Input data can be compared with pre-defined biomarker-disease assignments to define the reading's specific disease risk level. A user's specific reading record can be updated with the risk level determined. A system can transmit informatics, including specific alerts to a software app (user interface). A user can provide feedback to a software app after an alert & informatics, including diagnosis and prognosis after seeking medical advice. A software app can update a respective readings record with a diagnosis and prognosis. A software app can compare a disease risk level calculated with diagnosis and prognosis feedback, and can calculate and assign specificity and sensitivity to the data record. When a specificity or sensitivity is below a set range, a biomarker-disease definition can be updated. An algorithm can search through a readings record within a database for a specific disease with similar low specificity and sensitivity. A biomarker-disease definition can be updated if a statistically significant sample is found.

Figure 16:
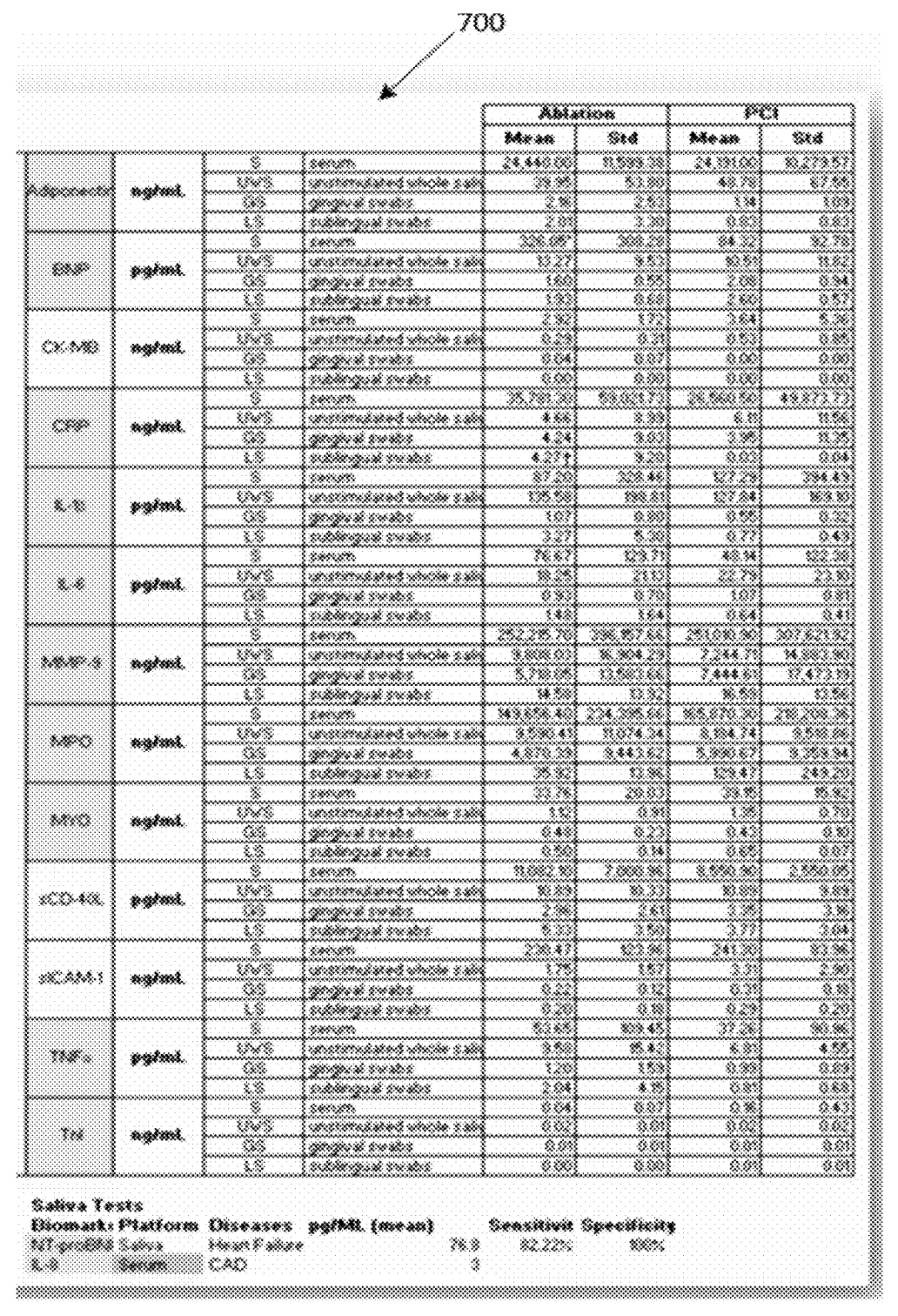

FIG. 16 displays a selection of biomarkers and the mean ablation and PCI detection concentrations from serum samples, unstimulated whole saliva samples, gingival swabs, and sublingual swabs.

Figure 17A:
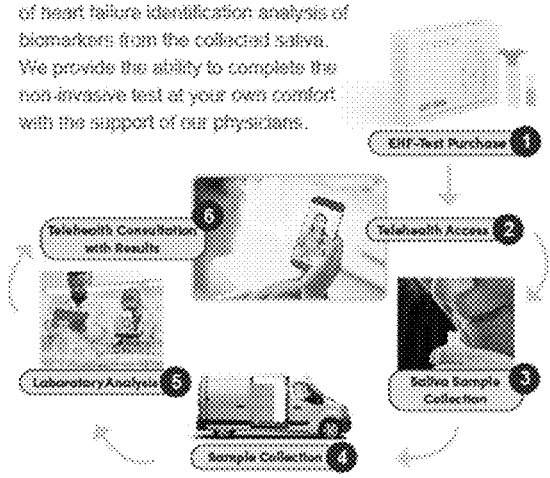
FIG. 17A shows saliva sample collection, delivery, and laboratory analysis, followed by a telehealth consultation with results.
Figure 17B:
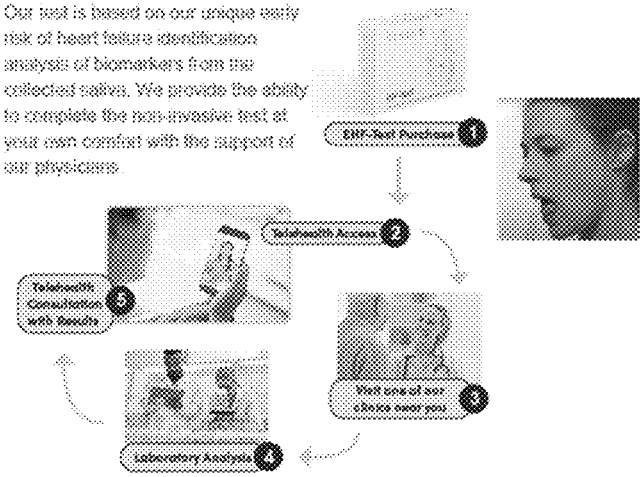
FIG. 17B shows saliva a clinic visit for sample collection, followed by a telehealth consultation with results.

FIG. 17 depicts different ways in which a detection can occur and a risk value shown to a subject or healthcare professional. FIG. 17A shows saliva sample collection, delivery, and laboratory analysis, followed by a telehealth consultation with results. FIG. 17A shows saliva a clinic visit for sample collection, followed by a telehealth consultation with results.

Figure 18A:
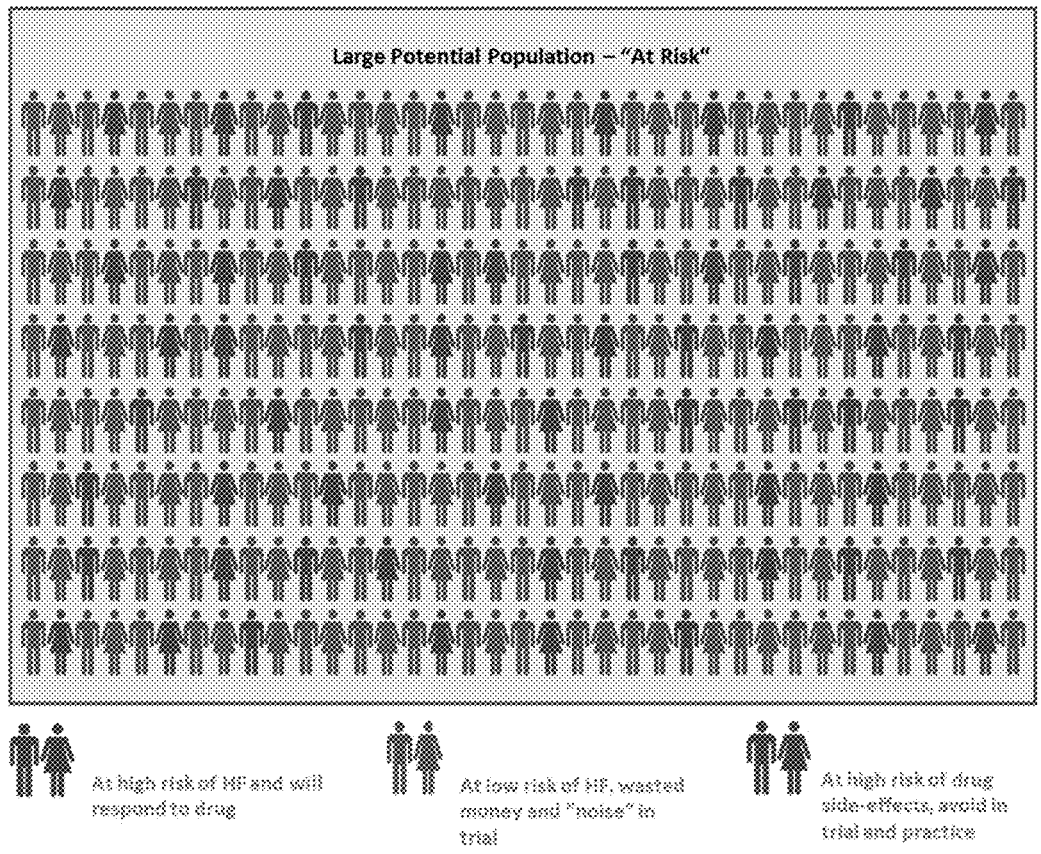
FIG. 18A depicts how different subjects within a population can be stratified into high risk of heart failure groups, low risk of heart failure groups, and high risk of drug side-effects groups, allowing actionable clinical decisions to be made based on the categorization of risk.
Figure 18B:
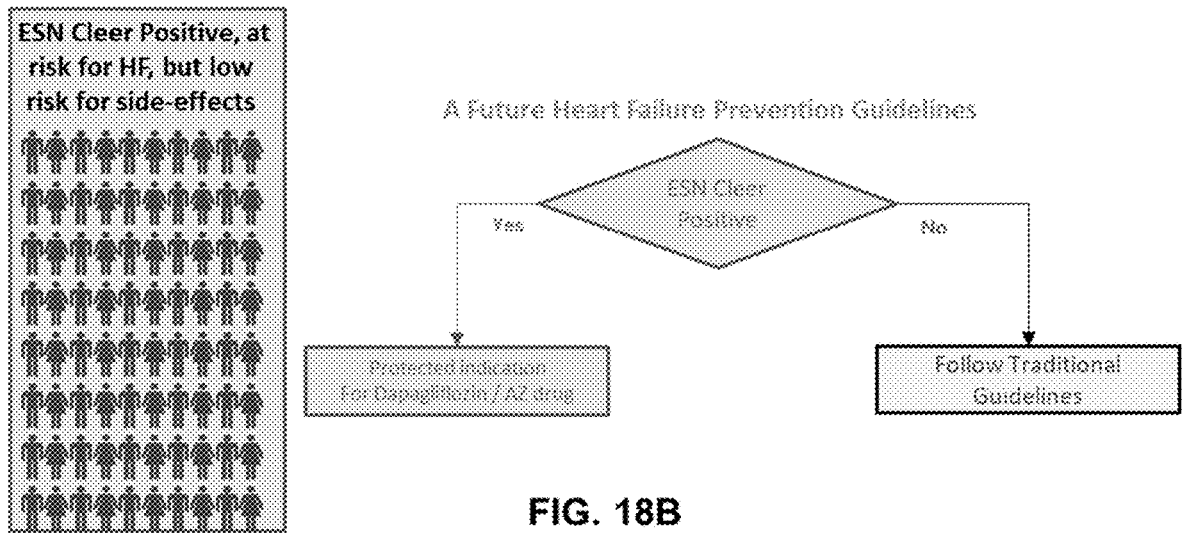
FIG. 18B depicts how individuals who are identified as being high risk for heart failure, but low risk for side effects can be given a protected indication for dapagliflozin or an AZ drug.

FIG. 18A depicts how different subjects within a population can be stratified into high risk of heart failure groups, low risk of heart failure groups, and high risk of drug side-effects groups, allowing actionable clinical decisions to be made based on the categorization of risk. FIG. 18B depicts how individuals who are identified as being high risk for heart failure, but low risk for side effects can be given a protected indication for dapagliflozin or an AZ drug.

Figure 19:
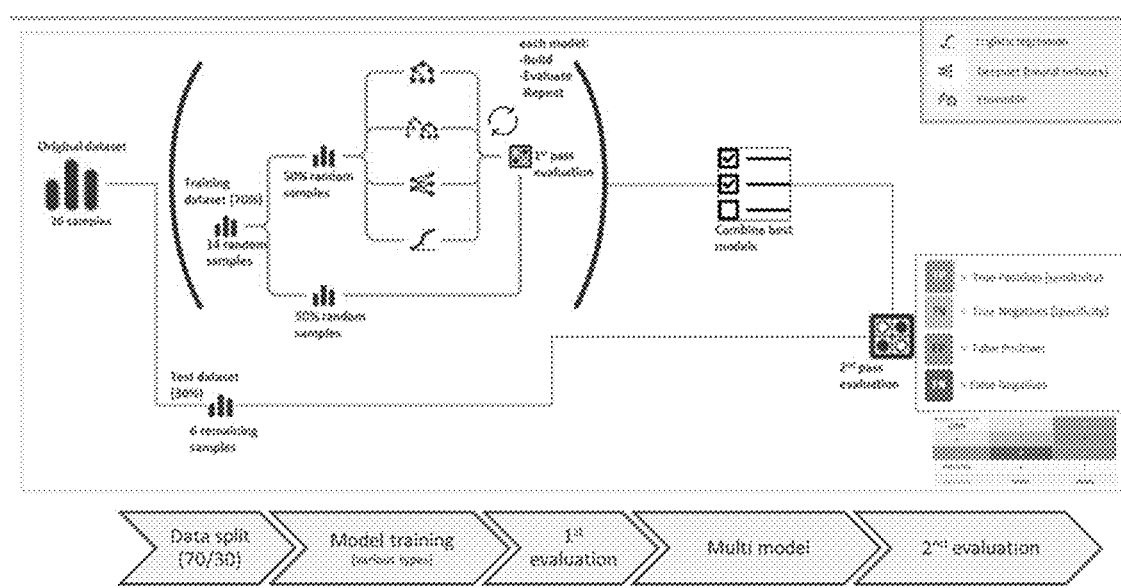
FIG. 19 depicts how data was processed from an original dataset of 20 samples. A Training dataset of 14 samples (70%) was selected at random for machine learning using logistic regression, deepnet (neural network), and ensemble. Half of these samples were used to create the first model. The remaining 50% were used for a first pass evaluation of the model, after which the best models were combined. A second pass evaluation was then performed using the six remaining samples. TP=True Positives (sensitivity), TN=True Negatives (specificity), FP=False Positives, and FN=False Negatives.

FIG. 19 depicts how data was processed from an original dataset of 20 samples. A Training dataset of 14 samples (70%) was selected at random for machine learning using logistic regression, deepnet (neural network), and ensemble. Half of these samples were used to create the first model. The remaining 50% were used for a first pass evaluation of the model, after which the best models were combined. A second pass evaluation was then performed using the six remaining samples. TP=True Positives (sensitivity), TN=True Negatives (specificity), FP=False Positives, and FN=False Negatives.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Embodiments

1. A method comprising:
   (a) contacting a first compound with a second compound present in a biological sample from a first subject that does not currently have or has not been diagnosed with heart failure, wherein the second compound when present in the biological sample at an increased level or a decreased level, relative to a reference level, is indicative of developing the heart failure within a time period of from about 1 week to about 5 years;
   (b) detecting binding of the first compound with the second compound; and
   (c) administering a treatment to the subject, wherein the administering prevents an occurrence of a heart failure over the time period when the treatment is administered over the time period.
2. The method of embodiment 1, wherein the reference level is derived from a plurality of biological samples that are each from a second subject.
3. The method of embodiment 2, wherein the second subject does not currently have or has not been diagnosed with the heart failure.
4. The method of embodiment 2, wherein the second subject has a non-heart failure disease, has been diagnosed with a non-heart failure disease, or a combination thereof.
5. The method of embodiment 4, wherein the non-heart failure disease comprises a cardiac disease.
6. The method of embodiment 2, wherein the second subject has heart failure, has been diagnosed with heart failure, or a combination thereof.
7. The method of embodiment 6, wherein the second subject was not hospitalized in the 12 months prior to collection of a biological sample from the second subject.
8. The method of embodiment 7, wherein the second subject was not hospitalized from about 1 week to about 3 months prior to the collection of the biological sample from the second subject.
9. The method of any one of embodiments 6-8, wherein the heart failure of the second subject is mild.
10. The method of any one of embodiments 6-8, wherein the heart failure of the second subject is severe.
11. The method of any one of embodiments 1-10, wherein the time period is from about one month to about three months.
12. The method of any one of embodiments 1-10, wherein the time period is from about three months to about eighteen months.
13. The method of any one of embodiments 1-12, wherein the treatment further prevents an occurrence of the heart failure in the first subject over a period of time that is longer than the time period of the treatment.
14. The method of embodiment 1, wherein the first compound comprises a polypeptide.
15. The method of embodiment 14, wherein the polypeptide comprises an antibody, an aptamer, or a functional fragment thereof.
16. The method of any one of embodiments 1-15, wherein the first compound comprises a fluorophore, a chromophore, a fluorescence-resonance energy transfer (FRET) donor, a FRET acceptor, or any combination thereof.
17. The method of any one of embodiments 1-16, wherein the second compound is not substantially present in a subject that has heart failure, a diagnosis of heart failure, or a combination thereof.
18. The method of any one of embodiments 1-17, wherein the second compound is at least partially present in a subject that has heart failure, a diagnosis of heart failure, or a combination thereof.
19. The method of any one of embodiments 1-17, wherein the second compound is present at a decreased level in the biological sample from the first subject, relative to the reference level.
20. The method of any one of embodiments 1-17, wherein the second compound is present at an increased level in the biological sample from the first subject, relative to the reference level.
21. The method of any one of embodiments 2-17, wherein the second compound is present at a decreased level in the biological sample from the first subject, relative to the reference level, wherein the reference level is derived from a biological sample from the second subject that developed the heart failure within a time period of about 12 months prior to collection of the biological sample from the second subject.
22. The method of any one of embodiments 2-17, wherein the second compound is present at an increased level in the biological sample from the first subject, relative to the reference level, wherein the reference level is derived from a biological sample from the second subject that developed the heart disease within a time period of about 12 months prior to collection of the biological sample from the second subject.
23. The method of any one of embodiments 1-22, wherein the second compound comprises a polypeptide.
24. The method of embodiment 23, wherein the polypeptide does not comprise a natriuretic peptide.
25. The method of embodiment 24, wherein the polypeptide comprises at least about 70% sequence identity to a polypeptide recited in Table 1, Table 7, a salt of any of these, or any combination thereof, as determined by BLAST.
26. The method of any one of embodiments 2-17 or 23-25, wherein the method distinguishes a first subject who develops heart failure without the administering over the time period from the second subject, wherein the second subject does not develop heart failure over the time period.
27. The method of embodiment 26, wherein the method distinguishes the first subject from the second subject with an accuracy of at least about 90%, with a confidence level of at least about 95%.
28. The method of any one of embodiments 1-27, wherein the biological sample comprises amniotic fluid, amniotic sac, aqueous humor, bile, blood, blood plasma, breast milk, cerebrospinal fluid (CSF), cerebrospinal fluid rhinorrhea, chyle, chyme, endolymph, extracellular fluid, exudate, gastric acid, hemolacria, hemolymph, interstitial fluid, lymph, mucus, pericardial fluid, perilymph, peritoneal fluid, perspiration, phlegm, pus, rheum, saliva, semen, sweat, synovial fluid, tears, transcellular fluid, transudate, urine, vaginal lubricant, vitreous body, vomit, or any combination thereof.

29. The method of any one of embodiments 1-27, wherein the biological sample comprises urine.

30. The method of any one of embodiments 1-27, wherein the biological sample comprises saliva.

31. The method of embodiment 30, wherein the biological sample is obtained using an oral sample collection device.

32. The method of embodiment 31, wherein the oral sample collection device comprises the first compound, and wherein the device is configured to perform the contacting when the saliva is input into the oral sample collection device.

33. The method of embodiment 31 or 32, wherein the oral sample collection device comprises a wireless transmitter.

34. The method of embodiment 33, wherein the wireless transmitter comprises a Bluetooth transmitter, an RF transmitter, a cellular signal transmitter, a Wi-fi transmitter, or any combination thereof.

35. The method of any one of embodiments 31-34, wherein the oral sample collection device comprises a wireless receiver.

36. The method of embodiment 35, wherein the wireless receiver comprises a Bluetooth receiver, an RF transmitter, a cellular signal receiver, a Wi-fi receiver, or any combination thereof.

37. The method of embodiment 31, wherein the oral sample collection device comprises an oral swab.

38. The method of any one of embodiments 31-37, wherein a concentration of the second compound is enriched in the oral sample collection device after binding to the first compound, relative to a concentration of the second compound present in the biological sample.

39. The method of any one of embodiments 1-38, further comprising, with the aid of a computer processor, executing an algorithm selecting a treatment from a database prior to the administering.

40. The method of embodiment 39, wherein the database is at least transiently stored on a computer readable memory.

41. The method of embodiment 39 or 40, wherein the database comprises a treatment formulary of medicaments or interventions.

42. The method of any one of embodiments 39-41, wherein the treatment comprises a medicament.

43. The method of embodiment 42, wherein the medicament comprises a drug or a biologic that is licensed or approved for a condition by the United States Federal Drug Agency (USFDA) anytime as of or after Apr. 1, 2020.

44. The method of embodiment 43, wherein the drug or the biologic is not licensed or approved by the USFDA for heart failure anytime as of or after May 1, 2020.

45. The method of embodiment 42, wherein the medicament comprises a drug or a biologic that is not licensed or approved by the USFDA for any condition anytime as of or after May 1, 2020.

46. The method of any one of embodiments 42-45, wherein the medicament comprises a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator cardioxyl, an omecamtiv mecarbil, a relaxin, a serelaxin, a staroxime, bucindolol, a phosphodiesterase 5 inhibitor, a vasopressin inhibitor, a levosimendan, a sodium-glucose cotransporter-2 (SGLT2) inhibitor, an If channel blocker, an alpha blocker, a beta receptor blocker, a beta blocker, an ACE inhibitor, a stereoisomer of any of these, a salt of any of these, or any combination thereof.

47. The method of embodiment 46, wherein the medicament comprises the beta receptor blocker or the salt thereof, wherein the beta receptor blocker or salt thereof comprise at least one stereocenter in an S-configuration.

48. The method of embodiment 47, wherein the beta receptor blocker comprises a long acting beta blocker.

49. The method of embodiment 47, wherein the beta receptor blocker comprises a short acting beta blocker.

50. The method of embodiment 48 or 49, wherein the long acting beta blocker or salt thereof or the short acting beta blocker or the salt thereof comprises pindolol, oxprenolol, atenolol, acebutolol, bisoprolol, bucindolol, carvedilol, metoprolol, nadolol, nebivolol, oxprenolol, propranolol, a stereoisomer of any of these, a polymorph of any of these, a diastereomer of any of these, a salt of any of these, or any combination thereof.

51. The method of embodiment 47, wherein the long acting or short acting beta blocker or the salt thereof comprise S-pindolol, S-oxprenolol, S-atenolol, S-acebutolol, S-bisoprolol, S-bucindolol, S-carvedilol, S-metoprolol, S-nadolol, S-nebivolol, S-Oxprenolol, S-propranolol, a stereoisomer of any of these, a polymorph of any of these, a diastereomer of any of these, a salt of any of these, or any combination thereof.

52. The method of embodiment 46, wherein the medicament comprises the statin or the salt thereof, wherein the statin or the salt thereof comprises atorvastatin, fluvastatin, lovastatin, pravastatin, rosuvastatin, simvastatin, pitavastatin, a salt of any of these, or any combination thereof.

53. The method of embodiment 46, wherein the medicament comprises the blood thinner or the salt thereof, wherein the blood thinner or the salt thereof comprises apixaban, dabigatran, edoxaban, fondaparinux, heparin, rivaroxaban, warfarin, a salt of any of these, or any combination thereof.

54. The method of embodiment 46, wherein the medicament comprises the phosphodiesterase 5 inhibitor or the salt thereof, wherein the phosphodiesterase 5 inhibitor or the salt thereof comprises amrinone, milrinone, avanafil, lodenafil, mirodenafil, sildenafil, tadalafil, vardenafil, udenafil, zaprinast, benzaminenafil, a salt of any of these, or any combination thereof.

55. The method of embodiment 46, wherein the medicament comprises the vasopressin inhibitor or the salt thereof, wherein the vasopressin inhibitor or the salt thereof comprises conivaptan, relcovaptan, nelivaptan, lixivaptan, mozavaptan, satavaptan, tolvaptan, demeclocycline, lithium, a salt of any of these, or any combination thereof.

56. The method of embodiment 46, wherein the medicament comprises the SGLT2 inhibitor or the salt thereof, wherein the SGLT2 inhibitor or the salt thereof comprises dapagliflozin, empagliflozin, canagliflozin, sotagliflozin, ertugliflozin, ipragliflozin, luseogliflozin, remogliflozin etabonate, sergliflozin etabonate, tofogliflozin a stereoisomer of any of these, a salt of any of these, or any combination thereof.

57. The method of embodiment 46, wherein the medicament comprises the aldosterone antagonist or the salt thereof, wherein the aldosterone antagonist or the salt thereof comprises spironolactone, eplerenone, finerenone, canrenoate, a stereoisomer of any of these, a salt of any of these, or any combination thereof.

58. The method of embodiment 46, wherein the medicament comprises the aldosterone synthesis inhibitor or the salt thereof, wherein the aldosterone synthesis inhibitor or the salt thereof comprises fadrozol, FAD 286, LCI699, a salt of any of these, or any combination thereof.

59. The method of embodiment 46, wherein the medicament comprises the angiotensin receptor antagonist or the salt thereof, wherein the angiotensin receptor antagonist or salt thereof comprises a sartan, candesartan, irbesartan, valsartan, telmisartan, eprosartan, olmesartan, azilsartan, fimasartan, sacubitril/valsartan, losartan, EXP 3174, amlodipine, a stereoisomer of any of these, a salt of any of these, or any combination thereof.

60. The method of embodiment 46, wherein the medicament comprises the ACE inhibitor or the salt thereof, wherein the ACE inhibitor or the salt thereof comprises benazepril, captopril, enalapril, fosinopril, lisinopril, moexipril, omapatrilat, perindopril, quinapril, ramipril, trandolapril, a salt of any of these, or any combination thereof.

61. The method of embodiment 46, wherein the medicament comprises the alpha blocker or the salt thereof, wherein the alpha blocker or the salt thereof comprises phenoxybenzamine, phentolamine, tolazoline, trazodone, alfuzosin, doxazosin, prazosin, tamsulosin, terazosin, silodosin, atipamezole, idazoxan, mirtazapine, yohimbine, a salt of any of these, or any combination thereof.

62. The method of embodiment 46, wherein the medicament comprises the guanylate cyclase stimulator or the salt thereof, wherein the guanylate cyclase stimulator or the salt thereof comprises a guanylate cyclase activator, adempas, riociguat, a salt of any of these or a combination thereof.

63. The method of embodiment 46, wherein the medicament comprises the inotrope or the salt thereof, wherein the inotrope comprises a cardiac inotrope or a salt thereof.

64. The method of embodiment 63, wherein the cardiac inotrope or salt thereof comprises a positive cardiac inotrope or a salt thereof.

65. The method of embodiment 64, wherein the positive cardiac inotrope or a salt thereof comprises a cardiotonic drug, a cardiotonic agent, a cardiostimulatory drug, a cardiostimulatory agent, any salt thereof, or any combination thereof.

66. The method of embodiment 64, wherein the positive cardiac inotrope or a salt thereof comprises a cardiac glycoside or a salt thereof.

67. The method of embodiment 66, wherein the cardiac glycoside or the salt thereof comprises a cardenolide, a bufadienolide, a salt of either of these, or any combination thereof.

68. The method of embodiment 67, wherein the cardiac glycoside or the salt thereof comprises the cardenolide or the salt thereof, and wherein the cardenolide or the salt thereof comprises a convallotoxin, an antiarin, a strophanthin, a digoxin, a digitoxin, an oleandrin, an adonitoxin, a salt of any of these, or any combination thereof.

69. The method of embodiment 67, wherein the cardiac glycoside or the salt thereof comprises the bufadienolide or the salt thereof, and wherein the bufadienolide or the salt thereof comprises a scillarenin, a proscillaridine A, a daigremontianin, a hellebore, a salt of any of these, or any combination thereof.

70. The method of embodiment 46, wherein the medicament comprises the cardiac inotrope or the salt thereof, wherein the cardiac inotrope or the salt thereof comprises a myosin activator or a salt thereof.

71. The method of embodiment 70, wherein the myosin activator or the salt thereof comprises an omecamtiv mecarbil or a salt thereof.

72. The method of embodiment 46, wherein the medicament comprises the cardiac inotrope or the salt thereof, wherein the cardiac inotrope or the salt thereof comprises a negative cardiac inotrope or a salt thereof.

73. The method of embodiment 72, wherein the negative cardiac inotrope or the salt thereof comprises a beta-blocker, a calcium-channel blocker, an anti-arrhythmic medicine, a salt of any of these, or any combination thereof.

74. The method of any one of embodiments 39-41, wherein the treatment comprises an intervention.

75. The method of embodiment 74, wherein the intervention comprises exercise, a selective diet, meditation, instructions to see a cardiologist, instructions to dispense a medicament, instructions to receive an ultrasound, or any combination thereof.

76. The method of any one of embodiments 39-75, wherein the database comprises a plurality of second compounds.

77. A method comprising determining a probability score for a subject developing heart failure, the method comprising:
  (a) contacting a device comprising a sensor with a bodily fluid of a subject;
  (b) detecting a level of a biomarker in the bodily fluid of the subject using the device, wherein the detecting at least in part occurs within a body of the subject, and wherein the bodily fluid is not processed prior to the detecting; and
  (c) comparing the level of the biomarker with a reference level to determine a probability of developing heart failure.

78. The method of embodiment 77, wherein the subject does not currently have or has not been diagnosed with heart failure.

79. The method of embodiment 77, wherein the subject has not been diagnosed with heart failure.

80. The method of embodiment 78 or 79, wherein the subject is assigned a probability score of developing heart failure.

81. The method of embodiment 77, wherein the subject is assigned a probability score of developing heart failure.

82. The method of embodiment 81, wherein the probability score comprises low probability, medium probability, high probability, or very high probability.

83. The method of embodiment 82, further comprising administering a treatment to the subject, wherein a choice of treatment is selected at least in part based on the probability score.

84. The method of embodiment 77, wherein the reference level comprises a range of reference levels.

85. The method of embodiment 77, wherein the range of reference levels comprises data from a range of reference samples.

86. The method of embodiment 77, wherein the sensor comprises an antibody or a functional fragment thereof.

87. The method of embodiment 77, wherein the sensor comprises a fluorophore, a chromophore, fluorescence-resonance energy transfer (FRET) donor, a FRET acceptor, or any combination thereof.

88. The method of any one of embodiments 77-87, wherein the biomarker comprises a polypeptide.

89. The method of embodiment 88, wherein the polypeptide does not comprise a natriuretic peptide.

90. The method of embodiment 88, wherein the polypeptide comprises at least about 70% sequence identity to a polypeptide recited in Table 1, Table 7, a salt of any of these, or any combination thereof, as determined by BLAST.

91. The method of any one of embodiments 77-87, wherein the biomarker comprises a microbe.

92. The method of embodiment 91, further comprising determining a microbiome status of the subject.

93. The method of embodiment 92, further comprising correlating the microbiome status with known databases to determine a probability score for the subject developing heart failure.

94. The method of any one of embodiments 77-93, wherein the biological sample comprises blood.

95. The method of any one of embodiments 77-94, wherein the biological sample comprises saliva.

96. The method of embodiment 95, wherein the biological sample is obtained using an oral sample collection device.

97. The method of any one of embodiments 77-96, wherein the device comprises a wireless transmitter.

98. The method of embodiment 97, wherein the wireless transmitter is a Bluetooth transmitter, an RF transmitter, a cellular signal transmitter, a Wi-fi transmitter, or any combination thereof.

99. The method of any one of embodiments 77-98, wherein the device comprises a wireless receiver.

100. The method of embodiment 99, wherein the wireless receiver is a Bluetooth receiver, an RF receiver, a cellular signal receiver, a Wi-fi receiver, or any combination thereof.

101. The method of embodiment 96, wherein the oral sample collection device comprises an oral swab.

102. The method of any one of embodiments 77-102, further comprising administering a treatment to the subject.

103. The method of embodiment 102, wherein a choice of treatment administered is at least partially determined by a level of a biomarker detected in the bodily fluid of the subject.

104. The method of embodiment 102, further comprising selecting a treatment from a database prior to the administering.

105. The method of embodiment 104, wherein the database is at least transiently stored on a computer readable memory.

106. The method of embodiment 104 or 105, wherein the database comprises a treatment formulary of medicaments or interventions.

107. The method of any one of embodiments 102-106, wherein the treatment comprises a medicament.

108. The method of embodiment 107, wherein the medicament comprises a drug or biologic that is licensed or approved for a condition by the United States Federal Drug Agency (USFDA) anytime as of or after Apr. 1, 2020.

109. The method of embodiment 108, wherein the drug or the biologic is not licensed or approved by the USFDA for heart failure anytime as of or after Apr. 1, 2020.

110. The method of embodiment 107, wherein the medicament comprises a drug or biologic that is not licensed or approved by the USFDA for any condition anytime as of or after Apr. 1, 2020.

111. The method of any one of embodiments 102-110, wherein the medicament comprises a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator, cardioxyl, omecamtiv mecarbil, relaxin, serelaxin, staroxime, bucindolol, a phosphodiesterase 5 inhibitor, a vasopressin inhibitor, levosimendan, a sodium-glucose cotransporter-2 (SGLT2) inhibitor, an If channel blocker, an alpha blocker, a beta blocker, a beta receptor blocker, an ACE inhibitor, a stereoisomer of any of these, or a salt of any of these, or any combination thereof.

112. The method of embodiment 111, wherein the medicament comprises the beta receptor blocker or salt thereof, and wherein the beta receptor blocker or salt thereof comprise at least one stereocenter in an S-configuration.

113. The method of embodiment 112, wherein the beta receptor blocker comprises a long acting beta blocker.

114. The method of embodiment 112, wherein the beta receptor blocker comprises a short acting beta blocker.

115. The method of embodiment 113 or 114, wherein the long acting beta blocker or the short acting beta blocker comprises pindolol, oxprenolol, atenolol, acebutolol, bisoprolol, metoprolol, nadolol, nebivolol, propranolol, a stereoisomer of any of these, a polymorph of any of these, a diastereomer of any of these, a salt of any of these, or any combination thereof.

116. The method of embodiment 112, wherein the long acting or short acting beta blockers comprise S-pindolol, S-oxprenolol, S-atenolol, S-acebutolol, S-bisoprolol, S-metoprolol, S-nadolol, S-nebivolol, S-propranolol, a stereoisomer of any of these, a polymorph of any of these, a diastereomer of any of these, a salt of any of these, or any combination thereof.

117. The method of embodiment 111, wherein the medicament comprises the statin or salt thereof, and wherein the statin or salt thereof comprises atorvastatin, fluvastatin, lovastatin, pravastatin, rosuvastatin, simvastatin, pitavastatin, a salt of any of these, or any combination thereof.

118. The method of embodiment 111, wherein the medicament comprises the blood thinner or the salt thereof, and wherein the blood thinner or salt thereof comprises apixaban, dabigatran, edoxaban, fondaparinux, heparin, rivaroxaban, warfarin, a salt of any of these, or any combination thereof.

119. The method of embodiment 111, wherein the medicament comprises the phosphodiesterase 5 inhibitor or the salt thereof, and wherein the phosphodiesterase 5 inhibitor comprises amrinone, milrinone, avanafil, lodenafil, mirodenafil, sildenafil, tadalafil, vardenafil, udenafil, zaprinast, benzaminenafil, carvedilol, a salt of any of these, or any combination thereof.

120. The method of embodiment 111, wherein the medicament comprises the vasopressin inhibitor or the salt thereof, and wherein the vasopressin inhibitor or the salt thereof comprises conivaptan, relcovaptan, nelivaptan, lixivaptan, mozavaptan, satavaptan, tolvaptan, demeclocycline, lithium, a salt of any of these, or any combination thereof.

121. The method of embodiment 111, wherein the medicament comprises the SGLT2 inhibitor or the salt thereof, and wherein the SGLT2 inhibitor or the salt thereof comprises dapagliflozin, empagliflozin, canagliflozin, sotagliflozin, ertugliflozin, ipragliflozin, luseogliflozin, remogliflozin etabonate, sergliflozin etabonate, tofogliflozin a stereoisomer of any of these, a salt of any of these, or any combination thereof.

122. The method of embodiment 111, wherein the medicament comprises the aldosterone antagonist, or the salt thereof, and wherein the aldosterone antagonist or the salt thereof comprises spironolactone, eplerenone, finerenone, canreoate, a stereoisomer of any of these, a salt of any of these, or any combination thereof.

123. The method of embodiment 111, wherein the medicament comprises the aldosterone synthesis inhibitor or the salt thereof, and wherein the aldosterone synthesis inhibitor or the salt thereof comprises fadrozol, FAD 286, LCI699, a salt of any of these, or any combination thereof.

124. The method of embodiment 111, wherein the medicament comprises the angiotensin receptor antagonist or the salt thereof, and wherein the angiotensin receptor antagonist or the salt thereof comprises a sartan, candesartan, irbesartan, valsartan, telmisartan, eprosartan, Olmesartan, azilsartan, fimasartan, sacubitril/valsartan, losartan, EXP 3174, amlodipine, a stereoisomer of any of these, a salt of any of these, or any combination thereof.

125. The method of embodiment 111, wherein the medicament comprises the ACE inhibitor or the salt thereof, and wherein the ACE inhibitor or the salt thereof comprises benazepril, captopril, enalapril, fosinopril, lisinopril, moexipril, perindopril, quinapril, ramipril, trandolapril, or any combination thereof.

126. The method of embodiment 111, wherein the medicament comprises the alpha blocker or the salt thereof, and wherein the alpha blocker or the salt thereof comprises phenoxybenzamine, phentolamine, tolazoline, trazodone, alfuzosin, doxazosin, prazosin, tamsulosin, terazosin, silodosin, atipamezole, idazoxan, mirtazapine, yohimbine, or any combination thereof.

127. The method of embodiment 111, wherein the medicament comprises the guanylate cyclase stimulator or the salt thereof, and wherein the guanylate cyclase stimulator or the salt thereof comprises a guanylate cyclase activator, adempas, riociguat, a salt of any of these, or any combination thereof.

128. The method of embodiment 111, wherein the medicament comprises the inotrope or the salt thereof, and wherein the inotrope comprises a cardiac inotrope or a salt thereof.

129. The method of embodiment 128, wherein the cardiac inotrope or the salt thereof comprises a positive cardiac inotrope or a salt thereof.

130. The method of embodiment 129, wherein the positive cardiac inotrope or the salt thereof comprises a cardiotonic drug, a cardiotonic agent, a cardiostimulatory drug, a cardiostimulatory agent, any salt thereof, or any combination thereof.

131. The method of embodiment 130, wherein the positive cardiac inotrope or the salt thereof comprises a cardiac glycoside or a salt thereof.

132. The method of embodiment 131, wherein the cardiac glycoside or the salt thereof comprises a cardenolide, a bufadienolide, a salt of either of these, or any combination thereof.

133. The method of embodiment 132, wherein the cardiac glycoside or the salt thereof comprises the cardenolide, and wherein the cardenolide comprises a convallotoxin, an antiarin, a strophanthin, a digoxin, a digitoxin, an oleandrin, an adonitoxin, a salt of any of these, or any combination thereof.

134. The method of embodiment 132, wherein the cardiac glycoside or the salt thereof comprises the bufadienolide, and wherein the bufadienolide comprises a scillarenin, a proscillaridine A, a daigremontianin, a hellebore, a salt of any of these, or any combination thereof.

135. The method of embodiment 130, wherein the positive cardiac inotrope or the salt thereof comprises a myosin activator or a salt thereof.

136. The method of embodiment 135, wherein the myosin activator or the salt thereof comprises an omecamtiv mecarbil or a salt thereof.

137. The method of embodiment 128, wherein the cardiac inotrope comprises a negative cardiac inotrope or a salt thereof.

138. The method of embodiment 137, wherein the negative cardiac inotrope or the salt thereof comprises a beta-blocker, a calcium-channel blocker, an anti-arrhythmic medicine, a salt of any of these, or any combination thereof.

139. The method of embodiment 74, wherein the intervention comprises exercise, a selective diet, meditation, or any combination thereof.

140. The method of embodiment 139, wherein the diet comprises a supplement.

141. The method of embodiment 140, wherein the supplement comprises fish oil.

142. The method of any one of embodiments 1-141, further comprising monitoring a subject.

143. The method of embodiment 120, wherein the monitoring comprises monitoring a disease onset, disease progression, disease regression, or any combination thereof.

144. The method of any one of embodiments 1-76 or 83-143, further comprising monitoring the effectiveness of the treatment.

145. The method of any one of embodiments 119-121, wherein the monitoring comprises measuring heart rate, blood pressure, EKG readings, or any combination thereof over a time period.

146. A system comprising:
(a) a computer processor,
(b) a computer readable memory operatively coupled to the computer processor, wherein the computer readable memory at least transiently stores:
  (i) a database that comprises a treatment formulary of medicaments or interventions, and a plurality of biomarkers predictive of a probability of developing heart failure within a time period of from about 1 week to about 5 years; and
  (ii) an algorithm that, when executed by the computer processor, selects a treatment from the treatment formulary based on a biomarker selected from the plurality of compounds.

147. The system of embodiment 146, wherein the system further comprises a wireless transmitter or a wireless receiver.

148. The system of embodiment 147, wherein the system is configured for wireless communication to a device.

149. The system of embodiment 146, wherein the system is configured for wired communication to a device.

150. The system of embodiment 146-149, wherein the device is an oral sample collection device.

151. The system of embodiment 150, wherein the oral sample collection device comprises a compound, and wherein the oral sample collection device is configured to contact the compound with a biomarker present in saliva when the saliva is input into the oral sample collection device.

152. The system of embodiment 150 or 151, wherein the oral sample collection device comprises a wireless transmitter.

153. The system of embodiment 152, wherein the wireless transmitter is a Bluetooth transmitter, an RF transmitter, a cellular signal transmitter, a Wi-fi transmitter, or any combination thereof.

154. The system of any one of embodiments 150-153, wherein the oral sample collection device comprises a wireless receiver.

155. The system of embodiment 154, wherein the wireless receiver is a Bluetooth receiver, an RF transmitter, a cellular signal receiver, a Wi-fi receiver, or any combination thereof.

156. The system of embodiment 150, wherein the oral sample collection device comprises an oral swab.

157. The system of any one of embodiments 147-156, wherein the system is configured to access the database via the wireless transmitter or the wireless receiver, wherein the database is stored on a server.

158. The system of embodiment 157, wherein the server is a cloud-based server.

159. A kit comprising the first compound of embodiment 1 and an oral sample collection device.

160. The kit of embodiment 159, wherein the first compound is present in the oral sample collection device.

161. The kit of embodiment 159 or 160, wherein the first compound is a polypeptide.

162. The kit of embodiment 161, wherein the polypeptide comprises at least about 70% sequence identity to a polypeptide recited in Table 1, Table 7, a salt of any of these, or any combination thereof, as determined by BLAST.

163. A method of treating heart failure comprising:
(a) measuring one or more compounds present in a biological sample from a subject that does not currently have heart failure or that has not been diagnosed with heart failure, wherein an increased or decreased level of the compound relative to a reference level is indicative of a risk of developing heart failure within a time period;
(b) determining a risk score of the subject developing heart failure within a time period based on the increased or decreased levels of the one or more compounds; and
(c) administering a treatment for the heart failure to the subject based on the risk score.

164. The method of embodiment 163, wherein the one or more compounds is one or more biomarkers.

165. The method of embodiment 164, wherein the one or more biomarkers is a polypeptide comprising at least 70% sequence identity to AMPN, AMD, CALM3, KI21A, ACBP, IGA2, a salt of any of these, or any combination thereof.

166. The method of embodiment 164, wherein the one or more biomarkers comprises at least two polypeptides comprising at least 70% sequence identity to at least two of AMPN, AMD, CALM3, KI21A, ACBP, IGA2, S10A7, a salt of any of these, or any combination thereof.

167. The method of embodiment 164, wherein the one or more biomarkers comprises at least three polypeptides comprising at least 70% sequence identity to at least three of AMPN, AMD, CALM3, KI21A, ACBP, IGA2, S10A7, a salt of any of these, or any combination thereof.

168. The method of embodiment 164, wherein the one or more biomarkers comprises at least four polypeptides comprising at least 70% sequence identity to at least four of AMPN, AMD, CALM3, KI21A, ACBP, IGA2, S10A7, a salt of any of these, or any combination thereof.

169. The method of embodiment 164, wherein the one or more biomarkers comprises at least five polypeptides comprising at least 70% sequence identity to at least five of AMPN, AMD, CALM3, KI21A, ACBP, IGA2, S10A7, a salt of any of these, or any combination thereof.

170. The method of embodiment 165, wherein the polypeptide comprises at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity to AMPN, AMD, CALM3, KI21A, ACBP, IGA2, a salt of any of these, or any combination thereof.

171. The method of any one of embodiments 166-169, wherein the polypeptides comprise at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity to AMPN, AMD, CALM3, KI21A, ACBP, IGA2, S10A7, a salt of any of these, or any combination thereof.

172. The method of any one of embodiments 167-171, wherein the treatment for the heart failure administered to the subject is determined at least in part by the number of biomarkers that are expressed at an increased or decreased level relative to the reference level.

173. The method of any one of embodiments 164-171, wherein the treatment for the heart failure administered to the subject is determined at least in part by the quantitative level of a biomarker relative to the reference level.

174. The method of any one of embodiments 163-173, wherein the subject is classified as being low risk, medium risk or high risk of developing heart failure within a time period.

175. The method of embodiment 174, wherein the subject is determined to be at low risk of developing heart failure within ten years, and wherein the treatment prescribed comprises dietary intervention, exercise, or a combination thereof.

176. The method of embodiment 174, wherein the subject is determined to be at medium risk of developing heart failure within a time period, and wherein the treatment prescribed comprises administering a statin, an anti-inflammatory, a blood thinner, dietary intervention, exercise, or any combination thereof.

177. The method of embodiment 174, wherein the subject is determined to be at high risk of developing heart failure within the next six months, and wherein the treatment prescribed comprises administering a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator, cardioxyl, omecamtiv mecarbil, relaxin, serelaxin, staroxime, bucindolol, a phosphodiesterase 5 inhibitor, a vasopressin inhibitor, levosimendan, a sodium-glucose cotransporter-2 (SGLT2) inhibitor, an If channel blocker, an alpha blocker, a beta blocker, a beta receptor blocker, an ACE inhibitor, a stereoisomer of any of these, or a salt of any of these, or any combination thereof.

178. The method of any one of embodiments 163-177, wherein the biological sample comprises amniotic fluid, amniotic sac, aqueous humor, bile, blood, blood plasma, breast milk, cerebrospinal fluid (CSF), cerebrospinal fluid rhinorrhea, chyle, chyme, endolymph, extracellular fluid, exudate, gastric acid, hemolacria, hemolymph, interstitial fluid, lymph, mucus, pericardial fluid, perilymph, peritoneal fluid, perspiration, phlegm, pus, rheum, saliva, semen, sweat, synovial fluid, tears, transcellular fluid, transudate, urine, vaginal lubricant, vitreous body, vomit, or any combination thereof.

179. The method of any one of embodiments 163-177, wherein the biological sample comprises urine.

180. The method of any one of embodiments 163-177, wherein the biological sample comprises saliva.

181. The method of embodiment 180, wherein the biological sample is obtained using an oral sample collection device.

182. The method of embodiment 181, wherein the oral sample collection device comprises a detection compound, and wherein the device is configured to perform the contacting when the saliva is input into the oral sample collection device.

183. The method of embodiment 181 or 182, wherein the oral sample collection device comprises a wireless transmitter.

184. The method of embodiment 183, wherein the wireless transmitter comprises a Bluetooth transmitter, an RF transmitter, a cellular signal transmitter, a Wi-fi transmitter, or any combination thereof.

185. The method of any one of embodiments 181-184, wherein the oral sample collection device comprises a wireless receiver.

186. The method of embodiment 185, wherein the wireless receiver comprises a Bluetooth receiver, an RF transmitter, a cellular signal receiver, a Wi-fi receiver, or any combination thereof.

187. The method of any one of embodiments 181-186, wherein the oral sample collection device comprises an oral swab.

188. The method of any one of embodiments 182-187, wherein a concentration of the one or more compounds present in a biological sample is enriched in the oral sample collection device after binding to the detection compound, relative to the concentration of the compound present in the biological sample.

189. The method of any one of embodiments 163-188, further comprising, with the aid of a computer processor, executing an algorithm selecting a treatment from a database prior to the administering.

190. The method of embodiment 189, wherein the database is at least transiently stored on a computer readable memory.

191. The method of embodiment 189 or 190, wherein the database comprises a treatment formulary of medicaments or interventions.

192. The method of any one of embodiments 189-191, wherein the treatment comprises a medicament.

193. The method of embodiment 192, wherein the medicament comprises a drug or a biologic that is licensed or approved for a condition by the United States Federal Drug Agency (USFDA) anytime as of or after Apr. 1, 2020.

194. The method of embodiment 193, wherein the drug or the biologic is not licensed or approved by the USFDA for heart failure anytime as of or after May 1, 2020.

195. The method of embodiment 192, wherein the medicament comprises a drug or a biologic that is not licensed or approved by the USFDA for any condition anytime as of or after May 1, 2020.

196. The method of any one of embodiments 192-195, wherein the medicament comprises a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator cardioxyl, an omecamtiv mecarbil, a relaxin, a serelaxin, a staroxime, bucindolol, a phosphodiesterase 5 inhibitor, a vasopressin inhibitor, a levosimendan, a sodium-glucose cotransporter-2 (SGLT2) inhibitor, an If channel blocker, an alpha blocker, a beta receptor blocker, a beta blocker, an ACE inhibitor, a stereoisomer of any of these, a salt of any of these, or any combination thereof.

197. The method of embodiment 196, wherein the medicament comprises the beta receptor blocker or the salt thereof, wherein the beta receptor blocker or salt thereof comprise at least one stereocenter in an S-configuration.

198. The method of embodiment 197, wherein the beta receptor blocker comprises a long acting beta blocker.

199. The method of embodiment 197, wherein the beta receptor blocker comprises a short acting beta blocker.

200. The method of embodiment 198 or 199, wherein the long acting beta blocker or salt thereof or the short acting beta blocker or the salt thereof comprises pindolol, oxprenolol, atenolol, acebutolol, bisoprolol, bucindolol, carvedilol, metoprolol, nadolol, nebivolol, oxprenolol, propranolol, a stereoisomer of any of these, a polymorph of any of these, a diastereomer of any of these, a salt of any of these, or any combination thereof.

201. The method of embodiment 197, wherein the long acting or short acting beta blocker or the salt thereof comprise S-pindolol, S-oxprenolol, S-atenolol, S-acebutolol, S-bisoprolol, S-bucindolol, S-carvedilol, S-metoprolol, S-nadolol, S-nebivolol, S-Oxprenolol, S-propranolol, a stereoisomer of any of these, a polymorph of any of these, a diastereomer of any of these, a salt of any of these, or any combination thereof.

202. The method of embodiment 196, wherein the medicament comprises the statin or the salt thereof, wherein the statin or the salt thereof comprises atorvastatin, fluvastatin, lovastatin, pravastatin, rosuvastatin, simvastatin, pitavastatin, a salt of any of these, or any combination thereof.

203. The method of embodiment 196, wherein the medicament comprises the blood thinner or the salt thereof, wherein the blood thinner or the salt thereof comprises apixaban, dabigatran, edoxaban, fondaparinux, heparin, rivaroxaban, warfarin, a salt of any of these, or any combination thereof.

204. The method of embodiment 196, wherein the medicament comprises the phosphodiesterase 5 inhibitor or the salt thereof, wherein the phosphodiesterase 5 inhibitor or the salt thereof comprises amrinone, milrinone, avanafil, lodenafil, mirodenafil, sildenafil, tadalafil, vardenafil, udenafil, zaprinast, benzaminenafil, a salt of any of these, or any combination thereof.

205. The method of embodiment 196, wherein the medicament comprises the vasopressin inhibitor or the salt thereof, wherein the vasopressin inhibitor or the salt thereof comprises conivaptan, relcovaptan, nelivaptan, lixivaptan, mozavaptan, satavaptan, tolvaptan, demeclocycline, lithium, a salt of any of these, or any combination thereof.

206. The method of embodiment 196, wherein the medicament comprises the SGLT2 inhibitor or the salt thereof, wherein the SGLT2 inhibitor or the salt thereof comprises dapagliflozin, empagliflozin, canagliflozin, sotagliflozin, ertugliflozin, ipragliflozin, luseogliflozin, remogliflozin etabonate, sergliflozin etabonate, tofogliflozin a stereoisomer of any of these, a salt of any of these, or any combination thereof.

207. The method of embodiment 196, wherein the medicament comprises the aldosterone antagonist or the salt thereof, wherein the aldosterone antagonist or the salt thereof comprises spironolactone, eplerenone, finerenone, canrenoate, a stereoisomer of any of these, a salt of any of these, or any combination thereof.

208. The method of cembodiment laim 196, wherein the medicament comprises the aldosterone synthesis inhibitor or the salt thereof, wherein the aldosterone synthesis inhibitor or the salt thereof comprises fadrozol, FAD 286, LCI699, a salt of any of these, or any combination thereof.

209. The method of embodiment 196, wherein the medicament comprises the angiotensin receptor antagonist or the salt thereof, wherein the angiotensin receptor antagonist or salt thereof comprises a sartan, candesartan, irbesartan, valsartan, telmisartan, eprosartan, olmesartan, azilsartan, fimasartan, sacubitril/valsartan, losartan, EXP 3174, amlodipine, a stereoisomer of any of these, a salt of any of these, or any combination thereof.

210. The method of embodiment 196, wherein the medicament comprises the ACE inhibitor or the salt thereof, wherein the ACE inhibitor or the salt thereof comprises benazepril, captopril, enalapril, fosinopril, lisinopril, moexipril, omapatrilat, perindopril, quinapril, ramipril, trandolapril, a salt of any of these, or any combination thereof.

211. The method of embodiment 196, wherein the medicament comprises the alpha blocker or the salt thereof, wherein the alpha blocker or the salt thereof comprises phenoxybenzamine, phentolamine, tolazoline, trazodone, alfuzosin, doxazosin, prazosin, tamsulosin, terazosin, silodosin, atipamezole, idazoxan, mirtazapine, yohimbine, a salt of any of these, or any combination thereof.

212. The method of embodiment 196, wherein the medicament comprises the guanylate cyclase stimulator or the salt thereof, wherein the guanylate cyclase stimulator or the salt thereof comprises a guanylate cyclase activator, adempas, riociguat, a salt of any of these or a combination thereof.

213. The method of embodiment 196, wherein the medicament comprises the inotrope or the salt thereof, wherein the inotrope comprises a cardiac inotrope or a salt thereof.

214. The method of embodiment 213, wherein the cardiac inotrope or salt thereof comprises a positive cardiac inotrope or a salt thereof.

215. The method of embodiment 213, wherein the positive cardiac inotrope or a salt thereof comprises a cardiotonic drug, a cardiotonic agent, a cardiostimulatory drug, a cardiostimulatory agent, any salt thereof, or any combination thereof.

216. The method of embodiment 213, wherein the positive cardiac inotrope or a salt thereof comprises a cardiac glycoside or a salt thereof.

217. The method of embodiment 216, wherein the cardiac glycoside or the salt thereof comprises a cardenolide, a bufadienolide, a salt of either of these, or any combination thereof.

218. The method of embodiment 217, wherein the cardiac glycoside or the salt thereof comprises the cardenolide or the salt thereof, and wherein the cardenolide or the salt thereof comprises a convallotoxin, an antiarin, a strophanthin, a digoxin, a digitoxin, an oleandrin, an adonitoxin, a salt of any of these, or any combination thereof.

219. The method of embodiment 218, wherein the cardiac glycoside or the salt thereof comprises the bufadienolide or the salt thereof, and wherein the bufadienolide or the salt thereof comprises a scillarenin, a proscillaridine A, a daigremontianin, a hellebore, a salt of any of these, or any combination thereof.

220. The method of embodiment 196, wherein the medicament comprises the cardiac inotrope or the salt thereof, wherein the cardiac inotrope or the salt thereof comprises a myosin activator or a salt thereof.

221. The method of embodiment 220, wherein the myosin activator or the salt thereof comprises an omecamtiv mecarbil or a salt thereof.

222. The method of embodiment 196, wherein the medicament comprises the cardiac inotrope or the salt thereof, wherein the cardiac inotrope or the salt thereof comprises a negative cardiac inotrope or a salt thereof.

223. The method of embodiment 222, wherein the negative cardiac inotrope or the salt thereof comprises a beta-blocker, a calcium-channel blocker, an anti-arrhythmic medicine, a salt of any of these, or any combination thereof.

224. The method of any one of embodiments 163-191, wherein the treatment comprises an intervention.

225. The method of embodiment 224, wherein the intervention comprises exercise, a selective diet, meditation, instructions to see a cardiologist, instructions to dispense a medicament, instructions to receive an ultrasound, or any combination thereof.

226. The method of any one of embodiments 189-225, wherein the database comprises a plurality of the compounds present in the biological sample from the subject.

227. A method of using a machine learning model to determine a risk of a subject developing heart failure comprising:
(a) measuring a level of one or more compounds present in a biological sample from the subject that does not currently have heart failure or that has not been diagnosed with heart failure, wherein an increased or decreased level of the compound relative to a reference level is indicative of a risk of developing heart failure within a time period;
(b) clustering the level of the one or more compounds present in the biological sample using the machine learning model;
(c) identifying a cluster of the one or more compound present in the biological sample, wherein the cluster represents the plurality of biomarker levels associated with a risk of a subject developing heart failure; and
(d) determining the risk of the subject developing heart failure within a time period.

228. The method of embodiment 227, wherein the one or more compounds is one or more biomarkers.

229. The method of embodiment 228, wherein the one or more biomarkers is a polypeptide comprising at least 70% sequence identity to AMPN, AMD, CALM3, KI21A, ACBP, IGA2, a salt of any of these, or any combination thereof.

230. The method of embodiment 228, wherein the one or more biomarkers comprises at least two polypeptides comprising at least 70% sequence identity to at least two of AMPN, AMD, CALM3, KI21A, ACBP, IGA2, S10A7, a salt of any of these, or any combination thereof.

231. The method of embodiment 228, wherein the one or more biomarkers comprises at least three polypeptides comprising at least 70% sequence identity to at least three of AMPN, AMD, CALM3, KI21A, ACBP, IGA2, S10A7, a salt of any of these, or any combination thereof.

232. The method of embodiment 228, wherein the one or more biomarkers comprises at least four polypeptides comprising at least 70% sequence identity to at least four of AMPN, AMD, CALM3, KI21A, ACBP, IGA2, S10A7, a salt of any of these, or any combination thereof.

233. The method of embodiment 228, wherein the one or more biomarkers comprises at least five polypeptides comprising at least 70% sequence identity to at least five of AMPN, AMD, CALM3, KI21A, ACBP, IGA2, S10A7, a salt of any of these, or any combination thereof.

234. The method of embodiment 229, wherein the polypeptide comprises at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity to AMPN, AMD, CALM3, KI21A, ACBP, IGA2, a salt of any of these, or any combination thereof.

235. The method of any one of embodiments 230-233, wherein the polypeptides comprise at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% sequence identity to AMPN, AMD, CALM3, KI21A, ACBP, IGA2, S10A7, a salt of any of these, or any combination thereof.

236. The method of any one of embodiments 231-235, wherein the treatment for the heart failure administered to the subject is determined at least in part by the number of biomarkers that are expressed at an increased or decreased level relative to a reference level.

237. The method of any one of embodiments 228-235, wherein the treatment for the heart failure administered to the subject is determined at least in part by the quantitative level of a biomarker relative to a reference level.

238. The method of any one of embodiments 226-237, wherein the subject is classified as being low risk, medium risk or high risk of developing heart failure within a time period.

239. The method of embodiment 238, wherein the subject is determined to be at low risk of developing heart failure, and the treatment prescribed comprises dietary intervention, exercise, or a combination thereof.

240. The method of embodiment 238, wherein the subject is determined to be at medium risk of developing heart failure, and the treatment prescribed comprises administering a statin, an anti-inflammatory, a blood thinner, dietary intervention, exercise, or any combination thereof.

241. The method of embodiment 238, wherein the subject is determined to be at high risk of developing heart failure within the next six months, and the treatment prescribed comprises administering a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator, cardioxyl, omecamtiv mecarbil, relaxin, serelaxin, staroxime, bucindolol, a phosphodiesterase 5 inhibitor, a vasopressin inhibitor, levosimendan, a sodium-glucose cotransporter-2 (SGLT2) inhibitor, an If channel blocker, an alpha blocker, a beta blocker, a beta receptor blocker, an ACE inhibitor, a stereoisomer of any of these, or a salt of any of these, or any combination thereof.

242. The method of any one of embodiments 227-241, wherein the biological sample comprises amniotic fluid, amniotic sac, aqueous humor, bile, blood, blood plasma, breast milk, cerebrospinal fluid (CSF), cerebrospinal fluid rhinorrhea, chyle, chyme, endolymph, extracellular fluid, exudate, gastric acid, hemolacria, hemolymph, interstitial fluid, lymph, mucus, pericardial fluid, perilymph, peritoneal fluid, perspiration, phlegm, pus, rheum, saliva, semen, sweat, synovial fluid, tears, transcellular fluid, transudate, urine, vaginal lubricant, vitreous body, vomit, or any combination thereof.

243. The method of any one of embodiments 227-241, wherein the biological sample comprises urine.

244. The method of any one of embodiments 227-241, wherein the biological sample comprises saliva.

245. The method of embodiment 244, wherein the biological sample is obtained using an oral sample collection device.

246. The method of embodiment 245, wherein the oral sample collection device comprises a detection compound, and wherein the device is configured to perform the contacting when the saliva is input into the oral sample collection device.

247. The method of embodiment 245 or 246, wherein the oral sample collection device comprises a wireless transmitter.

248. The method of embodiment 247, wherein the wireless transmitter comprises a Bluetooth transmitter, an RF transmitter, a cellular signal transmitter, a Wi-fi transmitter, or any combination thereof.

249. The method of any one of embodiments 245-248, wherein the oral sample collection device comprises a wireless receiver.

250. The method of embodiment 249, wherein the wireless receiver comprises a Bluetooth receiver, an RF transmitter, a cellular signal receiver, a Wi-fi receiver, or any combination thereof.

251. The method of any one of embodiments 245-250, wherein the oral sample collection device comprises an oral swab.

252. The method of any one of embodiments 246-251, wherein a concentration of the one or more compounds present in a biological sample is enriched in the oral sample collection device after binding to the detection compound, relative to the concentration of the compound present in the biological sample.

253. The method of any one of embodiments 226-252, further comprising, with the aid of a computer processor, executing an algorithm selecting a treatment from a database prior to the administering.

254. The method of embodiment 253, wherein the database is at least transiently stored on a computer readable memory.

255. The method of claim 253 or 254, wherein the database comprises a treatment formulary of medicaments or interventions.

256. The method of any one of embodiment s 253-255, wherein the treatment comprises a medicament.

257. The method of embodiment 256, wherein the medicament comprises a drug or a biologic that is licensed or approved for a condition by the United States Federal Drug Agency (USFDA) anytime as of or after Apr. 1, 2020.

258. The method of embodiment 257, wherein the drug or the biologic is not licensed or approved by the USFDA for heart failure anytime as of or after May 1, 2020.

259. The method of embodiment 256, wherein the medicament comprises a drug or a biologic that is not licensed or approved by the USFDA for any condition anytime as of or after May 1, 2020.

260. The method of any one of embodiments 256-259, wherein the medicament comprises a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator cardioxyl, an omecamtiv mecarbil, a relaxin, a serelaxin, a staroxime, bucindolol, a phosphodiesterase 5 inhibitor, a vasopressin inhibitor, a levosimendan, a sodium-glucose cotransporter-2 (SGLT2) inhibitor, an If channel blocker, an alpha blocker, a beta receptor blocker, a beta blocker, an ACE inhibitor, a stereoisomer of any of these, a salt of any of these, or any combination thereof 261. The method of embodiment 227, wherein the machine learning model clusters the level of the one or more compounds present in the biological sample using a linear regression, a neural network, an ensemble, or any combination thereof.

What is claimed is:

1. A method of treating heart failure comprising:
(a) measuring two or more biomarkers present in a biological sample from a subject that does not currently have heart failure or that has not been diagnosed with heart failure, wherein an increased or decreased level of the two or more biomarkers relative to a reference level is indicative of a risk of developing heart failure within a time period, wherein the two or more biomarkers comprise a first polypeptide comprising at least 70% sequence identity to CALM3 (calmodulin-3) or a salt thereof, and wherein the two or more biomarkers further comprise a second polypeptide comprising at least 70% sequence identity to a member selected from the group consisting of
AMPN (Aminopeptidase N)
AMD (Peptidyl-glycine alpha-amidating monooxygenase)
KI21A (Kinesin-like protein KIF21A)
ACBP (Acyl-CoA-binding protein)
IGA2 (Immunoglobulin alpha-2 heavy chain)
S10A7 (Protein S100-A7), a salt of any of these, and any combination thereof;
(b) determining a risk score of the subject developing heart failure within the time period based on the increased or decreased levels of the two or more-biomarkers; and
(c) administering a treatment for the heart failure to the subject based on the risk score, wherein:
(i) the subject is determined to be at low risk of developing heart failure within about ten years, and wherein the treatment prescribed comprises dietary intervention, exercise, or a combination thereof;
(ii) the subject is determined to be at medium risk of developing heart failure within about five years, and wherein the treatment prescribed comprises administering a statin, an anti-inflammatory, a blood thinner, dietary intervention, exercise, or any combination thereof; or
(iii) the subject is determined to be at high risk of developing heart failure within about six months, and wherein the treatment prescribed comprises administering a statin, an anti-inflammatory, a blood thinner, an aldosterone antagonist, a mineralocorticoid receptor antagonist, an aldosterone synthesis inhibitor, a myosin activator, an inotrope, a guanylate cyclase stimulator, a guanylate cyclase activator, omecamtiv mecarbil, relaxin, serelaxin, staroxime, bucindolol, a phosphodiesterase 5 inhibitor, a vasopressin inhibitor, levosimendan, a sodium-glucose cotransporter-2 (SGLT2) inhibitor, an $I_f$ channel blocker, an alpha blocker, a beta blocker, a beta receptor blocker, an angiotensin-converting enzyme (ACE) inhibitor, a stereoisomer of any of these, a salt of any of these, or any combination thereof.

2. The method of claim 1, wherein the treatment for heart failure administered to the subject is determined at least in part by the quantitative level of the two or more biomarkers relative to the reference level.

3. The method of claim 1, wherein the biological sample comprises amniotic fluid, amniotic sac, aqueous humor, bile, blood, blood plasma, breast milk, cerebrospinal fluid (CSF), cerebrospinal fluid rhinorrhea, chyle, chyme, endolymph, extracellular fluid, exudate, gastric acid, hemolacria, hemolymph, interstitial fluid, lymph, mucus, pericardial fluid, perilymph, peritoneal fluid, perspiration, phlegm, pus, rheum, saliva, semen, sweat, synovial fluid, tears, transcellular fluid, transudate, urine, vaginal lubricant, vitreous body, vomit, or any combination thereof.

4. The method of claim 1, wherein the biological sample comprises saliva.

5. The method of claim 4, wherein the biological sample is obtained using an oral sample collection device.

6. The method of claim 5, wherein the oral sample collection device comprises a detection compound that contacts one of the two or more biomarkers in the saliva when the saliva is input into the oral sample collection device.

7. The method of claim 5, wherein the oral sample collection device comprises a wireless transmitter.

8. The method of claim 7, wherein the wireless transmitter comprises a Bluetooth transmitter, a radio frequency (RF) transmitter, a cellular signal transmitter, a Wi-fi transmitter, or any combination thereof.

9. The method of claim 5, wherein the oral sample collection device comprises a wireless receiver.

10. The method of claim 9, wherein the wireless receiver comprises a Bluetooth receiver, a radio frequency (RF) transmitter, a cellular signal receiver, a Wi-fi receiver, or any combination thereof.

11. The method of claim 5, wherein the oral sample collection device comprises an oral swab.

12. The method of claim 5, wherein a concentration of the two or more biomarkers present in the biological sample is enriched in the oral sample collection device after contacting the detection compound, relative to the concentration of the two or more biomarkers present in the biological sample.

13. The method of claim 1, further comprising, with the aid of a computer processor, executing an algorithm selecting a treatment from a database prior to the administering.

14. The method of claim 13, wherein the database is at least transiently stored on a computer readable memory.

15. The method of claim 13, wherein the database comprises a treatment formulary of medicaments or interventions.

16. The method of claim 1, wherein the second polypeptide comprises at least 70% sequence identity to KI21A, S10A7, a salt of any of these, or any combination thereof.

17. The method of claim 1, wherein the method further comprises measuring a third polypeptide, wherein the second polypeptide and the third polypeptide comprise at least two polypeptides comprising at least 70% sequence identity to at least two of AMPN, AMD, KI21A, ACBP, IGA2, S10A7, a salt of any of these, or any combination thereof.

18. The method of claim 17, wherein the method further comprises measuring a fourth polypeptide, wherein the second polypeptide, the third polypeptide, and the fourth polypeptide comprise at least three polypeptides comprising at least 70% sequence identity to at least three of AMPN, AMD, KI21A, ACBP, IGA2, S10A7, a salt of any of these, or any combination thereof.

19. The method of claim 17, wherein the method further comprises measuring a fifth polypeptide, wherein the second polypeptide, the third polypeptide, the fourth polypeptide, and the fifth polypeptide comprise at least four polypeptides comprising at least 70% sequence identity to at least four of AMPN, AMD, KI21A, ACBP, IGA2, S10A7, a salt of any of these, or any combination thereof.

20. The method of claim 1, wherein measuring in (a) comprises measuring via mass spectrometry.

* * * * *